United States Patent
David et al.

(10) Patent No.: US 12,180,165 B2
(45) Date of Patent: *Dec. 31, 2024

(54) HUMAN TLR8-SELECTIVE AGONISTS

(71) Applicant: University of Kansas, Lawrence, KS (US)

(72) Inventors: Sunil A. David, Lawrence, KS (US); Mallesh Beesu, Lawrence, KS (US); Giuseppe Caruso, Lawrence, KS (US); Alex Salyer, Marion, OH (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 398 days.

This patent is subject to a terminal disclaimer.

(21) Appl. No.: 17/472,371

(22) Filed: Sep. 10, 2021

(65) Prior Publication Data

US 2022/0002251 A1 Jan. 6, 2022

Related U.S. Application Data

(63) Continuation of application No. 15/754,193, filed as application No. PCT/US2016/047791 on Aug. 19, 2016, now Pat. No. 11,130,736.

(60) Provisional application No. 62/208,019, filed on Aug. 21, 2015.

(51) Int. Cl.
| C07D 215/38 | (2006.01) |
| A61K 45/06 | (2006.01) |
| A61P 37/02 | (2006.01) |
| A61K 39/39 | (2006.01) |

(52) U.S. Cl.
CPC ............ *C07D 215/38* (2013.01); *A61K 45/06* (2013.01); *A61P 37/02* (2018.01); *A61K 39/39* (2013.01)

(58) Field of Classification Search
None
See application file for complete search history.

(56) References Cited

U.S. PATENT DOCUMENTS

| 9,296,698 B2 | 3/2016 | Cheng et al. | |
| 2014/0135359 A1* | 5/2014 | Martineau | A61K 31/421 514/460 |

FOREIGN PATENT DOCUMENTS

| WO | WO-2012/080953 | 6/2012 |
| WO | WO-2015/023958 | 2/2015 |
| WO | WO-2015/095780 | 6/2015 |

OTHER PUBLICATIONS

Chemical Abstract Registry No. 203506-20-1 indexed in the Registry File on STN CAS Online Apr. 2, 1998.*
Chemical Abstract Registry No. 1273805-54-1, indexed in the Registry File on STN CAS Online Apr. 3, 2011.
Chemical Abstract Registry No. 1495291-70-7, indexed in the Registry File on STN CAS Online Dec. 15, 2013.
Chemical Abstract Registry No. 1692842-61-7, indexed in the Registry File on STN CAS Online Apr. 27, 2015.
Final Office Action issued in U.S. Appl. No. 15/754,193 on Apr. 14, 2021, 9 pgs.
Final Office Action issued in U.S. Appl. No. 15/754,193 on Jul. 22, 2020, 13 pgs.
Hari Prasad Kokatla et al: "Structure-Based Design of Novel Human Toll-like Receptor 8 Agonists", CHEMMEDCHEM, vol. 9, No. 4, Jan. 28, 2014 (Jan. 28, 2014), pp. 719-723, XP002788547, DE ISSN: 1860-7179, DOI: 10.1002/cmdc.201300573.
International Preliminary Report on Patentability re Application No. PCT/US2016/047791 issued Feb. 27, 2018; 5 pgs.
Ito et al., "A medium-term rat liver bioassay for rapid in vivo detection of carcinogenic potential of chemicals." Cancer Science, 2003, 94, 3-8.
Mallesh Beesu et al: "Structure-Based Design of Human TLR8-Specific Agonists with Augmented Potency and Adjuvanticity", Journal of Medicinal Chemistry, vol. 58, No. 19, pp. 7833-7849, XP002788548, ISSN: 0022-2623, DOI: 10.1021/acs.jmedchem.5b01087, (published on Sep. 9, 2015).
Nasr et al., "7-Aminoquinolines. A Novel Class of Agents Active against Herpesviruses." Journal of Medicinal Chemistry, 1988, 31, 1347-1351.
Non-Final Office Action issued in U.S. Appl. No. 15/754,193 on Jun. 13, 2019, 17 pages.
Non-Final Office Action issued in U.S. Appl. No. 15/754,193 on Oct. 1, 20, 9 pgs.
Non-Final Office Action issued in U.S. Appl. No. 15/754,193 on Dec. 19, 19, 12 pgs.
Notice of Allowance issued in U.S. Appl. No. 15/754,193 on May 25, 2021, 9 pgs.
Office Action issued in U.S. Appl. No. 15/754,193 on Feb. 25, 2019, 10 pgs.
PCT International Search Report and Written Opinion mailed Mar. 2, 2017 for International Application No. PCT/US2016/047791.

(Continued)

*Primary Examiner* — Po-Chih Chen
(74) *Attorney, Agent, or Firm* — Foley & Lardner LLP

(57) ABSTRACT

The disclosure provides human toll-like receptor modulators of general Formula (II), wherein $R^1$, $R^2$, $R^3$, $R^4$, $R^5$, $R^6$, $R^7$, $R^8$ are defined herein.

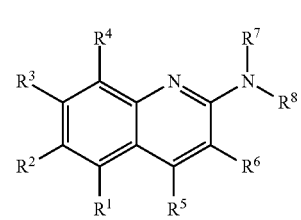

12 Claims, 10 Drawing Sheets

(56) References Cited

OTHER PUBLICATIONS

Supplemental European Search Report re Application No. EP16839885 dated Feb. 26, 2019, 8 pgs.
Yoo, Euna: "Determinants of Activity at Human to 11-like Receptors 7 and. 8: Quantitative Structure-Activity Relationship (QSAR) of Diverse Heterocyclic Scaffolds", Journal of Medicinal Chemistry, vol. 57, No. 19, Sep. 5, 2014 (Sep. 5, 2014), pp. 7955-7970, XP002788546, ISSN: 0022-2623, DOI : 10.1021/jm500744f.

* cited by examiner

1

2

3

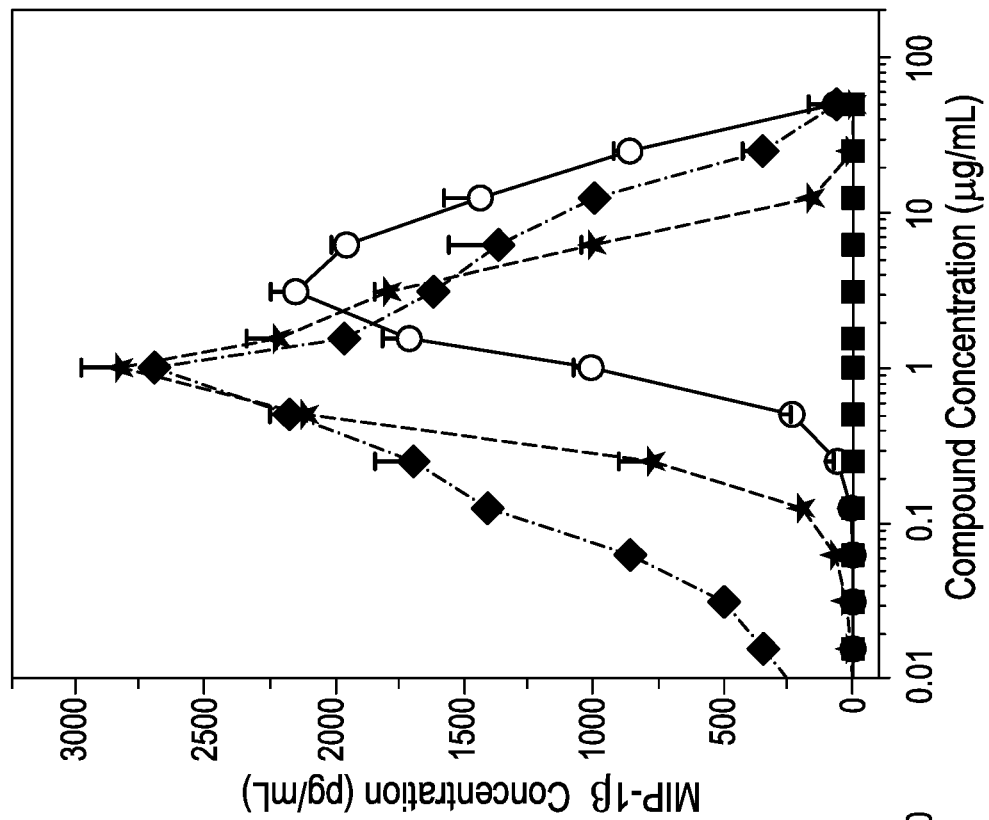
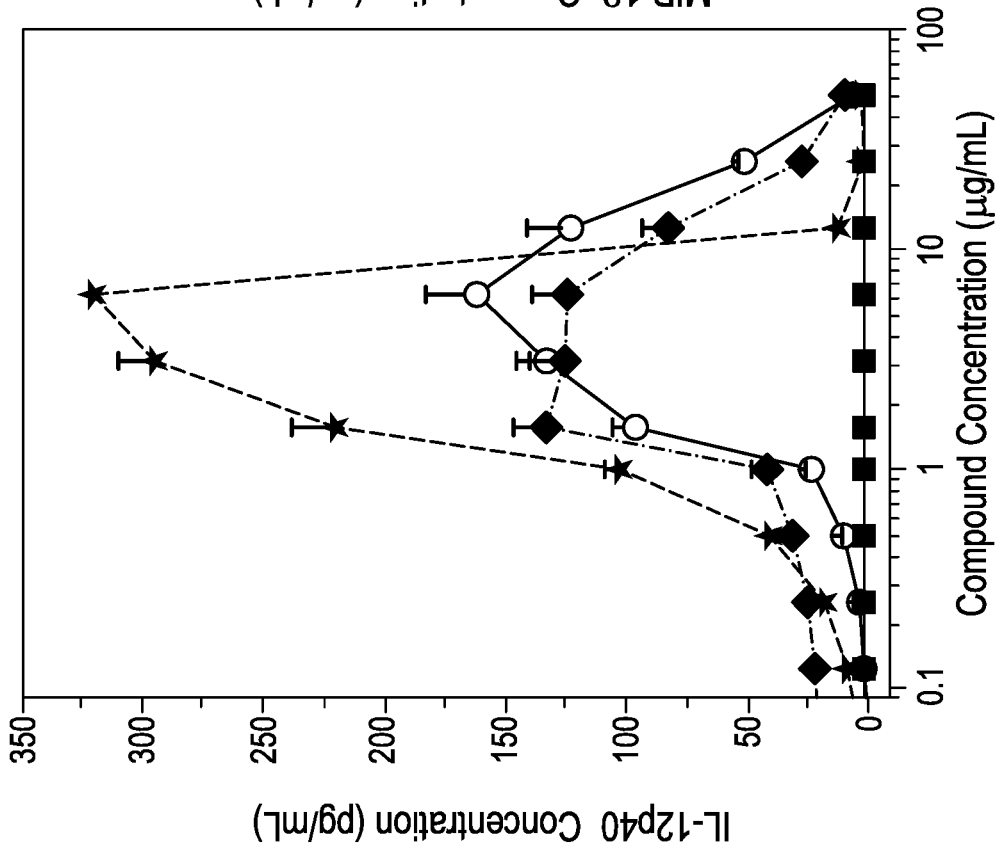
FIGURE 3C
FIGURE 3D

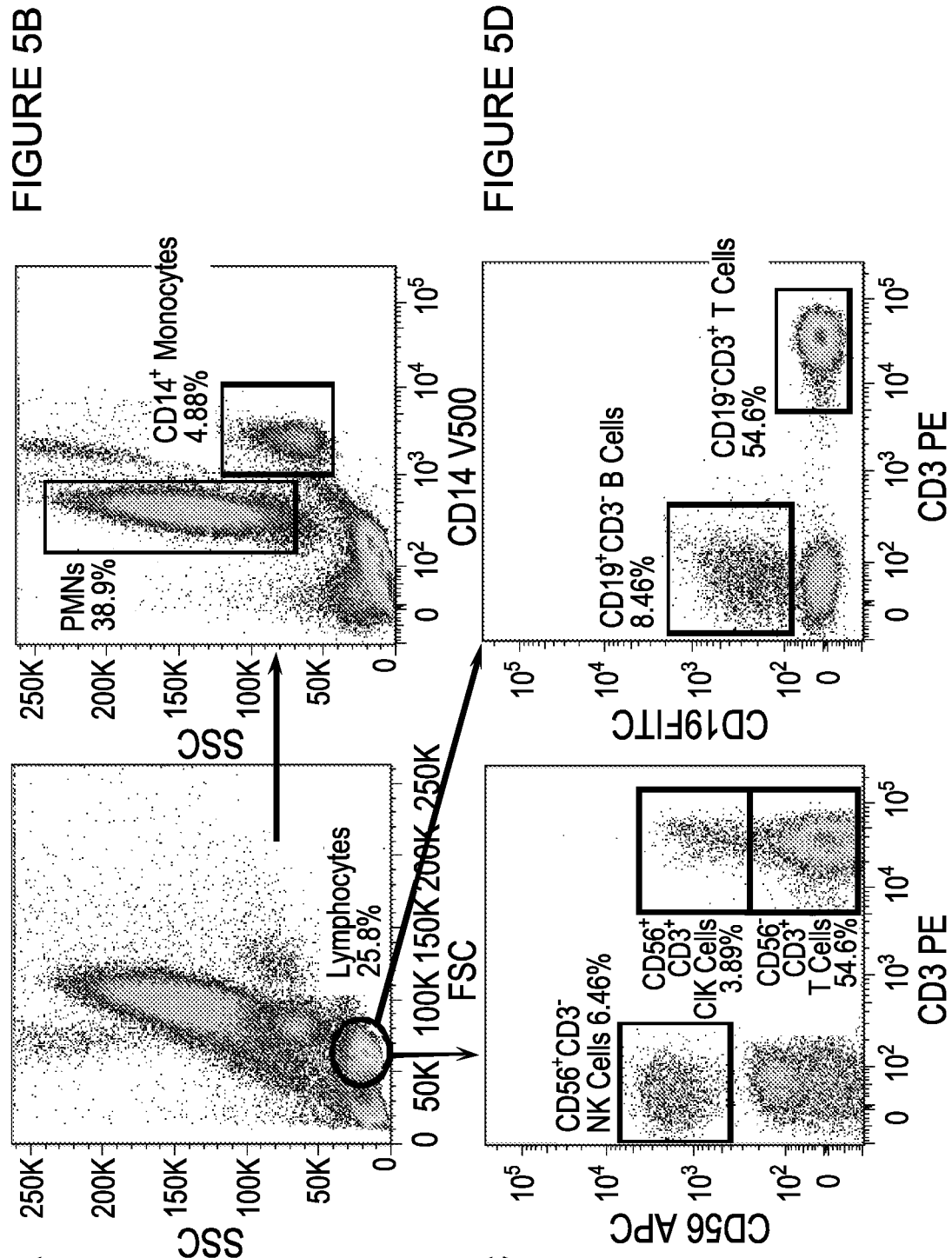

HUMAN TLR8-SELECTIVE AGONISTS

CROSS REFERENCE

This application is a continuation of U.S. application Ser. No. 15/754,193, filed Feb. 21, 2018, which is a U.S. National Phase Application under 35 U.S.C. § 371 of International Application No. PCT/US2016/047791, filed Aug. 19, 2016, which claims the benefit of U.S. Provisional Application No. 62/208,019, filed Aug. 21, 2015.

STATEMENT AS TO FEDERALLY SPONSORED RESEARCH

This invention was made with government support under grant number HHSN272201400056C awarded by the National Institutes of Health. The government has certain rights in the invention.

FIELD OF THE INVENTION

Embodiments of the invention are directed to compounds which are Toll-Like Receptor (TLR)-8 agonists. In particular, the compounds are TLR8-specific agonists which modulate immune responses or can be used as adjuvants.

BACKGROUND

The Centers for Disease Control and Prevention (CDC) has declared vaccination and the control of infectious diseases to be among the greatest public health achievements of the 20th century. Vaccines afford protection by the induction of immune responses, both humoral and cellular, specifically directed against the pathogen. A significant trend in contemporary vaccinology is the design of highly effective subunit vaccines, and the majority of modern subunit vaccines which utilize highly purified, recombinantly-expressed protein immunogens are reliant on vaccine adjuvants to provide the initial, innate immune-activating signals which determine the specificity, magnitude, quality, and durability of downstream adaptive immune responses.

With few exceptions, the majority of currently available vaccines contain a single adjuvant—'alum' introduced by Alexander Glenny in 1926 (Glenny, A. T.; et al., *J. Path. Bact.* 1926, 29, 38-45). 'Alum' (a mixture of aluminum phosphate and aluminum hydroxide), appears to promote a T helper 2 (Th2)-skewed antibody response, and is virtually ineffective at inducing cytotoxic T lymphocyte or mucosal IgA antibody responses (Gupta, R. K.; Siber, G. R. *Vaccine* 1995, 13, 1263-1276; Gupta, R. K. *Adv. Drug Deliv. Rev.* 1998, 32, 155-172). Indeed, alum-adjuvanted pertussis subunit vaccines (Klein, N. P. *Hum. Vaccin. Immunother.* 2014, 10, 2684-2690), which supplanted killed whole-cell pertussis vaccines in the 1990s, induce immunity that rapidly wanes (Sheridan, S. L. et al. *Exp. Rev. Vaccines* 2014, 13, 1081-1106; Lavine, J. S. et al. *Vaccine* 2012, 30, 544-51; Suryadevara, M. et al. *Hum. Vaccin. Immunother.* 2015, 11, 1744-1747); the short-lived immunity is thought to contribute to the recent re-emergence of pertussis in the United States (Clark, T. A. *J. Infect. Dis.* 2014, 209, 978-981; Cherry, J. D. *New Eng. J. Med.* 2012, 367, 785-787) and elsewhere in the world (Zepp, F. et al. *Lancet Infect. Dis.* 2011, 11, 557-570; Hara, M. et al. *BMC Infect. Dis.* 2015, 15, 45). In experimental models of pertussis, alum-adjuvanted acellular pertussis vaccines protected baboons in the short term from severe pertussis-like symptoms, but failed to prevent colonization of *B. pertussis*, allowing transmission of the pathogen to unvaccinated animals (Warfel, J. M. *Proc. Natl. Acad. Sci* USA 2014, 111, 787-792); killed whole-cell pertussis vaccines, on the other hand, elicited strong *B. pertussis*-specific Th17 and Th1 memory, indicating that both durability and quality of immune responses are pivotal in the induction and maintenance of long-term sterilizing immunity.

Innate immune signals evoked by vaccine adjuvants include those originating from Toll-like receptors (TLRs) (Hoffmann, J. et al. *Curr. Opin. Immunol.* 2013, 25, 1-3; Kumagai, Y. et al. *J. Allergy Clin. Immunol.* 2010, 125, 985-992; Kawai, T. et al. *Nat. Immunol.* 2010, 11, 373-384), as well as RIG-I-like receptors (Loo, Y. M. et al. *Immunity.* 2011, 34, 680-692) and NOD-like receptors (NLRs) (Kersse, K. et al. *Cytokine Growth Factor Rev.* 2011, 22, 257-276; Clarke, T. B. et al. *Immunol. Rev.* 2011, 243, 9-25). There are 10 functional TLRs encoded in the human genome, which are trans-membrane proteins with an extracellular domain having leucine-rich repeats (LRR) and a cytosolic domain called the Toll/IL-1 receptor (TIR) domain. The ligands for these receptors are highly conserved molecules such as lipopolysaccharides (LPS) (recognized by TLR4), lipopeptides (TLR2 in combination with TLR1 or TLR6), flagellin (TLR5), single stranded RNA (TLR7 and TLR8), double stranded RNA (TLR3), CpG motif-containing DNA (recognized by TLR9), and profilin present on uropathogenic bacteria (TLR11). TLR1, -2, -4, -5, and -6 recognize extracellular stimuli, while TLR3, -7, -8 and -9 function within the endolysosomal compartment.

The current understanding of how the engagement of innate immune receptors by vaccine adjuvants leads to the deployment and amplification of immunogen-specific adaptive immune responses (Hoffmann, J. et al. *Curr. Opin. Immunol.* 2013, 25, 1-3; Kumagai, Y. et al. *J. Allergy Clin. Immunol.* 2010, 125, 985-992; Cottalorda, A. et al. *Eur. J Immunol.* 2006, 36, 1684-1693), and the maintenance of immunological memory is incomplete, and may involve multiple mechanisms and pathways; these may include (i) enhanced antigen uptake and presentation by professional antigen presenting cells (APCs) (Xu, W. et al. *Front. Immunol.* 2014, 4, 504; Platt, A. M. et al. *Adv. Immunol.* 2013, 120, 51-68; Teijeira, A. et al. *Front. Immunol.* 2013, 4, 433; Teijeira, A.; et al. *Semin. Immunopathol.* 2014, 36, 261-274), (ii) amplification of cross-talk (Jenkins, M. K. et al. *Annu. Rev. Immunol.* 2001, 19, 23-45; Garside, P. et al. *Science* 1998, 281, 96-99; Miga, A. J. et al. *Eur. J. Immunol.* 2001, 31, 959-965) between naïve B lymphocytes recognizing the immunogen, and rare naïve CD4+ T cells expressing T cell antigen receptors (TCRs) specific for antigen-derived peptide/major histocompatibility complex class II molecules (MHCII) displayed by such naïve B cells, (iii) accelerated differentiation of CD4+ T cells into follicular helper T cells (Tfh) (Breitfeld, D. et al. *J. Exp. Med.* 2000, 192, 1545-1552; Hale, J. S. et al. *Front. Immunol.* 2015, 6, 16; Crotty, S. *Nat. Rev. Immunol.* 2015, 15, 185-189; Crotty, S. *Annu. Rev. Immunol.* 2011, 29, 621-663), and, (iv) subsequent B lymphocyte differentiation events leading to immunoglobulin affinity maturation (McHeyzer-Williams, L. J. et al. *Curr. Opin. Immunol.* 2009, 21, 266-273; Nurieva, R. I. et al. *Cell. Molec. Immunol.* 2010, 7, 190-19), and the generation of antigen-specific memory B cells and plasma cells (Hauser, A. E. et al. *Ann. NY Acad. Sci.* 2003, 987, 266-269; Borghesi, L. et al. *Immunol. Res.* 2006, 36, 27-32; Johnson, K. et al. *Molec. Immunol.* 2005, 42, 749-761).

The need for the development of safe and effective vaccine adjuvants has fueled the exploration of a variety of innate immune stimuli, which include agonists of TLR2

(Salunke, D. B. et al. *J. Med. Chem.* 2012, 55, 3353-3363; Salunke, D. B. et al. *J. Med Chem.* 2013, 56, 5885-5900; Wu, W. et al. *J Med. Chem.* 2010, 53, 3198-3213), TLR7 (Shukla, N. M. et al. *Bioorg. Med. Chem. Lett.* 2009, 19, 2211-2214; Shukla, N. M. et al. *J. Med. Chem.* 2010, 53, 4450-4465; Shukla, N. M. et al. *Bioorg. Med. Chem. Lett.* 2010, 20, 6384-6386; Shukla, N. M. et al. *Bioorg. Med. Chem. Lett.* 2011, 21, 3232-3236; Shukla, N. M. et al. *Med. Chem.* 2011, 19, 3801-3811; Shukla, N. M. et al. *J Med Chem.* 2012, 55, 1106-1116; Shukla, N. M. et al. *PLoS ONE.* 2012, 7, e43612; Yoo, E. et al. *Org. Biomol. Chem.* 2013, 11, 6526-6545; Yoo, E. et al. *J. Med. Chem.* 2014, 57, 7955-7970), TLR8 (Salunke, D. B et al. *J. Med. Chem.* 2012, 55, 8137-8151; Kokatla, H. P. et al. *Org. Biomol. Chem.* 2013, 11, 1179-1198; Kokatla, H. P. et al. *J. Med. Chem.* 2013, 56, 6871-6885; Kokatla, H. P. et al. *Chem. Med. Chem.* 2014, 9, 719-723; Beesu, M. et al. *J. Med. Chem.* 2014, 57, 7325-7341), nucleotide oligomerization domain 1 (NOD1) (Agnihotri, G. et al *J. Med. Chem.* 2011, 54, 1490-1510.), as well as C—C chemokine receptor type 1 (CCR1) (Ukani, R. et al. *Bioorg. Med. Chem. Lett.* 2012, 22, 293-295). Structure-activity relationship studies have proven useful in providing tools with which to examine how these different classes of innate immune signaling molecules affect and modulate pathways linking the innate and adaptive immune systems described above.

SUMMARY

The present disclosure provides a compound represented by Formula (II):

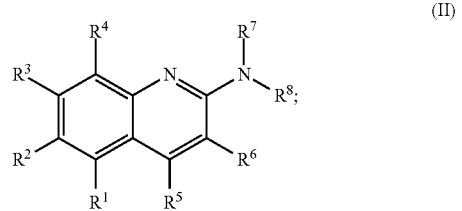

(II)

or a salt thereof, wherein:

$R^1$, $R^2$, $R^3$, $R^4$, and $R^5$ are independently selected from the group consisting of: H, halogen, —$OR^{10}$, —$N(R^{10})_2$, —$SR^{10}$, —CN, —$NO_2$, —$OC(O)R^{50}$, —$C(O)R^{10}$, —$C(O)OR^{10}$, —$C(O)N(R^{10})_2$, —$S(O)_2R^{10}$, —$S(O)_2OR^{10}$, optionally substituted $C_{1-20}$ alkyl, optionally substituted $C_{2-20}$ alkenyl, optionally substituted $C_{2-20}$ alkynyl, optionally substituted $C_{3-20}$ carbocycle, and optionally substituted 3- to 20-membered heterocycle, wherein at least one of $R^1$ and $R^3$ is selected from the group consisting of —$OR^{10}$, —$N(R^{10})_2$, —$SR^{10}$, —$OC(O)R^{10}$, —$C(O)R^{10}$, —$C(O)OR^{10}$, —$C(O)N(R^{10})_2$, —$S(O)_2R^{10}$, —$S(O)_2OR^1$, optionally substituted $C_{1-20}$ alkyl, optionally substituted $C_{2-20}$ alkenyl, optionally substituted $C_{2-20}$ alkynyl, optionally substituted $C_{3-20}$ carbocycle, and optionally substituted 3- to 20-membered heterocycle;

$R^6$ is selected from the group consisting of —$OR^{11}$, —$N(R^{11})_2$, —$SR^{11}$, optionally substituted $C_{1-20}$ alkyl, optionally substituted $C_{2-20}$ alkenyl, and optionally substituted $C_{2-20}$ alkynyl;

$R^7$ and $R^8$ are independently selected from H, optionally substituted $C_{1-10}$ alkyl, optionally substituted $C_{2-10}$ alkenyl, optionally substituted $C_{2-10}$ alkynyl, optionally substituted $C_{3-12}$ carbocycle and optionally substituted 3- to 12-membered heterocycle;

$R^{10}$ is independently selected at each occurrence from the group consisting of H, optionally substituted $C_{1-10}$ alkyl, optionally substituted $C_{2-10}$ alkenyl, optionally substituted $C_{2-10}$ alkynyl, optionally substituted $C_{3-12}$ carbocycle and optionally substituted 3- to 12-membered heterocycle; and $R^{11}$ is independently selected at each occurrence from the group consisting of optionally substituted $C_{1-10}$ alkyl, optionally substituted $C_{2-10}$ alkenyl, and optionally substituted $C_{2-10}$ alkynyl.

In certain embodiments, at least one of $R^1$ and $R^3$ is selected from the group consisting of —$OR^{10}$, —$N(R^{10})_2$, —$OC(O)R^{10}$, —$C(O)R^{10}$, —$C(O)OR^{10}$, —$C(O)N(R^{10})_2$, —$S(O)_2R^{10}$, —$S(O)_2OR^{10}$, optionally substituted $C_{1-20}$ alkyl, optionally substituted $C_{2-20}$ alkenyl, and optionally substituted $C_{2-20}$ alkynyl. In some embodiments, at least one of $R^1$ and $R^3$ is selected from the group consisting of optionally substituted $C_{1-20}$ alkyl, optionally substituted $C_{2-20}$ alkenyl, and optionally substituted $C_{2-20}$ alkynyl.

In some embodiments, $R^1$ is optionally substituted $C_{1-10}$ alkyl. In some embodiments, $R^1$ is optionally substituted $C_{1-5}$ alkyl. In some embodiments, $R^1$ is selected from the group consisting of: optionally substituted $C_{1-20}$ alkyl, optionally substituted $C_{2-20}$ alkenyl, optionally substituted $C_{2-20}$ alkynyl, wherein the $C_{1-20}$ alkyl, $C_{2-20}$ alkenyl, $C_{2-20}$ alkynyl optional substituents are one or more substituents independently selected from the group consisting of: halogen, —CN, —$NO_2$, —$OR^{50}$, —$SR^{50}$, —$N(R^{50})_2$, —$NR^{50}C(N(R^{50}))N(R^{50})_2$, —$OC(O)R^{50}$, —$C(O)R^{50}$, —$C(O)OR^{50}$, —$C(O)N(R^{50})_2$, —$S(O)_2R^{50}$, —$S(O)_2OR^{50}$, $C_{3-12}$ carbocycle, and 3- to 12-membered heterocycle, wherein the $C_{3-12}$ carbocycle and 3- to 12-membered heterocycle are optionally substituted with one or more substituents selected from the group consisting of halogen, —CN, —$NO_2$, —$OR^{50}$, —$SR^{50}$, —$N(R^{50})_2$, $C_{1-10}$ alkyl, $C_{1-10}$ haloalkyl, —$C_{1-10}$ alkyl-$N(R^{50})_2$, —$C_{1-10}$ alkyl-$OR^{50}$, and —$C_{1-10}$ alkyl-$C(O)N(R^{50})_2$; and optionally substituted $C_{3-20}$ carbocycle and optionally substituted 3- to 20-membered heterocycle, wherein the $C_{3-20}$ carbocycle and 3- to 20-membered heterocycle optional substituents are one or more substituents independently selected from the group consisting of: halogen, —CN, —$NO_2$, —$OR^{50}$, —$SR^{50}$, —$N(R^{50})_2$, $C_{1-10}$ alkyl, $C_{1-10}$ haloalkyl, —$C_{1-10}$ alkyl-$N(R^{50})_2$, —$C_{1-10}$ alkyl-$OR^{50}$, and —$C_{1-10}$ alkyl-$C(O)N(R^{50})_2$; and wherein $R^{50}$ at each occurrence is independently selected from the group consisting of hydrogen, $C_{1-10}$ alkyl, and $C_{1-10}$ haloalkyl. In some embodiments, $R^1$ is substituted with —$N(R^{50})_2$.

In some embodiments, $R^1$ is selected from:

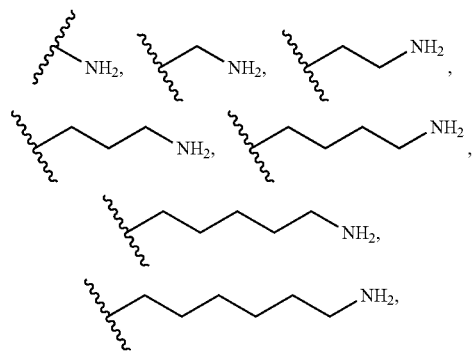

-continued

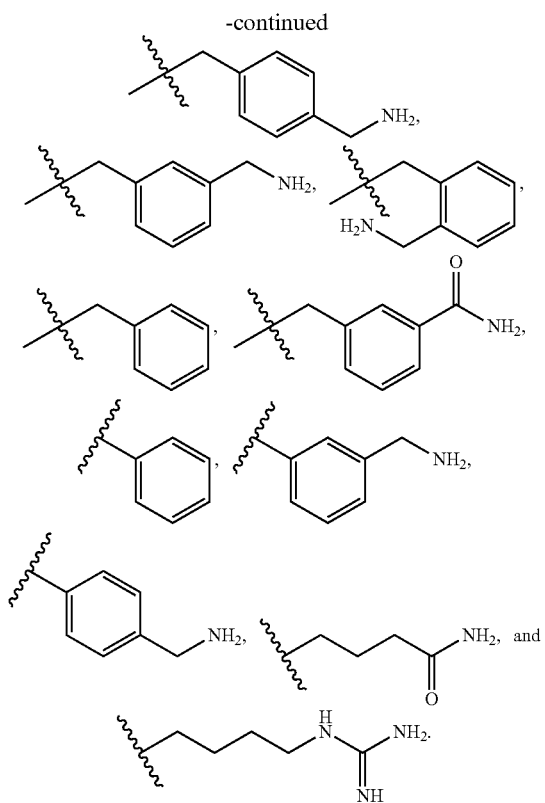

In some embodiments, $R^1$ is selected from H, halogen, and —CN. In some embodiments, $R^1$ is hydrogen. In some embodiments, $R^1$ is $C_{1-20}$ alkyl, $C_{2-20}$ alkenyl, $C_{2-20}$ alkynyl, $C_{3-20}$ carbocycle or 3- to 20-membered heterocycle any of which is substituted with $N(R^{50})_2$ and $R^3$ is selected from H, halogen, and —CN, such as $R^3$ is hydrogen.

In some embodiments, $R^3$ is optionally substituted $C_{1-10}$ alkyl. In some embodiments, $R^3$ is optionally substituted $C_{1-5}$ alkyl. In some embodiments, $R^3$ is selected from the group consisting of: optionally substituted $C_{1-20}$ alkyl, optionally substituted $C_{2-20}$ alkenyl, optionally substituted $C_{2-20}$ alkynyl, wherein the $C_{1-20}$ alkyl, $C_{2-20}$ alkenyl, and $C_{2-20}$ alkynyl optional substituents are one or more substituents independently selected from the group consisting of: halogen, —CN, —NO$_2$, —OR$^{50}$, —SR$^{50}$, —N(R$^{50}$)$_2$, —NR$^{50}$C(N(R$^{50}$))N(R$^{50}$)$_2$, —OC(O)R$^{50}$, —C(O)R$^{50}$, —C(O)OR$^{50}$, —C(O)N(R$^{50}$)$_2$, —S(O)$_2$R$^{50}$, —S(O)$_2$OR$^{50}$, $C_{3-12}$ carbocycle, and 3- to 12-membered heterocycle, wherein the $C_{3-12}$ carbocycle and 3- to 12-membered heterocycle are optionally substituted with one or more substituents selected from the group consisting of halogen, —CN, —NO$_2$, —OR$^{50}$, —SR$^{50}$, —N(R$^{50}$)$_2$, $C_{1-10}$ alkyl, $C_{1-10}$ haloalkyl, —$C_{1-10}$ alkyl-N(R$^{50}$)$_2$, —$C_{1-10}$ alkyl-OR$^{50}$, and —$C_{1-10}$ alkyl-C(O)N(R$^{10}$)$_2$; and optionally substituted $C_{3-20}$ carbocycle and optionally substituted 3- to 20-membered heterocycle, wherein the $C_{3-20}$ carbocycle and 3- to 20-membered heterocycle optional substituents are one or more substituents independently selected from the group consisting of: halogen, —CN, —NO$_2$, —OR$^{50}$, —SR$^{50}$, —N(R$^{50}$)$_2$, $C_{1-10}$ alkyl, $C_{1-10}$ haloalkyl, —$C_{1-10}$ alkyl-N(R$^{50}$)$_2$, —$C_{1-10}$ alkyl-OR$^{50}$, and —$C_{1-10}$ alkyl-C(O)N(R$^{50}$)$_2$; and wherein $R^{50}$ at each occurrence is independently selected from the group consisting of hydrogen, $C_{1-10}$ alkyl, and $C_{1-10}$ haloalkyl. In some embodiments, $R^3$ is substituted with —N(R$^{50}$)$_2$.

In some embodiments, $R^3$ is selected from:

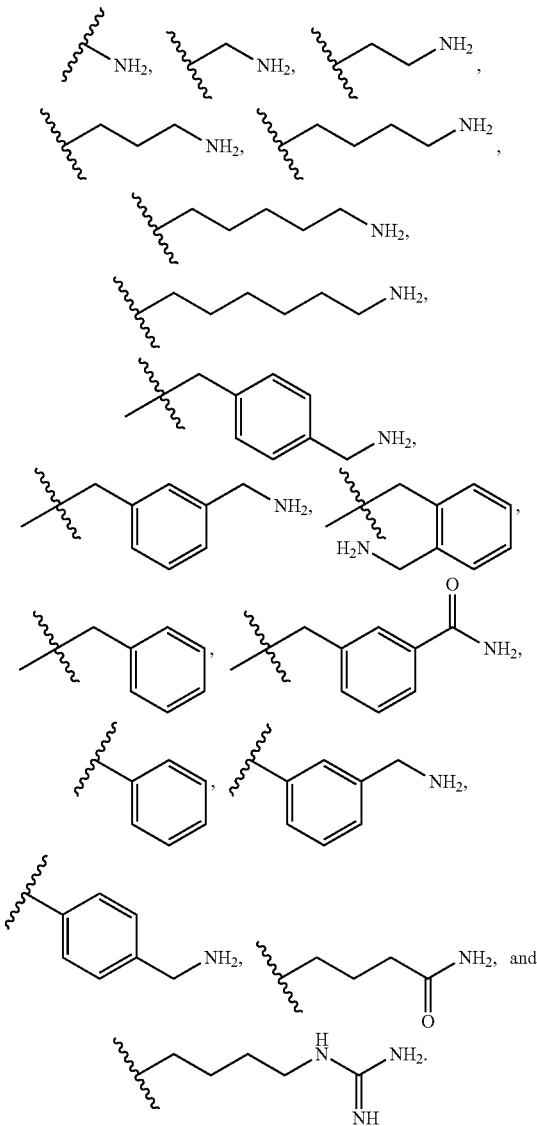

In some embodiments, $R^3$ is selected from H, halogen, and —CN. In some embodiments, $R^3$ is hydrogen. In some embodiments, $R^3$ is $C_{1-20}$ alkyl, $C_{2-20}$ alkenyl, $C_{2-20}$ alkynyl, $C_{3-20}$ carbocycle or 3- to 20-membered heterocycle any of which is substituted with —N(R$^{50}$)$_2$ and $R^1$ is selected from H, halogen, and —CN, such as $R^1$ is hydrogen.

In some embodiments, $R^2$, $R^4$, and $R^5$ are independently selected from the group consisting of: H, halogen, —OR$^{10}$, —N(R$^{10}$)$_2$, —SR$^{10}$, —CN, —NO$_2$, —OC(O)R$^{10}$, —C(O)R$^{10}$, —C(O)OR$^{10}$, —C(O)N(R$^{10}$)$_2$, —S(O)$_2$R$^{10}$, —S(O)$_2$OR$^{10}$, and optionally substituted $C_{1-20}$ alkyl. In some embodiments, $R^2$, $R^4$, and $R^5$ are independently selected from the group consisting of: H, halogen, —OR$^{10}$, —N(R$^{10}$)$_2$, —SR$^{10}$, —CN, —NO$_2$, and optionally substituted $C_{1-20}$ alkyl. In some embodiments, $R^2$, $R^4$, and $R^5$ are independently selected from the group consisting of: optionally substituted $C_{1-20}$ alkyl, optionally substituted $C_{2-20}$ alkenyl, optionally substituted $C_{2-20}$ alkynyl, wherein the $C_{1-20}$ alkyl, $C_{2-20}$ alkenyl, and $C_{2-20}$ alkynyl optional substituents are one or more substituents independently selected from the group consisting of: halogen, —CN, —NO$_2$, —OR$^{50}$, —SR$^{50}$, —N(R$^{50}$)$_2$, —NR$^{50}$C(N(R$^{50}$))N(R$^{50}$)$_2$, —OC(O)R$^{50}$, —C(O)R$^{50}$, —C(O)OR$^{50}$, —C(O)N(R$^{50}$)$_2$, —S(O)$_2$R$^{50}$, —S(O)$_2$OR$^{50}$, C$_{3-12}$ carbocycle, and 3- to 12-membered heterocycle, wherein the C$_{3-12}$ carbocycle and 3- to 12-membered heterocycle are optionally substituted with one or more substituents selected from the group consisting of halogen, —CN, —NO$_2$, —OR$^{50}$, —SR$^{50}$, —N(R$^{50}$)$_2$, C$_{1-10}$ alkyl, C$_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and optionally substituted C$_{3-20}$ carbocycle and optionally substituted 3- to 20-membered heterocycle, wherein C$_{3-20}$ carbocycle and 3- to 20-membered heterocycle optional substituents are one or more substituents independently selected from the group consisting of: halogen, —CN, —NO$_2$, —OR$^{50}$, —SR$^{50}$, —N(R$^{50}$)$_2$, C$_{1-10}$ alkyl, C$_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and wherein R$^{50}$ at each occurrence is independently selected from the group consisting of hydrogen, C$_{1-10}$ alkyl, and C$_{1-10}$ haloalkyl.

In some embodiments, R$^2$ is hydrogen. In some embodiments, R$^4$ is hydrogen. In some embodiments, R$^5$ is hydrogen.

In some embodiments, R$^{10}$ is selected from the group consisting of: optionally substituted C$_{1-20}$ alkyl, optionally substituted C$_{2-20}$ alkenyl, optionally substituted C$_{2-20}$ alkynyl, wherein the C$_{1-20}$ alkyl, C$_{2-20}$ alkenyl, and C$_{2-20}$ alkynyl optional substituents are one or more substituents independently selected from the group consisting of: halogen, —CN, —NO$_2$, —OR$^{50}$, —SR$^{50}$, —N(R$^{50}$)$_2$, —NR$^{50}$C(N(R$^{50}$))N(R$^{50}$)$_2$, —OC(O)R$^{50}$, —C(O)R$^{50}$, —C(O)OR$^{50}$, —C(O)N(R$^{50}$)$_2$, —S(O)$_2$R$^{50}$, —S(O)$_2$OR$^{50}$, C$_{3-12}$ carbocycle, and 3- to 12-membered heterocycle, wherein the C$_{3-12}$ carbocycle and 3- to 12-membered heterocycle are optionally substituted with one or more substituents selected from the group consisting of halogen, —CN, —NO$_2$, —OR$^{50}$, —SR$^{50}$, —N(R$^{50}$)$_2$, C$_{1-10}$ alkyl, C$_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and optionally substituted C$_{3-20}$ carbocycle and optionally substituted 3- to 20-membered heterocycle, wherein the C$_{3-20}$ carbocycle and 3- to 20-membered heterocycle optional substituents are one or more substituents independently selected from the group consisting of: halogen, —CN, —NO$_2$, —OR$^{50}$, —SR$^{50}$, —N(R$^{50}$)$_2$, C$_{1-10}$ alkyl, C$_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and wherein R$^{50}$ at each occurrence is independently selected from the group consisting of hydrogen, C$_{1-10}$ alkyl, and C$_{1-10}$ haloalkyl.

In some embodiments, R$^6$ is selected from the group consisting of optionally substituted C$_{1-20}$ alkyl, optionally substituted C$_{2-20}$ alkenyl, and optionally substituted C$_{2-20}$ alkynyl. In some embodiments, R$^6$ is selected from the group consisting of optionally substituted C$_{1-10}$ alkyl, optionally substituted C$_{2-10}$ alkenyl, and optionally substituted C$_{1-20}$ alkynyl. In some embodiments, R$^6$ is selected from the group consisting of optionally substituted C$_{1-10}$ alkyl. In some embodiments, R$^6$ is selected from the group consisting of: optionally substituted C$_{1-20}$ alkyl, optionally substituted C$_{2-20}$ alkenyl, optionally substituted C$_{2-20}$ alkynyl, wherein the C$_{1-20}$ alkyl, C$_{2-20}$ alkenyl, and C$_{2-20}$ alkynyl optional substituents are one or more substituents independently selected from the group consisting of: halogen, —CN, —NO$_2$, —OR$^{50}$, —SR$^{50}$, —N(R$^{50}$)$_2$, —NR$^{50}$C(N(R$^{50}$))N(R$^{50}$)$_2$, —OC(O)R$^{50}$, —C(O)R$^{50}$, —C(O)OR$^{50}$, —C(O)N(R$^{50}$)$_2$, —S(O)$_2$R$^{50}$, —S(O)$_2$OR$^{50}$, C$_{3-12}$ carbocycle, and 3- to 12-membered heterocycle, wherein the C$_{3-12}$ carbocycle, and 3- to 12-membered heterocycle are optionally substituted with one or more substituents selected from the group consisting of halogen, —CN, —NO$_2$, —OR$^{50}$, —SR$^{50}$, —N(R$^{50}$)$_2$, C$_{1-10}$ alkyl, C$_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and optionally substituted C$_{3-20}$ carbocycle and optionally substituted 3- to 20-membered heterocycle, wherein the C$_{3-20}$ carbocycle and 3- to 20-membered heterocycle optional substituents are one or more substituents independently selected from the group consisting of: halogen, —CN, —NO$_2$, —OR$^{50}$, —SR$^{50}$, —N(R$^{50}$)$_2$, C$_{1-10}$ alkyl, C$_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and wherein R$^{50}$ at each occurrence is independently selected from the group consisting of hydrogen, C$_{1-10}$ alkyl, and C$_{1-10}$ haloalkyl. In some embodiments, R$^6$ is:

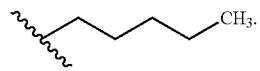 [SMILES: *CCCCC]

In some embodiments, R$^7$ and R$^8$ are independently selected from H and optionally substituted C$_{1-10}$ alkyl. In some embodiments, R$^7$ and R$^8$ are each H. In some embodiments, R$^7$ and R$^8$ are independently selected from the group consisting of: optionally substituted C$_{1-20}$ alkyl, optionally substituted C$_{2-20}$ alkenyl, optionally substituted C$_{2-20}$ alkynyl, wherein the C$_{1-20}$ alkyl, C$_{2-20}$ alkenyl, and C$_{2-20}$ alkynyl optional substituents are one or more substituents independently selected from the group consisting of: halogen, —CN, —NO$_2$, —OR$^{50}$, —SR$^{50}$, —N(R$^{50}$)$_2$, —NR$^{50}$C(N(R$^{50}$))N(R$^{50}$)$_2$, —OC(O)R$^{50}$, —C(O)R$^{50}$, —C(O)OR$^{50}$, —C(O)N(R$^{50}$)$_2$, —S(O)$_2$R$^{50}$, —S(O)$_2$OR$^{50}$, C$_{3-12}$ carbocycle, and 3- to 12-membered heterocycle, wherein the C$_{3-12}$ carbocycle, and 3- to 12-membered heterocycle are optionally substituted with one or more substituents selected from the group consisting of halogen, —CN, —NO$_2$, —OR$^{50}$, —SR$^{50}$, —N(R$^{50}$)$_2$, C$_{1-10}$ alkyl, C$_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and optionally substituted C$_{3-20}$ carbocycle and optionally substituted 3- to 20-membered heterocycle, wherein the C$_{3-20}$ carbocycle and 3- to 20-membered heterocycle optional substituents are one or more substituents independently selected from the group consisting of: halogen, —CN, —NO$_2$, —OR$^{50}$, —SR$^{50}$, —N(R$^{50}$)$_2$, C$_{1-10}$ alkyl, C$_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and wherein R$^{50}$ at each occurrence is independently selected from the group consisting of hydrogen, C$_{1-10}$ alkyl, and C$_{1-10}$ haloalkyl. In some embodiments, a compound of the present disclosure is represented by the Formula:

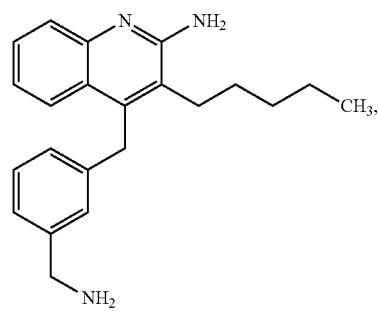

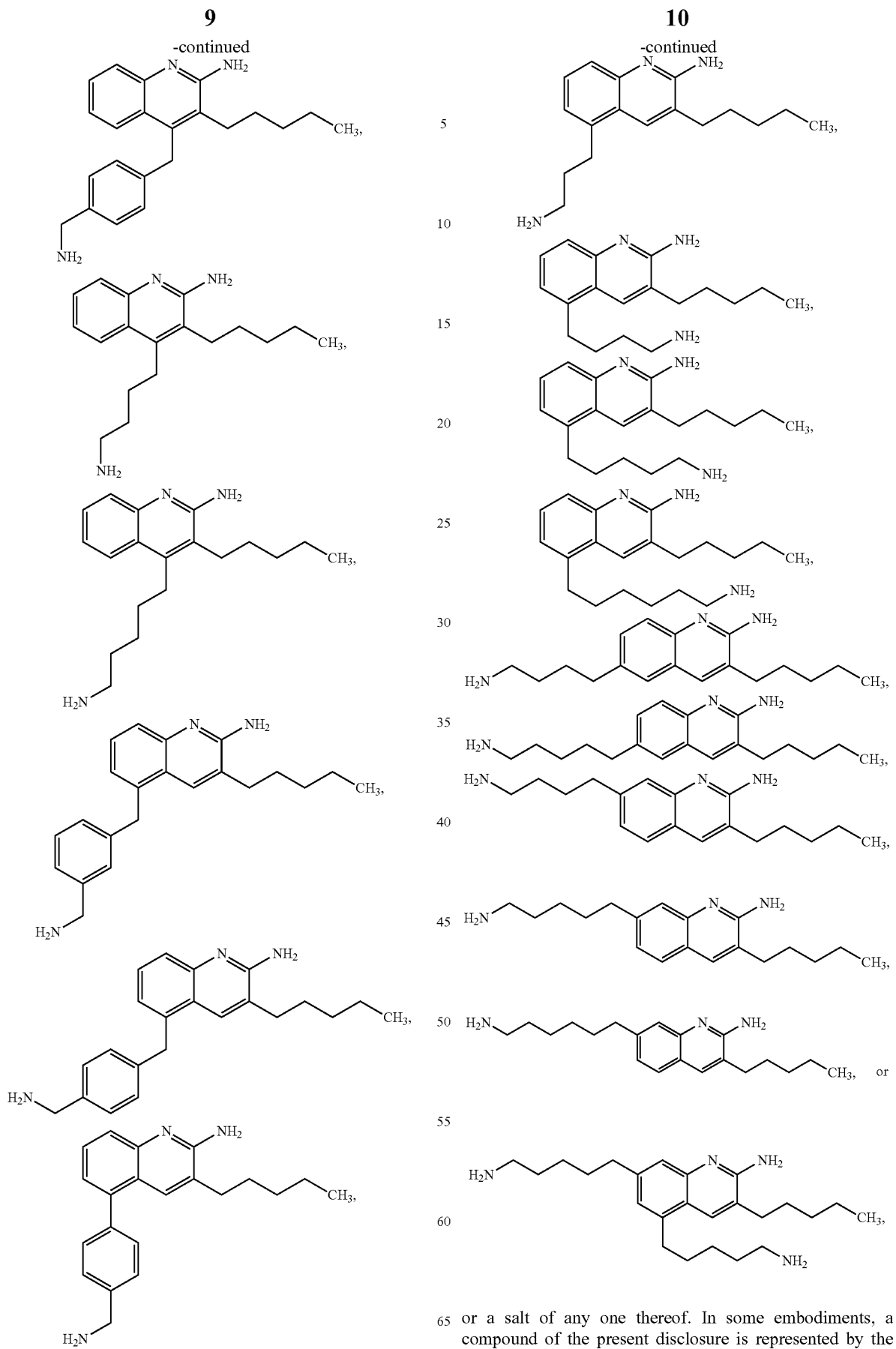
or a salt of any one thereof. In some embodiments, a compound of the present disclosure is represented by the Formula:

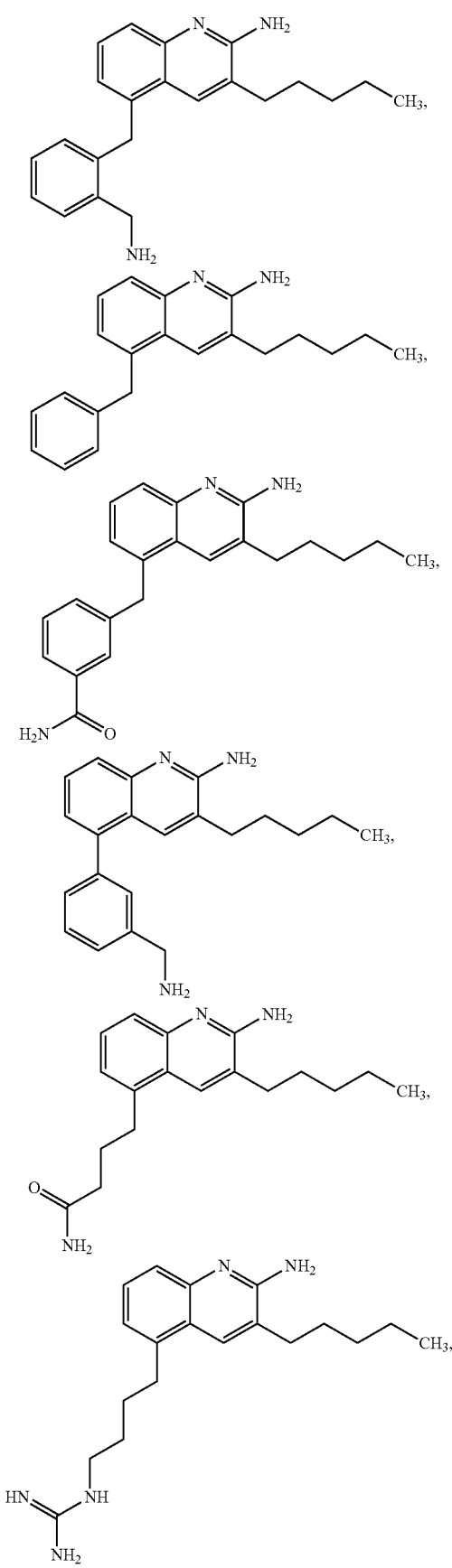

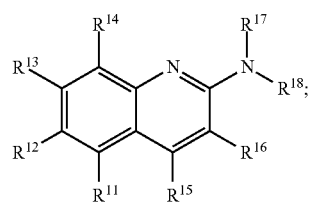

or a salt of any one thereof.

In some embodiments, the present disclosure provides a pharmaceutical composition comprising a compound or salt disclosed herein and pharmaceutically acceptable excipient. In some embodiments, the composition further comprises a vaccine.

In some aspects, the present disclosure provides a method for modulating activity of a human toll-like receptor, comprising administering to a subject in need thereof, a compound of formula (III):

$$\text{(III)}$$

or a salt thereof, wherein:

$R^{11}$, $R^{12}$, $R^{13}$, $R^{14}$, and $R^{15}$ are independently selected from the group consisting of: H, halogen, $-OR^{20}$, $-N(R^{20})_2$, $-SR^{20}$, $-CN$, $-NO_2$, $-OC(O)R^{20}$, $-C(O)R^{20}$, $-C(O)OR^{20}$, $-C(O)NR^{20}$, $-S(O)_2R^{20}$, $-S(O)_2OR^{20}$, optionally substituted $C_{3-20}$ carbocycle, optionally substituted $C_{1-20}$ alkyl, optionally substituted $C_{2-20}$ alkenyl, optionally substituted $C_{2-20}$ alkynyl, and optionally substituted 3- to 20-membered heterocycle, wherein at least one of $R^{11}$, $R^{12}$, $R^{13}$, and $R^{14}$ is selected from the group consisting of $-OR^{20}$, $-NR^{20}_2$, $-OC(O)R^{20}$, $-C(O)R^{20}$, $-C(O)OR^{20}$, $-C(O)NR^{20}$, $-S(O)_2R^{20}$, $-S(O)_2OR^{20}$, optionally substituted $C_{3-20}$ carbocycle, optionally substituted $C_{1-20}$ alkyl, optionally substituted $C_{2-20}$ alkenyl, optionally substituted $C_{2-20}$ alkynyl, and optionally substituted 3- to 20-membered heterocycle;

$R^{16}$ is optionally substituted $C_{1-20}$ alkyl, $-OR^{21}$, $-N(R^{21})_2$, $-SR^{21}$, optionally substituted $C_{2-20}$ alkenyl, and optionally substituted $C_{2-20}$ alkynyl;

$R^{17}$ and $R^{18}$ are independently selected from H, optionally substituted $C_{1-10}$ alkyl, optionally substituted $C_{2-10}$ alkenyl, optionally substituted $C_{2-10}$ alkynyl, optionally substituted $C_{3-12}$ carbocycle and optionally substituted 3- to 12-membered heterocycle;

$R^{20}$ is independently selected at each occurrence from the group consisting of H, optionally substituted $C_{1-10}$ alkyl, optionally substituted $C_{2-10}$ alkenyl, optionally substituted $C_{2-10}$ alkynyl, optionally substituted 3- to 12-membered heterocycle and optionally substituted $C_{3-12}$ carbocycle; and $R^{21}$ is independently selected at each occurrence from the group consisting of optionally substituted $C_{1-10}$ alkyl, optionally substituted $C_{2-10}$ alkenyl, and optionally substituted $C_{2-10}$ alkynyl.

In some embodiments, a method of the current disclosure comprises modulating the activity of the human toll-like receptor, comprising agonizing the human toll-like receptor. In some embodiments, a human toll-like receptor comprises hTLR8. In some embodiments, a method further comprises administering a vaccine to the subject before, in conjunction with, or after administration of the compound or salt.

In some aspects, the present disclosure provides a method of increasing an immune response to an antigen or vaccine, wherein the method comprises administering to a subject in need thereof a compound of Formula (III):

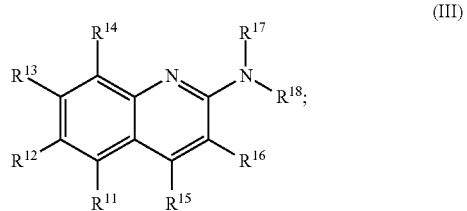

(III)

or a salt thereof, wherein:

$R^{11}$, $R^{12}$, $R^{13}$, $R^{14}$, and $R^{15}$ are independently selected from the group consisting of: H, halogen, $-OR^{20}$, $-N(R^{20})_2$, $-SR^{20}$, $-CN$, $-NO_2$, $-OC(O)R^{20}$, $-C(O)R^{21}$, $-C(O)OR^{20}$, $-C(O)NR^{20}$, $-S(O)_2R^{20}$, $-S(O)_2OR^{20}$, optionally substituted $C_{3-20}$ carbocycle, optionally substituted $C_{1-20}$ alkyl, optionally substituted $C_{2-20}$ alkenyl, optionally substituted $C_{2-20}$ alkynyl, and optionally substituted 3- to 20-membered heterocycle, wherein at least one of $R^{11}$, $R^{12}$, $R^{13}$, and $R^{14}$ is selected from the group consisting of $-OR^{20}$, $-NR^{20}{}_2$, $-OC(O)R^{20}$, $-C(O)R^{20}$, $-C(O)OR^{20}$, $-C(O)NR^{20}$, $-S(O)_2R^{20}$, $-S(O)_2OR^{20}$, optionally substituted $C_{3-20}$ carbocycle, optionally substituted $C_{1-20}$ alkyl, optionally substituted $C_{2-20}$ alkenyl, optionally substituted $C_{2-20}$ alkynyl, and optionally substituted 3- to 20-membered heterocycle;

$R^{16}$ is selected from the group consisting of optionally substituted $C_{1-20}$ alkyl, $-OR^{21}$, $-N(R^{20})_2$, $-SR^{21}$, optionally substituted $C_{2-20}$ alkenyl, and optionally substituted $C_{2-20}$ alkynyl;

$R^{17}$ and $R^{18}$ are independently selected from the group consisting of H, optionally substituted $C_{1-10}$alkyl, optionally substituted $C_{20}$alkenyl, optionally substituted $C_{2-10}$ alkynyl, optionally substituted $C_{3-12}$ carbocycle and optionally substituted 3- to 12-membered heterocycle;

$R^{20}$ is independently selected at each occurrence from the group consisting of H, optionally substituted $C_{1-10}$ alkyl, optionally substituted $C_{2-10}$ alkenyl, optionally substituted $C_{2-10}$ alkynyl, optionally substituted 3- to 12-membered heterocycle and optionally substituted $C_{3-12}$ carbocycle; and $R^{21}$ is independently selected at each occurrence from the group consisting of optionally substituted $C_{1-10}$ alkyl, optionally substituted $C_{2-10}$ alkenyl, and optionally substituted $C_{2-10}$ alkynyl.

Embodiments of the invention are directed to compounds, formulations and pharmaceutical compositions comprising one or more compounds having a general structural Formula I:

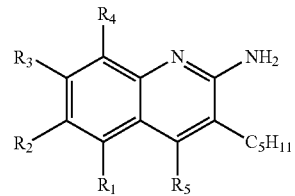

I wherein: $R_1$, $R_5$ are independently: H, $-OH$, $-OR'$, $-NH_2$, $-NHR'$, $-NR'_2$, $-SH$, $-SR'$, $-O-C(O)R'$, $-C(O)R'$, $(CH_2)_bNH_2$, $C_{(m+1)}H_{(2m+1)}$, $C_{(m+1)}H_{(2m+1)}NH_2$, $C_{(m+1)}H_{(2m+1)}CONH_2$, $C_{(m+1)}H_{(2m+1)}$, $CR'NH_2$, $C_{(m+1)}H_{(2m+1)}-C_{4-20}$ aryl-$C_{(m+1)}H_{(2m+1)}-NH_2$, $C_mH_{2m+2}$, $C_{4-20}$ aryl, $C_{1-20}$ alkyl, $C_{1-20}$ alkylamino, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, where m is an integer from 0 to 10, and b is an integer from 0 to 10; the $C_{4-20}$ aryl, $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl is unsubstituted or optionally substituted with a functional group comprising H, $-OH$, $-OR'$, $-NH_2$, $-NHR'$, $-NR'_2$, $-SH$, $-SR'$, $-O-C(O)R'$, $-C(O)R'$, $-CF_3$, $-OCF_3$, or an amino acid side chain or peptide fragment, the $C_{4-20}$ aryl, $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, and the $C_{1-6}$ alkyl is optionally interrupted by one or more O, S, or N atoms, or one or more groups comprising cycloalkyl, $C_{(m+1)}H_{(2m+1)}$, $C_{(m+1)}H_{(2m+1)}NH_2$, $CH-C(O)-O-$, $-O-C(O)-$, $-C(O)-$, $-C(O)-NH-$, $-NH-C(O)-$, $-NH-C(O)-O-$ and $-O-C(O)-NH-$, R' is H, OH, halogen, $NO_2$, $-NH_2$, CN, $-COOH$, heteroaryl having 1 to 4 N, O and/or S atoms, $C_{4-20}$ aryl, $C_{1-10}$ alkyl, $C_{2-10}$ alkenyl, $C_{2-10}$ alkynyl, $C_{4-10}$ heterocycle or $C_{4-10}$ heteroaryl;

the groups $R_2$, $R_3$, and $R_4$ are independently: H, $-OH$, $-NH_2$, $-CH_2$, $-COOH$, $-OR'$, $-NH_2$, $-NHR'$, $-NR'_2$, $-SH$, $-SR'$, $-O-C(O)R'$, $-C(O)R'$, $(CH_2)_bNH_2$ where m is an integer from 0 to 10, and b is an integer from 0 to 10, $C_{1-50}$ alkyl, the $C_{1-50}$ alkyl is unsubstituted or optionally substituted with a functional group comprising one or more of: H, $-OH$, $-OR'$, $-NH_2$, $-NHR'$, $-NR'_2$, $-SH$, $-SR'$, $-O-C(O)R'$, $-C(O)R'$, $-CF_3$, $-OCF_3$, an amino acid side chain or peptide fragment, where $R^1$ is selected from radicals consisting of H, heteroaryl having 1 to 4 N, O and/or S atoms, $C_{1-20}$ alkyl, $C_{1-20}$ alkylamino, $C_{2-10}$ alkenyl, $C_{2-10}$ alkynyl, $C_{4-10}$ heterocycle, $C_{4-10}$ heteroaryl, ammonium and salts thereof, sulfates, sulfonates, thiosulfonates, boronates, phosphates, phosphonate, guanidine, amidine, pyridine, pyridium, alkali metal groups, nitrates, chlorates, perchlorates, acetates, chloride, bromide, iodide and salts thereof, an alkali metal salt of sulfonic acid; an alkali metal salt of phosphonic acid; a pharmaceutically acceptable salt; a sugar or a polyhydroxy group.

In another embodiment, a pharmaceutical composition comprises one or more compounds having a general structure of Formula I.

Other aspects are described infra.

BRIEF DESCRIPTION OF THE DRAWINGS

FIGS. 3A-3D are graphs showing representative cytokine induction data (excerpted from a 63 cytokine panel) in human PBMCs. Means±SD on quadruplicates are shown.

FIGS. 5A-5D show the results from an eight-color flow cytometry and gating strategy for identification of B, T, NK lymphocytes, monocytes and granulocytes.

DETAILED DESCRIPTION

Figure 1:
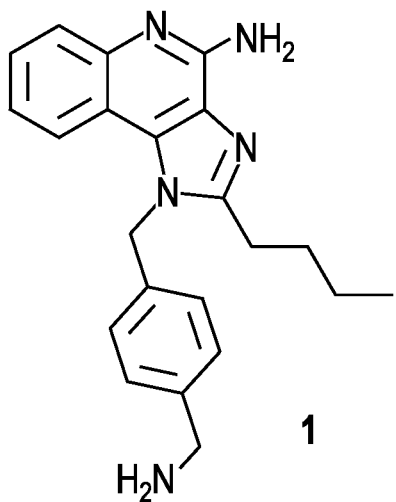
FIG. 1 shows three structures: dual TLR7/8-active $N^1$-4-aminomethylbenzyl-substituted imidazoquinoline (1); $N^1$-3-aminomethylbenzyl-substituted imidazoquinoline (2); and TLR8-agonistic 3-pentylquinolin-2-amine (3). Crystal structures of compounds 1 and 2 bound to human TLR8 are also shown. Dashed lines in yellow depict direct hydrogen bonds.
Figure 1:
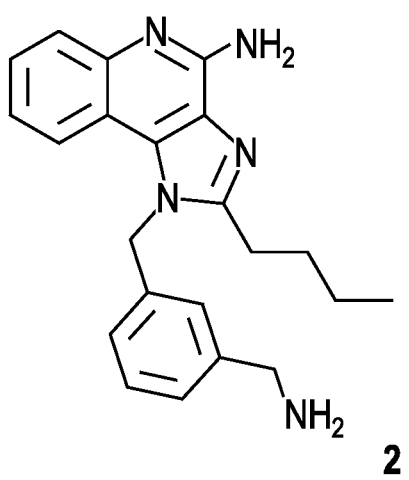
Figure 1:
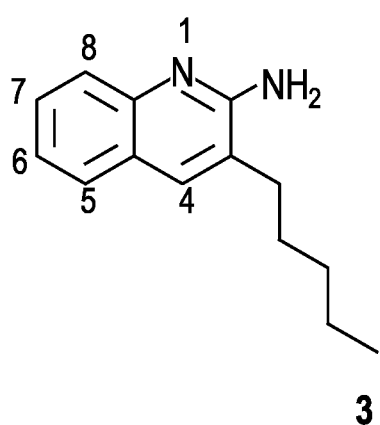
Figure 1:
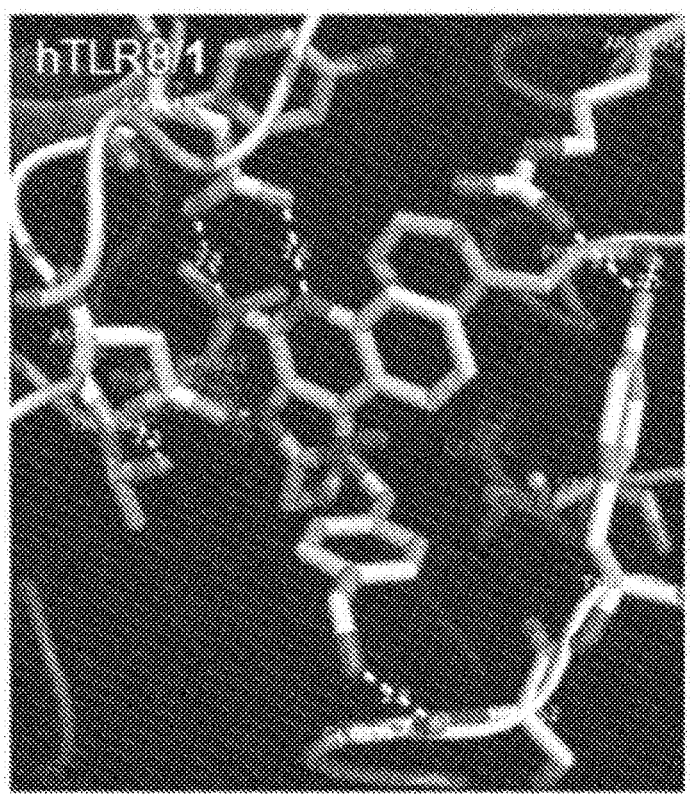
Figure 1:
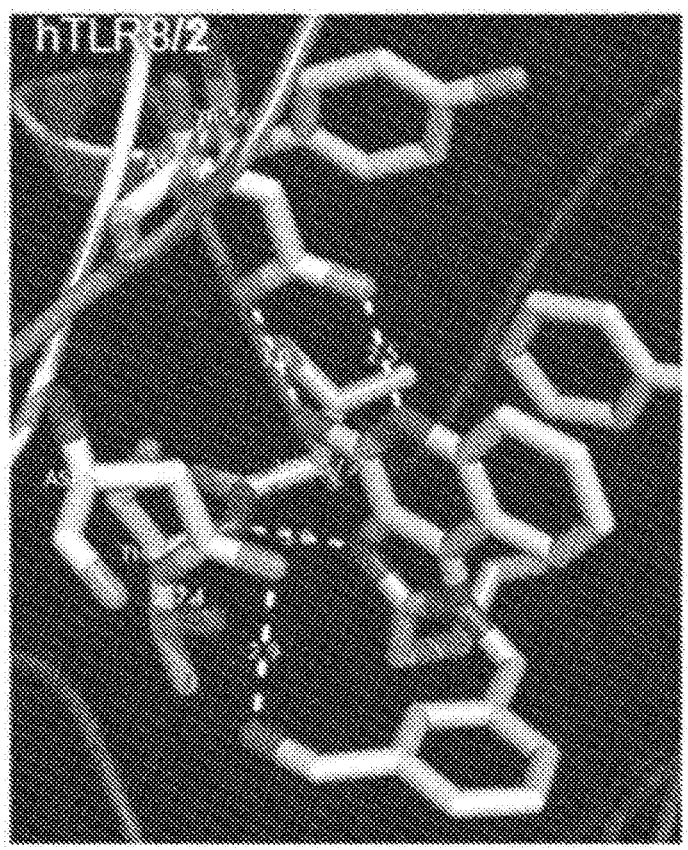

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

As used in this specification and the appended claims, the term "or" is generally employed in its sense including "and/or" unless the content clearly dictates otherwise.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value or range. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

The terms, "compound" and "compounds" as used herein refers to a compound encompassed by the generic formulae disclosed herein, any subgenus of those generic formulae, and any forms of the compounds, e.g. compounds 18a, 18b, etc., within the generic and subgeneric formulae. Unless specified otherwise, the term further includes the racemates and stereoisomers, of the compound or compounds.

The term "lower" as used herein refers to a group having between one and six carbons.

The term "alkyl" as used herein refers to a saturated straight, branched, or cyclic, primary, secondary, or tertiary hydrocarbon having from one to about fifty carbon atoms, typically $C_1$ to $C_{10}$, and specifically includes, for example, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. An alkyl group as used herein may be substituted unless otherwise indicated. Alkyl groups can be optionally substituted with one or more moieties including, but not limited to: halogens, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed, hydroxyl, amino, alkylamino, arylamino, aryloxy, nitro, cyano, sulfonic acid, sulfate, phosphonic acid, phosphate, or phosphonate, or as known to those skilled in the art, for example, as taught in T. W. Greene and P. G. M. Wuts, "Protective Groups in Organic Synthesis," $3^{rd}$ ed., John Wiley & Sons, 1999, hereby incorporated by reference. An alkyl group may contain one or more O, S, S(O), or $S(O)_2$ moieties. Examples of "alkyl" as used herein include, but are not limited to, methyl, ethyl, propyl, decyl, undecyl, octadecyl, nonadecyl, eicosyl, heneicosyl, decosyl, tricosyl, tetracosyl, and pentacosyl, n-butyl, t-butyl, n-pentyl, isobutyl, and isopropyl, and the like. In some embodiments the alkyl comprises 1, 2, 3, 4, 5, 6, 7, 8, 9, 10, 11, or 12 carbon atoms.

The term "$C_{x-y}$" or "$C_x$-$C_y$" when used in conjunction with a chemical moiety, such as alkyl, alkenyl, or alkynyl is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain. The terms "$C_{x-y}$ alkenyl" and "$C_{x-y}$ alkynyl" refer to substituted or unsubstituted unsaturated aliphatic groups analogous in length and possible substitution to the alkyls described above, but that contain at least one double or triple bond respectively. The term "$C_{x-y}$ carbocycle" refers to substituted or unsubstituted carbocycle that contains from x to y carbons in the ring.

The term "x- to y-membered" refers to the number of atoms in a chemical moiety. For example a 3- to 20-membered heterocycle is a heterocycle that contains from 3 to 20 ring atoms.

As used herein, "cycloalkyl" refers to a cyclic saturated hydrocarbon group having from about three to about fifty carbon atoms, optionally substituted with substituents, for example: halogens, halides, alkylhalides, selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes, by way of example, cyclopropyl, cyclobutyl, cyclopentyl, cyclohexyl, cycloheptyl, or cyclooctyl, and the like.

The term "carbocycle" as used herein refers to a saturated, unsaturated or aromatic ring in which each atom of the ring is carbon. Carbocycle includes, for example, 3- to 10-membered monocyclic rings, 6- to 12-membered bicyclic rings, and 6- to 12-membered bridged rings. Each ring of a polycyclic carbocycle may be selected from saturated, unsaturated, and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocycle. Exemplary carbocycles include cyclopentyl, cyclohexyl, cyclohexenyl, adamantyl, phenyl, indanyl, and naphthyl. A carbocycle may be optionally substituted with one or more substituents as described herein.

The terms "heterocycle" and "heterocyclic" as used herein are used interchangeably to refer to a three to about twelve-membered heterocyclic ring optionally aromatic or possessing one or more degrees of unsaturation, containing one or more heteroatomic substitutions, for example: —S—, —SO—, —SO$_2$—, —O—, or —N— and with optional substituents on the ring atoms including, but not limited to, halogens, halides, alkylhalides lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring optionally may be fused to one or more of another heterocyclic, cycloalkyl or aryl ring(s).

The term "alkenyl" as used herein refers to an unsaturated straight, branched, or cyclic, primary, secondary, or tertiary hydrocarbon of typically $C_1$ to $C_{10}$, that has one or more double bonds therein where the double bond can be unconjugated or conjugated to another unsaturated group (e.g., a polyunsaturated alkenyl) and can be unsubstituted or substituted, with multiple degrees of substitution being allowed. Substituents on alkenyl include, for example, halides, alkylhalides, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For example, and without limitation, the alkenyl can be vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, decenyl, undecenyl, dodecenyl, heptadecenyl, octadecenyl, nonadecenyl, eicosenyl, heneicosenyl, docosenyl, tricosenyl, tetracisenyl, pentacosenyl, phytyl, the branched chain isomers thereof, and polyunsaturated alkenes including octadec-9,12,-dienyl, octadec-9,12,15-trienyl, and eicos-5,8,11,14-tetraenyl. In certain embodiments, alkenyl groups are optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate.

The term "alkynyl" refers to an unsaturated straight, branched, or cyclic, primary, secondary, or tertiary hydrocarbon having from about two to about fifty carbons, typically $C_1$ to $C_{10}$, and at least one carbon-carbon triple bond, and wherein the alkynyl is optionally substituted with substituents comprising, hydroxyl, alkylamino, arylamino, alkoxy, aryloxy, nitro, cyano, sulfonic acid, sulfate, phosphonic acid, phosphate, phosphonate, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed.

The terms "alkylamino" or "arylamino" as used herein refer to an amino group that has one or two alkyl or aryl substituents, respectively. For example, alkylamino is a substituent such as —NH(CH$_3$), N(CH$_3$)$_2$, etc. and arylamino is a substituent such as —NH(Ph), N(Ph)$_2$.

The term "aryl" as used herein refers to a carbocyclic aromatic ring, such as phenyl, biphenyl, naphthyl, or anthracenyl. The term includes both substituted and unsubstituted moieties and includes for example, an optionally substituted benzene ring or an optionally substituted benzene ring system fused to one or more optionally substituted benzene rings, with multiple degrees of substitution being allowed. The aryl group can also be substituted with one or more moieties comprising: hydroxyl, amino, alkylamino, arylamino, alkoxy, aryloxy, nitro, cyano, sulfonic acid, sulfate, phosphonic acid, phosphate, or phosphonate. Substituents also include, but are not limited to, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, amino sulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, 2-napthyl, 1-naphthyl, 1-anthracenyl, and the like.

The term "acyl" as used herein refers to a carboxylic acid ester, represented by the formula —C(O)O—R* in which R* is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen (F, Cl, Br, I), $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. R* may be selected from alkyl, alkenyl, alkynyl, carbocycle, heterocycle, any of which are optionally substituted by a substituent described herein.

As used herein, the term "alkoxy" refers to an optionally substituted straight or branched chain alkyl-O— group wherein alkyl is as previously defined. For example, $C_{1-10}$ alkoxy means a straight or branched alkoxy containing at least 1, and at most 10, carbon atoms. Examples of "alkoxy" as used herein include, but are not limited to, methoxy, ethoxy, propoxy, prop-2-oxy, butoxy, but-2-oxy, 2-methyl-prop-1-oxy, 2-methylprop-2-oxy, pentoxy and hexyloxy. A $C_{1-4}$alkoxy group is preferred, for example methoxy, ethoxy, propoxy, prop-2-oxy, butoxy, but-2-oxy or 2-methylprop-2-oxy. Alkoxy may be substituted with one or more substituents described herein.

As used herein, the term "aryloxy" refers to an optionally substituted —O-aryl-O— group wherein aryl is as previously defined. Exemplary aryloxy groups include, but are not limited to, phenoxy (phenyl-O—). Aryloxy may be substituted by one or more substituents described herein.

As used herein, the term "heteroaryl" refers to an aromatic heterocycle. Heteroaryl may be optionally substituted. In certain embodiments, heteroaryl refers to an aromatic heterocycle comprising one or more heteroatoms. Heteroatoms may include, for example, N, O, Si, P, B, and S atoms. As used herein, the heteroaryl ring may be selected from monocyclic or bicyclic and fused or bridged ring systems rings wherein at least one of the rings in the ring system is aromatic, i.e., it contains a cyclic, delocalized (4n+2) π-electron system in accordance with the Hückel theory. The heteroatom(s) in the heteroaryl radical may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Heteroaryl groups having a total of from about 5 to about 14 carbon atom ring members and heteroatom ring members (and all combinations and subcombinations of ranges and specific numbers of carbon and heteroatom ring members) are preferred. Heteroaryl groups having a total of from about 5 to about 10 carbon atom ring members and heteroatom ring members (and all combinations and subcombinations of ranges and specific numbers of carbon and heteroatom ring members) are more preferred. Exemplary heteroaryl groups include, but are not limited to, pyrryl, furyl, pyridyl, pyridine-N-oxide, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Unless stated otherwise specifically in the specification, the term "heteroaryl" is meant to include heteroaryl radicals as defined above which are optionally substituted by one or more substituents such as those substituents described herein.

As used herein, the term "heteroarylalkyl" refers to an optionally substituted moiety comprising an alkyl radical bearing a heteroaryl substituent, each as defined above, having from about 6 to about 50 carbon atoms (and all combinations and subcombinations of ranges and specific numbers of carbon atoms therein), with from about 6 to about 25 carbon atoms being preferred. Non-limiting examples include 2-(1H-pyrrol-3-yl)ethyl, 3-pyridylmethyl, 5-(2H-tetrazolyl)methyl, and 3-(pyrimidin-2-yl)-2-methylcyclopentanyl.

In certain embodiments, a heterocycloalkyl ring system has a total of from about 3 to about 14 carbon atom ring members and heteroatom ring members (and all combinations and subcombinations of ranges and specific numbers of carbon and heteroatom ring members). In other embodiments, the heterocycloalkyl groups may be fused to one or more aromatic rings. In yet other embodiments, heterocycloalkyl moieties are attached via a ring carbon atom to the rest of the molecule. Exemplary heterocycloalkyl groups include, but are not limited to, azepanyl, tetrahydrofuranyl, hexahydropyrimidinyl, tetrahydrothienyl, piperidinyl, pyrrolidinyl, isoxazolidinyl, isothiazolidinyl, pyrazolidinyl, oxazolidinyl, imidazolidinyl, diazolidinyl, piperazinyl, 2-oxo-morpholinyl, morpholinyl, 2-oxo-piperidinyl, piperadinyl, decahydroquinolyl, octahydrochromenyl, octahydro-cyclopentapyranyl, 1,2,3,4,-tetrahydroquinolyl, 1,2,3,4-tetrahydroquinazolinyl, octahydro-[2]pyridinyl, decahydro-cyclooctafuranyl, 1,2,3,4-tetrahydroisoquinolyl, 2-oxoimidazolidinyl, and imidazolidinyl. In some embodiments, two moieties attached to a heteroatom may be taken together to form a heterocycloalkyl ring. In certain of these embodiments, 1 or 2 of the heterocycloalkyl ring carbon atoms may be replaced by other moieties which contain either one (—O—, —S—, —N(R)—) or two (—N(R)—C (=O)—, or —C(=O)N(R)—) ring replacement atoms.

When a moiety containing one ring replacement atom replaces a ring carbon atom, the resultant ring, after replacement of a ring atom by the moiety, will contain the same number of ring atoms as the ring before ring atom replacement. When a moiety containing two ring replacement atoms replaces a ring carbon atom, the resultant ring after replacement will contain one more ring atom than the ring prior to replacement by the moiety. For example, when a piperidine ring has one of its ring carbon atoms replaced by —N(R) C(=O)—, the resultant ring is a 7-membered ring containing 2 ring nitrogen atoms and the carbon of a carbonyl group in addition to 4 other carbon ring atoms ($CH_2$ groups) from the original piperidine ring.

"Cycloaliphatic" means a saturated or unsaturated, non-aromatic hydrocarbon moiety having from 1 to 3 rings, each ring having from 3 to 8 carbon atoms. Cycloaliphatic includes cycloalkyl, cycloalkenyl and cycloalkynyl monocyclic or polycyclic rings. "Cyclo-alkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties include cyclopropyl, cyclobutyl, cyclopentyl, and cyclohexyl.

"Heterocycloaliphatic" means a cycloaliphatic moiety wherein, in at least one ring thereof, up to three carbons have been replaced with a heteroatom independently selected from N, O, or S, where the N and S optionally may be oxidized and the N optionally may be quaternized. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like.

"Hydroxyalkyl," "haloalkyl," "alkylaryl," "cyanoaryl," and the like mean an alkyl, aryl, etc., moiety, as the case may be, substituted with one or more of the identified substituent (hydroxyl, halo, etc., as the case may be).

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. The term "substituted" as used herein refers to substitution with the named substituent or substituents, multiple degrees of substitution being allowed unless otherwise stated.

The term "optionally substituted" means that the group in question may be unsubstituted or it may be substituted one or several times, such as 1 to 3 times or 1 to 5 times. For example, an alkyl group that is "optionally substituted" with 1 to 5 chloro atoms, may be unsubstituted, or it may contain 1, 2, 3, 4, or 5 chlorine atoms. Typically, substituted chemical moieties include one or more substituents that replace hydrogen. Exemplary substituents include, for example, halo (e.g., F, Cl, Br, I), amino ($NH_2$), alkyl, alkylamino, cycloalkyl, alkylcycloalkyl, alkenyl, alkynyl, haloalkyl including trifluoroalkyl, aralkyl, aryl, heteroaryl, heteroarylalkyl, spiroalkyl, heterocyclyl, heterocycloalkyl, hydroxyl (—OH), alkoxyl, aryloxyl, aralkoxyl, nitro (—$NO_2$), cyano (—CN), amino (—$NH_2$), N-substituted amino (—NHR"), N,N-disubstituted amino (—N(R")R"), carboxyl (—COOH), —C(=O)R", —OR", —C(=O)OR", —C(=O)NHSO$_2$R", —NHC(=O)R", aminocarbonyl (—C(=O)NH$_2$), N-substituted aminocarbonyl (C(=O)NHR"), N,N-disubstituted aminocarbonyl (—C(=O)N(R")R"), thiolato (SR"), sulfonic acid and its esters (—$SO_3$R"), phosphonic acid and its mono-ester (—P(=O)(OR")(OH) and di-esters (—P(=O)(OR")(OR"), —S(=O)$_2$R", —S(=O)$_2$NH$_2$, —S(=O)$_2$NHR", —S(=O)$_2$NR"R", —SO$_2$NHC(=O)R", NHS(=O)$_2$R", —NR"S(=O)$_2$R", —CF$_3$, —CF$_2$CF$_3$, —NHC(=O)NHR", —NHC(=O)NR"R", —NR"C(=O)NHR", —NR"C(=O)NR"R", —NR"C(=O)R" and the like. In relation to the aforementioned substituents, each moiety "R" can be, independently, any of H, alkyl, cycloalkyl, alkenyl, aryl, aralkyl, heteroaryl, or heterocycloalkyl, or when (R"(R")) is attached to a nitrogen atom, R" and R" can be taken together with the nitrogen atom to which they are attached to form a 4- to 8-membered nitrogen heterocycle, wherein the heterocycloalkyl ring is optionally interrupted by one or more additional —O—, —S—, —SO, —SO$_2$—, —NH—, —N(alkyl)-, or —N(aryl) groups, for example. In certain embodiments, chemical moieties are substituted by at least one optional substituent, such as those provided hereinabove. In the present invention, when chemical moieties are substituted with optional substituents, the optional substituents are not further substituted unless otherwise stated. For example, when an R group is an alkyl moiety, it is optionally substituted, based on the definition of "alkyl" as set forth herein. In some embodiments, when R is alkyl substituted with optional aryl, the optional aryl substituent is not further substituted.

By way of illustration, substituents include, but are not limited to, alkyl (e.g. methyl, ethyl), alkylamino, alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —OCF$_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl)$_2$, and the like.

Where the moiety being substituted is an aliphatic moiety, substituents include, but not limited to: aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(=O)alkyl, —S(cycloalkyl), —SO$_2$(alkyl), —SO$_2$NH$_2$, —SO$_2$NH(alkyl), and —SO$_2$N(alkyl)$_2$. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are phenyl, cyano, halo, hydroxyl, nitro, C$_1$-C$_4$alkyoxy, O(C$_2$-C$_4$ alkylene)OH, and O(C$_2$-C$_4$ alkylene)halo.

Where the moiety being substituted is a cycloaliphatic, heterocycloaliphatic, aryl, or heteroaryl moiety, substituents include, but not limited to: alkyl, alkenyl, alkynyl, halo, haloalkyl, hydroxyl, hydroxyalkyl, cyano, nitro, alkoxy, —O(hydroxyalkyl), —O(haloalkyl), —O(aryl), —O(cycloalkyl), —O(heterocycloalkyl), alkylthio, arylthio, —C(=O)(alkyl), —C(=O)H, —CO$_2$H, —C(O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. In some embodiments, substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. In some embodiments, substituents are C$_1$-C$_4$ alkyl, cyano, nitro, halo, and C$_1$-C$_4$alkoxy.

When any variable occurs more than one time in any constituent or formula for a compound, its definition at each occurrence is independent of its definition at every other occurrence. Thus, for example, if the R$_5$ group is shown to be substituted with 0-2 substituents, then said group may optionally be substituted with up to two substituents and each substituent may be selected independently from the definition of optionally substituted defined above. Also, combinations of substituents and/or variables are permissible only if such combinations result in stable compounds.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a phenyl ring.

A "tautomer" refers to a molecule wherein a proton shift from one atom of a molecule to another atom of the same molecule is possible. Tautomers are included within the scope of the compounds described herein. The compounds presented herein, in certain embodiments, exist as tautomers. For example, where an alkene carbon of a compound is substituted with a hydroxyl group, both the enol and keto forms of the compound are included within the intended scope of the compounds described herein. In circumstances where tautomerization is possible, a chemical equilibrium of the tautomers will exist. The exact ratio of the tautomers depends on several factors, including physical state, temperature, solvent, and pH. Some examples of tautomeric equilibrium include:

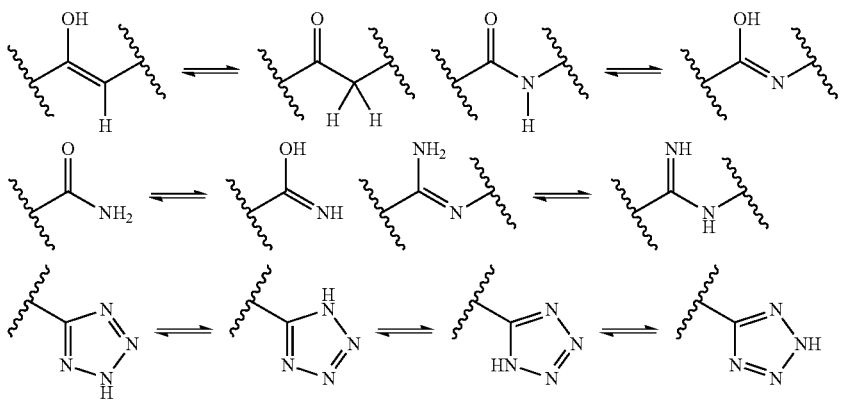

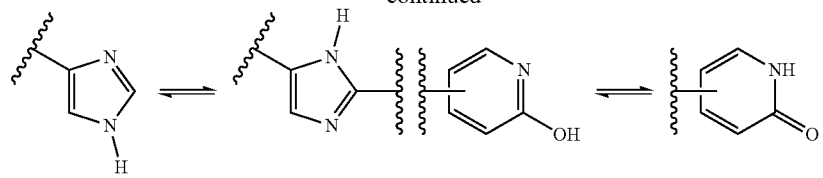
-continued

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334, 997. As described in U.S. Pat. Nos. 5,846,514 and 6,334, 997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. All isotopic variations of the compounds of the present invention, whether radioactive or not, are encompassed within the scope of the present invention.

In certain embodiments, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6 (10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64 (1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

As used herein, a "pharmaceutically acceptable" component/carrier etc is one that is suitable for use with humans and/or animals without undue adverse side effects (such as toxicity, irritation, and allergic response) commensurate with a reasonable benefit/risk ratio.

By "therapeutically effective amount" is meant an amount of a compound of the present invention effective to yield the desired therapeutic response. For example, an amount effective to delay the growth of a cancer, either a sarcoma or lymphoma, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

The term "prodrug" refers to any derivative of a compound of the embodiments that is capable of directly or indirectly providing a compound of the embodiments or an active metabolite or residue thereof when administered to a subject. Particularly favored derivatives and prodrugs are those that increase the bioavailability of the compounds of the embodiments when such compounds are administered to a subject (e.g., by allowing an orally administered compound to be more readily absorbed into the blood) or which enhance delivery of the parent compound to a biological compartment (e.g., the brain or lymphatic system) relative to the parent species. A general overview of prodrugs is provided in T. Higuchi and V. Stella, Pro-drugs as Novel Delivery Systems, Vol. 14 of the A.C.S. Symposium Series, and in Edward B. Roche, ed., Bioreversible.

The term "pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), *Handbook of Pharmaceutical Salts Properties*, Selection, and Use; 2002.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. Accordingly, "treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (2) inhibiting the state, disorder or condition, i.e., arresting, reducing or delaying the development of the disease or a relapse thereof (in case of maintenance treatment) or at least one clinical or subclinical symptom thereof; or (3) relieving the disease, i.e., causing regression of the state, disorder or condition or at least one of its clinical or subclinical symptoms. The benefit to an individual to be treated is either statistically significant or at least perceptible to the patient or to the physician.

The terms "patient", "subject" or "individual" are used interchangeably herein, and refers to a mammalian subject to be treated, with human patients being preferred. In certain embodiments, the methods of the invention find use in experimental animals, in veterinary application, and in the development of animal models for disease, including, but not limited to, rodents including mice, rats, and hamsters; and primates.

TLR8 Agonists

TLR8 is expressed predominantly in myeloid dendritic cells, monocytes, and monocyte-derived dendritic cells (Bekeredjian-Ding, I. et al. *J. Immunol.* 2006, 176, 7438-7446; Warshakoon, H. J. et al. *Hum. Vaccin.* 2009, 5, 381-394). Engagement by TLR8 agonists evokes a dominant proinflammatory cytokine profile, including tumor necrosis factor-α (TNF-α), interleukin (IL)-12, and IL-18, and appear uniquely potent in enhancing the production of Th1-polarizing cytokines TNF-α and IL-12 in APCs (Bohnenkamp, H. R. et al. *Cell. Immunol.* 2007, 247, 72-84; Philbin, V. J. et al. *Biochem. Soc. Trans.* 2007, 35, 1485-1491; Saruta, M. et al. *Eur. J. Immunol.* 2009, 39, 2195-2202). Small molecule agonists of TLR8 include: 2,3-diamino-furo[2,3-c]pyridines (Salunke, D. B. et al. *J. Med. Chem.* 2012, 55, 8137-8151), 4-amino-furo[2,3-c]quinolines (Kokatla, H. P. et al. *J. Med. Chem.* 2013, 56, 6871-6885), 3-alkyl-quinoline-2-amines (Kokatla, H. P. et al. *Chem. Med. Chem.* 2014, 9, 719-723), and 1-alkyl-2-aminobenzimidazoles (Beesu, M. et al. *J. Med. Chem.* 2014, 57, 7325-7341), all of which are pure TLR8 agonists with no detectable activity at TLR7.

Crystal structures of the ectodomain of human TLR8 (hTLR8) co-crystallized with two regioisomers of dual TLR7/8-agonistic N1-aminomethylbenzyl-substituted imidazoquinolines (1, 2) showed subtle differences in their interactions in the binding site of hTLR8 (FIG. 1); The $N^1$-substituent of 1 was observed to H-bond with a backbone carbonyl group, while in 2, a stronger salt-bridge was present, which fully explained the higher TLR8 activity of 2.

The present disclosure provides a library of compounds and resulting compositions having TLR8-specific agonistic activity.

In certain aspects, a compound of the disclosure is represented by Formula (II):

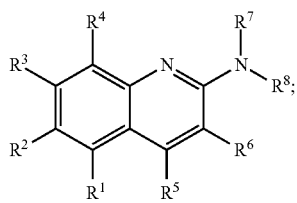

(II)

or a salt thereof, wherein:
$R^1$, $R^2$, $R^3$, $R^4$, and $R^5$ are independently selected from the group consisting of: H, halogen, —$OR^{10}$, —$N(R^{10})_2$, —$SR^{10}$, —CN, —$NO_2$, —$OC(O)R^{10}$, —$C(O)R^{10}$, —$C(O)OR^{10}$, —$C(O)N(R^{10})_2$, —$S(O)_2R^{10}$, —$S(O)_2OR^{10}$, optionally substituted $C_{1-20}$ alkyl, optionally substituted $C_{2-20}$ alkenyl, optionally substituted $C_{2-20}$ alkynyl, optionally substituted $C_{3-20}$ carbocycle, and optionally substituted 3- to 20-membered heterocycle;

$R^6$ is selected from the group consisting of —$OR^{11}$, —$N(R^{11})_2$, —$SR^{11}$, optionally substituted $C_{1-20}$ alkyl, optionally substituted $C_{2-20}$ alkenyl, and optionally substituted $C_{2-20}$ alkynyl;

$R^7$ and $R^8$ are independently selected from H, optionally substituted $C_{1-10}$ alkyl, optionally substituted $C_{2-10}$ alkenyl, optionally substituted $C_{2-10}$ alkynyl, optionally substituted $C_{3-12}$ carbocycle and optionally substituted 3- to 12-membered heterocycle;

$R^{10}$ is independently selected at each occurrence from the group consisting of H, optionally substituted $C_{1-10}$ alkyl, optionally substituted $C_{2-10}$ alkenyl, optionally substituted $C_{2-10}$ alkynyl, optionally substituted $C_{3-12}$ carbocycle and optionally substituted 3- to 12-membered heterocycle; and $R^{11}$ is independently selected at each occurrence from the group consisting of optionally substituted $C_{1-10}$ alkyl, optionally substituted $C_{2-10}$ alkenyl, and optionally substituted $C_{2-10}$ alkynyl.

certain embodiments, for a compound or salt of Formula (II), at least one of $R^1$ and $R^3$ is selected from the group consisting of —$OR^{10}$, —$N(R^{10})_2$, —$SR^{10}$, —$OC(O)R^{10}$, —$C(O)R^{10}$, —$C(O)OR^{10}$, —$C(O)N(R^{10})_2$, —$S(O)_2R^{10}$, —$S(O)_2OR^{10}$, optionally substituted $C_{1-20}$ alkyl, optionally substituted $C_{2-20}$ alkenyl, optionally substituted $C_{2-20}$ alkynyl, optionally substituted $C_{3-20}$ carbocycle, and optionally substituted 3- to 20-membered heterocycle. In certain embodiments, for a compound or salt of Formula (II), at least one of $R^1$ and $R^3$ may be selected from the group consisting of —$OR^{10}$, —$N(R^{10})_2$, —$OC(O)R^{10}$, —$C(O)R^{10}$, —$C(O)OR^{10}$, —$C(O)N(R^{10})_2$, —$S(O)_2R^{10}$, —$S(O)_2OR^{10}$, optionally substituted $C_{1-20}$ alkyl, optionally substituted $C_{2-20}$ alkenyl, and optionally substituted $C_{2-20}$ alkynyl. In certain embodiments, at least one of $R^1$ and $R^3$ is selected from the group consisting of optionally substituted $C_{1-20}$ alkyl, optionally substituted $C_{2-20}$ alkenyl, and optionally substituted $C_{2-20}$ alkynyl. In certain embodiments, at least one of $R^1$ and $R^3$ is selected from the group consisting of substituted $C_{1-20}$ alkyl, substituted $C_{2-20}$ alkenyl, and substituted $C_{2-20}$ alkynyl. In certain embodiments, at least one of $R^1$ and $R^3$ is optionally substituted $C_{1-20}$ alkyl. In certain embodiments, at least one of $R^1$ and $R^3$ is substituted $C_{1-20}$ alkyl. In certain embodiments, $R^1$ is optionally substituted $C_{1-10}$ alkyl. In certain embodiments, $R^1$ is optionally substituted $C_{1-5}$ alkyl. In certain embodiments, $R^1$ is substituted $C_{1-5}$ alkyl. In certain embodiments for a compound or salt of Formula (II), $R^1$ is selected from the group consisting of:

optionally substituted $C_{1-20}$ alkyl, optionally substituted $C_{2-20}$ alkenyl, optionally substituted $C_{2-20}$ alkynyl, wherein the $C_{1-20}$ alkyl, $C_{2-20}$ alkenyl, and $C_{2-20}$ alkynyl optional substituents are one or more substituents independently selected from the group consisting of: halogen, —CN, —$NO_2$, —$OR^{50}$, —$SR^{50}$, —$N(R^{50})_2$, —$NR^{50}C(N(R^{50}))N(R^{50})_2$, —$OC(O)R^{50}$, —$C(O)R^{50}$, —$C(O)OR^{50}$, —$C(O)N(R^{50})_2$, —$S(O)_2R^{50}$, —$S(O)_2OR^{50}$, $C_{3-12}$ carbocycle, and 3- to 12-membered heterocycle, wherein the $C_{3-12}$ carbocycle and 3- to 12-membered heterocycle are optionally substituted with one or more substituents selected from the group consisting of halogen, —CN, —$NO_2$, —$OR^{50}$, —$SR^{50}$, —$N(R^{50})_2$, $C_{1-10}$ alkyl, $C_{1-10}$ haloalkyl, —$C_{1-10}$ alkyl-N(R^{50})_2$, —$C_{1-10}$ alkyl-$OR^{50}$, and —$C_{1-10}$ alkyl-$C(O)N(R^{50})_2$; and optionally substituted C$_{3-20}$ carbocycle and optionally substituted 3- to 20-membered heterocycle, wherein the C$_{3-20}$ carbocycle and 3- to 20-membered heterocycle optional substituents are one or more substituents independently selected from the group consisting of halogen, —CN, —NO$_2$, —OR$^{50}$, —SR$^{50}$, —N(R$^{50}$)$_2$, C$_{1-10}$ alkyl, C$_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and wherein R$^{50}$ at each occurrence is independently selected from the group consisting of hydrogen, C$_{1-10}$ alkyl, and C$_{1-10}$ haloalkyl.

In certain embodiments for a compound or salt of Formula (II), R$^1$ is optionally substituted C$_{1-20}$ alkyl, wherein optional substituents are one or more substituents independently selected from the group consisting of: halogen, C$_{3-12}$ carbocycle, and 3- to 12-membered heterocycle, wherein carbocycle and heterocycle are optionally substituted with one or more substituents selected from the group consisting of halogen, —CN, —NO$_2$, —OR$^{50}$, —SR$^{50}$, —N(R$^{50}$)$_2$, C$_{1-10}$ alkyl, C$_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and wherein R$^{50}$ at each occurrence is independently selected from the group consisting of hydrogen, C$_{1-10}$ alkyl, and C$_{1-10}$ haloalkyl.

In certain embodiments for a compound or salt of Formula (II), R$^1$ is optionally substituted C$_{1-20}$ alkyl, wherein the alkyl is substituted by a C$_{3-12}$ carbocycle, wherein the carbocycle is optionally substituted with one or more substituents selected from the group consisting of halogen, —CN, —NO$_2$, —OR$^{50}$, —SR$^{50}$, —N(R$^{50}$)$_2$, C$_{1-10}$ alkyl, C$_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and wherein R$^{50}$ at each occurrence is independently selected from the group consisting of hydrogen, C$_{1-10}$ alkyl, and C$_{1-10}$ haloalkyl.

In certain embodiments for a compound or salt of Formula (II), R$^1$ is optionally substituted C$_{1-20}$ alkyl, wherein the alkyl is substituted by a C$_{3-12}$ carbocycle, wherein the carbocycle is optionally substituted with one or more substituents selected from the group consisting of C$_{1-10}$ alkyl, C$_{1-10}$ haloalkyl, —C$_{1-10}$ alkyl-N(R$^{50}$)$_2$, and —C$_{1-10}$ alkyl-C(O)N(R$^{50}$)$_2$; and wherein R$^{50}$ at each occurrence is independently selected from the group consisting of hydrogen, C$_{1-10}$ alkyl, and C$_{1-10}$ haloalkyl.

In certain embodiments for a compound or salt of Formula (II), R$^1$ is C$_{1-20}$ alkyl, wherein the alkyl is substituted by a C$_{3-12}$ carbocycle, wherein the carbocycle is substituted with one or more substituents selected from the group consisting of C$_{1-10}$ alkyl and —C$_{1-10}$ alkyl-N(R$^{50}$)$_2$, and wherein R$^{50}$ at each occurrence is independently selected from the group consisting of hydrogen, C$_{1-10}$ alkyl, and C$_{1-10}$ haloalkyl.

In certain embodiments for a compound or salt of Formula (II), R$^1$ is C$_{1-20}$ alkyl, wherein the alkyl is substituted by a C$_{3-12}$ carbocycle, wherein the carbocycle is substituted with one or more substituents selected from the group consisting of C$_{1-10}$ alkyl and —C$_{1-10}$ alkyl-N(R$^{50}$)$_2$, and wherein R$^{50}$ at each occurrence is independently selected from the group consisting of hydrogen, C$_{1-10}$ alkyl, and C$_{1-10}$ haloalkyl.

In certain embodiments for a compound or salt of Formula (II), R$^1$ is substituted with —N(R$^{50}$)$_2$. In certain embodiments for a compound or salt of Formula (II), R$^1$ is selected from:

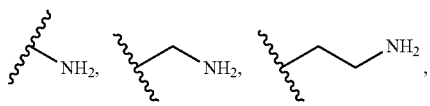

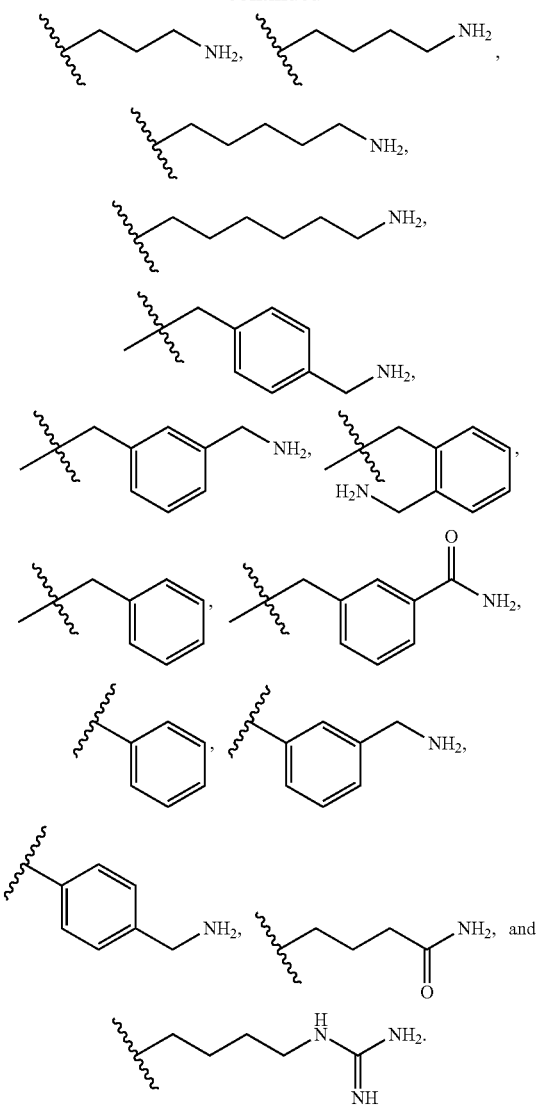

In certain embodiments for a compound or salt of Formula (II), R$^1$ is selected from:

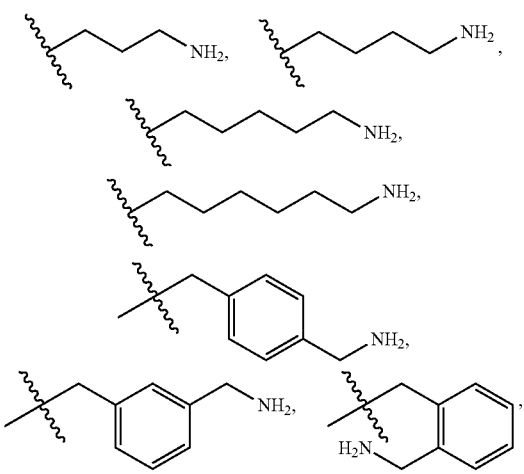

-continued

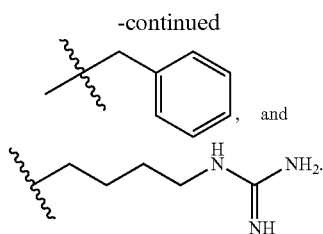, and

[structure showing chain with NH-C(=NH)-NH2 guanidine group]

In some embodiments for a compound or salt of Formula (II), $R^1$ is selected from H, halogen, and —CN. In some embodiments, $R^1$ is hydrogen.

In certain embodiments for a compound or salt of Formula (II), $R^1$ is $C_{1-20}$ alkyl, $C_{2-20}$ alkenyl, $C_{2-20}$ alkynyl, $C_{3-20}$ carbocycle or 3- to 20-membered heterocycle any of which is substituted with —N($R^{50}$)$_2$; $R^3$ is selected from H, halogen, and —CN, such as $R^3$ is hydrogen; and $R^{50}$ at each occurrence is independently selected from the group consisting of hydrogen, $C_{1-10}$ alkyl, and $C_{1-10}$ haloalkyl. In certain embodiments, $R^1$ is $C_{1-20}$ alkyl, $C_{2-20}$ alkenyl, $C_{2-20}$ alkynyl, any of which is substituted with —N($R^{50}$)$_2$; $R^3$ is selected from H, halogen, and —CN, such as $R^3$ is hydrogen; and $R^{50}$ at each occurrence is independently selected from the group consisting of hydrogen, $C_{1-10}$ alkyl, and $C_{1-10}$ haloalkyl. In certain embodiments, $R^1$ is $C_{1-20}$ alkyl substituted with —N($R^{50}$)$_2$, $R^3$ is selected from H, halogen, and —CN, such as $R^3$ is hydrogen; and $R^{50}$ at each occurrence is independently selected from the group consisting of hydrogen.

For a compound or salt of Formula (II), $R^1$ may be $C_{1-20}$ alkyl substituted with $C_{3-12}$ carbocycle or 3- to 12-membered heterocycle, wherein $C_{3-12}$ carbocycle and 3- to 12-membered heterocycle are optionally substituted with one or more substituents selected from the group consisting of halogen, —CN, —NO$_2$, —OR$^{50}$, —SR$^{50}$, —N($R^{10}$)$_2$, $C_{1-10}$ alkyl, $C_{1-10}$ haloalkyl, —$C_{1-10}$ alkyl-N($R^{50}$)$_2$, —$C_{1-10}$ alkyl-OR$^{50}$, and —$C_{1-10}$ alkyl-C(O)N($R^{50}$)$_2$—N($R^{50}$)$_2$; $R^3$ is selected from H, halogen, and —CN, such as $R^3$ is hydrogen; and $R^{50}$ at each occurrence is independently selected from the group consisting of hydrogen, $C_{1-10}$ alkyl, and $C_{1-10}$ haloalkyl.

In certain embodiments for a compound or salt of Formula (II), $R^1$ is $C_{1-20}$ alkyl substituted with $C_{3-12}$ carbocycle, wherein the $C_{3-12}$ carbocycle is optionally substituted with one or more substituents selected from the group consisting of halogen, —CN, —NO$_2$, OR$^{50}$, —SR$^{50}$, —N($R^{50}$)$_2$, $C_{1-10}$ alkyl, $C_{1-10}$ haloalkyl, —$C_{1-10}$ alkyl-N($R^{50}$)$_2$, —$C_{1-10}$ alkyl-OR$^{50}$, and —$C_{1-10}$ alkyl-C(O)N($R^{50}$)$_2$—N($R^{50}$)$_2$; $R^3$ is selected from H, halogen, and —CN, such as $R^3$ is hydrogen; and $R^{50}$ at each occurrence is independently selected from the group consisting of hydrogen, $C_{1-10}$ alkyl, and $C_{1-10}$ haloalkyl. In certain embodiments for a compound or salt of Formula (II), $R^1$ is $C_{1-10}$ alkyl substituted with aryl, wherein the aryl is optionally substituted with one or more substituents selected from the group consisting of halogen, —CN, —NO$_2$, —OR$^{50}$, —SR$^{50}$, —N($R^{50}$)$_2$, $C_{1-10}$ alkyl, $C_{1-10}$ haloalkyl, —$C_{1-10}$ alkyl-N($R^{50}$)$_2$, —$C_{1-10}$ alkyl-OR$^5$, and —$C_{1-10}$ alkyl-C(O)N($R^{50}$)$_2$—N($R^{50}$)$_2$; $R^3$ is selected from H, halogen, and —CN, such as $R^3$ is hydrogen; and $R^{50}$ at each occurrence is independently selected from the group consisting of hydrogen, $C_{1-10}$ alkyl, and $C_{1-10}$ haloalkyl.

For a compound or salt of Formula (II), $R^3$ may be optionally substituted $C_{1-10}$ alkyl. In certain embodiments, $R^3$ is optionally substituted $C_{1-5}$ alkyl.

For a compound or salt of Formula (II), $R^3$ may be selected from the group consisting of: optionally substituted $C_{1-20}$ alkyl, optionally substituted $C_{2-20}$ alkenyl, optionally substituted $C_{2-20}$ alkynyl, wherein the $C_{1-20}$ alkyl, $C_{2-20}$ alkenyl, and $C_{2-20}$ alkynyl optional substituents are one or more substituents independently selected from the group consisting of: halogen, —CN, —NO$_2$, —OR$^{50}$, —SR$^{50}$, —N($R^{50}$)$_2$, —NR$^{50}$C(N($R^{50}$))N($R^{50}$)$_2$, —OC(O)R$^{50}$, —C(O)R$^{50}$, —C(O)OR$^{50}$, —C(O)N($R^{50}$)$_2$, —S(O)$_2$R$^{50}$, —S(O)$_2$OR$^{50}$, $C_{3-12}$ carbocycle, and 3- to 12-membered heterocycle, wherein the $C_{3-12}$ carbocycle and 3- to 12-membered heterocycle are optionally substituted with one or more substituents selected from the group consisting of halogen, —CN, —NO$_2$, —OR$^{50}$, —SR$^{50}$, —N($R^{50}$)$_2$, $C_{1-10}$ alkyl, $C_{1-10}$ haloalkyl, —$C_{1-10}$ alkyl-N($R^{50}$)$_2$, —$C_{1-10}$ alkyl-OR$^{50}$, and —$C_{1-10}$ alkyl-C(O)N($R^{50}$)$_2$; and optionally substituted $C_{3-20}$ carbocycle and optionally substituted 3- to 20-membered heterocycle, wherein $C_{3-20}$ carbocycle and 3- to 20-membered heterocycle optional substituents are one or more substituents independently selected from the group consisting of halogen, —CN, —NO$_2$, —OR$^{50}$, —SR$^{50}$, —N($R^{50}$)$_2$, $C_{1-10}$ alkyl, $C_{1-10}$ haloalkyl, —$C_{1-10}$ alkyl-N($R^{50}$)$_2$, —$C_{1-10}$ alkyl-OR$^{50}$, and —$C_{1-10}$ alkyl-C(O)N($R^{50}$)$_2$; and wherein $R^{50}$ at each occurrence is independently selected from the group consisting of hydrogen, $C_{1-10}$ alkyl, and $C_{1-10}$ haloalkyl.

In certain embodiments, for a compound or salt of Formula (II), $R^3$ is optionally substituted $C_{1-20}$ alkyl, wherein optional substituents are one or more substituents independently selected from the group consisting of: halogen, $C_{3-12}$ carbocycle, and 3- to 12-membered heterocycle, wherein the $C_{3-12}$ carbocycle, and 3- to 12-membered heterocycle are optionally substituted with one or more substituents selected from the group consisting of halogen, —CN, —NO$_2$, —OR$^{50}$, —SR$^5$, —N($R^{50}$)$_2$, $C_{1-10}$ alkyl, $C_{1-10}$ haloalkyl, —$C_{1-10}$ alkyl-N($R^{50}$)$_2$, —$C_{1-10}$ alkyl-OR$^{50}$, and —$C_{1-10}$ alkyl-C(O)N($R^{50}$)$_2$; and wherein $R^{50}$ at each occurrence is independently selected from the group consisting of hydrogen, $C_{1-10}$ alkyl, and $C_{1-10}$ haloalkyl.

In certain embodiments, for a compound or salt of Formula (II), $R^3$ is optionally substituted $C_{1-20}$ alkyl, wherein the alkyl is substituted by a $C_{3-12}$ carbocycle, wherein the carbocycle is optionally substituted with one or more substituents selected from the group consisting of halogen, —CN, —NO$_2$, —OR$^{50}$, —SR$^{50}$, —N($R^{50}$)$_2$, $C_{1-10}$ alkyl, $C_{1-10}$ haloalkyl, —$C_{1-10}$ alkyl-N($R^{50}$)$_2$, —$C_{1-10}$ alkyl-OR$^{50}$, and —$C_{1-10}$ alkyl-C(O)N($R^{50}$)$_2$; and wherein $R^{50}$ at each occurrence is independently selected from the group consisting of hydrogen, $C_{1-10}$ alkyl, and $C_{1-10}$ haloalkyl.

In certain embodiments, for a compound or salt of Formula (II), $R^3$ is optionally substituted $C_{1-20}$ alkyl, wherein the alkyl is substituted by a $C_{3-12}$ carbocycle, wherein the $C_{3-12}$ carbocycle is optionally substituted with one or more substituents selected from the group consisting of $C_{1-10}$ alkyl, $C_{1-10}$ haloalkyl, —$C_{1-10}$ alkyl-N($R^{50}$)$_2$, and —$C_{1-10}$ alkyl-C(O)N($R^{50}$)$_2$; and wherein $R^{50}$ at each occurrence is independently selected from the group consisting of hydrogen, $C_{1-10}$ alkyl, and $C_{1-10}$ haloalkyl.

In certain embodiments, $R^3$ is $C_{1-20}$ alkyl, wherein the $C_{1-20}$ alkyl is substituted by a $C_{3-12}$ carbocycle, wherein the carbocycle is substituted with one or more substituents selected from the group consisting of $C_{1-10}$ alkyl and —$C_{1-10}$ alkyl-N($R^{50}$)$_2$, and wherein $R^{50}$ at each occurrence is independently selected from the group consisting of hydrogen, $C_{1-10}$ alkyl, and $C_{1-10}$ haloalkyl.

In certain embodiments, $R^3$ is $C_{1-20}$ alkyl, wherein the $C_{1-20}$ alkyl is substituted by a $C_{3-12}$ carbocycle, wherein the carbocycle is substituted with one or more substituents selected from the group consisting of $C_{1-10}$ alkyl and —$C_{1-10}$ alkyl-$N(R^{50})_2$, and wherein $R^{50}$ at each occurrence is independently selected from the group consisting of hydrogen, $C_{1-10}$ alkyl, and $C_{1-10}$ haloalkyl.

In certain embodiments, $R^3$ is substituted with —$N(R^{50})_2$. In certain embodiments, $R^3$ is selected from:

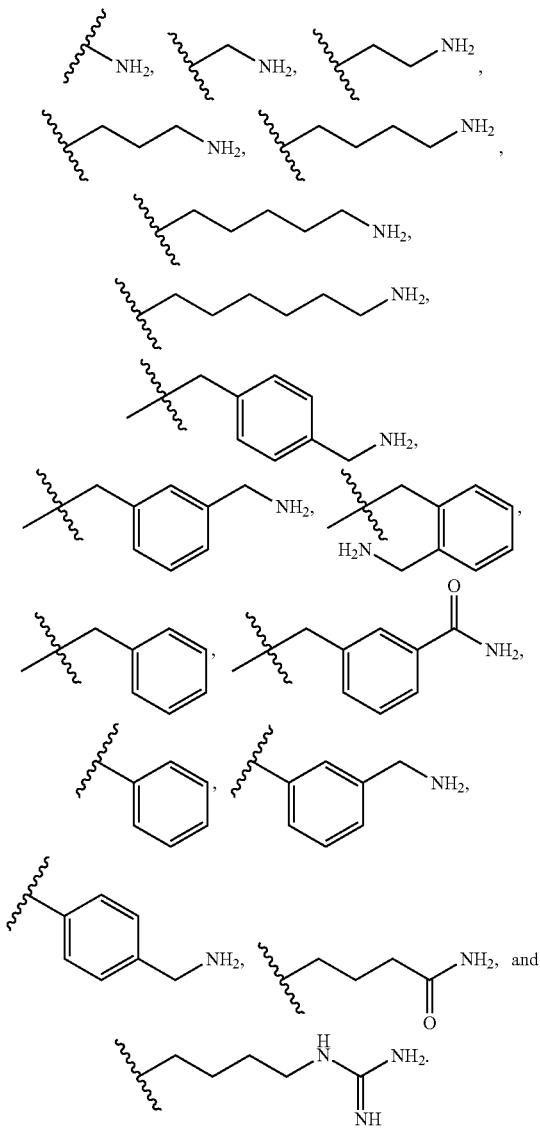

In certain embodiments, $R^3$ is selected from:

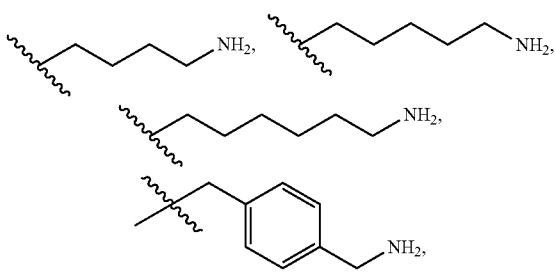

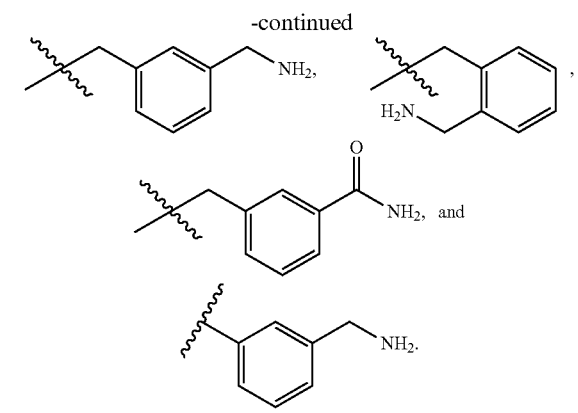

In certain embodiments, $R^3$ is selected from H, halogen, and —CN. In certain embodiments, $R^3$ is hydrogen. In certain embodiments, $R^3$ is halogen, wherein halogen is selected from fluorine, chloride, and bromine. In certain embodiments, $R^3$ is —CN.

In certain embodiments, $R^1$ is selected from H, halogen, and —CN. In certain embodiments, $R^1$ is hydrogen. In certain embodiments, $R^1$ is halogen, wherein halogen is selected from fluorine, chloride, and bromine. In certain embodiments, $R^1$ is —CN.

In certain embodiments for a compound or salt of Formula (II), $R^3$ is $C_{1-20}$ alkyl, $C_{2-20}$ alkenyl, $C_{2-20}$ alkynyl, $C_{3-20}$ carbocycle or 3- to 20-membered heterocycle any of which is substituted with —$N(R^{50})_2$; $R^1$ is selected from H, halogen, and —CN, such as $R^1$ is hydrogen; and $R^{50}$ at each occurrence is independently selected from the group consisting of hydrogen, $C_{1-10}$ alkyl, and $C_{1-10}$ haloalkyl. In certain embodiments, $R^3$ is $C_{1-20}$ alkyl, $C_{2-20}$ alkenyl, $C_{2-20}$ alkynyl, any of which is substituted with —$N(R^{50})_2$; $R^1$ is selected from H, halogen, and —CN, such as $R^1$ is hydrogen; and $R^{50}$ at each occurrence is independently selected from the group consisting of hydrogen, $C_{1-10}$ alkyl, and $C_{1-10}$ haloalkyl. In certain embodiments, $R^3$ is $C_{1-20}$ alkyl substituted with —$N(R^{50})_2$, $R^1$ is selected from H, halogen, and —CN, such as $R^1$ is hydrogen; and $R^{50}$ at each occurrence is independently selected from the group consisting of hydrogen.

For a compound or salt of Formula (II), $R^3$ may be $C_{1-20}$ alkyl substituted with $C_{3-12}$ carbocycle or 3- to 12-membered heterocycle, wherein $C_{3-12}$ carbocycle and 3- to 12-membered heterocycle are optionally substituted with one or more substituents selected from the group consisting of halogen, —CN, —$NO_2$, —$OR^{50}$, —$SR^{50}$, —$N(R^{50})_2$, $C_{1-10}$ alkyl, $C_{1-10}$ haloalkyl, —$C_{1-10}$ alkyl-$N(R^{50})_2$, —$C_{1-10}$ alkyl-$OR^{50}$, and —$C_{1-10}$ alkyl-$C(O)N(R")_2$—$N(R^{50})_2$; $R^1$ is selected from H, halogen, and —CN, such as $R^1$ is hydrogen; and $R^{50}$ at each occurrence is independently selected from the group consisting of hydrogen, $C_{1-10}$ alkyl, and $C_{1-10}$ haloalkyl.

In certain embodiments for a compound or salt of Formula (II), $R^3$ is $C_{1-20}$ alkyl substituted with $C_{3-12}$ carbocycle, wherein the $C_{3-12}$ carbocycle is optionally substituted with one or more substituents selected from the group consisting of halogen, —CN, —$NO_2$, —$OR^{50}$, —$SR^{50}$, —$N(R^{50})_2$, $C_{1-10}$ alkyl, $C_{1-10}$ haloalkyl, —$C_{1-10}$ alkyl-$N(R^{50})_2$, —$C_{1-10}$ alkyl-$OR^{50}$, and —$C_{1-10}$ alkyl-$C(O)N(R^{50})_2$—$N(R^{50})_2$; $R^1$ is selected from H, halogen, and —CN, such as $R^1$ is hydrogen; and $R^{50}$ at each occurrence is independently selected from the group consisting of hydrogen, $C_{1-10}$ alkyl, and $C_{1-10}$ haloalkyl. In certain embodiments for a compound or salt of Formula (II), $R^3$ is $C_{1-10}$ alkyl substituted with aryl, wherein the aryl is optionally substituted with one or more substituents selected from the group consisting of halogen, —CN, —NO$_2$, —OR$^{50}$, —SR$^5$, —N(R$^{50}$)$_2$, $C_{1-10}$ alkyl, $C_{1-10}$ haloalkyl, —$C_{1-10}$ alkyl-N(R$^{50}$)$_2$, —$C_{1-10}$ alkyl-OR$^{50}$, and —$C_{1-10}$ alkyl-C(O)N(R$^{50}$)$_2$—N(R$^{50}$)$_2$; $R^1$ is selected from H, halogen, and —CN, such as $R^1$ is hydrogen; and $R^{50}$ at each occurrence is independently selected from the group consisting of hydrogen, $C_{1-10}$ alkyl, and $C_{1-10}$ haloalkyl.

In certain embodiments, for a compound or salt of Formula (II), $R^2$, $R^4$, and $R^5$ are independently selected from the group consisting of: H, halogen, —OR$^{10}$, —N(R$^{10}$)$_2$, —SR$^{10}$, —CN, —NO$_2$, —OC(O)R$^{10}$, —C(O)R$^{10}$, —C(O)OR$^{10}$, —C(O)N(R$^{10}$)$_2$, —S(O)$_2$R$^{10}$, —S(O)$_2$OR$^{10}$, and optionally substituted $C_{1-20}$ alkyl. In certain embodiments, $R^2$, $R^4$, and $R^5$ are independently selected from the group consisting of: H, halogen, —OR$^{10}$, —N(R$^{10}$)$_2$, —SR$^{10}$, —CN, —NO$_2$, and optionally substituted $C_{1-20}$ alkyl. In certain embodiments, $R^2$, $R^4$, and $R^5$ are independently selected from the group consisting of: optionally substituted $C_{1-20}$ alkyl, optionally substituted $C_{2-20}$ alkenyl, optionally substituted $C_{2-20}$ alkynyl, wherein the $C_{1-20}$ alkyl, $C_{2-20}$ alkenyl, and $C_{2-20}$ alkynyl optional substituents are one or more substituents independently selected from the group consisting of: halogen, —CN, —NO$_2$, —OR$^{50}$, —SR$^{50}$, —N(R$^{50}$)$_2$, —NR$^{50}$C(N(R$^{50}$))N(R$^{50}$)$_2$, —OC(O)R$^{50}$, —C(O)R$^{50}$, —C(O)OR$^{50}$, —C(O)N(R$^{50}$)$_2$, —S(O)$_2$R$^{50}$, —S(O)$_2$OR$^{50}$, $C_{3-12}$ carbocycle, and 3- to 12-membered heterocycle, wherein the $C_{3-12}$ carbocycle and 3- to 12-membered heterocycle are optionally substituted with one or more substituents selected from the group consisting of: halogen, —CN, —NO$_2$, —OR$^{50}$, —SR$^{50}$, —N(R$^{50}$)$_2$, $C_{1-10}$ alkyl, $C_{1-10}$ haloalkyl, —$C_{1-10}$ alkyl-N(R$^{50}$)$_2$, —$C_{1-10}$ alkyl-OR$^{50}$, and —$C_{1-10}$ alkyl-C(O)N(R$^{50}$)$_2$; and optionally substituted $C_{3-20}$ carbocycle and optionally substituted 3- to 20-membered heterocycle, wherein $C_{3-20}$ carbocycle and 3- to 20-membered heterocycle optional substituents are one or more substituents independently selected from the group consisting of: halogen, —CN, —NO$_2$, —OR$^{50}$, —SR$^{50}$, —N(R$^{50}$)$_2$, $C_{1-10}$ alkyl, $C_{1-10}$ haloalkyl, —$C_{1-10}$ alkyl-N(R$^{50}$)$_2$, —$C_{1-10}$ alkyl-OR$^{50}$, and —$C_{1-10}$ alkyl-C(O)N(R$^{50}$)$_2$; and wherein $R^{50}$ at each occurrence is independently selected from the group consisting of hydrogen, $C_{1-10}$ alkyl, and $C_{1-10}$ haloalkyl.

In certain embodiments, for a compound or salt of Formula (II), $R^2$, $R^4$, and $R^5$ may be independently selected from the group consisting of: optionally substituted $C_{1-20}$ alkyl, wherein optional substituents of $C_{1-20}$ alkyl are one or more substituents independently selected from the group consisting of: halogen, —CN, —NO$_2$, —OR$^{50}$, —SR$^{50}$, —N(R$^{50}$)$_2$, —NR$^{50}$C(N(R$^{50}$))N(R$^{50}$)$_2$, —OC(O)R$^{50}$, —C(O)R$^{50}$, —C(O)OR$^{50}$, —C(O)N(R$^{50}$)$_2$, $C_{3-12}$ carbocycle, wherein $C_{3-12}$ carbocycle is optionally substituted with one or more substituents selected from the group consisting of halogen, $C_{1-10}$ alkyl, $C_{1-10}$ haloalkyl, —$C_{1-10}$ alkyl-N(R$^{50}$)$_2$, —$C_{1-10}$ alkyl-OR$^{50}$, and —$C_{1-10}$ alkyl-C(O)N(R$^{50}$)$_2$; and optionally substituted $C_{3-20}$ carbocycle and optionally substituted 3- to 20-membered heterocycle, wherein the $C_{3-20}$ carbocycle and 3- to 20-membered heterocycle optional substituents are one or more substituents independently selected from the group consisting of: halogen, —N(R$^{50}$)$_2$, $C_{1-10}$ alkyl, $C_{1-10}$ haloalkyl, —$C_{1-10}$ alkyl-N(R$^{50}$)$_2$, —$C_{1-10}$ alkyl-OR$^{50}$, and —$C_{1-10}$ alkyl-C(O)N(R$^{50}$)$_2$; and wherein $R^{50}$ at each occurrence is independently selected from the group consisting of hydrogen, $C_{1-10}$ alkyl, and $C_{1-10}$ haloalkyl.

In certain embodiments, for a compound or salt of Formula (II), $R^2$, $R^4$, and $R^5$ may be independently selected from the group consisting of: optionally substituted $C_{1-20}$ alkyl, wherein the $C_{1-20}$ alkyl optional substituents are one or more substituents independently selected from the group consisting of: halogen and $C_{3-12}$ carbocycle, wherein the $C_{3-12}$ carbocycle is optionally substituted with one or more substituents selected from the group consisting of halogen, $C_{1-10}$ alkyl, $C_{1-10}$ haloalkyl, —$C_{1-10}$ alkyl-N(R$^{50}$)$_2$, and wherein $R^{50}$ at each occurrence is independently selected from the group consisting of hydrogen, $C_{1-10}$ alkyl, and $C_{1-10}$ haloalkyl.

In certain embodiments, for a compound or salt of Formula (II), $R^2$ is $C_{1-20}$ alkyl or hydrogen. In certain embodiments, $R^2$ is hydrogen. In certain embodiments, $R^4$ is $C_{1-20}$ alkyl or hydrogen. In certain embodiments, $R^4$ is hydrogen. In certain embodiments, $R^5$ is $C_{1-20}$ alkyl or hydrogen. In certain embodiments, $R^5$ is hydrogen.

In certain embodiments, for a compound or salt of Formula (II), $R^{10}$ may be selected from the group consisting of: optionally substituted $C_{1-20}$ alkyl, optionally substituted $C_{2-20}$ alkenyl, optionally substituted $C_{2-20}$ alkynyl, wherein optional substituents are one or more substituents independently selected from the group consisting of: halogen, —CN, —NO$_2$, —OR$^{50}$, —SR$^{50}$, —N(R$^{50}$)$_2$, —NR$^{50}$C(N(R$^{50}$))N(R$^{50}$)$_2$, —OC(O)R$^{50}$, —C(O)R$^{50}$, —C(O)OR$^{50}$, —C(O)N(R$^{50}$)$_2$, —S(O)$_2$R$^{50}$, —S(O)$_2$OR$^{50}$, $C_{3-12}$ carbocycle, and 3- to 12-membered heterocycle, wherein carbocycle and heterocycle are optionally substituted with one or more substituents selected from the group consisting of halogen, —CN, —NO$_2$, —OR$^{50}$, —SR$^{50}$, —N(R$^{50}$)$_2$, $C_{1-10}$ alkyl, $C_{1-10}$ haloalkyl, —$C_{1-10}$ alkyl-N(R$^{50}$)$_2$, —$C_{1-10}$ alkyl-OR$^{50}$, and —$C_{1-10}$ alkyl-C(O)N(R$^{50}$)$_2$; and optionally substituted $C_{3-20}$ carbocycle and optionally substituted 3- to 20-membered heterocycle, wherein optional substituents are one or more substituents independently selected from the group consisting of: halogen, —CN, —NO$_2$, —OR$^{50}$, —SR$^{50}$, —N(R$^{50}$)$_2$, $C_{1-10}$ alkyl, $C_{1-10}$ haloalkyl, —$C_{1-10}$ alkyl-N(R$^{50}$)$_2$, —$C_{1-10}$ alkyl-OR$^{50}$, and —$C_{1-10}$ alkyl-C(O)N(R$^{50}$)$_2$; and wherein $R^{50}$ at each occurrence is independently selected from the group consisting of hydrogen, $C_{1-10}$ alkyl, and $C_{1-10}$ haloalkyl.

In certain embodiments, for a compound or salt of Formula (II), $R^{10}$ may be optionally substituted $C_{1-20}$ alkyl, wherein the $C_{1-20}$ alkyl optional substituents are one or more substituents independently selected from the group consisting of: halogen, —CN, —NO$_2$, —OR$^{50}$, —SR$^{50}$, —N(R$^{50}$)$_2$, —NR$^{50}$C(N(R$^{50}$))N(R$^{50}$)$_2$, —OC(O)R$^{50}$, —C(O)R$^{50}$, —C(O)OR$^5$, —C(O)N(R$^{50}$)$_2$, —S(O)$_2$R$^{50}$, —S(O)$_2$OR$^{50}$, $C_{3-12}$ carbocycle, and 3- to 12-membered heterocycle, wherein the $C_{3-12}$ carbocycle and 3- to 12-membered heterocycle are optionally substituted with one or more substituents selected from the group consisting of halogen, —N(R$^{50}$)$_2$, $C_{1-10}$ alkyl, $C_{1-10}$ haloalkyl, —$C_{1-10}$ alkyl-N(R$^{50}$)$_2$, —$C_{1-10}$ alkyl-OR$^{50}$, and —$C_{1-10}$ alkyl-C(O)N(R$^{50}$)$_2$; and optionally substituted $C_{3-20}$ carbocycle, wherein the $C_{3-20}$ carbocycle optional substituents are one or more substituents independently selected from the group consisting of: halogen, —N(R$^{50}$)$_2$, $C_{1-10}$ alkyl, $C_{1-10}$ haloalkyl, —$C_{1-10}$ alkyl-N(R$^{50}$)$_2$, —$C_{1-10}$ alkyl-OR$^{50}$, and —$C_{1-10}$ alkyl-C(O)N(R$^{50}$)$_2$; and wherein $R^{50}$ at each occurrence is independently selected from the group consisting of hydrogen, $C_{1-10}$ alkyl, and $C_{1-10}$ haloalkyl.

In certain embodiments, for a compound or salt of Formula (II), $R^{10}$ is optionally substituted $C_{1-20}$ alkyl. In certain embodiments, for a compound or salt of Formula (II), $R^{10}$ may be optionally substituted $C_{1-20}$ alkyl, wherein the $C_{1-20}$ alkyl optional substituents are one or more substituents independently selected from the group consisting of: halogen, —CN, —NO$_2$, —OR$^{50}$, —SR$^{50}$, —N(R$^{50}$)$_2$, —NR$^{50}$C(N(R$^{50}$))N(R$^{50}$)$_2$, —OC(O)R$^{50}$, —C(O)R$^{50}$, —C(O)OR$^{50}$, —C(O)N(R$^{50}$)$_2$, —S(O)$_2$R$^{50}$, —S(O)$_2$OR$^{50}$, $C_{3-12}$ carbocycle, and 3- to 12-membered heterocycle. In certain embodiments, $R^{10}$ is $C_{1-20}$ alkyl. In certain embodiments, $R^{10}$ is $C_{1-10}$ alkyl. In certain embodiments, $R^{10}$ is $C_{1-5}$ alkyl. In certain embodiments, for a compound or salt of Formula (II), $R^6$ may be selected from the group consisting of optionally substituted $C_{1-20}$ alkyl, optionally substituted $C_{2-20}$ alkenyl, and optionally substituted $C_{2-20}$ alkynyl. In certain embodiments, $R^6$ is selected from the group consisting of optionally substituted $C_{1-10}$ alkyl, optionally substituted $C_{2-10}$ alkenyl, and optionally substituted $C_{1-20}$ alkynyl. In certain embodiments, $R^6$ is selected from the group consisting of optionally substituted $C_{1-10}$ alkyl. In certain embodiments, $R^6$ is selected from the group consisting of: optionally substituted $C_{1-20}$ alkyl, optionally substituted $C_{2-20}$ alkenyl, optionally substituted $C_{2-20}$ alkynyl, wherein the $C_{1-20}$ alkyl, $C_{2-20}$ alkenyl, and $C_{2-20}$ alkynyl optional substituents are one or more substituents independently selected from the group consisting of: halogen, —CN, —NO$_2$, —OR$^{50}$, —SR$^{50}$, —N(R$^{50}$)$_2$, —NR$^{50}$C(N(R$^{50}$))N(R$^{50}$)$_2$, —OC(O)R$^{50}$, —C(O)R$^{50}$, —C(O)OR$^{50}$, —C(O)N(R$^{50}$)$_2$, —S(O)$_2$R$^{50}$, —S(O)$_2$OR$^{50}$, $C_{3-12}$ carbocycle, and 3- to 12-membered heterocycle, wherein the $C_{3-12}$ carbocycle and 3- to 12-membered heterocycle are optionally substituted with one or more substituents selected from the group consisting of halogen, —CN, —NO$_2$, —OR$^{50}$, —SR$^{50}$, —N(R$^{50}$)$_2$, $C_{1-10}$ alkyl, $C_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and optionally substituted $C_{3-20}$ carbocycle and optionally substituted 3- to 20-membered heterocycle, wherein the $C_{3-20}$ carbocycle and 3- to 20-membered heterocycle optional substituents are one or more substituents independently selected from the group consisting of: halogen, —CN, —NO$_2$, —OR$^{50}$, —SR$^{50}$, —N(R$^{50}$)$_2$, $C_{1-10}$ alkyl, $C_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and wherein R$^{50}$ at each occurrence is independently selected from the group consisting of hydrogen, $C_{1-10}$ alkyl, and $C_{1-10}$ haloalkyl.

In certain embodiments for a compound or salt of Formula (II), $R^6$ is optionally substituted $C_{1-20}$ alkyl. In certain embodiments, $R^6$ is $C_{1-20}$ alkyl. In certain embodiments, $R^6$ is $C_{1-10}$ alkyl. In certain embodiments, $R^6$ is $C_{1-6}$ alkyl. In certain embodiments, $R^6$ is:

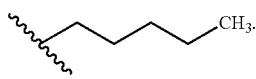 [SMILES: *CCCCC]

In certain embodiments for a compound or salt of Formula (II), $R^7$ and $R^8$ may be independently selected from H and optionally substituted $C_{1-10}$ alkyl. In certain embodiments, $R^7$ and $R^8$ are independently selected from the group consisting of: optionally substituted $C_{1-20}$ alkyl, optionally substituted $C_{2-20}$ alkenyl, optionally substituted $C_{2-20}$ alkynyl, wherein the $C_{1-20}$ alkyl, $C_{2-20}$ alkenyl, and $C_{2-20}$ alkynyl optional substituents are one or more substituents independently selected from the group consisting of: halogen, —CN, —NO$_2$, —OR$^{50}$, —SR$^{50}$, —N(R$^{50}$)$_2$, —NR$^{50}$C(N(R$^{50}$))N(R$^{50}$)$_2$, —OC(O)R$^{50}$, —C(O)R$^{50}$, —C(O)OR$^{50}$, —C(O)N(R$^{50}$)$_2$, —S(O)$_2$R$^{50}$, —S(O)$_2$OR$^{50}$, $C_{3-12}$ carbocycle, and 3- to 12-membered heterocycle, wherein the $C_{3-12}$ carbocycle and 3- to 12-membered heterocycle are optionally substituted with one or more substituents selected from the group consisting of halogen, —CN, —NO$_2$, —OR$^{50}$, —SR$^{50}$, —N(R$^{50}$)$_2$, $C_{1-10}$ alkyl, $C_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and optionally substituted $C_{3-20}$ carbocycle and optionally substituted 3- to 20-membered heterocycle, wherein the $C_{3-20}$ carbocycle and 3- to 20-membered heterocycle optional substituents are one or more substituents independently selected from the group consisting of: halogen, —CN, —NO$_2$, —OR$^{50}$, —SR$^{50}$, —N(R$^{50}$)$_2$, $C_{1-10}$ alkyl, $C_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and wherein R$^{50}$ at each occurrence is independently selected from the group consisting of hydrogen, $C_{1-10}$ alkyl, and $C_{1-10}$ haloalkyl.

In certain embodiments for a compound or salt of Formula (II), $R^7$ and $R^8$ are independently optionally substituted $C_{1-20}$ alkyl, wherein the $C_{1-20}$ alkyl optional substituents are one or more substituents independently selected from the group consisting of: halogen, —CN, —OR$^{50}$, —SR$^{50}$, —N(R$^{50}$)$_2$, —NR$^{50}$C(N(R$^{50}$))N(R$^{50}$)$_2$, —C(O)N(R$^{50}$)$_2$, —S(O)$_2$R$^{50}$, —S(O)$_2$OR$^{50}$, and optionally substituted $C_{3-20}$ carbocycle wherein the $C_{3-20}$ carbocycle optional substituents are one or more substituents independently selected from the group consisting of: halogen, —N(R$^{50}$)$_2$, —C$_{1-10}$ alkyl-N(R$^{50}$)$_2$, and —C$_{1-10}$ alkyl-OR$^{50}$; and wherein R$^{50}$ at each occurrence is independently selected from the group consisting of hydrogen, $C_{1-10}$ alkyl, and $C_{1-10}$ haloalkyl. In certain embodiments, $R^7$ is hydrogen. In certain embodiments, $R^8$ is hydrogen. In certain embodiments, each of $R^7$ and $R^8$ are hydrogen.

In certain embodiments for a compound or salt of Formula (II), is represented by the

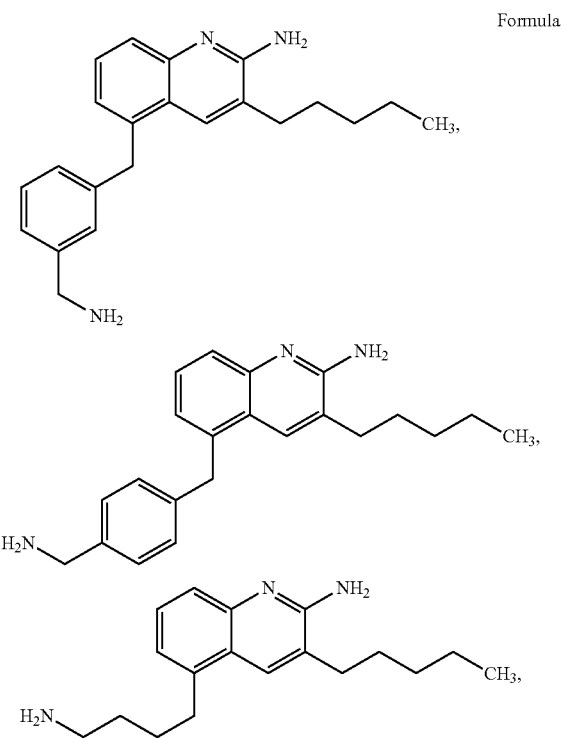

Formula

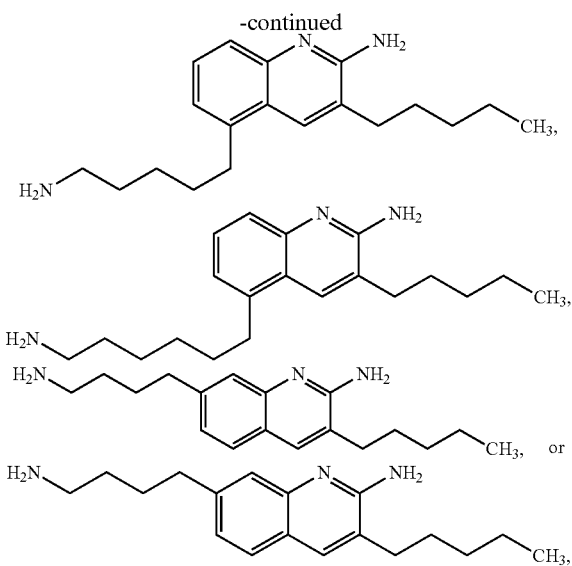

or a salt of any one thereof.

In certain embodiments for a compound or salt of Formula (II), $R^1$, $R^2$, $R^3$, $R^4$, and $R^5$ are independently selected from the group consisting of: H, halogen, —$OR^{10}$, —$N(R^{10})_2$, —$SR^{10}$, —CN, —$NO_2$, —$OC(O)R^{10}$, —$C(O)R^{10}$, —$C(O)OR^{10}$, —$C(O)N(R^{10})_2$, —$S(O)_2R^{10}$, —$S(O)_2OR^{10}$, optionally substituted $C_{1-20}$ alkyl, wherein at least one of $R^1$ and $R^3$ is selected from the group consisting of —$OR^{10}$, —$N(R^{10})_2$, —$SR^{10}$, —$OC(O)R^{10}$, —$C(O)R^{10}$, —$C(O)OR^{10}$, —$C(O)N(R^{10})_2$, —$S(O)_2R^{10}$, —$S(O)_2OR^{10}$, optionally substituted $C_{1-20}$ alkyl, optionally substituted $C_{2-20}$ alkenyl, optionally substituted $C_{2-20}$ alkynyl, optionally substituted $C_{3-20}$ carbocycle, and optionally substituted 3- to 20-membered heterocycle; $R^6$ is selected from the group consisting of —$OR^{11}$, —$N(R^{11})_2$, —$SR^{11}$, optionally substituted $C_{1-20}$ alkyl; $R^7$ and $R^8$ are independently selected from H, optionally substituted $C_{1-10}$ alkyl, optionally substituted $C_{3-12}$ carbocycle and optionally substituted 3- to 12-membered heterocycle; $R^{10}$ is independently selected at each occurrence from the group consisting of H, optionally substituted $C_{1-10}$ alkyl, optionally substituted $C_{3-12}$ carbocycle and optionally substituted 3- to 12-membered heterocycle; and R" is independently selected at each occurrence from the group consisting of optionally substituted $C_{1-10}$ alkyl.

In certain embodiments for a compound or salt of Formula (II), $R^1$, $R^2$, $R^3$, $R^4$, and $R^5$ are independently selected from the group consisting of: H, halogen, —$OR^{10}$, —$N(R^{10})_2$, —$SR^{10}$, optionally substituted $C_{1-20}$ alkyl, wherein at least one of $R^1$ and $R^3$ is selected from the group consisting of —$OR^{10}$, —$N(R^{10})_2$, —$SR^{10}$, —$OC(O)R^{10}$, —$C(O)R^{10}$, —$C(O)OR^{10}$, —$C(O)N(R^{10})_2$, —$S(O)_2R^{10}$, —$S(O)_2OR^{10}$, optionally substituted $C_{1-20}$ alkyl, optionally substituted $C_{3-20}$ carbocycle, and optionally substituted 3- to 20-membered heterocycle; $R^6$ is optionally substituted $C_{1-20}$ alkyl; $R^7$ and $R^8$ are independently selected from H, and optionally substituted $C_{1-10}$ alkyl; $R^{10}$ is independently selected at each occurrence from the group consisting of H, optionally substituted $C_{1-10}$ alkyl, and optionally substituted $C_{3-12}$ carbocycle; and R" is independently selected at each occurrence from the group consisting of optionally substituted $C_{1-10}$ alkyl.

In certain embodiments for a compound or salt of Formula (II), $R^1$, $R^2$, $R^3$, $R^4$, and $R^5$ are independently hydrogen or optionally substituted $C_{1-20}$ alkyl, wherein at least one of $R^1$ and $R^3$ is selected from the group consisting of —$OR^{10}$, —$N(R^{10})_2$, —$SR^{10}$, and optionally substituted $C_{1-20}$ alkyl; $R^6$ is $C_{1-20}$ alkyl; $R^7$ and $R^8$ are both H; $R^{10}$ is independently selected at each occurrence from the group consisting of H, and optionally substituted $C_{1-10}$ alkyl; and $R^{11}$ is independently selected at each occurrence from the group consisting of optionally substituted $C_{1-10}$ alkyl.

In certain embodiments for a compound or salt of Formula (II), $R^1$ is hydrogen or optionally substituted $C_{1-20}$ alkyl, wherein the $C_{1-20}$ alkyl is substituted by a $C_{3-12}$ carbocycle, wherein the $C_{3-12}$ carbocycle is substituted with one or more substituents selected from the group consisting of $C_{1-10}$ alkyl and —$C_{1-10}$ alkyl-$N(R^{50})_2$; $R^3$ is hydrogen or $C_{1-20}$ alkyl, wherein the $C_{1-20}$ alkyl is substituted by a $C_{3-12}$ carbocycle, wherein the $C_{3-12}$ carbocycle is substituted with one or more substituents selected from the group consisting of $C_{1-10}$ alkyl and —$C_{1-10}$ alkyl-$N(R^{50})_2$, $R^2$, R, and $R^5$ are independently hydrogen or optionally substituted $C_{1-20}$ alkyl, wherein at least one of $R^1$ and $R^3$ is selected from optionally substituted $C_{1-20}$ alkyl; wherein $R^{50}$ at each occurrence is independently selected from the group consisting of hydrogen, $C_{1-10}$ alkyl, and $C_{1-10}$ haloalkyl; $R^6$ is optionally substituted $C_{1-20}$ alkyl; $R^7$ is hydrogen or optionally substituted $C_{1-20}$ alkyl; $R^8$ is hydrogen or optionally substituted $C_{1-20}$ alkyl; $R^{10}$ is independently selected at each occurrence from the group consisting of H, and optionally substituted $C_{1-10}$ alkyl; and $R^{11}$ is independently selected at each occurrence from the group consisting of optionally substituted $C_{1-10}$ alkyl.

In certain embodiments for a compound or salt of Formula (II), $R^1$ is hydrogen or $C_{1-20}$ alkyl, wherein the $C_{1-20}$ alkyl is substituted by a $C_{3-12}$ carbocycle, wherein the $C_{3-12}$ carbocycle, e.g., phenyl, is substituted with one or more substituents selected from the group consisting of $C_{1-10}$ alkyl and —$C_{1-10}$ alkyl-$N(R^{50})_2$; $R^3$ is hydrogen; $R^2$, $R^4$, and $R^5$ are independently hydrogen or optionally substituted $C_{1-20}$ alkyl; $R^{50}$ at each occurrence is independently selected from the group consisting of hydrogen, $C_{1-10}$ alkyl, and $C_{1-10}$ haloalkyl; $R^6$ is optionally substituted $C_{1-10}$ alkyl, wherein the $C_{1-10}$ alkyl optional substituents are one or more substituents independently selected from the group consisting of: halogen, —$N(R^{50})_2$, and —$NR^{50}C(N(R^{50}))N(R^{50})_2$; $R^7$ is hydrogen or $C_{1-20}$ alkyl, e.g., methyl; $R^8$ is hydrogen or $C_{1-20}$ alkyl, e.g., methyl; $R^{10}$ is independently selected at each occurrence from the group consisting of H, and optionally substituted $C_{1-10}$ alkyl; and $R^{11}$ is independently selected at each occurrence from the group consisting of optionally substituted $C_{1-10}$ alkyl.

In certain embodiments for a compound or salt of Formula (II), $R^1$ is $C_{1-20}$ alkyl substituted by one or more of substituents selected from the group consisting of halogen, —CN, —$NO_2$, —$OR^{50}$, —$SR^{50}$, —$N(R^{50})_2$, —$NR^{50}C(N(R^{50}))N(R^{50})_2$, —$OC(O)R^{50}$, —$C(O)R^{50}$, —$C(O)OR^{30}$, —$C(O)N(R^{50})_2$, —$S(O)_2R^{50}$, —$S(O)_2OR^{50}$; $R^3$ is hydrogen; $R^2$, $R^4$, and $R^5$ are independently hydrogen or optionally substituted $C_{1-20}$ alkyl; $R^{50}$ at each occurrence is independently selected from the group consisting of hydrogen, $C_{1-10}$ alkyl, and $C_{1-10}$ haloalkyl; $R^6$ is $C_{1-10}$ alkyl; $R^{10}$ is independently selected at each occurrence from the group consisting of H, and $C_{1-10}$ alkyl; and $R^{11}$ is independently at each occurrence $C_{1-10}$ alkyl.

In certain embodiments for a compound or salt of Formula (II), $R^1$ is $C_{1-10}$ alkyl, e.g., $C_{1-5}$ alkyl, substituted by one or more of substituents selected from the group consisting of halogen, —CN, —$NO_2$, —$OR^{50}$, —$SR^{50}$, and —$N(R^{50})_2$; $R^3$ is hydrogen; $R^2$, $R^4$, and $R^5$ are independently hydrogen or optionally substituted $C_{1-20}$ alkyl; $R^{50}$ at each occurrence is independently selected from the group consisting of hydrogen, $C_{1-10}$ alkyl, and $C_{1-10}$ haloalkyl; $R^6$ is $C_{1-10}$ alkyl, e.g., $C_{1-5}$ alkyl; $R^{10}$ is independently selected at each occurrence from the group consisting of H, and $C_{1-10}$ alkyl; and $R^{11}$ is independently at each occurrence is $C_{1-10}$ alkyl.

In certain embodiments for a compound or salt of Formula (II), $R^1$ is hydrogen; $R^3$ is $C_{1-20}$ alkyl, wherein the alkyl is substituted by a phenyl, wherein the phenyl is substituted with one or more substituents selected from the group consisting of $C_{1-10}$ alkyl and —$C_{1-10}$ alkyl-$N(R^{50})_2$; $R^2$, $R^4$, and $R^5$ are independently hydrogen or optionally substituted $C_{1-20}$ alkyl; wherein $R^{50}$ at each occurrence is independently selected from the group consisting of hydrogen, $C_{1-10}$ alkyl, and $C_{1-10}$ haloalkyl; $R^6$ is $C_{1-10}$ alkyl; $R^{10}$ is independently selected at each occurrence from the group consisting of H, and $C_{1-10}$ alkyl; and $R^{11}$ is independently selected at each occurrence $C_{1-10}$ alkyl.

In certain embodiments for a compound or salt of Formula (II), $R^1$ is hydrogen; $R^3$ is $C_{1-20}$ alkyl, wherein the alkyl is substituted by a pyridyl, wherein the pyridyl is substituted with one or more substituents selected from the group consisting of $C_{1-10}$ alkyl and —$C_{1-10}$ alkyl-$N(R^{50})_2$; $R^2$, $R^4$, and $R^5$ are independently hydrogen or optionally substituted $C_{1-20}$ alkyl; wherein $R^{50}$ at each occurrence is independently selected from the group consisting of hydrogen, $C_{1-10}$ alkyl, and $C_{1-10}$ haloalkyl; $R^6$ is $C_{1-10}$ alkyl; $R^{10}$ is independently selected at each occurrence from the group consisting of H, and $C_{1-10}$ alkyl; and $R^{11}$ is independently at each occurrence $C_{1-10}$ alkyl.

In certain embodiments for a compound or salt of Formula (II), $R^3$ is $C_{1-10}$ alkyl, e.g., $C_{1-5}$ alkyl, substituted by one or more of substituents selected from the group consisting of halogen, —CN, —$NO_2$, —$OR^{50}$, —$SR^{50}$, and —$N(R^{50})_2$; $R^1$ is hydrogen; $R^2$, $R^4$, and $R^5$ are independently hydrogen or optionally substituted $C_{1-20}$ alkyl; $R^{50}$ at each occurrence is independently selected from the group consisting of hydrogen, $C_{1-10}$ alkyl, and $C_{1-10}$ haloalkyl; $R^6$ is $C_{1-10}$ alkyl, e.g., $C_{1-5}$ alkyl; $R^{10}$ is independently selected at each occurrence from the group consisting of H, and $C_{1-10}$ alkyl; and $R^{11}$ is independently at each occurrence is $C_{1-10}$ alkyl.

In certain embodiments, a compound is represented by Formula (III):

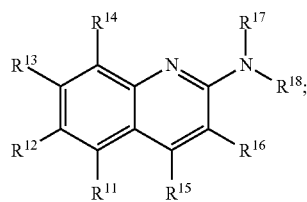

(III)

or a salt thereof, wherein:
$R^{11}$, $R^{12}$, $R^{13}$, $R^{14}$, and $R^{15}$ are independently selected from the group consisting of: H, halogen, —$OR^{20}$, —$N(R^{20})_2$, —$SR^{20}$, —CN, —$NO_2$, —OC(O)$R^{20}$, —C(O)$R^{20}$, —C(O)$OR^{20}$, —C(O)$NR^{20}$, —$S(O)_2R^{20}$, —$S(O)_2OR^{20}$, optionally substituted $C_{3-20}$ carbocycle, optionally substituted $C_{1-20}$ alkyl, optionally substituted $C_{2-20}$ alkenyl, optionally substituted $C_{2-20}$ alkynyl, and optionally substituted 3- to 20-membered heterocycle, $R^{16}$ is selected from the group consisting of optionally substituted $C_{1-20}$ alkyl, —$OR^{21}$, —$N(R^{21})_2$, —$SR^{21}$, optionally substituted $C_{2-20}$ alkenyl, and optionally substituted $C_{2-20}$ alkynyl;

$R^{17}$ and $R^{18}$ are independently selected from the group consisting of H, optionally substituted $C_{1-10}$ alkyl, optionally substituted $C_{2-10}$ alkenyl, optionally substituted $C_{2-10}$ alkynyl, optionally substituted $C_{3-12}$ carbocycle and optionally substituted 3- to 12-membered heterocycle;

$R^{20}$ is independently selected at each occurrence from the group consisting of H, optionally substituted $C_{1-10}$ alkyl, optionally substituted $C_{2-10}$ alkenyl, optionally substituted $C_{2-10}$ alkynyl, optionally substituted 3- to 12-membered heterocycle and optionally substituted $C_{3-12}$ carbocycle; and $R^{21}$ is independently selected at each occurrence from the group consisting of optionally substituted $C_{1-10}$ alkyl, optionally substituted $C_{2-10}$ alkenyl, and optionally substituted $C_{2-10}$ alkynyl.

In certain embodiments, a compound is represented by Formula (III):

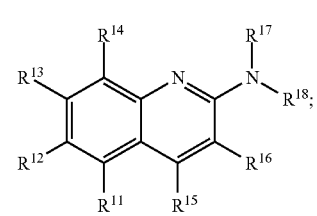

(III)

or a salt thereof, wherein:
$R^{11}$, $R^{12}$, $R^{13}$, $R^{14}$, and $R^{15}$ are independently selected from the group consisting of: H, halogen, —$OR^{20}$, —$N(R^{20})_2$, —$SR^{20}$, —CN, —$NO_2$, —OC(O)$R^{20}$, —C(O)$R^{20}$, —C(O)$OR^{20}$, —C(O)$NR^{20}$, —$S(O)_2R^{20}$, —$S(O)_2OR^{20}$, optionally substituted $C_{3-20}$ carbocycle, optionally substituted $C_{1-20}$ alkyl, optionally substituted $C_{2-20}$ alkenyl, optionally substituted $C_{2-20}$ alkynyl, and optionally substituted 3- to 20-membered heterocycle,
wherein at least one of $R^{11}$, $R^{12}$, $R^{13}$, and $R^{14}$ is selected from the group consisting of —$OR^{20}$, —$NR^{20}_2$, —OC(O)$R^{20}$, —C(O)$R^{20}$, —C(O)$OR^{20}$, —C(O)$NR^{20}$, —$S(O)_2R^{20}$, —$S(O)_2OR^{20}$, optionally substituted $C_{3-20}$ carbocycle, optionally substituted $C_{1-20}$ alkyl, optionally substituted $C_{2-20}$ alkenyl, optionally substituted $C_{2-20}$ alkynyl, and optionally substituted 3- to 20-membered heterocycle;

$R^{16}$ is selected from the group consisting of optionally substituted $C_{1-20}$ alkyl, —$OR^{21}$, —$N(R^{21})_2$, —$SR^{21}$, optionally substituted $C_{2-20}$ alkenyl, and optionally substituted $C_{2-20}$ alkynyl;

$R^{17}$ and $R^{18}$ are independently selected from the group consisting of H, optionally substituted $C_{1-10}$ alkyl, optionally substituted $C_{2-10}$ alkenyl, optionally substituted $C_{2-10}$ alkynyl, optionally substituted $C_{3-12}$ carbocycle and optionally substituted 3- to 12-membered heterocycle;

$R^{20}$ is independently selected at each occurrence from the group consisting of H, optionally substituted $C_{1-10}$ alkyl, optionally substituted $C_{2-10}$ alkenyl, optionally substituted $C_{2-10}$ alkynyl, optionally substituted 3- to 12-membered heterocycle and optionally substituted $C_{3-12}$ carbocycle; and $R^{21}$ is independently selected at each occurrence from the group consisting of optionally substituted $C_{1-10}$ alkyl, optionally substituted $C_{2-10}$ alkenyl, and optionally substituted $C_{2-10}$ alkynyl.

In certain embodiments for a compound or salt of Formula (III), at least one of $R^{11}$, $R^{12}$, $R^{13}$, and $R^{14}$ may be selected from the group consisting of —$OR^{20}$, —$N(R^{20})_2$, —$OC(O)R^{20}$, —$C(O)R^{20}$, —$C(O)R^{20}$, —$C(O)N(R^{20})_2$, —$S(O)R^{20}$, —$S(O)R^{20}$, optionally substituted $C_{1-20}$ alkyl, optionally substituted $C_{2-20}$ alkenyl, and optionally substituted $C_{2-20}$ alkynyl. In certain embodiments, at least one of $R^{11}$, $R^{12}$, $R^{13}$, and $R^{14}$ is selected from the group consisting of optionally substituted $C_{1-20}$ alkyl, optionally substituted $C_{2-20}$ alkenyl, and optionally substituted $C_{2-20}$ alkynyl. In certain embodiments, at least one of $R^{11}$, $R^{12}$, $R^{13}$, and $R^{14}$ is optionally substituted $C_{1-20}$ alkyl. In certain embodiments, $R^{11}$ is optionally substituted $C_{1-10}$ alkyl. In certain embodiments, $R^{11}$ is optionally substituted $C_{1-5}$ alkyl. In certain embodiments, for a compound or salt of Formula (III), $R^{11}$ is selected from the group consisting of: optionally substituted $C_{1-20}$ alkyl, optionally substituted $C_{2-20}$ alkenyl, optionally substituted $C_{2-20}$ alkynyl, wherein the $C_{1-20}$ alkyl, $C_{2-20}$ alkenyl, and $C_{2-20}$ alkynyl optional substituents are one or more substituents independently selected from the group consisting of: halogen, —CN, —$NO_2$, —$OR^{60}$, —$SR^{60}$, —$N(R^{60})_2$, —$NR^{60}C(N(R^{60}))N(R^{60})_2$, —$OC(O)R^{60}$, —$C(O)R^{60}$, —$C(O)OR^{60}$, —$C(O)N(R^{60})_2$, —$S(O)_2R^{60}$, —$S(O)_2OR^{60}$, $C_{3-12}$ carbocycle, and 3- to 12-membered heterocycle, wherein the $C_{3-12}$ carbocycle and 3- to 12-membered heterocycle are optionally substituted with one or more substituents selected from the group consisting of halogen, —CN, —$NO_2$, —$OR^{60}$, —$SR^{60}$, —$N(R^{60})_2$, $C_{1-10}$ alkyl, $C_{1-10}$ haloalkyl, —$C_{1-10}$ alkyl-$N(R^{60})_2$, —$C_{1-10}$ alkyl-$OR^{60}$, and —$C_{1-10}$ alkyl-$C(O)N(R^{60})_2$; and optionally substituted $C_{3-20}$ carbocycle and optionally substituted 3- to 20-membered heterocycle, wherein the $C_{3-12}$ carbocycle and 3- to 12-membered heterocycle optional substituents are one or more substituents independently selected from the group consisting of halogen, —CN, —$NO_2$, —$OR^{60}$, —$SR^{60}$, —$N(R^{60})_2$, $C_{1-10}$ alkyl, $C_{1-10}$ haloalkyl, —$C_{1-10}$ alkyl-$N(R^{60})_2$, —$C_{1-10}$ alkyl-$OR^{60}$, and —$C_{1-10}$ alkyl-$C(O)N(R^{60})_2$; and wherein $R^{60}$ at each occurrence is independently selected from the group consisting of hydrogen, $C_{1-10}$ alkyl, and $C_{1-10}$ haloalkyl.

In certain embodiments, for a compound or salt of Formula (III), $R^{11}$ is optionally substituted $C_{1-20}$ alkyl, wherein the $C_{1-20}$ alkyl optional substituents are one or more substituents independently selected from the group consisting of: halogen, $C_{3-12}$ carbocycle, and 3- to 12-membered heterocycle, wherein the $C_{3-12}$ carbocycle and 3- to 12-membered heterocycle are optionally substituted with one or more substituents selected from the group consisting of halogen, —CN, —$NO_2$, —$OR^{60}$, —$SR^{60}$, —$N(R^{60})_2$, $C_{1-10}$ alkyl, $C_{1-10}$ haloalkyl, —$C_{1-10}$ alkyl-$N(R^{60})_2$, —$C_{1-10}$ alkyl-$OR^{60}$, and —$C_{1-10}$ alkyl-$C(O)N(R^{60})_2$; and wherein $R^{60}$ at each occurrence is independently selected from the group consisting of hydrogen, $C_{1-10}$ alkyl, and $C_{1-10}$ haloalkyl.

In certain embodiments, for a compound or salt of Formula (III), $R^{11}$ is optionally substituted $C_{1-20}$ alkyl, wherein the $C_{1-20}$ alkyl is substituted by a $C_{3-12}$ carbocycle, wherein the $C_{3-12}$ carbocycle is optionally substituted with one or more substituents selected from the group consisting of halogen, —CN, —$NO_2$, —$OR^{60}$, —$SR^{60}$, —$N(R^{60})_2$, $C_{1-10}$ alkyl, $C_{1-10}$ haloalkyl, —$C_{1-10}$ alkyl-$N(R^{60})_2$, —$C_{1-10}$ alkyl-$OR^{60}$, and —$C_{1-10}$ alkyl-$C(O)N(R^{60})_2$; and wherein $R^{60}$ at each occurrence is independently selected from the group consisting of hydrogen, $C_{1-10}$ alkyl, and $C_{1-10}$ haloalkyl.

In certain embodiments, for a compound or salt of Formula (III), $R^{11}$ is optionally substituted $C_{1-20}$ alkyl, wherein the $C_{1-20}$ alkyl is substituted by a $C_{3-12}$ carbocycle, wherein the $C_{3-12}$ carbocycle is optionally substituted with one or more substituents selected from the group consisting of $C_{1-10}$ alkyl, $C_{1-10}$ haloalkyl, —$C_{1-10}$ alkyl-$N(R^{60})_2$, and —$C_{1-10}$ alkyl-$C(O)N(R^{60})_2$; and wherein $R^{60}$ at each occurrence is independently selected from the group consisting of hydrogen, $C_{1-10}$ alkyl, and $C_{1-10}$ haloalkyl.

In certain embodiments, for a compound or salt of Formula (III), $R^{11}$ is $C_{1-20}$ alkyl, wherein the $C_{1-20}$ alkyl is substituted by a $C_{3-12}$ carbocycle, wherein the $C_{3-12}$ carbocycle is substituted with one or more substituents selected from the group consisting of $C_{1-10}$ alkyl and —$C_{1-10}$ alkyl-$N(R^{60})_2$, and wherein $R^{60}$ at each occurrence is independently selected from the group consisting of hydrogen, $C_{1-10}$ alkyl, and $C_{1-10}$ haloalkyl.

In certain embodiments, for a compound or salt of Formula (III), $R^{11}$ is $C_{1-20}$ alkyl, wherein the $C_{1-20}$ alkyl is substituted by a $C_{3-12}$ carbocycle, wherein the $C_{3-12}$ carbocycle is substituted with one or more substituents selected from the group consisting of $C_{1-10}$ alkyl and —$C_{1-10}$ alkyl-$N(R^{60})_2$, and wherein $R^{60}$ at each occurrence is independently selected from the group consisting of hydrogen, $C_{1-10}$ alkyl, and $C_{1-10}$ haloalkyl.

In certain embodiments, for a compound or salt of Formula (III), $R^{11}$ is substituted with —$N(R^{60})_2$. In certain embodiments, $R^{11}$ is selected from:

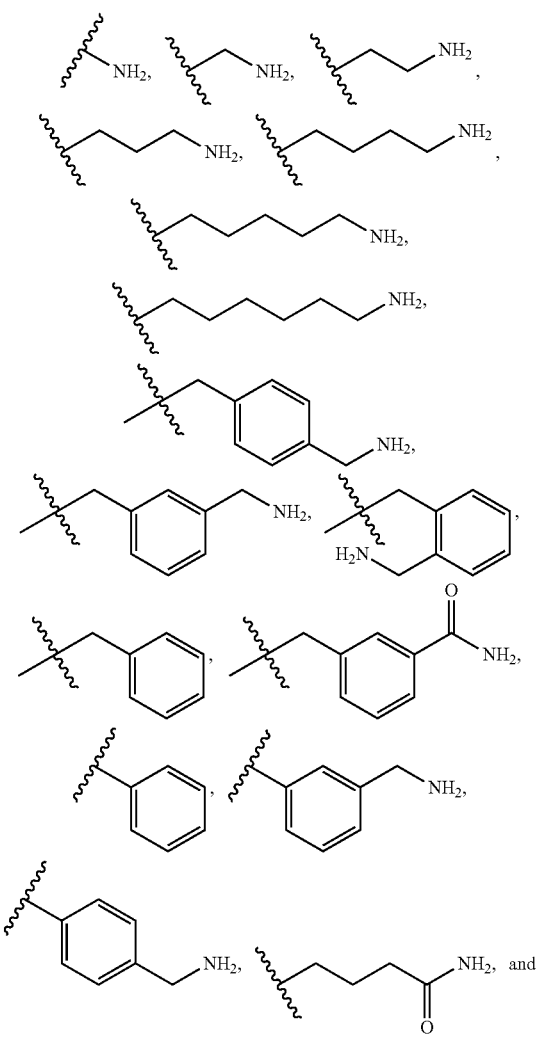

-continued

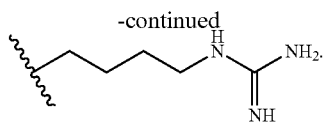

In certain embodiments, for a compound or salt of Formula (III) $R^{11}$ is selected from:

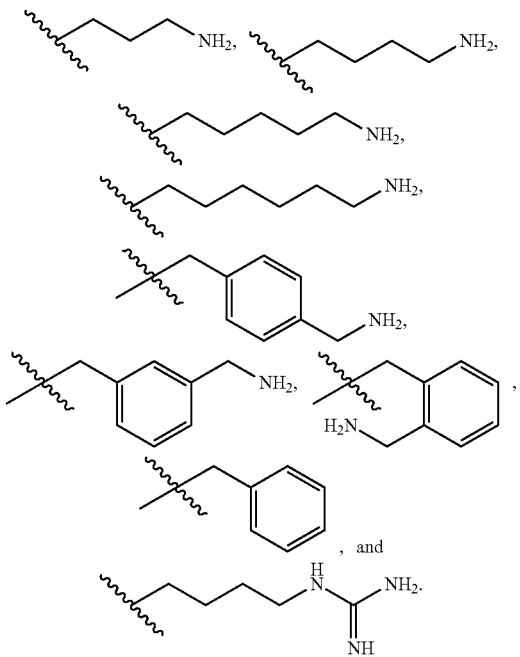

In certain embodiments, for a compound or salt of Formula (III), $R^{13}$ may be optionally substituted $C_{1-10}$ alkyl. In certain embodiments, R is optionally substituted $C_{1-5}$ alkyl. In certain embodiments, for a compound or salt of Formula (III), $R^{13}$ is selected from the group consisting of: optionally substituted $C_{1-20}$ alkyl, optionally substituted $C_{2-20}$ alkenyl, optionally substituted $C_{2-20}$ alkynyl, wherein the $C_{1-20}$ alkyl, $C_{2-20}$ alkenyl, and $C_{2-20}$ alkynyl optional substituents are one or more substituents independently selected from the group consisting of: halogen, —CN, —NO$_2$, —OR$^{60}$, —SR$^{60}$, —N(R$^{60}$)$_2$, —NR$^{60}$C(N(R$^{60}$))N(R$^{60}$)$_2$, —OC(O)R$^{60}$, —C(O)R$^{60}$, —C(O)OR$^{60}$, —C(O)N(R$^{60}$)$_2$, —S(O)$_2$R$^{60}$, —S(O)$_2$OR$^{60}$, $C_{3-12}$ carbocycle, and 3- to 12-membered heterocycle, wherein the $C_{3-12}$ carbocycle and the 3- to 12-membered heterocycle are optionally substituted with one or more substituents selected from the group consisting of halogen, —CN, —NO$_2$, —OR$^{60}$, —SR$^{60}$, —N(R$^{60}$)$_2$, $C_{1-10}$ alkyl, $C_{1-10}$ haloalkyl, —$C_{1-10}$ alkyl-N(R$^{60}$)$_2$, —$C_{1-10}$ alkyl-O R$^{60}$, and —$C_{1-10}$ alkyl-C(O)N(R$^{60}$)$_2$; and optionally substituted $C_{3-20}$ carbocycle and optionally substituted 3- to 20-membered heterocycle, wherein the $C_{3-20}$ carbocycle and 3- to 20-membered heterocycle optional substituents are one or more substituents independently selected from the group consisting of: halogen, —CN, —NO$_2$, —OR$^{60}$, —SR$^{60}$, —N(R$^{60}$)$_2$, $C_{1-10}$ alkyl, $C_{1-10}$ haloalkyl, —$C_{1-10}$ alkyl-N(R$^{60}$)$_2$, —$C_{1-10}$ alkyl-OR$^{60}$, and —$C_{1-10}$ alkyl-C(O)N(R$^{60}$)$_2$; and wherein R$^{60}$ at each occurrence is independently selected from the group consisting of hydrogen, $C_1$, alkyl, and $C_{1-10}$ haloalkyl.

In certain embodiments, for a compound or salt of Formula (III), $R^{13}$ is optionally substituted $C_{1-20}$ alkyl, wherein $C_{1-20}$ alkyl optional substituents are one or more substituents independently selected from the group consisting of: halogen, $C_{3-12}$ carbocycle, and 3- to 12-membered heterocycle, wherein the $C_{3-12}$ carbocycle and the 3- to 12-membered heterocycle are optionally substituted with one or more substituents selected from the group consisting of halogen, —CN, —NO$_2$, —OR$^{60}$, —SR$^{11}$, —N(R$^{60}$)$_2$, $C_{1-10}$ alkyl, $C_{1-10}$ haloalkyl, —$C_{1-10}$ alkyl-N(R$^{60}$)$_2$, —$C_{1-10}$ alkyl-OR$^{60}$, and —$C_{1-10}$ alkyl-C(O)N(R$^{60}$)$_2$; and wherein R$^{60}$ at each occurrence is independently selected from the group consisting of hydrogen, $C_{1-10}$ alkyl, and $C_{1-10}$ haloalkyl.

In certain embodiments, for a compound or salt of Formula (III), $R^{13}$ is optionally substituted $C_{1-20}$ alkyl, wherein the $C_{1-20}$ alkyl is substituted by a $C_{3-12}$ carbocycle, wherein the $C_{3-12}$ carbocycle is optionally substituted with one or more substituents selected from the group consisting of halogen, —CN, —NO$_2$, —OR$^{60}$, —SR$^{60}$, —N(R$^{60}$)$_2$, $C_{1-10}$ alkyl, $C_{1-10}$ haloalkyl, —$C_{1-10}$ alkyl-N(R$^{60}$)$_2$, —$C_{1-10}$ alkyl-OR$^{60}$, and —$C_{1-10}$ alkyl-C(O)N(R$^{60}$)$_2$; and wherein R$^{60}$ at each occurrence is independently selected from the group consisting of hydrogen, $C_{1-10}$ alkyl, and $C_{1-10}$ haloalkyl.

In certain embodiments, for a compound or salt of Formula (III), $R^{13}$ is optionally substituted $C_{1-20}$ alkyl, wherein the $C_{1-20}$ alkyl is substituted by a $C_{3-12}$ carbocycle, wherein the $C_{3-12}$ carbocycle is optionally substituted with one or more substituents selected from the group consisting of $C_{1-10}$ alkyl, $C_{1-10}$ haloalkyl, —$C_{1-10}$ alkyl-N(R$^{60}$)$_2$, and —$C_{1-10}$ alkyl-C(O)N(R$^{60}$)$_2$; and wherein R$^{60}$ at each occurrence is independently selected from the group consisting of hydrogen, $C_{1-10}$ alkyl, and $C_{1-10}$ haloalkyl.

In certain embodiments, for a compound or salt of Formula (III), $R^{12}$ is $C_{1-20}$ alkyl, wherein the $C_{1-20}$ alkyl is substituted by a $C_{3-12}$ carbocycle, wherein the $C_{3-12}$ carbocycle is substituted with one or more substituents selected from the group consisting of $C_{1-10}$ alkyl and —$C_{1-10}$ alkyl-N(R$^{60}$)$_2$, and wherein R$^{60}$ at each occurrence is independently selected from the group consisting of hydrogen, $C_{1-10}$ alkyl, and $C_{1-10}$ haloalkyl. In certain embodiments, $R^{13}$ is $C_{1-20}$ alkyl, wherein the $C_{1-20}$ alkyl is substituted by a $C_{3-12}$ carbocycle, wherein the $C_{3-12}$ carbocycle is substituted with one or more substituents selected from the group consisting of $C_{1-10}$ alkyl and —$C_{1-10}$ alkyl-N(R$^{60}$)$_2$, and wherein R$^{60}$ at each occurrence is independently selected from the group consisting of hydrogen, $C_{1-10}$ alkyl, and $C_{1-10}$ haloalkyl.

In certain embodiments, for a compound or salt of Formula (III), $R^{13}$ is $C_{1-20}$ alkyl, wherein the $C_{1-20}$ alkyl is substituted by a $C_{3-12}$ carbocycle, wherein the $C_{3-12}$ carbocycle is substituted with one or more substituents selected from the group consisting of $C_{1-10}$ alkyl and —$C_{1-10}$ alkyl-N(R$^{60}$)$_2$, and wherein R$^{60}$ at each occurrence is independently selected from the group consisting of hydrogen, $C_{1-10}$ alkyl, and $C_{1-10}$ haloalkyl. In certain embodiments, $R^{13}$ is $C_{1-20}$ alkyl, wherein the $C_{1-20}$ alkyl is substituted by a $C_{3-12}$ carbocycle, wherein the $C_{3-12}$ carbocycle is substituted with one or more substituents selected from the group consisting of $C_{1-10}$ alkyl and —$C_{1-10}$ alkyl-N(R$^{60}$)$_2$, and wherein R$^{60}$ at each occurrence is independently selected from the group consisting of hydrogen, $C_{1-10}$ alkyl, and $C_{1-10}$ haloalkyl.

In certain embodiments, for a compound or salt of Formula (III), $R^1$ is $C_{1-20}$ alkyl, wherein the $C_{1-20}$ alkyl is substituted by a $C_{3-12}$ carbocycle, wherein the $C_{3-12}$ carbocycle is substituted with one or more substituents selected from the group consisting of $C_{1-10}$ alkyl and —$C_{1-10}$ alkyl-N(R$^{60}$)$_2$, and wherein R$^{60}$ at each occurrence is independently selected from the group consisting of hydrogen, $C_{1-10}$ alkyl, and $C_{1-10}$ haloalkyl. In certain embodiments, $R^{13}$ is $C_{1-20}$ alkyl, wherein the $C_{1-20}$ alkyl is substituted by a $C_{3-12}$ carbocycle, wherein the $C_{3-2}$ carbocycle is substituted with one or more substituents selected from the group consisting of $C_{1-10}$ alkyl and —$C_{1-10}$ alkyl-$N(R^{60})_2$, and wherein $R^{60}$ at each occurrence is independently selected from the group consisting of hydrogen, $C_{1-10}$ alkyl, and $C_{1-10}$ haloalkyl.

In certain embodiments, for a compound or salt of Formula (III), one of $R^{11}$, $R^{12}$, $R^{13}$, and $R^{14}$ is substituted with —$N(R^{60})_2$. In certain embodiments, one of $R^{11}$, $R^{12}$, $R^{13}$, and $R^{14}$ is selected from:

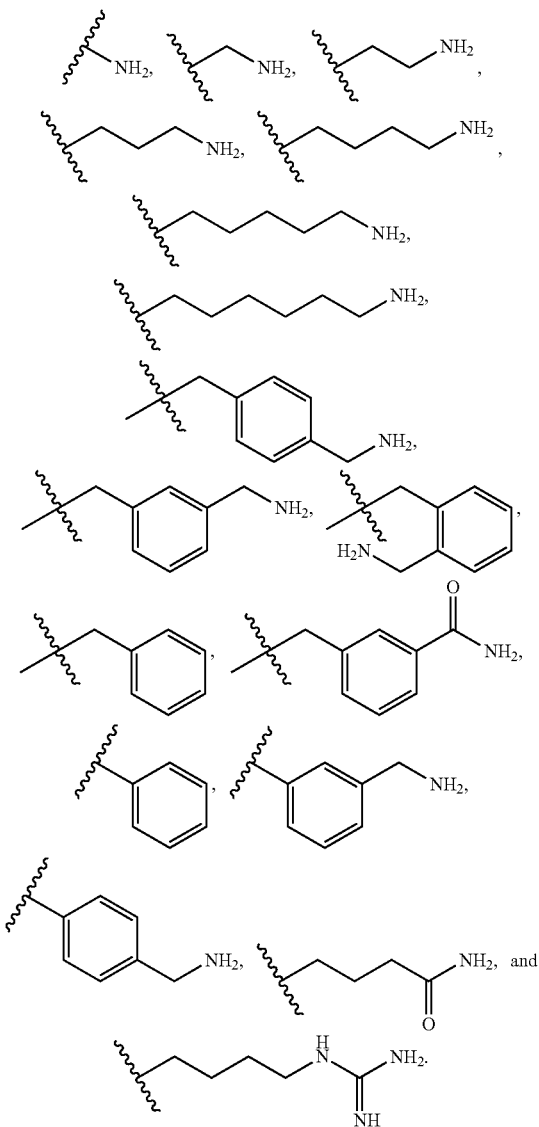

In certain embodiments, for a compound or salt of Formula (III), one of $R^{11}$, $R^{12}$, $R^{13}$ and $R^{14}$ is selected from:

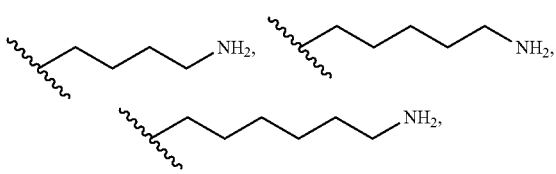

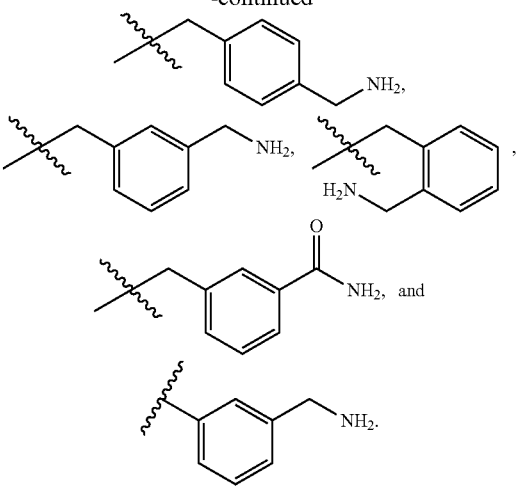

In certain embodiments, for a compound or salt of Formula (III), one of $R^{11}$, $R^{12}$, $R^{13}$, and $R^{14}$ is selected from H, halogen, and —CN. In certain embodiments, $R^{11}$ is hydrogen. In certain embodiments, $R^{11}$ is halogen, wherein halogen is selected from fluorine, chloride, and bromine. In certain embodiments, $R^{11}$ is —CN.

In certain embodiments, for a compound or salt of Formula (III), $R^{12}$ is hydrogen. In certain embodiments, $R^{12}$ is halogen, wherein halogen is selected from fluorine, chloride, and bromine. In certain embodiments, $R^{12}$ is —CN. In certain embodiments, $R^{13}$ is hydrogen. In certain embodiments, $R^{13}$ is halogen, wherein halogen is selected from fluorine, chloride, and bromine. In certain embodiments, $R^{13}$ is —CN. In certain embodiments, $R^{14}$ is hydrogen. In certain embodiments, $R^{14}$ is halogen, wherein halogen is selected from fluorine, chloride, and bromine. In certain embodiments, $R^{14}$ is —CN.

In certain embodiments, for a compound or salt of Formula (III), $R^{12}$, $R^{14}$, and $R^{15}$ are independently selected from the group consisting of: H, halogen, —$OR^{20}$, —$N(R^{20})_2$, —$SR^{20}$, —CN, —$NO_2$, —$OC(O)R^{20}$, —$C(O)R^{20}$, —$C(O)OR^{20}$, —$C(O)N(R^{20})_2$, —$S(O)_2R^{20}$, —$S(O)_2OR^{20}$, and optionally substituted $C_{1-20}$ alkyl. In certain embodiments, $R^{12}$, $R^{14}$, and $R^{15}$ are independently selected from the group consisting of: H, halogen, —$OR^{20}$, —$N(R^{20})_2$, —$SR^{20}$, —CN, —$NO_2$, and optionally substituted $C_{1-20}$ alkyl. In certain embodiments, $R^{12}$, $R^{14}$, and $R^{15}$ are independently selected from the group consisting of: optionally substituted $C_{1-20}$ alkyl, optionally substituted $C_{2-20}$ alkenyl, optionally substituted $C_{2-20}$ alkynyl, wherein the $C_{1-20}$ alkyl, $C_{2-20}$ alkenyl, and $C_{2-20}$ alkynyl optional substituents are one or more substituents independently selected from the group consisting of: halogen, —CN, —$NO_2$, —$OR^{60}$, —$SR^{60}$, —$N(R^{60})_2$, —$NR^{60}C(N(R^{60}))N(R^{60})_2$, —$OC(O)R^{60}$, —$C(O)R^{60}$, —$C(O)OR^{60}$, —$C(O)N(R^{60})_2$, —$S(O)_2R^{60}$, —$S(O)_2OR^{60}$, $C_{3-12}$ carbocycle, and 3- to 12-membered heterocycle, wherein the $C_{3-12}$ carbocycle and 3- to 12-membered heterocycle are optionally substituted with one or more substituents selected from the group consisting of halogen, —CN, —$NO_2$, —$OR^{60}$, —$SR^{60}$, —$N(R^{60})_2$, $C_{1-10}$ alkyl, $C_{1-10}$ haloalkyl, —$C_{1-10}$ alkyl-$N(R^{60})_2$, —$C_{1-10}$ alkyl-$OR^{60}$, and —$C_{1-10}$ alkyl-$C(O)N(R^{60})_2$; and optionally substituted $C_{3-20}$ carbocycle and optionally substituted 3- to 20-membered heterocycle, wherein the $C_{3-20}$ carbocycle and 3- to 20-membered heterocycle optional substituents are one or more independently selected from the group consisting of: halogen, —CN, —NO$_2$, —OR$^{60}$, —SR$^{60}$, —N(R$^{60}$)$_2$, C$_{1-10}$ alkyl, C$_{1-10}$ haloalkyl, —C$_{1-10}$ alkyl-N(R$^{60}$)$_2$, —C$_{1-10}$ alkyl-OR$^{60}$, and —C$_{1-10}$ alkyl-C(O)N(R$^{60}$)$_2$; and wherein R$^{60}$ at each occurrence is independently selected from the group consisting of hydrogen, C$_{1-10}$ alkyl, and C$_{1-10}$ haloalkyl.

In certain embodiments, for a compound or salt of Formula (III), R$^{12}$, R$^{14}$, and R$^{15}$ may be independently selected from the group consisting of: optionally substituted C$_{1-20}$ alkyl, wherein the C$_{1-20}$ alkyl optional substituents are one or more substituents independently selected from the group consisting of: halogen, —CN, —NO$_2$, —OR$^{60}$, —SR$^{60}$, —N(R$^{60}$)$_2$, —NR$^{60}$C(N(R$^{60}$))N(R$^{60}$)$_2$, —OC(O)R$^{60}$, —C(O)R$^{60}$, —C(O)OR$^{60}$, —C(O)N(R$^{60}$)$_2$, C$_{3-12}$ carbocycle, wherein the C$_{3-12}$ carbocycle is optionally substituted with one or more substituents selected from the group consisting of halogen, C$_{1-10}$ alkyl, C$_{1-10}$ haloalkyl, —C$_{1-10}$ alkyl-N(R$^{60}$)$_2$, —C$_{1-10}$ alkyl-OR$^{60}$, and —C$_{1-10}$ alkyl-C(O)N(R$^{60}$)$_2$; and optionally substituted C$_{3-20}$ carbocycle and optionally substituted 3- to 20-membered heterocycle, wherein the C$_{3-20}$ carbocycle and 3- to 20-membered heterocycle optional substituents are one or more substituents independently selected from the group consisting of: halogen, —N(R$^{60}$)$_2$, C$_{1-10}$ alkyl, C$_{1-10}$ haloalkyl, —C$_{1-10}$ alkyl-N(R$^{60}$)$_2$, —C$_{1-10}$ alkyl-OR$^{60}$, and —C$_{1-10}$ alkyl-C(O)N(R$^{60}$)$_2$; and wherein R$^{60}$ at each occurrence is independently selected from the group consisting of hydrogen, C$_{1-10}$ alkyl, and C$_{1-10}$ haloalkyl.

In certain embodiments, for a compound or salt of Formula (III), R$^{12}$, R$^{14}$, and R$^{15}$ may be independently selected from the group consisting of: optionally substituted C$_{1-20}$ alkyl, wherein C$_{1-20}$ alkyl optional substituents are one or more substituents independently selected from the group consisting of: halogen and C$_{3-12}$ carbocycle, wherein C$_{3-12}$ carbocycle is optionally substituted with one or more substituents selected from the group consisting of halogen, C$_{1-10}$ alkyl, C$_{1-10}$ haloalkyl, —C$_{1-10}$ alkyl-N(R$^{60}$)$_2$, and wherein R$^{60}$ at each occurrence is independently selected from the group consisting of hydrogen, C$_{1-10}$ alkyl, and C$_{1-10}$ haloalkyl.

In certain embodiments, for a compound or salt of Formula (III), R$^{12}$ is C$_{1-20}$ alkyl or hydrogen. In certain embodiments, R$^{12}$ is hydrogen. In certain embodiments, R$^{14}$ is C$_{1-20}$ alkyl or hydrogen. In certain embodiments, R$^{14}$ is hydrogen. In certain embodiments, R$^5$ is C$_{1-20}$ alkyl or hydrogen. In certain embodiments, R$^{15}$ is hydrogen.

In certain embodiments, for a compound or salt of Formula (III), R$^{20}$ may be selected from the group consisting of: optionally substituted C$_{1-20}$ alkyl, optionally substituted C$_{2-20}$ alkenyl, optionally substituted C$_{2-20}$ alkynyl, wherein the C$_{1-20}$ alkyl, C$_{2-20}$ alkenyl, and C$_{2-20}$ alkynyl optional substituents are one or more substituents independently selected from the group consisting of: halogen, —CN, —NO$_2$, —OR$^{60}$, —SR$^{60}$, —N(R$^{60}$)$_2$, —NR$^{60}$C(N(R$^{60}$))N(R$^{60}$)$_2$, —OC(O)R$^{60}$, —C(O)R$^{60}$, —C(O)OR$^{60}$, —C(O)N(R$^{60}$)$_2$, —S(O)$_2$R$^{60}$, —S(O)$_2$OR$^{60}$, C$_{3-12}$ carbocycle, and 3- to 12-membered heterocycle, wherein the C$_{3-12}$ carbocycle and 3- to 12-membered heterocycle are optionally substituted with one or more substituents selected from the group consisting of halogen, —CN, —NO$_2$, —OR$^{60}$, —SR$^{60}$, —N(R$^{60}$)$_2$, C$_{1-10}$ alkyl, C$_{1-10}$ haloalkyl, —C$_{1-10}$ alkyl-N(R$^{60}$)$_2$, —C$_{1-10}$ alkyl-OR$^{60}$, and —C$_{1-10}$ alkyl-C(O)N(R$^{60}$)$_2$; and wherein R$^{60}$ at each occurrence is independently selected from the group consisting of hydrogen, C$_{1-10}$ alkyl, and C$_{1-10}$ haloalkyl.

In certain embodiments, for a compound or salt of Formula (III), R$^{20}$ may be optionally substituted C$_{1-20}$ alkyl, wherein C$_{1-20}$ alkyl optional substituents are one or more substituents independently selected from the group consisting of: halogen, —CN, —NO$_2$, —OR$^{60}$, —SR$^{60}$, —N(R$^{60}$)$_2$, —NR$^{60}$C(N(R$^{60}$))N(R$^{60}$)$_2$, —OC(O)R$^{60}$, —C(O)R$^{60}$, —C(O)OR$^{60}$, —C(O)N(R$^{60}$)$_2$, —S(O)$_2$R$^{60}$, —S(O)$_2$OR$^{60}$, C$_{3-12}$ carbocycle, and 3- to 12-membered heterocycle, wherein the C$_{3-12}$ carbocycle and 3- to 12-membered heterocycle are optionally substituted with one or more substituents selected from the group consisting of halogen, —N(R$^{60}$)$_2$, C$_{1-10}$ alkyl, C$_{1-10}$ haloalkyl, —C$_{1-10}$ alkyl-N(R$^{60}$)$_2$, —C$_{1-10}$ alkyl-OR$^{60}$, and —C$_{1-10}$ alkyl-C(O)N(R$^{60}$)$_2$; and optionally substituted C$_{3-20}$ carbocycle, wherein the C$_{3-20}$ carbocycle optional substituents are one or more substituents independently selected from the group consisting of: halogen, —N(R$^6$))$_2$, C$_{1-10}$ alkyl, C$_{1-10}$ haloalkyl, —C$_{1-10}$ alkyl-N(R$^{60}$)$_2$, —C$_{1-10}$ alkyl-OR$^{60}$, and —C$_{1-10}$ alkyl-C(O)N(R$^{60}$)$_2$; and wherein R$^{60}$ at each occurrence is independently selected from the group consisting of hydrogen, C$_{1-10}$ alkyl, and C$_{1-10}$ haloalkyl.

In certain embodiments, for a compound or salt of Formula (III), R$^{20}$ may be optionally substituted C$_{1-20}$ alkyl, wherein C$_{1-20}$ alkyl optional substituents are one or more substituents independently selected from the group consisting of: halogen, —CN, —NO$_2$, —OR$^{60}$, —SR$^{60}$, —N(R$^{60}$)$_2$, —NR$^{60}$C(N(R$^{60}$))N(R$^{60}$)$_2$, —OC(O)R$^{60}$, —C(O)R$^{60}$, —C(O)O R$^{60}$, —C(O)N(R$^{60}$)$_2$, —S(O)$_2$R$^{60}$, —S(O)$_2$OR$^{60}$, —C$_{3-12}$ carbocycle, and 3- to 12-membered heterocycle. In certain embodiments, R$^{20}$ is optionally substituted C$_{1-20}$ alkyl. In certain embodiments, R$^{20}$ is C$_{1-20}$ alkyl. In certain embodiments, R$^{20}$ is C$_{1-10}$ alkyl. In certain embodiments, R$^{20}$ is C$_{1-5}$ alkyl.

In certain embodiments, for a compound or salt of Formula (III), R$^{16}$ may be selected from the group consisting of optionally substituted C$_{1-20}$ alkyl, optionally substituted C$_{2-20}$ alkenyl, and optionally substituted C$_{2-20}$ alkynyl. In certain embodiments, R$^{16}$ is selected from the group consisting of optionally substituted C$_{1-10}$ alkyl, optionally substituted C$_{2-10}$ alkenyl, and optionally substituted C$_{1-20}$ alkynyl. In certain embodiments, R$^{16}$ is selected from the group consisting of optionally substituted C$_{1-10}$ alkyl. In certain embodiments, R$^{16}$ is selected from the group consisting of: optionally substituted C$_{1-20}$ alkyl, optionally substituted C$_{2-20}$ alkenyl, optionally substituted C$_{2-20}$ alkynyl, wherein the C$_{1-20}$ alkyl, C$_{2-20}$ alkenyl, and C$_{2-20}$ alkynyl optional substituents are one or more substituents independently selected from the group consisting of: halogen, —CN, —NO$_2$, —OR$^{60}$, —SR$^{60}$, —N(R$^{60}$)$_2$, —NR$^{60}$C(N(R$^{60}$))N(R$^{60}$)$_2$, —OC(O)R$^{60}$, —C(O)R$^{60}$, —C(O)OR$^{60}$, —C(O)N(R$^{60}$)$_2$, —S(O)$_2$R$^{60}$, —S(O)$_2$OR$^{60}$, C$_{3-12}$ carbocycle, and 3- to 12-membered heterocycle, wherein the C$_{3-12}$ carbocycle and 3- to 12-membered heterocycle are optionally substituted with one or more substituents selected from the group consisting of halogen, —CN, —NO$_2$, —OR$^{60}$, —SR$^{60}$, —N(R$^{60}$)$_2$, C$_{1-10}$ alkyl, C$_{1-10}$ haloalkyl, —C$_{1-10}$ alkyl-N(R$^{60}$)$_2$, —C$_{1-10}$ alkyl-OR$^{60}$, and —C$_{1-10}$ alkyl-C(O)N(R$^{60}$)$_2$; and optionally substituted C$_{3-20}$ carbocycle and optionally substituted 3- to 20-membered heterocycle, wherein the C$_{3-20}$ carbocycle and 3- to 20-membered heterocycle optional substituents are one or more substituents independently selected from the group consisting of: halogen, —CN, —NO$_2$, —OR$^{60}$, —SR$^{60}$, —N(R$^{60}$)$_2$, C$_{1-10}$ alkyl, C$_{1-10}$ haloalkyl, —C$_{1-10}$ alkyl-N(R$^{60}$)$_2$, —C$_{1-10}$ alkyl-OR$^{60}$, and —C$_{1-10}$ alkyl-C(O)N(R$^{60}$)$_2$; and wherein R$^{60}$ at each occurrence is independently selected from the group consisting of hydrogen, C$_{1-10}$ alkyl, and C$_{1-10}$ haloalkyl.

In certain embodiments, for a compound or salt of Formula (III), R$^{16}$ is optionally substituted C$_{1-20}$ alkyl, wherein C$_{1-20}$ alkyl optional substituents are one or more substituents independently selected from the group consisting of: halogen, —CN, —NO$_2$, —OR$^{60}$, —SR$^{60}$, —N(R$^{60}$)$_2$, —NR$^{60}$C(N(R$^{60}$))N(R$^{60}$)$_2$, —OC(O)R$^{60}$, —C(O)R$^{60}$, —C(O)O R$^{60}$, —C(O)N(R$^{60}$)$_2$, —S(O)$_2$R$^{60}$, —S(O)$_2$OR$^{60}$, C$_{3-12}$ carbocycle, and 3- to 12-membered heterocycle, and wherein R$^{60}$ at each occurrence is independently selected from the group consisting of hydrogen, C$_{1-10}$ alkyl, and C$_{1-10}$ haloalkyl. In certain embodiments, R$^{16}$ is optionally substituted C$_{1-20}$ alkyl, wherein C$_{1-20}$ alkyl optional substituents are one or more substituents independently selected from the group consisting of: halogen, —N(R$^{60}$)$_2$, —NR$^{60}$C(N(R$^{60}$))N(R$^{60}$)$_2$, —C(O)N(R$^{60}$)$_2$, —S(O)$_2$R$^{60}$, —S(O)$_2$OR$^{60}$, and wherein R$^{60}$ at each occurrence is independently selected from the group consisting of hydrogen, C$_{1-10}$ alkyl, and C$_{1-10}$ haloalkyl.

In certain embodiments, R$^{16}$ is optionally substituted C$_{1-20}$ alkyl. In certain embodiments, R$^{16}$ is C$_{1-20}$ alkyl. In certain embodiments, R$^{16}$ is C$_{1-10}$ alkyl. In certain embodiments, R$^{16}$ is C$_{1-6}$ alkyl. In certain embodiments, R$^{16}$ is:

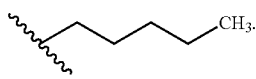 [SMILES: *CCCCC]

In certain embodiments, for a compound or salt of Formula (III), R$^{17}$ and R$^{18}$ may be independently selected from H and optionally substituted C$_{1-10}$alkyl. In certain embodiments, R$^{17}$ and R$^{18}$ are independently selected from the group consisting of: optionally substituted C$_{1-20}$ alkyl, optionally substituted C$_{2-20}$ alkenyl, optionally substituted C$_{2-20}$ alkynyl, wherein the C$_{1-20}$ alkyl, C$_{2-20}$ alkenyl, and C$_{2-20}$ alkynyl optional substituents are one or more substituents independently selected from the group consisting of: halogen, —CN, —NO$_2$, —OR$^{60}$, —SR$^{60}$, —N(R$^{60}$)$_2$, —NR$^{60}$C(N(R$^{60}$))N(R$^{60}$)$_2$, —OC(O)R$^{60}$, —C(O)R$^{60}$, —C(O)OR$^{60}$, —C(O)N(R$^{60}$)$_2$, —S(O)$_2$R$^{60}$, —S(O)$_2$OR$^{60}$, C$_{3-12}$ carbocycle, and 3- to 12-membered heterocycle, wherein the C$_{3-12}$ carbocycle and 3- to 12-membered heterocycle are optionally substituted with one or more substituents selected from the group consisting of halogen, —CN, —NO$_2$, —OR$^{60}$, —SR$^{60}$, —N(R$^{60}$)$_2$, C$_{1-10}$ alkyl, C$_{1-10}$ haloalkyl, —C$_{1-10}$ alkyl-N(R$^{60}$)$_2$, —C$_{1-10}$ alkyl-OR$^{60}$, and —C$_{1-10}$ alkyl-C(O)N(R$^{60}$)$_2$; and optionally substituted C$_{3-20}$ carbocycle and optionally substituted 3- to 20-membered heterocycle, wherein the C$_{3-20}$ carbocycle and 3- to 20-membered heterocycle optional substituents are one or more substituents independently selected from the group consisting of: halogen, —CN, —NO$_2$, —OR$^{60}$, —SR$^{60}$, —N(R$^{60}$)$_2$, C$_{1-10}$ alkyl, C$_{1-10}$ haloalkyl, —C$_{1-10}$ alkyl-N(R$^{60}$)$_2$, —C$_{1-10}$ alkyl-OR$^{60}$, and —C$_{1-10}$ alkyl-C(O)N(R$^{60}$)$_2$; and wherein R$^{60}$ at each occurrence is independently selected from the group consisting of hydrogen, C$_{1-10}$ alkyl, and C$_{1-10}$ haloalkyl.

In certain embodiments, for a compound or salt of Formula (III), R$^{17}$ and R$^{18}$ are independently optionally substituted C$_{1-20}$ alkyl, wherein C$_{1-20}$ alkyl optional substituents are one or more substituents independently selected from the group consisting of:

halogen, —CN, —NO$_2$, —OR$^{60}$, —SR$^{60}$, —N(R$^{60}$)$_2$, —NR$^{60}$C(N(R$^{60}$))N(R$^{60}$)$_2$, —OC(O)R$^{60}$, —C(O)R$^{60}$, —C(O)OR$^{60}$, —C(O)N(R$^{60}$)$_2$, —S(O)$_2$R$^{60}$, —S(O)$_2$OR$^{60}$, and optionally substituted C$_{3-20}$ carbocycle and optionally substituted 3- to 20-membered heterocycle, wherein the C$_{3-20}$ carbocycle and optionally substituted 3- to 20-membered heterocycle optional substituents are one or more substituents independently selected from the group consisting of: halogen, —N(R$^{60}$)$_2$, C$_{1-10}$ alkyl, C$_{1-10}$ haloalkyl, —C$_{1-10}$ alkyl-N(R$^{60}$)$_2$, —C$_{1-10}$ alkyl-OR$^{60}$, and —C$_{1-10}$ alkyl-C(O)N(R$^{60}$)$_2$; and wherein R$^{60}$ at each occurrence is independently selected from the group consisting of hydrogen, C$_{1-10}$ alkyl, and C$_{1-10}$ haloalkyl.

In certain embodiments, for a compound or salt of Formula (III), R$^{17}$ and R$^{18}$ are independently optionally substituted C$_{1-20}$ alkyl, wherein C$_{1-20}$ alkyl optional substituents are one or more substituents independently selected from the group consisting of: halogen, —CN, —NO$_2$, —OR$^{60}$, —SR$^{11}$, —N(R$^{60}$)$_2$, —NR$^{60}$C(N(R$^{60}$))N(R$^{60}$)$_2$, —OC(O)R$^{60}$, —C(O)R$^{60}$, —C(O)OR$^{60}$, —C(O)N(R$^{60}$)$_2$, —S(O)$_2$R$^{60}$, —S(O)$_2$OR$^{60}$, optionally substituted C$_{3-20}$ carbocycle, wherein C$_{3-20}$ carbocycle optional substituents are one or more substituents independently selected from the group consisting of: halogen, —N(R$^{60}$)$_2$, —C$_{1-10}$ alkyl-N(R$^{60}$)$_2$, and —C$_{1-10}$ alkyl-OR$^{60}$; and wherein R$^{60}$ at each occurrence is independently selected from the group consisting of hydrogen, C$_{1-10}$ alkyl, and C$_{1-10}$ haloalkyl. In certain embodiments, R$^7$ is hydrogen. In certain embodiments, R$^{18}$ is hydrogen.

In one embodiment a compound comprises a compound of general structural Formula I:

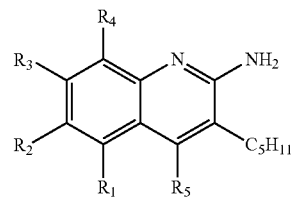

I wherein: R$_1$, R$_5$ are independently: H, —OH, —OR', —NH$_2$, —NHR', —NR'$_2$, —SH, —SR', —O—C(O)R', —C(O)R', (CH$_2$)$_b$NH$_2$, C$_{(m+1)}$H$_{(2m+1)}$, C$_{(m+1)}$H$_{(2m+1)}$NH$_2$, C$_{(m+1)}$H$_{(2m+1)}$CONH$_2$, C$_{(m+1)}$H$_{(2m+1)}$, CR'NH$_2$, C$_{(m+1)}$H$_{(2m+1)}$—C$_{4-20}$ aryl-C$_{(m+1)}$H$_{(2m+1)}$—NH$_2$, C$_m$H$_{2m+2}$, C$_{4-20}$ aryl, C$_{1-20}$ alkyl, C$_{1-20}$ alkylamino, C$_{2-20}$ alkenyl, C$_{2-20}$ alkynyl, C$_{4-20}$ heterocycle, C$_{4-20}$ heteroaryl, C$_{4-20}$ alkyl heterocycle, C$_{7-20}$ alkyl heteroaryl, C$_{1-20}$ alkyoxyl, where m is an integer from 0 to 10, and b is an integer from 0 to 10.

The C$_{4-20}$ aryl, C$_{1-20}$ alkyl, C$_{2-20}$ alkenyl, C$_{2-20}$ alkynyl, C$_{4-20}$ heterocycle, C$_{4-20}$ heteroaryl, C$_{4-20}$ alkyl heterocycle, C$_{7-20}$ alkyl heteroaryl, C$_{1-20}$ alkyoxyl is unsubstituted or optionally substituted with a functional group comprising H, —OH, —OR', —NH$_2$, —NHR', —NR'$_2$, —SH, —SR', —O—C(O)R', —C(O)R', —CF$_3$, —OCF$_3$, or an amino acid side chain or peptide fragment, the C$_{4-20}$ aryl, C$_{1-20}$ alkyl, C$_{2-20}$ alkenyl, C$_{2-20}$ alkynyl, C$_{4-20}$ heterocycle, C$_{4-20}$ heteroaryl, C$_{4-20}$ alkyl heterocycle, C$_{7-20}$ alkyl heteroaryl, C$_{1-20}$ alkyoxyl, and the C$_{1-6}$ alkyl is optionally interrupted by one or more O, S, or N atoms, or one or more groups comprising cycloalkyl, C$_{(m+1)}$H$_{(2m+1)}$, C$_{(m+1)}$H$_{(2m+1)}$NH$_2$, CH—C(O)—O—, —O—C(O)—, —C(O)—, —C(O)—NH—, —NH—C(O)—, —NH—C(O)—O— and —O—C(O)—NH—, R' is H, OH, halogen, NO$_2$, —NH$_2$, CN, —COOH, heteroaryl having 1 to 4 N, O and/or S atoms, $C_{4-20}$ aryl, $C_{1-10}$ alkyl, $C_{2-10}$ alkenyl, $C_{2-10}$ alkynyl, $C_{4-10}$ heterocycle or $C_{4-10}$ heteroaryl.

The groups $R_2$, $R_3$, and $R_4$ are independently: H, —OH, —NH$_2$, —CH$_2$, —COOH, —OR', —NH$_2$, —NHR', —NR'$_2$, —SH, —SR', —O—C(O)R', —C(O)R', $(CH_2)_b$NH$_2$ where m is an integer from 0 to 10, and b is an integer from 0 to 10, $C_{1-50}$ alkyl, the $C_{1-50}$ alkyl is unsubstituted or optionally substituted with a functional group comprising one or more of: H, —OH, —OR', —NH$_2$, —NHR', —NR'$_2$, —SH, —SR', —O—C(O)R', —C(O)R', —CF$_3$, —OCF$_3$, an amino acid side chain or peptide fragment, where $R^1$ is selected from radicals consisting of H, heteroaryl having 1 to 4 N, O and/or S atoms, $C_{1-20}$ alkyl, $C_{1-20}$ alkylamino, $C_{2-10}$ alkenyl, $C_{2-10}$ alkynyl, $C_{4-10}$ heterocycle, $C_{4-10}$ heteroaryl, ammonium and salts thereof, sulfates, sulfonates, thiosulfonates, boronates, phosphates, phosphonate, guanidine, amidine, pyridine, pyridium, alkali metal groups, nitrates, chlorates, perchlorates, acetates, chloride, bromide, iodide and salts thereof, an alkali metal salt of sulfonic acid; an alkali metal salt of phosphonic acid; a pharmaceutically acceptable salt; a sugar or a polyhydroxy group.

In other embodiments, $R_1$ is selected from the group of: H, —OH, —NH$_2$, $(CH_2)_b$NH$_2$, $C_{(m+1)}H_{(2m+1)}$, $C_{(m+1)}H_{(2m+1)}$NH$_2$, $C_{(m+1)}H_{(2m+1)}$—CO—NH$_2$, $C_{(m+1)}H_{(2m+1)}$, CR'NH$_2$, $C_{(m+1)}H_{(2m+1)}$—$C_{4-20}$ aryl-$C_{(m+1)}H_{(2m+1)}$—NH$_2$, $C_{4-20}$ aryl, $C_{1-20}$ alkyl, $C_{1-20}$ alkylamino, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, where m is an integer from 0 to 10, and b is an integer from 0 to 10.

In another embodiment, $R_1$ is $C_{(m+1)}H_{(2m+1)}$NH$_2$ where m is an integer from 0 to 10, and b is an integer from 0 to 10, $C_{1-10}$ alkyl, or $C_{1-10}$ alkyl substituted with a functional group selected from the group consisting of —OH, —OR', —NH$_2$, —NHR', —NR'$_2$, —O—C(O)R', —C(O)R', —CF$_3$, and —OCF$_3$, where $R^1$ is selected from the groups consisting of H and $C_{1-5}$ alkyl.

In one embodiment, $R_1$ is H, $(CH_2)_{2-5}$NH$_2$, a pentyl amine ($C_5H_{11}$NH$_2$), or a $C_{1-20}$ alkylamino having a formula $(CH_2)_b$NH$_2$ where b is an integer from 0 to 10. In another embodiment, the $R_9$ group is H or $C_5H_{11}$NH$_2$.

In another embodiment, the $R_3$ is H, $(CH_2)_{2-5}$NH$_2$ a pentyl amine ($C_5H_{11}$NH$_2$), or a $C_{1-20}$ alkylamino having a formula $(CH_2)_b$NH$_2$ where b is an integer from 0 to 10. In another embodiment, $R_3$ is H or $C_5H_{11}$NH$_2$.

In another embodiment, $R_2$, $R_4$ and $R_5$ are H.

Some of the exemplary compounds are listed on Table 1. For example, a composition can comprise one of the following selected compounds. The following compounds are listed for demonstration purposes. The compounds in the present disclosure include but are not limited to:

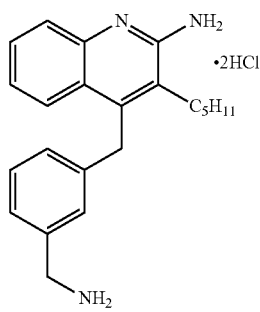

9a 4-(3-(Aminomethyl)benzyl)-3-pentylquinolin-2-amine dihydrochloride (9a)

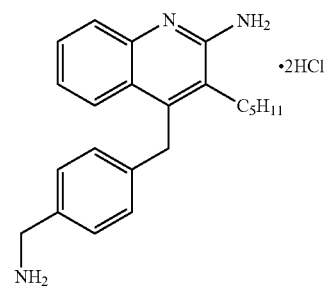

9b 4-(4-(Aminomethyl)benzyl)-3-pentylquinolin-2-amine dihydrochloride (9b)

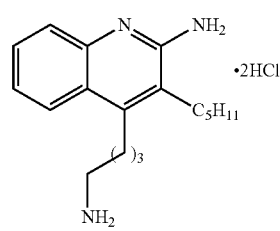

14a 4-(4-Aminobutyl)-3-pentylquinolin-2-amine dihydrochloride (14a)

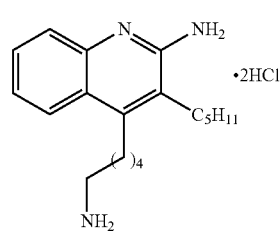

14b 4-(5-Aminopentyl)-3-pentylquinolin-2-amine dihydrochloride (14b)

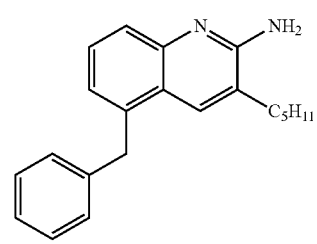

17d

5-Benzyl-3-pentylquinolin-2-amine (17d)
5-(2-(Aminomethyl)benzyl)-3-pentylquinolin-2-amine (18c)
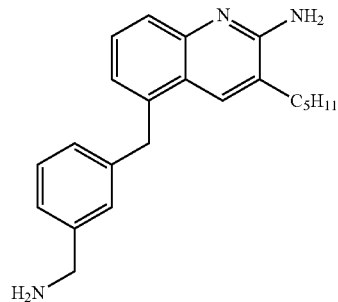
5-(3-(Aminomethyl)benzyl)-3-pentylquinolin-2-amine (18a)
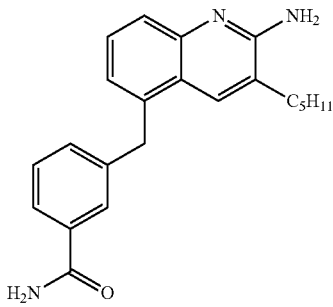
3-((2-Amino-3-pentylquinolin-5-yl)methyl)benzamide (18d)
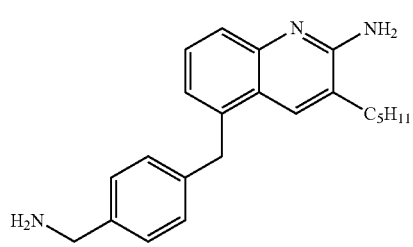
5-(4-(Aminomethyl)benzyl)-3-pentylquinolin-2-amine (18b)
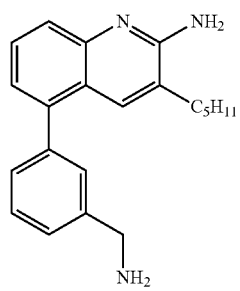
5-(3-(Aminomethyl)phenyl)-3-pentylquinolin-2-amine (20a)
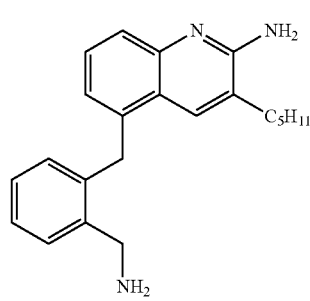
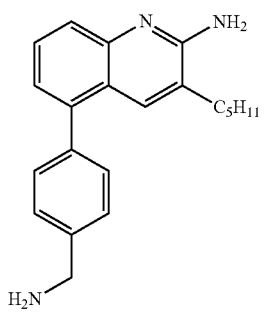

5-(4-(Aminomethyl)phenyl)-3-pentylquinolin-2-amine (20b)
5-(6-Aminohexyl)-3-pentylquinolin-2-amine (34c)
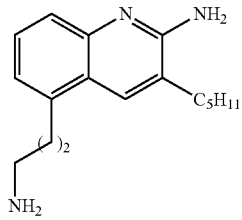
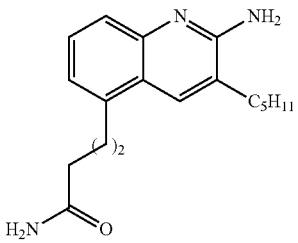
5-(3-Aminopropyl)-3-pentylquinolin-2-amine (23)
4-(2-Amino-3-pentylquinolin-5-yl)butanamide (34d)
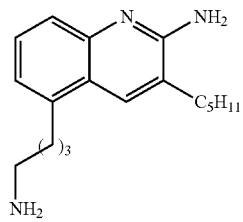
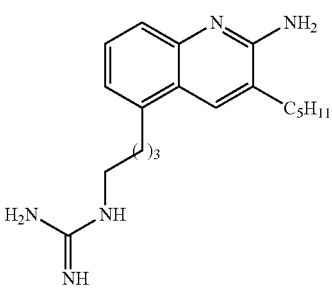
5-(4-Aminobutyl)-3-pentylquinolin-2-amine (34a)
1-(4-(2-Amino-3-pentylquinolin-5-yl)butyl)guanidine (34e)
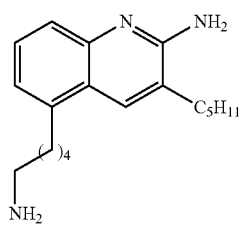
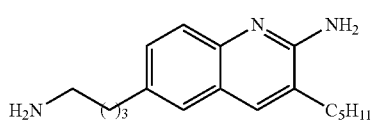
6-(4-Aminobutyl)-3-pentylquinolin-2-amine (35a)
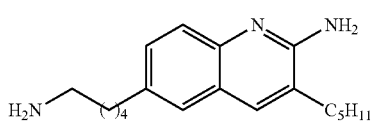
5-(5-Aminopentyl)-3-pentylquinolin-2-amine (34b)
6-(5-Aminopentyl)-3-pentylquinolin-2-amine (35b)
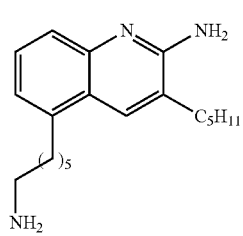
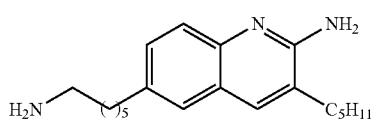

6-(6-Aminohexyl)-3-pentylquinolin-2-amine (35c)

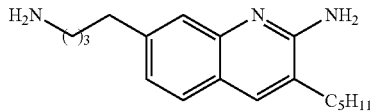

7-(4-Aminobutyl)-3-pentylquinolin-2-amine (36a)

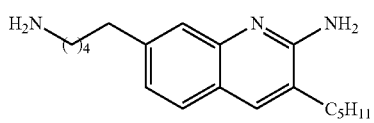

7-(5-Aminopentyl)-3-pentylquinolin-2-amine (36b)

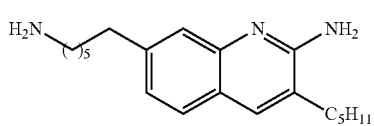

7-(6-Aminohexyl)-3-pentylquinolin-2-amine (36c)

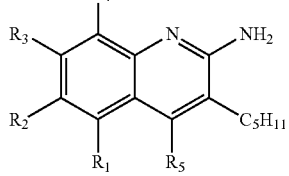

8-(4-Aminobutyl)-3-pentylquinolin-2-amine (37)

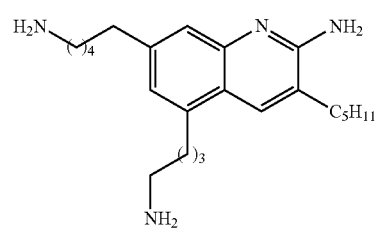

5,5'-(2-amino-3-pentylquinoline-5,7-diyl)bis(pentan-1-amine) (43)

In other embodiments, a pharmaceutical composition of a therapeutically effective amount of one or more compounds of general Formulas I:

I wherein: $R_1$, $R_5$ are independently: H, —OH, —OR', —NH$_2$, —NHR', —NR'$_2$, —SH, —SR', —O—C(O)R', —C(O)R', (CH$_2$)$_b$NH$_2$, C$_{(m+1)}$H$_{(2m+1)}$, C$_{(m+1)}$H$_{(2m+1)}$NH$_2$, C$_{(m+1)}$H$_{(2m+1)}$CONH$_2$, C$_{(m+1)}$H$_{(2m+1)}$, CR'NH$_2$, C$_{(m+1)}$H$_{(2m+1)}$—C$_{4-20}$ aryl-C$_{(m+1)}$H$_{(2m+1)}$—NH$_2$, C$_m$H$_{2m+2}$, C$_{4-20}$ aryl, C$_{1-20}$ alkyl, C$_{1-20}$ alkylamino, C$_{2-20}$ alkenyl, C$_{2-20}$ alkynyl, C$_{4-20}$ heterocycle, C$_{4-20}$ heteroaryl, C$_{4-20}$ alkyl heterocycle, C$_{7-20}$ alkyl heteroaryl, C$_{1-20}$ alkyoxyl, where m is an integer from 0 to 10, and b is an integer from 0 to 10; the C$_{4-20}$ aryl, C$_{1-20}$ alkyl, C$_{2-20}$ alkenyl, C$_{2-20}$ alkynyl, C$_{4-20}$ heterocycle, C$_{4-20}$ heteroaryl, C$_{4-20}$ alkyl heterocycle, C$_{7-20}$ alkyl heteroaryl, C$_{1-20}$ alkyoxyl is unsubstituted or optionally substituted with a functional group comprising H, —OH, —OR', —NH$_2$, —NHR', —NR'$_2$, —SH, —SR', —O—C(O)R', —C(O)R', —CF$_3$, —OCF$_3$, or an amino acid side chain or peptide fragment, the C$_{4-20}$ aryl, C$_{1-20}$ alkyl, C$_{2-20}$ alkenyl, C$_{2-20}$ alkynyl, C$_{4-20}$ heterocycle, C$_{4-20}$ heteroaryl, C$_{4-20}$ alkyl heterocycle, C$_{7-20}$ alkyl heteroaryl, C$_{1-20}$ alkyoxyl, and the C$_{1-6}$ alkyl is optionally interrupted by one or more O, S, or N atoms, or one or more groups comprising cycloalkyl, C$_{(m+1)}$H$_{(2m+1)}$, C$_{(m+1)}$H$_{(2m+1)}$NH$_2$, CH—C(O)—O—, —O—C(O)—, —C(O)—, —C(O)—NH—, —NH—C(O)—, —NH—C(O)—O— and —O—C(O)—NH—, R' is H, OH, halogen, NO$_2$, —NH$_2$, CN, —COOH, heteroaryl having 1 to 4 N, O and/or S atoms, C$_{4-20}$ aryl, C$_{1-10}$ alkyl, C$_{2-10}$ alkenyl, C$_{2-10}$ alkynyl, C$_{4-10}$ heterocycle or C$_{4-10}$ heteroaryl; the groups R$_2$, R$_3$, and R$_4$ are independently: H, —OH, —NH$_2$, —CH$_2$, —COOH, —OR', —NH$_2$, —NHR', —NR'$_2$, —SH, —SR', —O—C(O)R', —C(O)R', (CH$_2$)$_b$NH$_2$ where m is an integer from 0 to 10 and b is an integer from 0 to 10, C$_{1-50}$ alkyl, the C$_{1-50}$ alkyl is unsubstituted or optionally substituted with a functional group comprising one or more of: H, —OH, —OR', —NH$_2$, —NHR', —NR'$_2$, —SH, —SR', —O—C(O)R', —C(O)R', —CF$_3$, —OCF$_3$, an amino acid side chain or peptide fragment, where R$^1$ is selected from radicals consisting of H, heteroaryl having 1 to 4 N, O and/or S atoms, C$_{1-20}$ alkyl, C$_{1-20}$ alkylamino, C$_{2-10}$ alkenyl, C$_{2-10}$ alkynyl, C$_{4-10}$ heterocycle, C$_{4-10}$ heteroaryl, ammonium and salts thereof, sulfates, sulfonates, thiosulfonates, boronates, phosphates, phosphonate, guanidine, amidine, pyridine, pyridium, alkali metal groups, nitrates, chlorates, perchlorates, acetates, chloride, bromide, iodide and salts thereof, an alkali metal salt of sulfonic acid; an alkali metal salt of phosphonic acid; a pharmaceutically acceptable salt; a sugar, a polyhydroxy group or prodrugs thereof.

In another embodiment, a TLR8-specific agonist comprises one or more compounds of general Formula I:

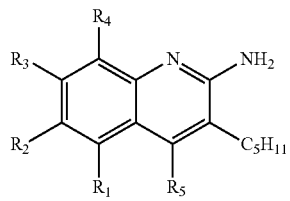

I wherein: $R_1$, $R_5$ are independently: H, —OH, —OR', —NH$_2$, —NHR', —NR'$_2$, —SH, —SR', —O—C(O)R', —C(O)R', (CH$_2$)$_b$NH$_2$, $C_{(m+1)}H_{(2m+1)}$, $C_{(m+1)}H_{(2m+1)}$NH$_2$, $C_{(m+1)}H_{(2m+1)}$CONH$_2$, $C_{(m+1)}H_{(2m+1)}$, CR'NH$_2$, $C_{(m+1)}H_{(2m+1)}$—C$_{4-20}$ aryl-$C_{(m+1)}H_{(2m+1)}$—NH$_2$, $C_mH_{2m+2}$, $C_{4-20}$ aryl, $C_{1-20}$ alkyl, $C_{1-20}$ alkylamino, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, where m is an integer from 0 to 10, and b is an integer from 0 to 10;

the $C_{4-20}$ aryl, $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl is unsubstituted or optionally substituted with a functional group comprising H, —OH, —OR', —NH$_2$, —NHR', —NR'$_2$, —SH, —SR', —O—C(O)R', —C(O)R', —CF$_3$, —OCF$_3$, or an amino acid side chain or peptide fragment, the $C_{4-20}$ aryl, $C_{1-20}$ alkyl, $C_{2-20}$ alkenyl, $C_{2-20}$ alkynyl, $C_{4-20}$ heterocycle, $C_{4-20}$ heteroaryl, $C_{4-20}$ alkyl heterocycle, $C_{7-20}$ alkyl heteroaryl, $C_{1-20}$ alkyoxyl, and the $C_{1-6}$ alkyl is optionally interrupted by one or more O, S, or N atoms, or one or more groups comprising cycloalkyl, $C_{(m+1)}H_{(2m+1)}$, $C_{(m+1)}H_{(2m+1)}$NH$_2$, CH—C(O)—O—, —O—C(O)—, —C(O)—, —C(O)—NH—, —NH—C(O)—, —NH—C(O)—O— and —O—C(O)—NH—, R' is H, OH, halogen, NO$_2$, —NH$_2$, CN, —COOH, heteroaryl having 1 to 4 N, O and/or S atoms, $C_{4-20}$ aryl, $C_{1-10}$ alkyl, $C_{2-10}$ alkenyl, $C_{2-10}$ alkynyl, $C_{4-10}$ heterocycle or $C_{4-10}$ heteroaryl;

the groups $R_2$, $R_3$, and $R_4$ are independently: H, —OH, —NH$_2$, —CH$_2$, —COOH, —OR', —NH$_2$, —NHR', —NR'$_2$, —SH, —SR', —O—C(O)R', —C(O)R', (CH$_2$)$_b$NH$_2$ where m is an integer from 0 to 10 and b is an integer from 0 to 10, $C_{1-50}$ alkyl, the $C_{1-50}$ alkyl is unsubstituted or optionally substituted with a functional group comprising one or more of: H, —OH, —OR', —NH$_2$, —NHR', —NR'$_2$, —SH, —SR', —O—C(O)R', —C(O)R', —CF$_3$, —OCF$_3$, an amino acid side chain or peptide fragment, where R' is selected from radicals consisting of H, heteroaryl having 1 to 4 N, O and/or S atoms, $C_{1-20}$ alkyl, $C_{1-20}$ alkylamino, $C_{2-10}$ alkenyl, $C_{2-10}$ alkynyl, $C_{4-10}$ heterocycle, $C_{4-10}$ heteroaryl, ammonium and salts thereof, sulfates, sulfonates, thiosulfonates, boronates, phosphates, phosphonate, guanidine, amidine, pyridine, pyridium, alkali metal groups, nitrates, chlorates, perchlorates, acetates, chloride, bromide, iodide and salts thereof, an alkali metal salt of sulfonic acid; an alkali metal salt of phosphonic acid; a pharmaceutically acceptable salt; a sugar, a polyhydroxy group or prodrugs thereof.

In certain embodiments, a TLR8-agonist comprises:

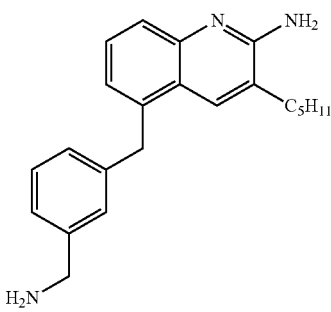

5-(3-(Aminomethyl)benzyl)-3-pentylquinolin-2-amine (18a)

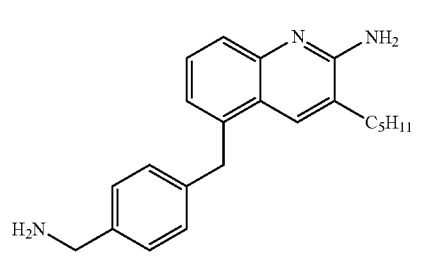

5-(4-(Aminomethyl)benzyl)-3-pentylquinolin-2-amine (18b)

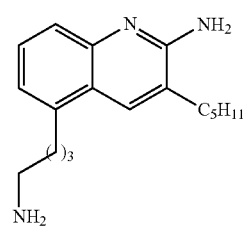

5-(4-Aminobutyl)-3-pentylquinolin-2-amine (34a)

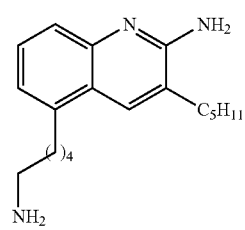

5-(5-Aminopentyl)-3-pentylquinolin-2-amine (34b)

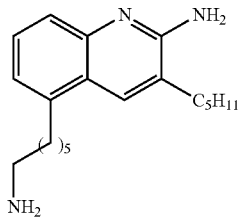

5-(6-Aminohexyl)-3-pentylquinolin-2-amine (34c)

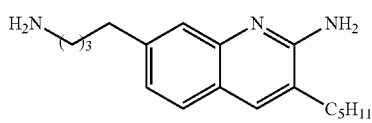

7-(4-Aminobutyl)-3-pentylquinolin-2-amine (36a)

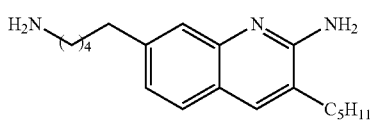

7-(5-Aminopentyl)-3-pentylquinolin-2-amine (36b)

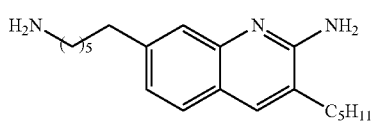

7-(6-Aminohexyl)-3-pentylquinolin-2-amine (36c)

or pharmaceutical salts thereof.

In one embodiment, compounds are synthesized by general scheme 1:

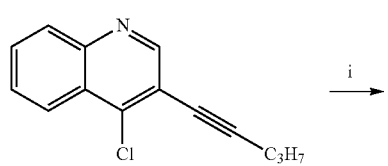

-continued

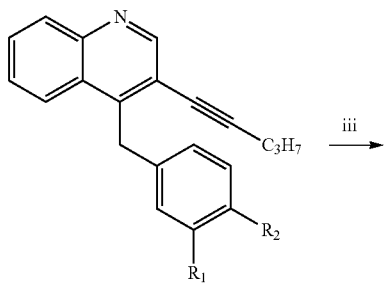

5a-b
6a-b
5a ($R_1$ = CN, $R_2$ = H)
5b ($R_1$ = H, $R_2$ = CN)

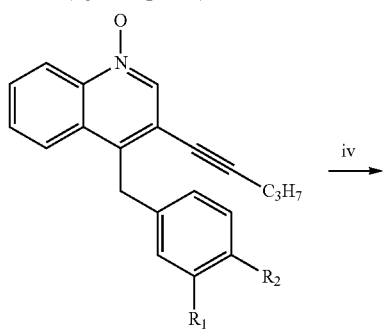

7a-b
6a-8a ($R_1$ = CH$_2$NHBoc, $R_2$ = H)
6b-8b ($R_1$ = H, $R_2$ = CH$_2$NHBoc)

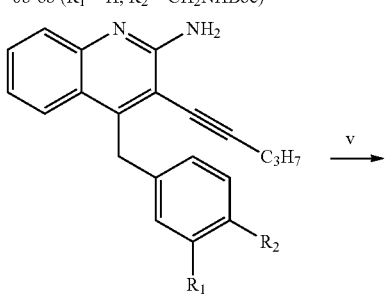

8a-b

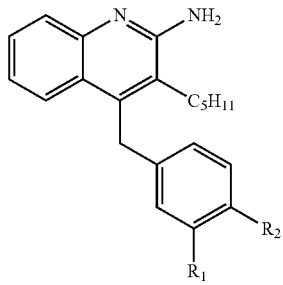

9a-b
9a ($R_1$ = CH$_2$NH$_2$, $R_2$ = H)
9b ($R_1$ = H, $R_2$ = CH$_2$NH$_2$)

Reagents: (i) 3-cyanobenzylzinc bromide (for 5a) or 4-cyanobenzylzinc bromide (for 5b), LiCl, DMF; (ii) (a) LiAlH$_4$, THF, (b) Boc$_2$O, CH$_3$OH; (iii) m-CPBA, CHCl$_3$; (iv) (a) benzoyl isocyanate, CH$_2$Cl$_2$, (b) NaOCH$_3$, CH$_3$OH; (v) (a) Pt/C, EtOAc, 30 psi, (b) HCl, 4M.

In another embodiment, compounds are synthesized by general scheme 2:

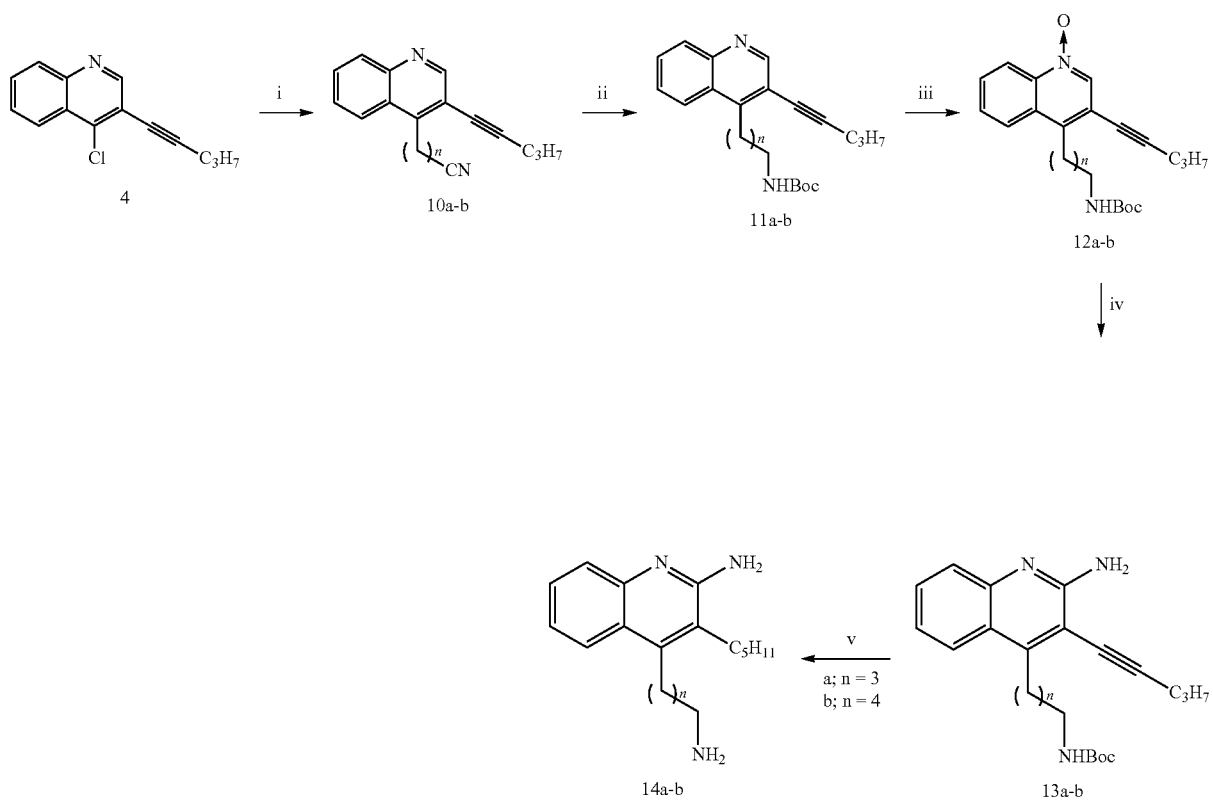

Reagents: (i) 3-cyanopropylzinc bromide (for 10a) or 4-cyanobutylzinc bromide (for 10b), Pd(PPh₃)₄, THF; (ii) (a) LiAlH₄, THF, (b) Boc₂O, CH₃OH; (iii) m-CPBA, CHCl₃; (iv) (a) benzoyl isocyanate, CH₂Cl₂, (b) NaOCH₃, CH₃OH; (v) (a) Pt/C, EtOAc, 30 psi, (b) HCl, 4M.

In another embodiment, compounds are synthesized by general scheme 3:

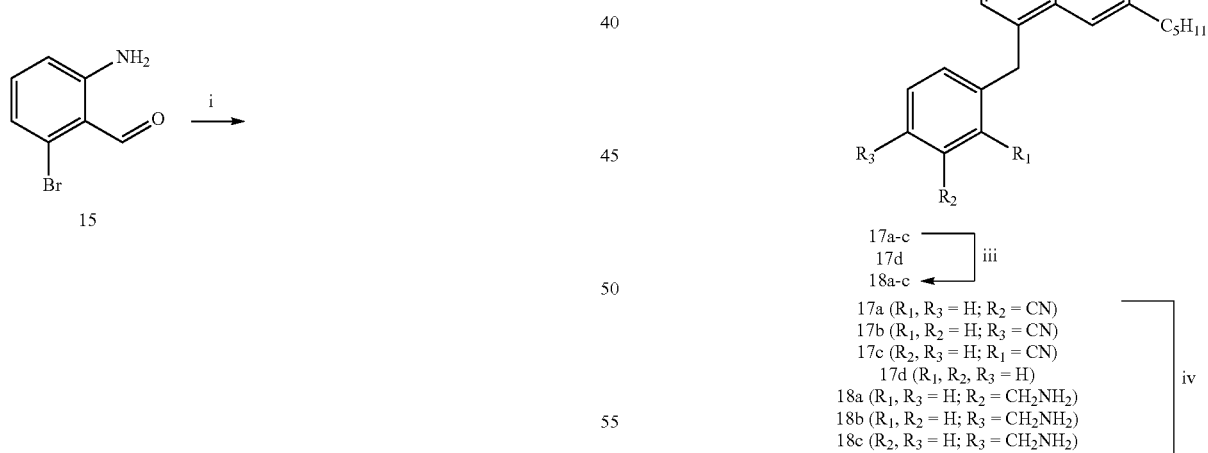

Reagents: (i) Heptanenitrile, t-BuOK, DMSO; (ii) 3-cyanobenzylzinc bromide (for 17a) or 4-cyanobenzylzinc bromide (for 17b) or 2-cyanobenzylzinc bromide (for 17c) or benzylzinc bromide (for 17d), Pd(PPh₃)₄, THF; (iii) LiAlH₄, THF; (iv) KOH, t-BuOH, 8 h.

In another embodiment, compounds are synthesized by general scheme 4:

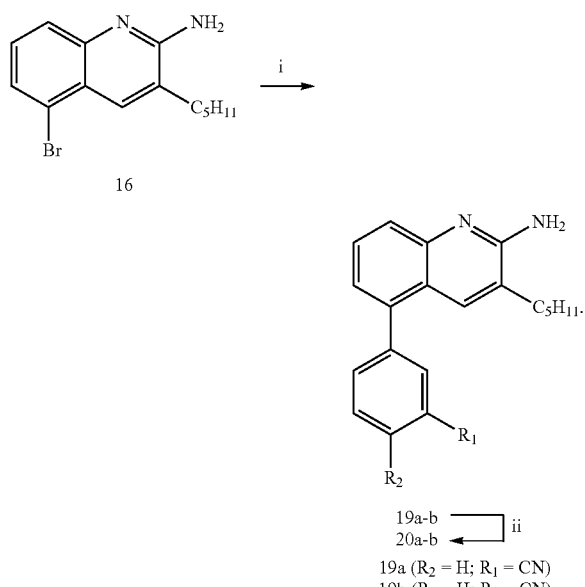

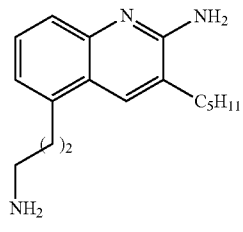

23

Reagents: (i) Acrylonitrile, Pd(OAc)$_2$, PPh$_3$, K$_2$CO$_3$, DMF; (ii) H$_2$, Pt/C, 30 psi, EtOAc; (iii) LiAlH$_4$, THF.

In another embodiment, compounds are synthesized by general scheme 6:

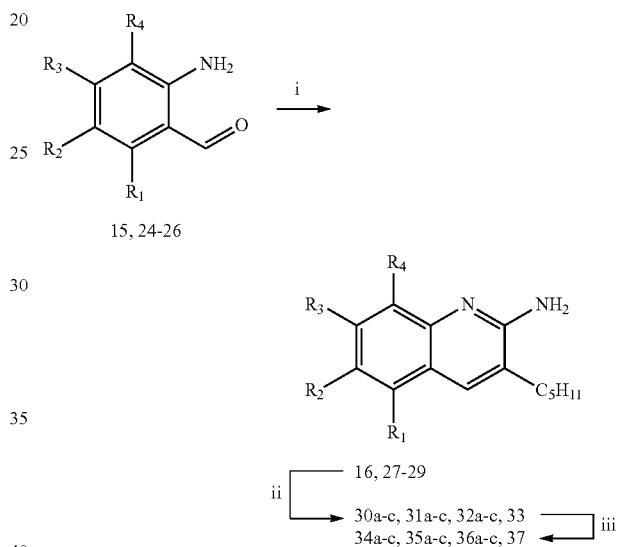

30a: R$_2$, R$_3$, R$_4$ = H, R$_1$ = n-C$_3$H$_7$CN
30b: R$_2$, R$_3$, R$_4$ = H, R$_1$ = n-C$_4$H$_9$CN
30c: R$_2$, R$_3$, R$_4$ = H, R$_1$ = n-C$_5$H$_{11}$CN
31a: R$_1$, R$_3$, R$_4$ = H, R$_2$ = n-C$_3$H$_7$CN
31b: R$_1$, R$_3$, R$_4$ = H, R$_2$ = n-C$_4$H$_9$CN
31c: R$_1$, R$_3$, R$_4$ = H, R$_2$ = n-C$_5$H$_{11}$CN
32a: R$_1$, R$_2$, R$_4$ = H, R$_3$ = n-C$_3$H$_7$CN
32b: R$_1$, R$_2$, R$_4$ = H, R$_3$ = n-C$_4$H$_9$CN
32c: R$_1$, R$_2$, R$_4$ = H, R$_3$ = n-C$_5$H$_9$CN
33: R$_1$, R$_2$, R$_3$ = H, R$_4$ = n-C$_3$H$_7$CN

34a: R$_2$, R$_3$, R$_4$ = H, R$_1$ = n-C$_4$H$_9$NH$_2$
34b: R$_2$, R$_3$, R$_4$ = H, R$_1$ = n-C$_5$H$_{11}$NH$_2$
34c: R$_2$, R$_3$, R$_4$ = H, R$_1$ = n-C$_6$H$_{13}$NH$_2$
34d: R$_2$, R$_3$, R$_4$ = H, R$_1$ = n-C$_3$H$_7$CONH$_2$
34e: R$_2$, R$_3$, R$_4$ = H, R$_1$ = n-C$_4$H$_9$NH(CNH)NH$_2$
35a: R$_1$, R$_3$, R$_4$ = H, R$_2$ = n-C$_4$H$_9$NH$_2$
35b: R$_1$, R$_3$, R$_4$ = H, R$_2$ = n-C$_5$H$_{11}$NH$_2$
35c: R$_1$, R$_3$, R$_4$ = H, R$_2$ = n-C$_6$H$_{13}$NH$_2$
36a: R$_1$, R$_2$, R$_4$ = H, R$_3$ = n-C$_4$H$_9$NH$_2$
36b: R$_1$, R$_2$, R$_4$ = H, R$_3$ = n-C$_5$H$_{11}$NH$_2$
36c: R$_1$, R$_2$, R$_4$ = H, R$_3$ = n-C$_6$H$_{13}$NH$_2$
37: R$_1$, R$_2$, R$_3$ = H, R$_4$ = n-C$_4$H$_9$NH$_2$

Reagents: (i) Heptanenitrile, t-BuOK, DMSO; (ii) 3-cyanopropylzinc bromide (for 30a-32a and 33) or 4-cyanobutylzinc bromide (for 30b-32b) or 5-cyanopentylzinc bromide (for 30c-32c), Pd(PPh$_3$)$_4$, THF; (iii) LiAlH$_4$, THF; (iv) KOH, t-BuOH, 8 h; (v) 1H-pyrazole-1-carboxamidine HCl, Et$_3$N, MeOH.

In another embodiment, compounds are synthesized by general scheme 7:

In another embodiment, compounds are synthesized by general scheme 5:

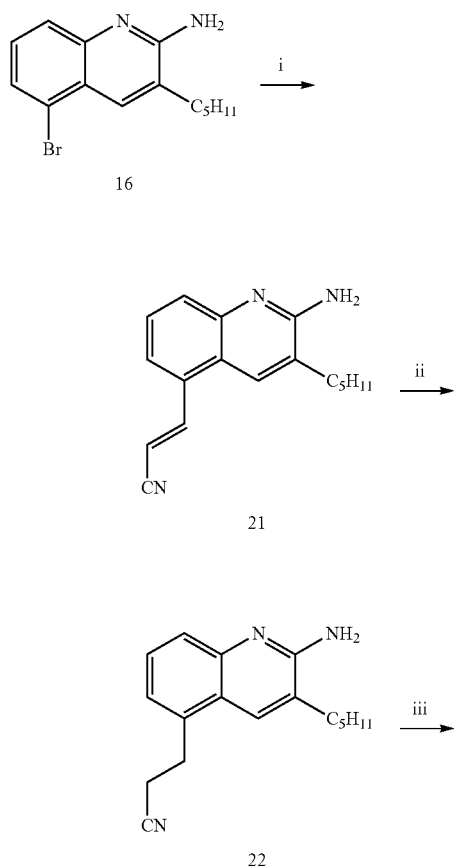

Reagents: (i) 3-cyanophenylboronic acid (for 19a) or 4-cyanophenylboronic acid (for 19b), Pd(dppf)Cl$_2$, K$_2$CO$_3$, 1,4-dioxane; (ii) LiAlH$_4$, THF, 5 h.

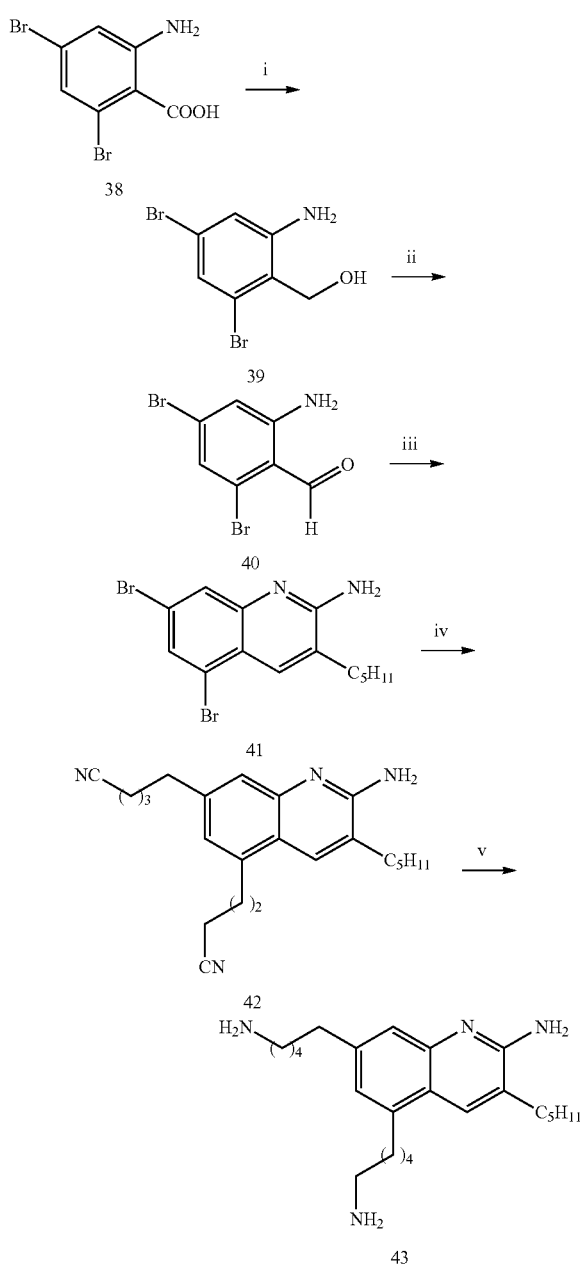

Reagents: (i) LiAlH4, THF; (i) MnO$_2$, DCM; (iii) heptanenitrile, t-BuOK, DMSO; (iv) 4-cyanobutylzinc bromide, Pd(PPh$_3$)$_4$, THF; (v) LiAlH$_4$, THF, 4 h.

In another embodiment, one or more compounds or salts of general Formulas (I), (II) or (III) are administered as a pharmaceutical composition.

In other embodiments, a pharmaceutical composition comprises an effective and therapeutically effective amount of one or more compounds or salts of Formulas (I), (II) or (III).

Uses

In embodiments, one or more compounds or salts of Formulas (I), (II) or (III) are TLR8 specific agonists. Engagement of the human toll-like receptor (hTLR)-8 by TLR8 agonists evokes a distinct cytokine profile, e.g. TNF-α, IL-6, IL-12, etc) which favors the development of Type 1 helper T cells ($T_H1$). Type 1 helper ($T_H1$), but not type 2 helper ($T_H2$), cells produce interleukin (IL)-2, gamma-interferon (IFN-γ) and tumor necrosis factor-α, whereas $T_H2$, but not $T_H1$, cells express IL-4, IL-5, IL-6, IL-10, IL-12, IL-13, etc. The different cytokine patterns lead to different functions of the two types of T cell. In general, $T_H2$ cells are excellent helpers for B-cell antibody secretion, particularly IgE responses. On the other hand $T_H1$ cells induce delayed-type hypersensitivity reactions. Most allergen- or helminthic antigen-specific CD4$^+$ human T cell clones have a $T_H2$ phenotype, whereas the majority of T-cell clones specific for mycobacterial antigens or antigens responsible for type IV hypersensitivity exhibit a $T_H1$ phenotype. Selective or preferential activation of CD4$^+$ T-cell subsets secreting defined patterns of cytokines is of major importance in determining the class of immune effector function, thus influencing both protection and immunopathology.

Strongly $T_H1$-biasing TLR8 agonists would be useful as candidate vaccine adjuvants for the newborn. Maternal immunoglobulins acquired passive transplacental passage, confer protection to the neonate for the first few weeks of life; thereafter, the newborn is susceptible to a wide range of pathogens until early infancy. The very young do not mount adequate adaptive immune responses and, consequently, even highly effective vaccines that confer excellent protection in adults fail to elicit strong immune responses in them. The neonatal immunophenotype is characterized by decreased production of both type I and type II interferons, as well as $T_H1$-biasing cytokines such as TNF-α, IL-12, IL-18, IL-23, the preferential induction of memory B lymphocytes rather than immunoglobulin-secreting plasma cells, as well as a pronounced type 2 helper ($T_H2$) skewing of T-cell responses.

Accordingly, in one preferred embodiment, one or more compounds of Formulas (I), (II) or (III) modulate an immune response in vitro or in vivo. In another preferred embodiment, one or more compounds of Formulas (I), (II) or (III) are administered as a vaccine adjuvant.

In another embodiment, a pharmaceutical composition comprising an effective amount of one or more compounds of Formulas (I), (II) or (III) are administered to a patient in need thereof, either alone, in combination with another therapeutic agent or as part of a therapy. The therapeutic agent can be, for example, a vaccine, chemotherapy, radiotherapy, immuno therapy, surgery, antibiotics, anti-fungal, etc.

In another embodiment, a pharmaceutical composition comprising an effective amount of one or more compounds of Formulas (I), (II) or (III), is administered to a patient in need thereof, as an adjuvant. The compounds can, for example, stimulate an immune response to a weakly immunogenic antigen, vaccine etc.

In some aspects, a method comprising administering any of the compositions provided herein to a subject in an amount effective to modulate an immune response is provided. In some embodiments, the composition is in an amount effective to induce or enhance an immune response. In some embodiments, the composition is in an amount effective to suppress an immune response. In some embodiments, the composition is in an amount effective to direct or redirect an immune response. In some embodiments, the method is for prophylaxis and/or treatment of the diseases or disorders which would benefit by an enhanced immune response.

In some embodiments, where the method is to induce or enhance an immune response, the subject has or is susceptible to having cancer, an infectious disease, a non-autoimmune metabolic or degenerative disease, an atopic disease, or an addiction. In some embodiments, the subject has been exposed to or may be exposed to a toxin. In some embodiments, the subject has been exposed to or may be exposed to a toxin from a chemical weapon. In some embodiments, the method raises high titer antibodies that bind and neutralize the offending agent before it reaches its effector site (e.g., the brain).

In some embodiments, the infectious disease is a chronic viral infection. In some embodiments, the chronic viral infection is HIV, HPV, HBV, or HCV infection.

In some aspects, the compositions comprising compounds of Formulas (I), (II) or (III) are administered with immunomodulatory agents that stimulate various cells of the immune system. For example, B cells, T cells, antigen-presenting cells (APCs). In some preferred embodiments, the compounds induce a $T_H1$ type immune response.

In some embodiments, an immunomodulatory agent may comprise isolated and/or recombinant proteins or peptides, vaccines, carbohydrates, glycoproteins, glycopeptides, proteoglycans, inactivated organisms and viruses, dead organisms and virus, genetically altered organisms or viruses, and cell extracts. In some embodiments, an immunomodulatory agent may comprise nucleic acids, carbohydrates, lipids, and/or small molecules. In some embodiments, an immunomodulatory agent is one that elicits an immune response. In some embodiments, an immunomodulatory agent is an antigen. In some embodiments, an immunomodulatory agent is used as a vaccine. In some embodiments, an immunomodulatory agent is any protein and/or other antigen derived from a pathogen. The pathogen may be a virus, bacterium, fungus, protozoan, parasite, etc. In some embodiments, an immunomodulatory agent may be in the form of whole killed organisms, peptides, proteins, glycoproteins, glycopeptides, proteoglycans, carbohydrates, or combinations thereof.

Pharmaceutical Compositions

As discussed above, the invention also includes pharmaceutical compositions containing compounds having a general Formulas (I), (II) or (III). In some embodiments, the compositions are suitable for internal use and include an effective amount of a pharmacologically active conjugate of the invention, alone or in combination, with one or more pharmaceutically acceptable carriers.

The patient having pathology, e.g. the patient treated by the methods of this invention can be a mammal, or more particularly, a human. In practice, the agents are administered in amounts which will be sufficient to exert their desired biological activity.

The pharmaceutical compositions of the invention may contain, for example, more than one type of compounds of Formulas (I), (II) or (III). In some examples, a pharmaceutical composition of the invention, containing one or more compounds of the invention, is administered in combination with another useful composition such as, a vaccine, antibodies, an anti-inflammatory agent, an immunostimulator, a chemotherapeutic agent, an antiviral agent, or the like. Furthermore, the compositions of the invention may be administered in combination with a cytotoxic, cytostatic, or chemotherapeutic agent such as an alkylating agent, antimetabolite, mitotic inhibitor or cytotoxic antibiotic. In general, the currently available dosage forms of the known therapeutic agents for use in such combinations will be suitable.

In certain embodiments, a method of modulating an immune response in vitro or in vivo, comprises contacting a cell or administering to a subject in need thereof, a composition comprising one or more compounds of general Formulas (I), (II) or (III). Examples of such compounds, comprise:

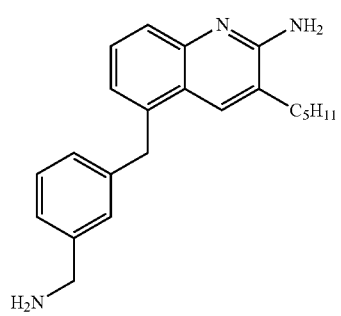

5-(3-(Aminomethyl)benzyl)-3-pentylquinolin-2-amine (18a)

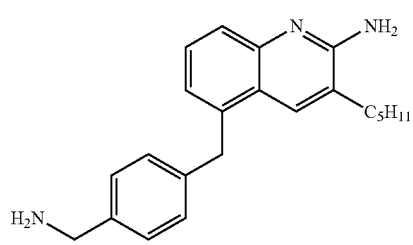

5-(4-(Aminomethyl)benzyl)-3-pentylquinolin-2-amine (18b)

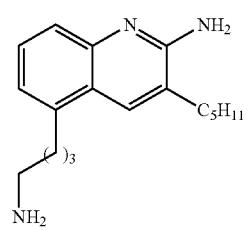

5-(4-Aminobutyl)-3-pentylquinolin-2-amine (34a)

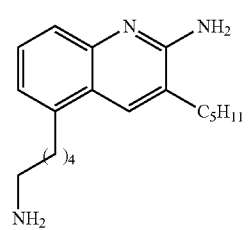

5-(5-Aminopentyl)-3-pentylquinolin-2-amine (34b)

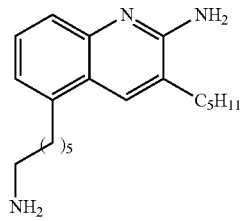

5-(6-Aminohexyl)-3-pentylquinolin-2-amine (34c)

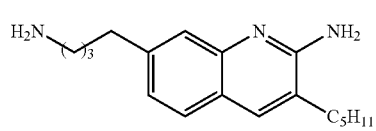

7-(4-Aminobutyl)-3-pentylquinolin-2-amine (36a)

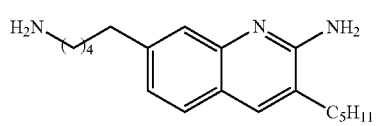

7-(5-Aminopentyl)-3-pentylquinolin-2-amine (36b)

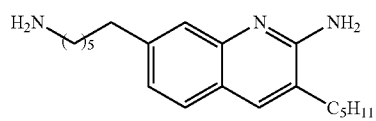

7-(6-Aminohexyl)-3-pentylquinolin-2-amine (36c)

or pharmaceutical salts thereof.

An immunomodulatory agent such as a vaccine, can be administered to the subject before, in conjunction with, or after administration of the composition.

In another embodiment, a method of increasing an immune response in a subject to an immunomodulatory agent such as, for example, an antigen or vaccine, comprises administering the immunomodulatory agent to the subject; administering a composition comprising an effective amount of one or more compounds of general Formulas (I), (II) or (III). These compounds, for example, comprise one or more of:

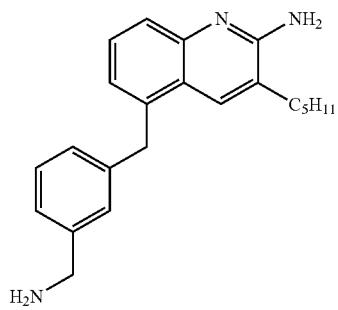

5-(3-(Aminomethyl)benzyl)-3-pentylquinolin-2-amine (18a)

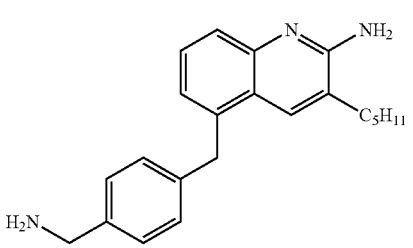

5-(4-(Aminomethyl)benzyl)-3-pentylquinolin-2-amine (18b)

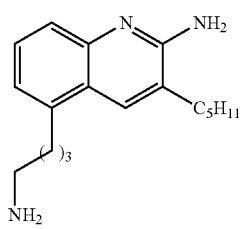

5-(4-Aminobutyl)-3-pentylquinolin-2-amine (34a)

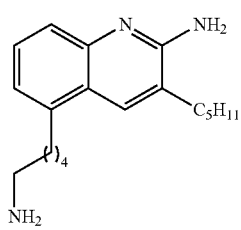

5-(5-Aminopentyl)-3-pentylquinolin-2-amine (34b)

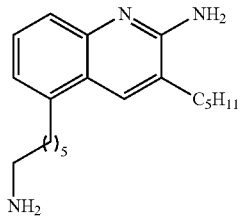

5-(6-Aminohexyl)-3-pentylquinolin-2-amine (34c)

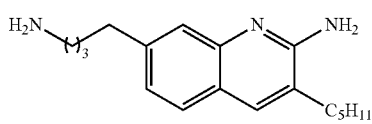

7-(4-Aminobutyl)-3-pentylquinolin-2-amine (36a)

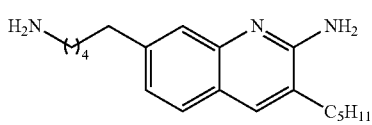

7-(5-Aminopentyl)-3-pentylquinolin-2-amine (36b)

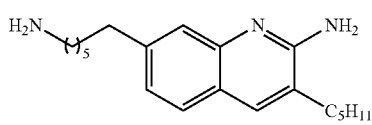

7-(6-Aminohexyl)-3-pentylquinolin-2-amine (36c)

or pharmaceutical salts thereof.

As discussed infra, the composition comprising the one or more compounds of general Formulas (I), (II) or (III), are pre-administered before administration of the antigen or vaccine, co-administered with the antigen or vaccine, or post-administration of the antigen or vaccine.

Combination therapy (or "co-therapy") includes the administration of the compositions and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

Combination therapy may, but generally is not, intended to encompass the administration of two or more of these therapeutic agents as part of separate monotherapy regimens that incidentally and arbitrarily result in the combinations of the present invention. Combination therapy is intended to embrace administration of compounds of Formulas (I), (II) or (III) in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the therapeutic agents are administered is not narrowly critical unless noted otherwise. Combination therapy also can embrace the administration of the therapeutic agents as described above in further combination with other biologically active ingredients. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Therapeutic or pharmacological compositions of the present invention will generally comprise an effective amount of the active component(s), dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

For any agent used in the methods of the invention, the therapeutically effective amount or dose can be estimated initially from activity assays in cell cultures and/or animals. For example, a dose can be formulated in animal models to achieve a circulating concentration range that includes the $IC_{50}$ as determined by activity assays (e.g., the concentration of the test compound, which achieves a half-maximal inhibition of the proliferation activity). Such information can be used to more accurately determine useful doses in humans.

Toxicity and therapeutic efficacy of the peptides described herein can be determined by standard pharmaceutical procedures in experimental animals, e.g., by determining the $IC_{50}$ and the $LD_{50}$ (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. Dosage amount and interval may be adjusted individually to provide plasma levels of the active moiety which are sufficient to maintain therapeutic effects, termed the minimal effective concentration (MEC). The MEC will vary for each preparation, but can be estimated from in vitro and/or in vivo data, e.g., the concentration necessary to achieve 50-90% inhibition of a proliferation of certain cells may be ascertained using the assays described herein. Dosages necessary to achieve the MEC will depend on individual characteristics and route of administration. HPLC assays or bioassays can be used to determine plasma concentrations. Dosage intervals can also be determined using the MEC value. Preparations should be administered using a regimen, which maintains plasma levels above the MEC for 10-90% of the time, preferably between 30-90% and most preferably 50-90%. Depending on the severity and responsiveness of the condition to be treated, dosing can also be a single administration of a slow release composition described hereinabove, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, etc.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or other known methods.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

The pharmaceutical compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

The compositions of the present invention can be administered in intravenous (both bolus and infusion), intraperitoneal, subcutaneous or intramuscular form, all using forms well known to those of ordinary skill in the pharmaceutical arts. Injectables can be prepared in conventional forms, either as liquid solutions or suspensions.

Parenteral injectable administration is generally used for subcutaneous, intramuscular or intravenous injections and infusions. Additionally, one approach for parenteral administration employs the implantation of a slow-release or sustained-released systems, which assures that a constant level of dosage is maintained.

Furthermore, preferred compositions for the present invention can be administered in intranasal form via topical use of suitable intranasal vehicles, inhalants, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, suppositories, ointments, lotions, aerosol sprays and gels, wherein the concentration of active ingredient would typically range from 0.01% to 15%, w/w or w/v.

The active compound defined above, may be also formulated as suppositories, using for example, polyalkylene glycols, for example, propylene glycol, as the carrier. In some embodiments, suppositories are advantageously prepared from fatty emulsions or suspensions.

The compounds of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564. For example, the molecules described herein can be provided as a complex with a lipophilic compound or non-immunogenic, high molecular weight compound constructed using methods known in the art. An example of nucleic-acid associated complexes is provided in U.S. Pat. No. 6,011,020.

The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

If desired, the pharmaceutical composition to be administered may also contain minor amounts of non-toxic auxiliary substances such as wetting or emulsifying agents, pH buffering agents, and other substances such as for example, sodium acetate, and triethanolamine oleate. The dosage regimen utilizing the molecules is selected in accordance with a variety of factors including type, species, age, weight, sex and medical condition of the patient; the severity of the condition to be treated; the route of administration; the renal and hepatic function of the patient; and the particular molecule or salt thereof employed. An ordinarily skilled physician or veterinarian can readily determine and prescribe the effective amount of the drug required to prevent, counter or arrest the progress of the condition. Compounds of the present invention may be administered in a single daily dose, or the total daily dosage may be administered in divided doses of two, three or four times daily.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention.

EXAMPLES

The invention has been described in detail with reference to preferred embodiments thereof. However, it will be appreciated that those skilled in the art, upon consideration of this disclosure, may make modifications and improvements within the spirit and scope of the invention. The following non-limiting examples are illustrative of the invention.

Example 1: Structure-Based Design of Human TLR8-Specific Agonists with Augmented Potency and Adjuvanticity Previous work, by the inventors, on identifying small molecule agonists of TLR8 include: 2,3-diamino-furo[2,3-c]pyridines (Salunke, D. B. et al. *J. Med. Chem.* 2012, 55, 8137-8151), 4-amino-furo[2,3-c]quinolines (Kokatla, H. P. et al. *J. Med. Chem.* 2013, 56, 6871-6885), 3-alkyl-quinoline-2-amines (Kokatla, H. P. et al. *Chem. Med. Chem.* 2014, 9, 719-723), and 1-alkyl-2-aminobenzimidazoles (Beesu, M. et al. *J. Med. Chem.* 2014, 57, 7325-7341), all of which are pure TLR8 agonists with no detectable activity at TLR7.

Crystal structures of the ectodomain of human TLR8 (hTLR8) co-crystallized with two regioisomers of dual TLR7/8-agonistic N1-aminomethylbenzyl-substituted imidazoquinolines (1, 2) (Shukla, N. M. et al. *J. Med. Chem.* 2010, 53, 4450-4465) showed subtle differences in their interactions in the binding site of hTLR8 (FIG. 1). The N1-substituent of 1 was observed to H-bond with a backbone carbonyl group, while in 2, a stronger salt-bridge was present, which fully explained the higher TLR8 activity of 2. The questions addressed herein were whether the TLR8-agonistic potency of the best-in-class compound of the 3-alkyl-quinoline-2-amine series could be further enhanced by 'designing in' functional groups which would mimic the ionic H-bond observed in the hTLR8/2 complex.

A focused and hypothesis-driven exploration of introducing alkylamino groups at all possible positions on the quinoline core is reported herein. These studies led to the identification of a novel TLR8 agonist which was ~20-fold more potent than the parent compound.

Materials and Methods

Abbreviations: APCs, Antigen-presenting cells; CD, Cluster of differentiation; EC50, Half-maximal effective concentration; ESI-TOF, Electrospray ionization-time of flight; HEK, Human embryonic kidney; IFN, Interferon; IL, Interleukin; MHC, Major histocompatibility complex; MPL®, monophosphoryl lipid A; NF-κB, Nuclear factor-κB; NK, Natural killer; NLR, Nod-like receptor; NOD-1 and -2, Nucleotide-binding oligomerization domain-containing protein 1 and 2; PBMCs, Peripheral blood mononuclear cells; sAP, Secreted alkaline phosphatase; Th1, Helper T lymphocyte, type 1; Th2, Helper T lymphocyte, type 2; TLR, Toll-like receptor; TNF-α, Tumor necrosis factor-α.

Chemistry: All of the solvents and reagents used were obtained commercially and used as such unless noted otherwise. Moisture- or air-sensitive reactions were conducted under nitrogen atmosphere in oven-dried (120° C.) glass apparatus. Solvents were removed under reduced pressure using standard rotary evaporators. Flash column chromatography was carried out using RediSep Rf 'Gold' high performance silica columns on CombiFlash Rf instruments unless otherwise mentioned, while thin-layer chromatography was carried out on silica gel CCM pre-coated aluminum sheets. Purity for all final compounds was confirmed to be greater than 98% by LC-MS using a Zorbax Eclipse Plus 4.6 mm×150 mm, 5 µm analytical reverse phase $C_{18}$ column with $H_2O$—$CH_3CN$ and $H_2O$-MeOH gradients and an Agilent 6520 ESI-QTOF Accurate Mass spectrometer (mass accuracy of 5 ppm) operating in the positive ion acquisition mode. Compound 4 was synthesized as previously described (Kokatla, H. P. *Chem. Med. Chem.* 2014, 9, 719-723).

3-((3-(Pent-1-yn-1-yl)quinolin-4-yl)methyl)benzonitrile (5a). To a solution of compound 4 (230 mg, 1 mmol) in DMF (5 mL) were added 3-cyanobenzylzinc bromide (4 mL, 2 mmol, 0.5 M in THF) and LiCl (85 mg, 2 mmol). The resulting reaction mixture was stirred for 24 h at room temperature under nitrogen atmosphere. The reaction mixture was diluted with water and extracted with EtOAc (3×30 mL). The combined organic layer was dried over $Na_2SO_4$ and concentrated under reduced pressure. The crude material was purified by flash chromatography (40% EtOAc/hexanes) to obtain the compound 5a as a pale yellow solid (179 mg, 58%). $^1H$ NMR (500 MHz, $CDCl_3$) δ 8.93 (s, 1H), 8.10 (dd, J=1.2, 8.4 Hz, 1H), 7.87 (dd, J=1.3, 8.3 Hz, 1H), 7.67 (ddd, J=1.3, 6.9, 8.4 Hz, 1H), 7.55-7.50 (m, 2H), 7.49-7.46 (m, 1H), 7.44-7.41 (m, 1H), 7.34 (t, J=7.7 Hz, 1H), 4.65 (s, 2H), 2.47 (t, J=7.0 Hz, 2H), 1.73-1.52 (m, 2H), 1.02 (t, J=7.4 Hz, 3H). 13C NMR (126 MHz, $CDCl_3$) δ 152.89, 147.08, 145.67, 140.55, 132.90, 132.02, 130.52, 130.36, 129.55, 129.51, 127.65, 126.62, 123.91, 119.01, 118.90, 112.77, 98.31, 77.53, 35.56, 22.20, 21.80, 13.70. MS (ESI-TOF) for $C_{22}H_{18}N_2[M+H]+$ calculated 311.1543, found 311.1441.

Compound 5b was synthesized similarly as compound 5a.

4-((3-(Pent-1-yn-1-yl)quinolin-4-yl)methyl)benzonitrile (5b). 4-Cyanobenzylzinc bromide was used as reagent. Pale yellow solid (201 mg, 65%). $^1H$ NMR (500 MHz, $CDCl_3$) δ 8.93 (s, 1H), 8.09 (dd, J=0.8, 8.4 Hz, 1H), 7.84 (dd, J=0.8, 8.5 Hz, 1H), 7.67 (ddd, J=1.4, 6.9, 8.4 Hz, 1H), 7.56-7.48 (m, 3H), 7.32-7.26 (m, 2H), 4.69 (s, 2H), 2.46 (t, J=7.0 Hz, 2H), 1.74-1.51 (m, 2H), 1.01 (t, J=7.4 Hz, 3H). $^{13}C$ NMR (126 MHz, CDCl3) δ 152.87, 147.07, 145.59, 144.64, 132.54, 130.50, 129.55, 129.18, 127.61, 126.68, 123.97, 119.08, 118.94, 110.49, 98.24, 77.50, 36.17, 22.19, 21.79, 13.69. MS (ESI-TOF) for $C_{22}H_{18}N_2$ $[M+H]^+$ calculated 311.1543, found 311.1504.

4-(3-(Aminomethyl)benzyl)-3-pentylquinolin-2-amine dihydrochloride (9a). A solution of compound 5a (155 mg, 0.5 mmol) in THE (5 mL) was added slowly to a solution of $LiAlH_4$ (2.5 mL, 2.5 mmol, 1.0 M in THF) in THE (5 mL)

at 0° C. under nitrogen atmosphere. The reaction mixture was stirred for 1 h at 25° C. and 5 h at 75° C. The reaction mixture was cooled to room temperature and quenched carefully with ice-cold water. The resulting mixture was basified with 10% NaOH (to pH=8.0) and extracted with $CH_2Cl_2$ (3×30 mL). The combined organic layer was dried over $Na_2SO_4$ and concentrated under reduced pressure to obtain the residue. The residue was dissolved in MeOH and di-t-butyl dicarbamate (109 mg, 0.5 mmol) was added and stirred under nitrogen for 1 h. The solvent was removed under vacuum. The resulting residue was purified by flash chromatography (20% EtOAc/hexanes) to obtain the compound 6a as a pale yellow solid (134 mg, 65%). MS (ESI-TOF) for $C_{27}H_{30}N_2O_2$ [M+H]$^+$ calculated 415.2380, found 415.2266. To a stirred solution of substrate 6a (124 mg, 0.3 mmol) in $CHCl_3$ was added m-CPBA (134 mg, 0.6 mmol). The resulting reaction mixture was stirred for 4 h at room temperature. The reaction mixture was diluted with water and extracted with $CH_2Cl_2$ (3×20 mL). The combined organic layer was dried over $Na_2SO_4$, concentrated under reduced pressure, and the crude material was purified by flash chromatography (10% MeOH/$CH_2Cl_2$) to obtain 7a as a yellow solid (98 mg, 76%). MS (ESI-TOF) for $C_{27}H_{30}N_2O_3$ [M+H]$^+$ calculated 431.2329, found 431.2122. To a stirred solution of 7a (86 mg, 0.2 mmol) in $CH_2Cl_2$ was added benzoyl isocyanate (88 mg, 0.6 mmol). The resulting reaction mixture was stirred at 55° C. for 1 h. After completion of reaction (monitored by TLC), the solvent was removed under reduced pressure. The residue was re-dissolved in MeOH (5 mL), NaOMe (54 mg, 1 mmol) was added and refluxed for 2 h. The solvent was removed and the crude material was purified by flash chromatography (10% MeOH/$CH_2Cl_2$) to obtain 8a as an off-white solid (67 mg, 78%). MS (ESI-TOF) for $C_{27}H_{31}N_3O_2$ [M+H]$^+$ calculated 430.2489, found 430.2303. To a solution of compound 8a (43 mg, 0.1 mmol) in anhydrous EtOAc (10 mL) was added a catalytic amount of Pt/C, and the reaction mixture was subjected to hydrogenation at 30 psi for 30 min. The reaction mixture was filtered, and the filtrate concentrated under reduced pressure. The crude material was purified by flash chromatography (10% MeOH/$CH_2Cl_2$) to obtain N-Boc protected benzylamine as a white solid (32 mg). MS (ESI-TOF) for $C_{27}H_{35}N_3O_2$ [M+H]$^+$ calculated 434.2802, found 434.2612. To a stirred solution of N-Boc protected benzylamine (32 mg) in 1,4-dioxane (1 mL) was added hydrogen chloride (1 mL, 4 M in dioxane), and the reaction mixture was stirred for 1 h at room temperature. Excess solvent was removed under reduced pressure and the resulted residue was thoroughly washed with diethyl ether to obtain the desired compound 9a as a white solid (28 mg, 69%). 1H NMR (500 MHz, MeOD) δ 7.97-7.91 (m, 1H), 7.77-7.64 (m, 2H), 7.43 (ddd, Jr 1.4, 7.0, 8.4 Hz, 1H), 7.38 (t, J=7.6 Hz, 1H), 7.36-7.31 (m, 1H), 7.28 (s, 1H), 7.18 (d, J=8.0 Hz, 1H), 4.62 (s, 2H), 4.06 (s, 2H), 2.81 (t, J=8.5 Hz, 2H), 1.58-1.49 (m, 2H), 1.47-1.39 (m, 2H), 1.36-1.25 (m, 2H), 0.89 (t, J=7.3 Hz, 3H). $^{13}$C NMR (126 MHz, MeOD) δ 155.07, 151.34, 140.27, 136.23, 135.28, 133.06, 130.87, 129.87, 129.62, 128.43, 127.13, 126.67, 126.32, 123.05, 118.59, 44.08, 34.87, 32.75, 29.22, 28.11, 23.67, 14.34. MS (ESI-TOF) for $C_{22}H_{27}N_3$[M+H]$^+$ calculated 334.2278, found 334.2238.

Compound 9b was synthesized similarly as compound 9a.

4-(4-(Aminomethyl)benzyl)-3-pentylquinolin-2-amine dihydrochloride (9b). White solid (30 mg, 74%). $^1$H NMR (500 MHz, MeOD) δ 7.91 (dd, J=1.2, 8.4 Hz, 1H), 7.79-7.64 (m, 2H), 7.44-7.37 (m, 3H), 7.22 (d, J=8.0 Hz, 2H), 4.62 (s, 2H), 4.07 (s, 2H), 2.79 (t, J=8.2 Hz, 2H), 1.57-1.47 (m, 2H), 1.46-1.38 (m, 2H), 1.36-1.27 (m, 2H), 0.89 (t, J=7.3 Hz, 3H). 13C NMR (126 MHz, MeOD) δ 155.04, 151.56, 140.37, 136.15, 133.09, 133.07, 130.67, 129.85, 127.14, 126.60, 126.20, 123.00, 118.56, 43.87, 34.72, 32.71, 29.19, 27.99, 23.62, 14.33. MS (ESI-TOF) for $C_{22}H_{27}N_3$[M+H]$^+$ calculated 334.2278, found 334.2257.

4-(3-(Pent-1-yn-1-yl)quinolin-4-yl)butanenitrile (10a). To a solution of compound 4 (229.7 mg, 1 mmol) in THF (4 mL) were added 3-cyanopropylzinc bromide (4 mL, 2 mmol, 0.5 M in THF) and Pd(PPh$_3$)$_4$ (115.5 mg, 0.1 mmol). The resulting reaction mixture was stirred for 12 h at 65° C. under nitrogen atmosphere. The reaction mixture was diluted with water and extracted with EtOAc (3×30 mL). The combined organic layer was dried over $Na_2SO_4$ and concentrated under reduced pressure. The crude material was purified by flash chromatography (20% EtOAc/hexanes) to obtain the compound 10a as a pale yellow oil (144 mg, 55%). $^1$H NMR (500 MHz, CDCl$_3$) δ 8.84 (s, 1H), 8.11-8.06 (m, 1H), 7.98 (dd, J=1.0, 8.9 Hz, 1H), 7.69 (ddd, J=1.3, 6.8, 8.3 Hz, 1H), 7.59 (ddd, J=1.3, 6.8, 8.3 Hz, 1H), 3.42 (t, J=7.7 Hz, 2H), 2.53 (t, J=7.0 Hz, 2H), 2.46 (t, J=7.0 Hz, 2H), 2.14-2.03 (m, 2H), 1.77-1.62 (m, 2H), 1.10 (t, J=7.4 Hz, 3H). 13C NMR (126 MHz, CDCl$_3$) δ 152.74, 147.14, 146.93, 130.56, 129.49, 127.51, 126.37, 123.25, 119.48, 118.15, 98.32, 77.10, 28.90, 25.79, 22.27, 21.83, 17.31, 13.81. MS (ESI-TOF) for $C_{18}H_{18}N_2$[M+H]$^+$ calculated 263.1543, found 263.1437.

Compound 10b was synthesized similarly as compound 10a.

5-(3-(Pent-1-yn-1-yl)quinolin-4-yl)pentanenitrile (10b). 4-Cyanobutylzinc bromide was used as reagent. Pale yellow oil (174 mg, 63%). $^1$H NMR (500 MHz, CDCl$_3$) δ 8.83 (s, 1H), 8.07 (dd, J=0.8, 8.5 Hz, 11H), 7.97 (dd, J=1.0, 8.5 Hz, 1H), 7.67 (ddd, J=1.4, 6.9, 8.3 Hz, 1H), 7.57 (ddd, J=1.3, 6.9, 8.3 Hz, 1H), 3.30 (t, J=7.5 Hz, 2H), 2.51 (t, J=7.0 Hz, 2H), 2.40 (t, J=7.0 Hz, 2H), 1.95-1.84 (m, 2H), 1.85-1.75 (m, 2H), 1.76-1.65 (m, 2H), 1.10 (t, J=7.4 Hz, 3H). $^{13}$C NMR (126 MHz, CDCl$_3$) δ 152.78, 148.54, 146.91, 130.45, 129.34, 127.22, 126.48, 123.54, 119.52, 117.88, 97.62, 77.51, 29.32, 29.02, 25.41, 22.33, 21.81, 17.20, 13.79. MS (ESI-TOF) for $C_{19}H_{20}N_2$[M+H]$^+$ calculated 277.1699, found 277.1581.

Compounds 14a and 14b were synthesized similarly as compound 9a.

4-(4-Aminobutyl)-3-pentylquinolin-2-amine dihydrochloride (14a). White solid (28 mg, 78%). $^1$H NMR (500 MHz, MeOD) δ 8.11 (d, J=8.1 Hz, 1H), 7.76 (ddd, J=1.2, 7.1, 8.4 Hz, 1H), 7.67 (dd, J=1.2, 8.4 Hz, 1H), 7.57 (ddd, J=1.2, 7.1, 8.3 Hz, 11H), 3.19 (t, J=8.2 Hz, 2H), 3.01 (t, J=7.6 Hz, 2H), 2.80 (t, J=8.2 Hz, 2H), 1.98-1.87 (m, 2H), 1.80-1.70 (m, 2H), 1.65-1.55 (m, 2H), 1.56-1.46 (m, 2H), 1.47-1.38 (m, 2H), 0.96 (t, J=7.2 Hz, 3H). $^{13}$C NMR (126 MHz, MeOD) δ 154.80, 154.01, 135.98, 133.05, 126.77, 126.45, 124.51, 122.47, 118.61, 40.50, 32.81, 29.52, 29.45, 28.86, 28.16, 27.56, 23.73, 14.42. MS (ESI-TOF) for $C_{18}H_{27}N_3$[M+H]$^+$ calculated 286.2278, found 286.2240.

4-(5-Aminopentyl)-3-pentylquinolin-2-amine dihydrochloride (14b). White solid (29 mg, 78%). $^1$H NMR (500 MHz, MeOD) δ 8.09 (d, J=8.2 Hz, 1H), 7.76 (ddd, J=1.2, 7.0, 8.3 Hz, 1H), 7.66 (d, J=7.6 Hz, 11H), 7.56 (ddd, J=1.2, 7.0, 8.3 Hz, 1H), 3.16 (t, J=6.7 Hz, 2H), 2.97 (t, J=7.5 Hz, 2H), 2.79 (t, J=8.4 Hz, 2H), 1.80-1.64 (m, 6H), 1.64-1.56 (m, 2H), 1.54-1.46 (m, 2H), 1.48-1.38 (m, 2H), 0.96 (t, J=7.3 Hz, 3H). $^{13}$C NMR (126 MHz, MeOD) δ 154.78, 154.54, 135.97, 133.00, 126.70, 126.41, 124.30, 122.51, 118.60, 40.61, 32.81, 30.92, 29.79, 29.52, 28.48, 27.85, 27.54, 23.73, 14.41. MS (ESI-TOF) for $C_{19}H_{29}N_3[M+H]^+$ calculated 300.2434, found 300.2397.

5-Bromo-3-pentylquinolin-2-amine (16). To a solution of compound 15 (200 mg, 1 mmol) in DMSO (3 mL) were added heptanenitrile (275 µL, 2 mmol) and t-BuOK (224 mg, 2 mmol). The resulting reaction mixture was stirred for 3 h at 60° C. under nitrogen atmosphere. The reaction mixture was diluted with water and extracted with EtOAc (3×50 mL). The combined organic layer was dried over $Na_2SO_4$ and concentrated under reduced pressure. The crude material was purified by flash chromatography (50% EtOAc/hexanes) to obtain the compound 16 as a off-white solid (220 mg, 75%). $^1$H NMR (500 MHz, DMSO-$d_6$) δ 7.82 (s, 1H), 7.49-7.40 (m, 2H), 7.34 (dd, J=7.6, 8.3 Hz, 1H), 6.58 (s, 2H), 2.62 (t, J=7.8 Hz, 2H), 1.66-1.57 (m, 2H), 1.44-1.29 (m, 4H), 0.89 (t, J=7.0 Hz, 3H). $^{13}$C NMR (126 MHz, DMSO-$d_6$) δ 157.75, 147.59, 132.61, 128.85, 126.08, 124.89, 124.73, 121.98, 120.40, 30.96, 30.29, 27.42, 22.06, 14.01. MS (ESI-TOF) for $C_{14}H_{17}BrN_2$ $[M+H]^+$ calculated 293.0648, found 293.0684.

3-((2-Amino-3-pentylquinolin-5-yl)methyl)benzonitrile (17a). To a solution of compound 16 (58.8 mg, 0.2 mmol) in THF (2 mL) were added 3-cyanobenzylzinc bromide (0.8 mL, 0.4 mmol, 0.5 M in THF) and $Pd(PPh_3)_4$ (11.6 mg, 0.01 mmol). The resulting reaction mixture was stirred at 65° C. under nitrogen atmosphere for 12 h. The reaction mixture was diluted with water and extracted with EtOAc (3×10 mL). The combined organic layer was dried over $Na_2SO_4$ and concentrated under reduced pressure. The crude material was purified by flash chromatography (60% EtOAc/hexanes) to obtain the compound 17a as a pale yellow solid (54 mg, 82%). $^1$H NMR (500 MHz, CDCl$_3$) δ 7.67 (s, 1H), 7.61 (d, J=8.5 Hz, 1H), 7.51-7.44 (m, 3H), 7.40-7.33 (m, 2H), 7.07 (d, J=7.0 Hz, 1H), 4.80 (s, 2H), 4.37 (s, 2H), 2.52 (t, J=7.6 Hz, 2H), 1.66-1.56 (m, 2H), 1.38-1.21 (m, 4H), 0.88 (t, J=7.1 Hz, 3H). $^{13}$C NMR (126 MHz, CDCl$_3$) δ 155.95, 147.28, 142.44, 134.55, 133.17, 132.16, 131.77, 130.13, 129.40, 128.69, 125.59, 124.49, 123.66, 122.91, 119.00, 112.68, 38.40, 31.52, 31.49, 27.56, 22.63, 14.15. MS (ESI-TOF) for $C_{22}H_{23}N_3[M+H]^+$ calculated 330.1965, found 330.1896.

Compounds 17b-d were synthesized similarly as compound 17a.

4-((2-Amino-3-pentylquinolin-5-yl)methyl)benzonitrile (17b). 4-Cyanobenzylzinc bromide was used as reagent. Pale yellow solid (55 mg, 83%). $^1$H NMR (500 MHz, CDCl$_3$) δ 7.66 (s, 1H), 7.62 (d, J=8.5 Hz, 1H), 7.56 (d, J=8.3 Hz, 2H), 7.48 (dd, J=7.0, 8.4 Hz, 1H), 7.30-7.25 (m, 2H), 7.09 (d, J=6.8 Hz, 1H), 4.81 (s, 2H), 4.41 (s, 2H), 2.52 (t, J=7.8 Hz, 2H), 1.66-1.53 (m, 2H), 1.39-1.19 (m, 4H), 0.89 (t, J=7.1 Hz, 3H). $^{13}$C NMR (126 MHz, CDCl$_3$) δ 155.95, 147.26, 146.62, 134.50, 132.44, 131.82, 129.42, 128.68, 125.56, 124.54, 123.63, 122.96, 119.07, 110.20, 39.00, 31.51, 31.45, 27.53, 22.63, 14.15. MS (ESI-TOF) for $C_{22}H23N_3$ $[M+H]^+$ calculated 330.1965, found 330.1899.

2-((2-Amino-3-pentylquinolin-5-yl)methyl)benzonitrile (17c). 2-Cyanobenzylzinc bromide was used as reagent. Pale yellow solid (45 mg, 68%). $^1$H NMR (500 MHz, CDCl$_3$) δ 7.71 (s, 1H), 7.69 (dd, J=1.1, 7.7 Hz, 1H), 7.61 (d, J=8.5 Hz, 1H), 7.47 (dd, J=7.1, 8.5 Hz, 1H), 7.39 (td, J=1.4, 7.7 Hz, 1H), 7.29 (td, J=1.2, 7.6 Hz, 1H), 7.07 (dd, J=1.1, 7.1 Hz, 1H), 7.00 (dd, J=0.6, 7.9 Hz, 1H), 4.81 (s, 2H), 4.57 (s, 2H), 2.53 (t, J=7.6 Hz, 2H), 1.67-1.60 (m, 2H), 1.38-1.22 (m, 4H), 0.87 (t, J=7.1 Hz, 3H). $^{13}$C NMR (126 MHz, CDCl3) δ 156.01, 147.18, 144.65, 134.08, 133.05, 132.87, 131.83, 129.79, 128.64, 126.92, 125.57, 124.59, 123.80, 123.06, 118.25, 112.43, 36.89, 31.56, 31.48, 27.55, 22.62, 14.16. MS (ESI-TOF) for $C_{22}H_{23}N_3[M+H]^+$ calculated 330.1965, found 330.2008.

5-Benzyl-3-pentylquinolin-2-amine (17d). Benzylzinc bromide was used as reagent. White solid (50 mg, 82%). $^1$H NMR (500 MHz, DMSO-$d_6$) δ 7.82 (s, 1H), 7.41-7.31 (m, 2H), 7.28-7.18 (m, 4H), 7.18-7.11 (m, 1H), 7.05-7.00 (m, 1H), 6.21 (s, 2H), 4.28 (s, 2H), 2.55-2.49 (m, 2H), 1.57-1.47 (m, 2H), 1.32-1.17 (m, 4H), 0.83 (t, J=7.2 Hz, 3H). $^{13}$C NMR (126 MHz, DMSO-$d_6$) δ 156.73, 147.10, 141.09, 136.57, 131.20, 128.43, 128.28, 127.75, 125.84, 123.78, 123.50, 122.48, 121.73, 37.77, 30.72, 30.31, 27.23, 22.06, 13.96. MS (ESI-TOF) for $C_{21}H_{24}N_2[M+H]^+$ calculated 305.2012, found 305.1951.

5-(3-(Aminomethyl)benzyl)-3-pentylquinolin-2-amine (18a). A solution of compound 17a (33 mg, 0.1 mmol) in THF (5 mL) was added slowly to a solution of $LiAlH_4$ (0.5 mL, 0.5 mmol, 1.0 M in THF) in THF (3 mL) at 0° C. under nitrogen atmosphere. The reaction mixture was stirred for 2 h at 25° C. and 2 h at 75° C. The reaction mixture was carefully quenched with ice-cold water (1 mL) at 0° C. and 10% NaOH (1 mL) was added. The resulting mixture was stirred for 10 min at room temperature, filtered through celite and washed with $CH_2Cl_2$ (15 mL). The resulting filtrate was dried over $Na_2SO_4$ and concentrated under reduced pressure and the crude material was purified by neutral-alumina column chromatography (20% MeOH/$CH_2Cl_2$) to obtain the compound 18a as a white solid (24 mg, 72%). $^1$H NMR (500 MHz, MeOD) δ 7.88 (s, 1H), 7.46-7.38 (m, 2H), 7.21 (t, J=7.5 Hz, 1H), 7.18-7.10 (m, 3H), 7.06 (d, J=7.4 Hz, 1H), 4.34 (s, 2H), 3.70 (s, 2H), 2.55 (t, J=7.5 Hz, 2H), 1.60 (p, J=7.6 Hz, 2H), 1.42-1.20 (m, 4H), 0.89 (t, J=7.1 Hz, 3H). $^{13}$C NMR (126 MHz, MeOD) δ 158.00, 147.60, 143.84, 142.65, 138.04, 133.82, 129.68, 129.58, 128.69, 128.24, 126.21, 125.12, 125.06, 124.29, 123.67, 46.67, 39.64, 32.47, 31.77, 28.68, 23.64, 14.41. MS (ESI-TOF) for $C_{22}H_{27}N_3[M+H]^+$ calculated 334.2278, found 334.2214.

Compounds 18b and 18c were synthesized similarly as compound 18a.

5-(4-(Aminomethyl)benzyl)-3-pentylquinolin-2-amine (18b). Compound 17b was used as reagent. White solid (25 mg, 75%). $^1$H NMR (500 MHz, MeOD) δ 7.87 (s, 1H), 7.51-7.37 (m, 2H), 7.22 (d, J=8.0 Hz, 2H), 7.14 (d, J=7.9 Hz, 2H), 7.12-7.09 (m, 1H), 4.32 (s, 2H), 3.72 (s, 2H), 2.54 (t, J=7.6 Hz, 2H), 1.68-1.48 (m, 2H), 1.40-1.21 (m, 4H), 0.89 (t, J=7.1 Hz, 3H). $^{13}$C NMR (126 MHz, MeOD) δ 158.00, 147.60, 141.33, 141.04, 138.13, 133.81, 129.74, 129.56, 128.59, 125.10, 124.98, 124.27, 123.63, 46.35, 39.28, 32.48, 31.78, 28.66, 23.64, 14.41. MS (ESI-TOF) for $C_{22}H_{27}N_3$ $[M+H]^+$ calculated 334.2278, found 334.2191.

5-(2-(Aminomethyl)benzyl)-3-pentylquinolin-2-amine (18c). Compound 17c was used as reagent. White solid (21 mg, 63%). $^1$H NMR (500 MHz, MeOD) δ 7.90 (s, 1H), 7.47-7.33 (m, 3H), 7.24 (td, J=1.3, 7.5 Hz, 1H), 7.15 (td, J=1.4, 7.5 Hz, 1H), 6.93 (dd, J=1.3, 7.7 Hz, 1H), 6.84 (dd, J=1.1, 7.1 Hz, 1H), 4.42 (s, 2H), 3.84 (s, 2H), 2.59 (t, J=7.8 Hz, 2H), 1.68-1.57 (m, 2H), 1.40-1.27 (m, 4H), 0.90 (t, J=7.1 Hz, 3H). 3C NMR (126 MHz, MeOD) δ 158.12, 147.46, 141.29, 139.25, 137.80, 133.50, 131.09, 129.58, 129.13, 128.27, 127.89, 125.42, 124.27, 124.19, 123.78, 43.84, 35.93, 32.58, 31.94, 28.87, 23.65, 14.42. MS (ESI-TOF) for $C_{22}H_{27}N_3[M+H]^+$ calculated 334.2278, found 334.2195.

3-((2-Amino-3-pentylquinolin-5-yl)methyl)benzamide (18d). To a solution of compound 17a (33 mg, 0.1 mmol) in t-BuOH (2 mL) was added potassium hydroxide (84 mg, 1.5 mmol). The reaction mixture was stirred for 8 h at 60° C. The reaction was allowed to cool to room temperature, the solvent was removed under reduced pressure and the crude solubilized in ethyl acetate. The organic layer was washed with water and saturated aqueous ammonium chloride, and dried over $Na_2SO_4$ and evaporated under reduced pressure. The residue was purified by silica gel flash-column chromatography (15% $MeOH/CH_2Cl_2$) to afford the compound (18d) as a white solid (18 mg, 52%). $^1$H NMR (500 MHz, MeOD) δ 7.88 (s, 1H), 7.78 (d, J=0.8 Hz, 1H), 7.68 (dt, J=1.9, 7.0 Hz, 1H), 7.49-7.43 (m, 2H), 7.38-7.27 (m, 2H), 7.16 (dd, J=3.2, 5.0 Hz, 1H), 4.42 (s, 2H), 2.56 (t, J=7.1 Hz, 2H), 1.58 (p, J=7.5 Hz, 2H), 1.36-1.27 (m, 2H), 1.28-1.19 (m, 2H), 0.86 (t, J=7.2 Hz, 3H). $^{13}$C NMR (126 MHz, MeOD) δ 172.26, 157.87, 147.04, 142.96, 137.61, 135.13, 134.03, 133.11, 129.84, 129.66, 128.98, 126.42, 125.39, 125.32, 124.08, 123.44, 39.47, 32.39, 31.68, 28.61, 23.59, 14.39. MS (ESI-TOF) for $C_{22}H_{25}N3O$ $[M+H]^+$ calculated 348.2070, found 348.2022.

3-(2-Amino-3-pentylquinolin-5-yl)benzonitrile (19a). To a stirred solution of compound 16 (59 mg, 0.2 mmol) in 1,4-dioxane (2 mL) were added 3-cyanophenylboronic acid (44 mg, 0.3 mmol), $Pd(dppf)Cl_2$ (14.6 mg, 0.02 mmol), and $K_2CO_3$ (83 mg, 0.6 mmol). The resulting reaction mixture was stirred for 12 h at 90° C. under nitrogen atmosphere. The reaction mixture was diluted with water and extracted with EtOAc (3×20 mL). The combined organic layer was dried over $Na_2SO_4$ and concentrated under reduced pressure, and crude material was purified by flash chromatography (60% EtOAc/hexanes) to obtain the compound 19a as a brownish solid (40 mg, 63%). $^1$H NMR (500 MHz, $CDCl_3$) δ 7.77-7.66 (m, 4H), 7.64-7.52 (m, 3H), 7.15 (dd, J=1.2, 7.1 Hz, 1H), 4.89 (s, 2H), 2.53 (t, J=7.6 Hz, 2H), 1.67-1.57 (m, 2H), 1.39-1.31 (m, 4H), 0.89 (t, J=6.9 Hz, 3H). $^{13}$C NMR (126 MHz, CDCl3) δ 156.25, 146.96, 141.74, 137.22, 134.46, 133.42, 132.79, 131.10, 129.35, 128.42, 126.31, 124.37, 123.92, 122.25, 118.90, 112.78, 31.69, 31.59, 27.74, 22.57, 14.15. MS (ESI-TOF) for $C_{21}H_{21}N_3[M+H]^+$ calculated 316.1808, found 316.1823.

Compound 19b was synthesized similarly as compound 19a.

4-(2-Amino-3-pentylquinolin-5-yl)benzonitrile (19b). 4-Cyanophenylboronic acid was used as reagent. Brownish solid (38 mg, 60%). $^1$H NMR (500 MHz, $CDCl_3$) δ 7.83-7.76 (m, 2H), 7.71 (d, Jr 8.4 Hz, 1H), 7.61 (s, 1H), 7.60-7.53 (m, 3H), 7.17 (dd, J=1.2, 7.2 Hz, 1H), 4.89 (s, 2H), 2.52 (t, J=7.7 Hz, 2H), 1.67-1.55 (m, 2H), 1.40-1.31 (m, 4H), 0.89 (t, J=7.0 Hz, 3H). $^{13}$C NMR (126 MHz, $CDCl_3$) δ 156.24, 146.97, 145.32, 137.73, 132.84, 132.32, 130.78, 128.40, 126.40, 124.35, 123.80, 122.09, 119.04, 111.30, 31.68, 31.56, 27.73, 22.57, 14.16. MS (ESI-TOF) for $C_{21}H_{21}N_3$ $[M+H]^+$ calculated 316.1808, found 316.1845.

Compounds 20a-b were synthesized similarly as compound 18a.

5-(3-(Aminomethyl)phenyl)-3-pentylquinolin-2-amine (20a). Compound 19a was used as reagent. White solid (21 mg, 66%). $^1$H NMR (500 MHz, MeOD) δ 7.73 (s, 1H), 7.58-7.39 (m, 5H), 7.30 (d, J=6.7 Hz, 1H), 7.16 (d, J=6.6 Hz, 1H), 3.88 (s, 2H), 2.56 (t, J=7.6 Hz, 2H), 1.68-1.53 (m, 2H), 1.38-1.29 (m, 4H), 0.90 (t, J=6.7 Hz, 3H). $^{13}$C NMR (126 MHz, MeOD) δ 158.28, 147.40, 144.04, 141.73, 141.28, 134.86, 130.00, 129.55, 129.53, 129.41, 127.59, 125.60, 124.69, 124.34, 123.07, 46.69, 32.56, 31.81, 28.73, 23.59, 14.39. MS (ESI-TOF) for $C_{21}H_{25}N_3[M+H]^+$ calculated 320.2121, found 320.2072.

5-(4-(Aminomethyl)phenyl)-3-pentylquinolin-2-amine (20b). Compound 19b was used as reagent. White solid (20 mg, 63%). $^1$H NMR (500 MHz, MeOD) δ 7.72 (s, 1H), 7.57-7.45 (m, 4H), 7.39 (d, J=8.1 Hz, 2H), 7.13 (dd, J=1.7, 6.6 Hz, 1H), 3.89 (s, 2H), 2.54 (t, J=7.6 Hz, 2H), 1.67-1.51 (m, 2H), 1.38-1.26 (m, 4H), 0.89 (t, J=7.0 Hz, 3H). $^{13}$C NMR (126 MHz, MeOD) δ 158.26, 147.42, 142.97, 141.07, 140.07, 134.82, 131.06, 129.43, 128.56, 125.58, 124.65, 124.33, 123.07, 46.45, 32.58, 31.88, 28.78, 23.57, 14.40. MS (ESI-TOF) for $C_{21}H_{25}N_3[M+H]+$ calculated 320.2121, found 320.2073.

5-(3-Aminopropyl)-3-pentylquinolin-2-amine (23). A solution of 16 (147 mg, 0.5 mmol) and acrylonitrile (66 μL, 1 mmol) in DMF (4 mL) was treated with $Pd(OAc)_2$ (11.2 mg, 0.05 mmol), $PPh_3$ (26.2 mg, 0.1 mmol) and $K_2CO_3$ (138 mg, 1 mmol). The resulting reaction mixture was stirred for 12 h at 110° C. under nitrogen atmosphere. The reaction mixture was diluted with water and extracted with EtOAc (3×20 mL). The combined organic layer was dried over $Na_2SO_4$ and concentrated under reduced pressure. The crude material was purified by flash chromatography (60% EtOAc/hexanes) to obtain the compound 21 as a pale yellow solid (73 mg, 55%). MS (ESI-TOF) for $C_{17}H_{19}N_3[M+H]^+$ calculated 266.1652, found 266.1663. To a solution of compound 21 (53 mg, 0.2 mmol) in anhydrous EtOAc (10 mL) was added a catalytic amount of Pt/C, and the reaction mixture was subjected to hydrogenation at 30 psi for 3 h. The reaction mixture was filtered, and the filtrate concentrated under reduced pressure. The crude material was purified using silica gel column chromatography (60% EtOAc/hexanes) to obtain compound 22 as white solid (40 mg, 75%). MS (ESI-TOF) for $C_{17}H_{21}N_3[M+H]^+$ calculated 268.1808, found 268.1821. A solution of compound 22 (27 mg, 0.1 mmol) in THF (5 mL) was added slowly to a solution of $LiAlH_4$ (0.5 mL, 0.5 mmol, 1.0 M in THF) in THF (3 mL) at 0° C. under nitrogen atmosphere. The reaction mixture was stirred for 2 h at 25° C. and 2 h at 60° C. The reaction mixture was carefully quenched with ice-cold water (1 mL) at 0° C. and 10% NaOH (1 mL) was added. The resulting mixture was stirred for 10 min at room temperature, filtered through celite and washed with $CH_2Cl_2$ (15 mL). The resulting filtrate was dried over $Na_2SO_4$ and concentrated under reduced pressure and the crude material was purified by flash neutral-alumina column chromatography (20% $MeOH/CH_2Cl_2$) to obtain the compound 23 as a white solid (15 mg, 55%). $^1$H NMR (500 MHz, MeOD) δ 7.99 (s, 1H), 7.40-7.37 (m, 2H), 7.09 (dd, J=2.8, 5.4 Hz, 1H), 3.02 (t, J=7.5 Hz, 2H), 2.73 (t, J=7.2 Hz, 2H), 2.68 (t, J=7.6 Hz, 2H), 1.92-1.80 (m, 2H), 1.78-1.68 (m, 2H), 1.48-1.40 (m, 4H), 0.95 (t, J=7.1 Hz, 3H). $^{13}$C NMR (126 MHz, MeOD) δ 158.00, 147.49, 139.44, 133.35, 129.58, 125.36, 123.72, 123.66, 123.41, 42.35, 35.26, 32.80, 32.15, 30.76, 29.17, 23.69, 14.46. MS (ESI-TOF) for $C_{17}H_{25}N_3$ $[M+H]^+$ calculated 272.2121, found 272.2155.

Compounds 27-29 were synthesized similarly as compound 16.

6-Bromo-3-pentylquinolin-2-amine (27). Compound 24 was used as reagent. White solid (230 mg, 78%). $^1$H NMR (500 MHz, $CDCl_3$) δ 7.74 (d, J=2.2 Hz, 1H), 7.58 (s, 11H), 7.56 (dd, J=2.2, 8.9 Hz, 11H), 7.51 (d, J=8.8 Hz, 11H), 4.87 (s, 2H), 2.57 (t, J=7.7 Hz, 2H), 1.78-1.66 (m, 2H), 1.45-1.36 (m, 4H), 0.93 (t, J=7.0 Hz, 3H). 13C NMR (126 MHz, CDCl3) δ 156.49, 145.21, 134.44, 132.05, 129.08, 127.43, 125.84, 124.79, 115.57, 31.76, 31.24, 27.56, 22.67, 14.17. MS (ESI-TOF) for $C_{14}H_{17}BrN_2$ $[M+H]^+$ calculated 293.0648, found 293.0654.

7-Bromo-3-pentylquinolin-2-amine (28). Compound 25 was used as reagent. Yellow solid (220 mg, 75%). $^1$H NMR (500 MHz, $CDCl_3$) δ 7.81 (d, J=2.2 Hz, 1H), 7.63 (s, 1H), 7.45 (d, J=8.5 Hz, 1H), 7.32 (dd, J=1.9, 8.5 Hz, 1H), 4.93 (s, 2H), 2.55 (t, J=7.9 Hz, 2H), 1.76-1.67 (m, 2H), 1.44-1.36 (m, 4H), 0.93 (t, J=7.0 Hz, 3H). $^{13}$C NMR (126 MHz, CDCl$_3$) δ 156.88, 147.41, 135.17, 128.30, 128.09, 125.98, 124.16, 123.19, 122.73, 31.79, 31.24, 27.56, 22.67, 14.17. MS (ESI-TOF) for C$_{14}$H$_{17}$BrN$_2$ [M+H]$^+$ calculated 293.0648, found 293.0669.

8-Bromo-3-pentylquinolin-2-amine (29). Compound 26 was used as reagent. Pale yellow solid (250 mg, 85%). $^1$H NMR (500 MHz, CDCl$_3$) δ 7.82 (dd, J=1.4, 7.5 Hz, 11H), 7.65 (s, 11H), 7.55 (dd, J=1.4, 7.9 Hz, 1H), 7.08 (t, J=7.7 Hz, 1H), 5.04 (s, 2H), 2.58 (t, J=7.5 Hz, 2H), 1.78-1.65 (m, 2H), 1.48-1.30 (m, 4H), 0.92 (t, J=7.0 Hz, 3H). $^{13}$C NMR (126 MHz, CDCl$_3$) δ 157.09, 143.79, 135.84, 132.41, 126.93, 125.67, 124.65, 122.94, 120.61, 31.76, 31.08, 27.58, 22.67, 14.16. MS (ESI-TOF) for C$_{14}$H$_{17}$BrN$_2$ [M+H]$^+$ calculated 293.0648, found 293.0675.

Compounds 30a-c, 31a-c, 32a-c and 33 were synthesized similarly as compound 17a.

4-(2-Amino-3-pentylquinolin-5-yl)butanenitrile (30a). Compound 16 and 3-cyanopropylzinc bromide were used as reagents. White solid (44 mg, 78%). $^1$H NMR (500 MHz, CDCl$_3$) δ 7.86 (s, 1H), 7.56 (d, J=8.4 Hz, 1H), 7.44 (d, J=7.1, 8.4 Hz, 1H), 7.10 (dd, J=1.1, 7.1 Hz, 1H), 4.83 (s, 2H), 3.15 (t, J=7.4 Hz, 2H), 2.62 (t, J=7.7 Hz, 2H), 2.36 (t, J=7.0 Hz, 2H), 2.12-2.01 (m, 2H), 1.79-1.68 (m, 2H), 1.45-1.37 (m, 4H), 0.93 (t, J=7.0 Hz, 3H). $^{13}$C NMR (126 MHz, CDCl$_3$) δ 155.95, 147.16, 135.47, 131.33, 128.61, 125.08, 123.79, 123.28, 122.75, 119.71, 31.84, 31.77, 31.02, 27.95, 26.64, 22.66, 16.84, 14.21. MS (ESI-TOF) for C$_{18}$H$_{23}$N$_3$[M+H]+ calculated 282.1965, found 282.1904.

5-(2-Amino-3-pentylquinolin-5-yl)pentanenitrile (30b). Compound 16 and 4-cyanobutylzinc bromide were used as reagents. Off-white solid (45 mg, 76%). $^1$H NMR (500 MHz, CDCl$_3$) δ 7.84 (s, 1H), 7.54 (d, J=8.4 Hz, 1H), 7.43 (dd, J=7.1, 8.4 Hz, 11H), 7.07 (dd, J=1.1, 7.1 Hz, 11H), 4.80 (s, 2H), 3.02 (t, J=7.5 Hz, 2H), 2.62 (t, J=7.6 Hz, 2H), 2.37 (t, J=7.1 Hz, 2H), 1.93-1.83 (m, 2H), 1.80-1.69 (m, 4H), 1.47-1.36 (m, 4H), 0.93 (t, J=7.1 Hz, 3H). $^{13}$C NMR (126 MHz, CDCl$_3$) δ 155.86, 147.12, 136.99, 131.59, 128.56, 124.66, 123.49, 123.01, 122.83, 119.68, 31.82, 31.77, 31.69, 29.93, 27.97, 25.25, 22.67, 17.27, 14.22. MS (ESI-TOF) for C$_{19}$H$_{25}$N$_3$[M+H]$^+$ calculated 296.2121, found 296.2068.

6-(2-Amino-3-pentylquinolin-5-yl)hexanenitrile (30c). Compound 16 and 5-cyanopentylzinc bromide were used as reagents. White solid (38 mg, 61%). $^1$H NMR (500 MHz, CDCl$_3$) δ 7.84 (s, 1H), 7.53 (d, J=8.4 Hz, 1H), 7.42 (dd, J=7.1, 8.4 Hz, 1H), 7.07 (dd, J=1.2, 7.0 Hz, 1H), 4.80 (s, 2H), 2.99 (t, J=7.6 Hz, 2H), 2.62 (t, J=7.7 Hz, 2H), 2.34 (t, J=7.1 Hz, 2H), 1.80-1.64 (m, 6H), 1.62-1.53 (m, 2H), 1.45-1.36 (m, 4H), 0.93 (t, J=7.0 Hz, 3H). $^{13}$C NMR (126 MHz, CDCl$_3$) δ 155.81, 147.02, 137.81, 131.78, 128.58, 124.38, 123.33, 122.91, 122.86, 119.84, 32.30, 31.79, 31.75, 30.36, 28.78, 27.98, 25.48, 22.68, 17.29, 14.22. MS (ESI-TOF) for C$_{20}$H$_{27}$N$_3$[M+H]$^+$ calculated 310.2278, found 310.2323.

4-(2-Amino-3-pentylquinolin-6-yl)butanenitrile (31a). Compound 27 and 3-cyanopropylzinc bromide were used as reagents. White solid (35 mg, 62%). $^1$H NMR (500 MHz, CDCl$_3$) δ 7.64 (s, 1H), 7.60 (d, J=8.5 Hz, 1H), 7.41 (d, J=2.0 Hz, 1H), 7.34 (dd, J=2.1, 8.5 Hz, 1H), 4.80 (s, 2H), 2.89 (t, J=7.3 Hz, 2H), 2.58 (t, J=7.7 Hz, 2H), 2.33 (t, J=7.1 Hz, 2H), 2.13-1.95 (m, 2H), 1.79-1.65 (m, 2H), 1.45-1.36 (m, 4H), 0.93 (t, J=7.1 Hz, 3H). $^{13}$C NMR (126 MHz, CDCl$_3$) δ 156.14, 145.35, 135.19, 133.81, 129.65, 126.26, 126.06, 124.58, 124.15, 119.73, 34.18, 31.80, 31.31, 27.71, 27.02, 22.69, 16.47, 14.19. MS (ESI-TOF) for C$_{18}$H$_{23}$N$_3$[M+H]$^+$ calculated 282.1965, found 282.1832.

5-(2-Amino-3-pentylquinolin-6-yl)pentanenitrile (31b). Compound 27 and 4-cyanobutylzinc bromide were used as reagents. Pale yellow solid (39 mg, 66%). $^1$H NMR (500 MHz, CDCl$_3$) δ 7.63 (s, 1H), 7.59 (d, J=8.5 Hz, 1H), 7.37 (d, J=1.9 Hz, 1H), 7.34 (dd, J=2.1, 8.5 Hz, 1H), 4.78 (s, 2H), 2.76 (t, J=7.4 Hz, 2H), 2.57 (t, J=7.8 Hz, 2H), 2.36 (t, J=7.1 Hz, 2H), 1.89-1.80 (m, 2H), 1.76-1.69 (m, 4H), 1.48-1.30 (m, 4H), 0.93 (t, J=7.0 Hz, 3H). $^{13}$C NMR (126 MHz, CDCl$_3$) δ 155.97, 145.13, 135.46, 135.22, 129.91, 125.82, 125.76, 124.56, 123.98, 119.80, 34.84, 31.80, 31.32, 30.41, 27.74, 24.96, 22.70, 17.26, 14.19. MS (ESI-TOF) for C$_{19}$H$_{25}$N$_3$[M+H]$^+$ calculated 296.2121, found 296.2146.

6-(2-Amino-3-pentylquinolin-6-yl)hexanenitrile (31c). Compound 27 and 5-cyanopentylzinc bromide were used as reagents. Pale yellow solid (40 mg, 65%). $^1$H NMR (500 MHz, CDCl$_3$) δ 7.63 (s, 1H), 7.58 (d, J=8.5 Hz, 1H), 7.37 (d, J=1.9 Hz, 1H), 7.34 (dd, J=2.1, 8.5 Hz, 1H), 4.77 (s, 2H), 2.73 (t, J=7.6 Hz, 2H), 2.57 (t, J=7.7 Hz, 2H), 2.33 (t, J=7.1 Hz, 2H), 1.78-1.61 (m, 6H), 1.56-1.46 (m, 2H), 1.44-1.36 (m, 4H), 0.93 (t, J=7.0 Hz, 3H). $^{13}$C NMR (126 MHz, CDCl3) δ 155.89, 145.03, 136.28, 135.24, 130.01, 125.75, 125.63, 124.55, 123.88, 119.93, 35.44, 31.81, 31.33, 30.77, 28.42, 27.76, 25.47, 22.70, 17.27, 14.19. MS (ESI-TOF) for C$_{20}$H$_{27}$N$_3$ [M+H]$^+$ calculated 310.2278, found 310.2309.

4-(2-Amino-3-pentylquinolin-7-yl)butanenitrile (32a). Compound 28 and 3-cyanopropylzinc bromide were used as reagents. Pale yellow solid (33 mg, 59%). $^1$H NMR (500 MHz, CDCl$_3$) δ 7.66 (s, 1H), 7.55 (d, J=8.1 Hz, 1H), 7.45 (s, 1H), 7.09 (dd, J=1.7, 8.1 Hz, 1H), 4.83 (s, 2H), 2.91 (t, J=7.3 Hz, 2H), 2.57 (t, J=7.6 Hz, 2H), 2.34 (t, J=7.1 Hz, 2H), 2.12-2.02 (m, 2H), 1.78-1.68 (m, 2H), 1.51-1.31 (m, 4H), 0.93 (t, J=7.0 Hz, 3H). $^{13}$C NMR (126 MHz, CDCl3) δ 156.54, 146.63, 140.61, 135.31, 127.40, 124.69, 123.73, 123.46, 123.24, 119.70, 34.72, 31.80, 31.27, 27.73, 26.85, 22.69, 16.52, 14.19. MS (ESI-TOF) for C$_{18}$H$_{23}$N$_3$[M+H]$^+$ calculated 282.1965, found 282.1978.

5-(2-Amino-3-pentylquinolin-7-yl)pentanenitrile (32b). Compound 28 and 4-cyanobutylzinc bromide were used as reagents. Off-white solid (36 mg, 61%). $^1$H NMR (500 MHz, CDCl$_3$) δ 7.66 (s, 1H), 7.54 (d, J=8.1 Hz, 1H), 7.43 (s, 1H), 7.09 (dd, J=1.7, 8.2 Hz, 1H), 4.81 (s, 2H), 2.79 (t, J=7.4 Hz, 2H), 2.57 (t, J=7.6 Hz, 2H), 2.34 (t, J=7.1 Hz, 2H), 1.94-1.81 (m, 2H), 1.77-1.63 (m, 4H), 1.45-1.36 (m, 4H), 0.93 (t, 3H). $^{13}$C NMR (126 MHz, CDCl$_3$) δ 156.44, 146.56, 142.18, 135.36, 127.15, 124.52, 123.82, 123.20, 123.00, 119.77, 35.26, 31.80, 31.26, 30.06, 27.75, 24.87, 22.69, 17.22, 14.19. MS (ESI-TOF) for C$_{19}$H$_{25}$N$_3$[M+H]$^+$ calculated 296.2121, found 296.2168.

6-(2-Amino-3-pentylquinolin-7-yl)hexanenitrile (32c). Compound 28 and 5-cyanopentylzinc bromide were used as reagents. Pale yellow solid (39 mg, 63%). MS (ESI-TOF) for C$_{20}$H$_{27}$N$_3$[M+H]$^+$ calculated 310.2278, found 310.2309.

4-(2-Amino-3-pentylquinolin-8-yl)butanenitrile (33). Compound 29 and 3-cyanopropylzinc bromide were used as reagents. Pale yellow solid (30 mg, 53%). $^1$H NMR (500 MHz, CDCl$_3$) δ 7.66 (s, 1H), 7.49 (dd, J=1.5, 8.0 Hz, 1H), 7.35 (dd, J=1.4, 7.1 Hz, 1H), 7.16 (dd, J=7.1, 8.0 Hz, 1H), 4.79 (s, 2H), 3.23 (t, J=7.2 Hz, 2H), 2.58 (t, J=7.6 Hz, 2H), 2.32 (t, J=7.1 Hz, 2H), 2.19-2.09 (m, 2H), 1.79-1.66 (m, 2H), 1.45-1.33 (m, 4H), 0.93 (t, J=7.1 Hz, 3H). $^{13}$C NMR (126 MHz, CDCl$_3$) δ 155.58, 145.03, 135.76, 135.33, 128.76, 125.91, 124.72, 123.64, 122.30, 120.54, 31.83, 31.28, 30.49, 27.78, 26.53, 22.70, 16.95, 14.19. MS (ESI-TOF) for C$_{18}$H$_{23}$N$_3$[M+H]$^+$ calculated 282.1965, found 282.2008.

Compounds 34a-c were synthesized similarly as compound 18a.

5-(4-Aminobutyl)-3-pentylquinolin-2-amine (34a). Compound 30a was used as reagent. White solid (20 mg, 70%). $^1$H NMR (500 MHz, MeOD) δ 7.95 (s, 1H), 7.42-7.35 (m, 2H), 7.08 (dd, J=3.1, 5.1 Hz, 1H), 3.00 (t, J=7.6 Hz, 2H), 2.69-2.63 (m, 4H), 1.78-1.64 (m, 4H), 1.61-1.50 (m, 2H), 1.46-1.40 (m, 4H), 0.95 (t, J=7.0 Hz, 3H). $^{13}$C NMR (126 MHz, MeOD) δ 157.97, 147.47, 139.74, 133.37, 129.56, 125.18, 123.77, 123.64, 123.41, 42.51, 33.75, 33.21, 32.72, 32.07, 29.82, 29.05, 23.68, 14.47. MS (ESI-TOF) for $C_{18}H_{27}N_3[M+H]^+$ calculated 286.2278, found 286.2218.

5-(5-Aminopentyl)-3-pentylquinolin-2-amine (34b). Compound 30b was used as reagent. White solid (21 mg, 70%). $^1$H NMR (500 MHz, MeOD) δ 7.94 (s, 1H), 7.42-7.32 (m, 2H), 7.06 (dd, J=2.9, 5.4 Hz, 1H), 2.98 (t, J=7.6 Hz, 2H), 2.67 (t, J=7.6 Hz, 2H), 2.62 (t, J=7.0 Hz, 2H), 1.78-1.65 (m, 4H), 1.57-1.47 (m, 2H), 1.49-1.39 (m, 6H), 0.95 (t, J=7.0 Hz, 3H). $^{13}$C NMR (126 MHz, MeOD) δ 157.96, 147.46, 139.91, 133.37, 129.57, 125.12, 123.73, 123.58, 123.39, 42.53, 33.77, 33.35, 32.69, 32.39, 32.04, 29.03, 27.94, 23.68, 14.47. MS (ESI-TOF) for $C_{19}H_{29}N_3[M+H]^+$ calculated 300.2434, found 300.2374.

5-(6-Aminohexyl)-3-pentylquinolin-2-amine (34c). Compound 30c was used as reagent. White solid (18 mg, 57%). $^1$H NMR (500 MHz, MeOD) δ 7.95 (s, 1H), 7.41-7.32 (m, 2H), 7.06 (dd, J=3.0, 5.3 Hz, 1H), 2.98 (t, J=7.6 Hz, 2H), 2.67 (t, J=7.4 Hz, 2H), 2.63 (t, J=7.0 Hz, 2H), 1.71 (dq, J=7.8, 15.5 Hz, 4H), 1.50-1.37 (m, 10H), 0.95 (t, J=7.0 Hz, 3H). $^{13}$C NMR (126 MHz, MeOD) δ 157.96, 147.45, 140.00, 133.37, 129.56, 125.08, 123.72, 123.55, 123.39, 42.40, 33.46, 33.34, 32.68, 32.51, 32.00, 30.48, 28.99, 27.93, 23.68, 14.47. MS (ESI-TOF) for $C_{20}H_{31}N_3[M+H]^+$ calculated 314.2591, found 314.2537.

Compound 34d was synthesized similarly as compound 18d.

4-(2-Amino-3-pentylquinolin-5-yl)butanamide (34d). Compound 30a was used as reagent. White solid (15 mg, 50%). $^1$H NMR (500 MHz, MeOD) δ 8.02 (s, 1H), 7.45-7.31 (m, 2H), 7.08 (dd, J=2.9, 5.4 Hz, 1H), 3.01 (t, J=7.7 Hz, 2H), 2.68 (t, J=7.7 Hz, 2H), 2.30 (t, J=7.3 Hz, 2H), 2.03-1.91 (m, 2H), 1.80-1.66 (m, 2H), 1.48-1.38 (m, 4H), 0.94 (t, J=7.0 Hz, 3H). $^{13}$C NMR (126 MHz, MeOD) δ 178.76, 157.96, 147.27, 139.18, 133.57, 129.64, 125.45, 123.92, 123.69, 123.43, 35.95, 32.85, 32.76, 32.13, 29.12, 28.38, 23.68, 14.47. MS (ESI-TOF) for $C_{18}H_{25}N_3O [M+H]^+$ calculated 300.2070, found 300.2025.

1-(4-(2-Amino-3-pentylquinolin-5-yl)butyl)guanidine (34e). 1H-Pyrazole-1-carboxamidine hydrochloride (16 mg, 0.11 mmol) and Et$_3$N (15.3 μL, 0.11 mmol) were added to a solution of compound 34a (28.5 mg, 0.1 mmol) in MeOH (2 mL), and the reaction mixture was stirred for 3 h at room temperature. The solvent was removed under reduced pressure and the crude material was purified by basic-alumina column chromatography (30% MeOH/CH$_2$Cl$_2$) to obtain 34e as a white solid (16 mg, 49%). $^1$H NMR (500 MHz, DMSO-d$_6$) δ 7.82 (s, 1H), 7.60 (t, J=5.7 Hz, 1H), 7.36-7.24 (m, 3H), 6.98 (dd, J=3.1, 5.3 Hz, 1H), 6.84 (s, 2H), 6.22 (s, 2H), 3.13 (q, J=6.9 Hz, 2H), 2.92 (t, J=7.5 Hz, 2H), 2.60 (t, J=7.6 Hz, 2H), 1.68-1.56 (m, 4H), 1.58-1.46 (m, 2H), 1.39-1.29 (m, 4H), 0.88 (t, J=7.0 Hz, 3H). $^{13}$C NMR (126 MHz, DMSO-d$_6$) δ 156.72, 156.66, 146.95, 137.62, 130.71, 127.62, 123.66, 123.27, 121.56, 121.26, 40.52, 31.08, 30.96, 30.56, 28.36, 27.64, 27.62, 22.03, 14.00. MS (ESI-TOF) for $C_{19}H_{29}N_5[M+H]^+$ calculated 328.2496, found 328.2444.

Compounds 35a-c, 36a-c and 37 were synthesized similarly as compound 18a.

6-(4-Aminobutyl)-3-pentylquinolin-2-amine (35a). Compound 31a was used as reagent. White solid (16 mg, 56%). $^1$H NMR (500 MHz, MeOD) δ 7.70 (s, 1H), 7.48-7.40 (m, 211), 7.36 (dd, J=2.0, 8.5 Hz, 11H), 2.73 (t, J=7.5 Hz, 2H), 2.66 (t, J=7.3 Hz, 2H), 2.62 (t, J=7.5 Hz, 2H), 1.76-1.66 (m, 4H), 1.57-1.47 (m, 2H), 1.46-1.39 (m, 4H), 0.94 (t, J=7.1 Hz, 3H). $^{13}$C NMR (126 MHz, MeOD) δ 158.06, 145.47, 137.66, 136.72, 131.08, 126.94, 125.75, 125.30, 124.97, 42.38, 36.34, 33.20, 32.78, 31.81, 29.96, 28.96, 23.68, 14.43. MS (ESI-TOF) for $C_{18}H27N_3 [M+H]^+$ calculated 286.2278, found 286.2283.

6-(5-Aminopentyl)-3-pentylquinolin-2-amine (35b). Compound 31b was used as reagent. Off-white solid (19 mg, 63%). $^1$H NMR (500 MHz, MeOD) δ 7.70 (s, 1H), 7.45 (d, J=8.5 Hz, 1H), 7.41 (s, 11H), 7.35 (dd, J=2.0, 8.5 Hz, 11H), 2.72 (t, J=7.6 Hz, 2H), 2.66-2.58 (m, 4H), 1.76-1.65 (m, 4H), 1.55-1.48 (m, 2H), 1.47-1.35 (m, 6H), 0.95 (t, J=6.9 Hz, 3H). $^{13}$C NMR (126 MHz, MeOD) δ 158.03, 145.42, 137.86, 136.72, 131.09, 126.88, 125.73, 125.30, 124.92, 42.50, 36.48, 33.66, 32.80, 32.61, 31.82, 28.97, 27.61, 23.68, 14.43. MS (ESI-TOF) for $C_{19}H_{29}N_3[M+H]^+$ calculated 300.2434, found 300.2487.

6-(6-Aminohexyl)-3-pentylquinolin-2-amine (35c). Compound 31c was used as reagent. Off-white solid (20 mg, 64%). $^1$H NMR (500 MHz, MeOD) δ 7.70 (s, 1H), 7.44 (d, J=8.5 Hz, 1H), 7.40 (s, 1H), 7.34 (dd, J=2.0, 8.5 Hz, 1H), 2.70 (t, J=7.6 Hz, 2H), 2.65-2.57 (m, 4H), 1.76-1.62 (m, 4H), 1.49-1.33 (m, 10H), 0.94 (t, J=7.0 Hz, 3H). $^{13}$C NMR (126 MHz, MeOD) δ 158.02, 145.41, 137.96, 136.71, 131.10, 126.86, 125.72, 125.30, 124.90, 42.52, 36.50, 33.73, 32.80, 32.70, 31.83, 30.18, 28.97, 27.89, 23.68, 14.44. MS (ESI-TOF) for $C_{20}H_{31}N_3[M+H]^+$ calculated 314.2591, found 314.2649.

7-(4-Aminobutyl)-3-pentylquinolin-2-amine (36a). Compound 32a was used as reagent. Off-white solid (19 mg, 67%). $^1$H NMR (500 MHz, MeOD) δ 7.71 (s, 1H), 7.53 (d, J=8.1 Hz, 1H), 7.33 (s, 1H), 7.10 (dd, J=1.7, 8.2 Hz, 1H), 2.75 (t, J=7.6 Hz, 2H), 2.65 (t, J=7.2 Hz, 2H), 2.61 (t, J=7.6 Hz, 2H), 1.78-1.65 (m, 4H), 1.58-1.48 (m, 2H), 1.46-1.39 (m, 4H), 0.94 (t, J=7.0 Hz, 3H). $^{13}$C NMR (126 MHz, MeOD) δ 158.52, 147.11, 144.79, 136.77, 128.05, 124.90, 124.62, 123.96, 123.62, 42.44, 36.97, 33.45, 32.77, 31.75, 29.78, 28.97, 23.68, 14.42. MS (ESI-TOF) for $C_{18}H_{27}N_3 [M+H]^+$ calculated 286.2278, found 286.2287.

7-(5-Aminopentyl)-3-pentylquinolin-2-amine (36b). Compound 32b was used as reagent. White solid (18 mg, 60%). $^1$H NMR (500 MHz, MeOD) δ 7.71 (s, 1H), 7.53 (d, J=8.1 Hz, J H), 7.32 (s, 1H), 7.08 (dd, J=1.7, 8.1 Hz, 1H), 2.74 (t, J=7.6 Hz, 2H), 2.65-2.58 (m, 4H), 1.76-1.66 (m, 4H), 1.56-1.47 (m, 2H), 1.46-1.36 (m, 6H), 0.94 (t, J=7.0 Hz, 3H). 13C NMR (126 MHz, MeOD) δ 158.52, 147.10, 144.96, 136.78, 128.02, 124.88, 124.64, 123.90, 123.58, 42.47, 37.08, 33.62, 32.78, 32.38, 31.75, 28.97, 27.62, 23.68, 14.43. MS (ESI-TOF) for $C_{19}H_{29}N_3[M+H]^+$ calculated 300.2434, found 300.2486.

7-(6-Aminohexyl)-3-pentylquinolin-2-amine (36c). Compound 32c was used as reagent. White solid (20 mg, 64%). $^1$H NMR (500 MHz, MeOD) δ 7.71 (d, J=0.9 Hz, 1H), 7.53 (d, J=8.2 Hz, 1H), 7.32 (s, 1H), 7.08 (dd, J=1.7, 8.1 Hz, 1H), 2.73 (t, J=7.6 Hz, 2H), 2.66-2.56 (m, 4H), 1.78-1.65 (m, 4H), 1.55-1.35 (m, 10H), 0.94 (t, J=7.1 Hz, 3H). $^{13}$C NMR (126 MHz, MeOD) δ 158.50, 147.09, 145.03, 136.78, 128.00, 124.86, 124.65, 123.89, 123.56, 42.40, 37.07, 33.42, 32.79, 32.43, 31.75, 30.14, 28.98, 27.85, 23.69, 14.43. MS (ESI-TOF) for $C_{20}H_{31}N_3[M+H]^+$ calculated 314.2591, found 314.2646.

8-(4-Aminobutyl)-3-pentylquinolin-2-amine (37). Compound 33 was used as reagent. White solid (17 mg, 60%). $^1$H NMR (500 MHz, MeOD) δ 7.68 (s, 1H), 7.44 (dd, J=1.5, 8.0 Hz, 1H), 7.32 (dd, J=1.4, 7.1 Hz, 1H), 7.10 (dd, J=7.1, 8.0 Hz, 1H), 3.06 (t, J=7.7 Hz, 2H), 2.69 (t, J=7.1 Hz, 2H), 2.62 (t, J=7.7 Hz, 2H), 1.81-1.68 (m, 4H), 1.61-1.51 (m, 2H), 1.46-1.39 (m, 4H), 0.94 (t, J=6.9 Hz, 3H). $^{13}$C NMR (126 MHz, MeOD) δ 157.96, 145.92, 137.83, 137.02, 129.40, 126.33, 125.61, 125.14, 122.79, 42.40, 33.63, 32.83, 32.10, 31.86, 28.96, 28.93, 23.69, 14.43. MS (ESI-TOF) for $C_{18}H_{27}N_3$ [M+H]$^+$ calculated 286.2278, found 286.2283.

2-Amino-4,6-dibromobenzaldehyde (40). A solution of compound 38 (737 mg, 2.5 mmol) in THF (20 mL) was added slowly to a solution of LiAlH$_4$ (10 mL, 10 mmol, 1.0 M in THF) in THF (10 mL) at 0° C. under nitrogen atmosphere. The reaction mixture was stirred for 4 h at 25° C. The reaction mixture was carefully quenched with ice-cold water (1 mL) at 0° C. and 10% NaOH (1 mL) was added. The resulting mixture was stirred for 10 min at room temperature, filtered through celite and washed with CH$_2$Cl$_2$ (50 mL). The resulting filtrate was dried over Na$_2$SO$_4$ and concentrated under reduced pressure and the crude material was purified by flash column chromatography (30% EtOAc/hexanes) to obtain the compound 39 as an off-white solid (386 mg, 55%). MS (ESI-TOF) for $C_7H_7Br_2NO$ [M+H]$^+$ calculated 279.8967, found 279.8975. To a solution of compound 39 (351 mg, 1.25 mmol) in CH$_2$Cl$_2$ (10 mL) was added MnO$_2$ (326 mg, 3.75 mmol, activated). The mixture was stirred for 6 h and then filtered over celite. The mixture was concentrated and purified by flash chromatography (20% EtOAc/hexanes) to give compound 40 as a yellow solid (286 mg, 82%). $^1$H NMR (400 MHz, CDCl$_3$) δ 10.33 (s, 1H), 7.07 (d, J=1.8 Hz, 1H), 6.81 (d, J=1.1 Hz, 1H), 6.56 (s, 2H). $^{13}$C NMR (126 MHz, CDCl$_3$) δ 194.69, 152.20, 130.08, 129.98, 124.03, 118.97, 113.96. MS (ESI-TOF) for $C_7H5 Br_2NO$ [M+H]$^+$ calculated 277.8811, found 277.8811.

Compound 41 was synthesized similarly as compound 16.

5,7-Dibromo-3-pentylquinolin-2-amine (41). Compound 40 was used as reagent. Off-white solid (242 mg, 65%). $^1$H NMR (400 MHz, CDCl$_3$) δ 7.96 (s, 1H), 7.77 (dd, J=0.8, 1.9 Hz, 1H), 7.61 (d, J=1.9 Hz, 1H), 4.98 (s, 2H), 2.58 (t, J=7.6 Hz, 2H), 1.81-1.68 (m, 2H), 1.48-1.36 (m, 4H), 0.94 (t, J=7.0 Hz, 3H). $^{13}$C NMR (126 MHz, CDCl$_3$) δ 157.24, 147.77, 134.54, 128.88, 128.00, 125.45, 122.50, 121.99, 121.86, 31.78, 31.35, 27.55, 22.65, 14.18. MS (ESI-TOF) for $C_{14}H_{16}Br_2N_2$[M+H]$^{30}$ calculated 370.9753, found 370.9747.

5,5'-(2-amino-3-pentylquinoline-5,7-diyl)bis(pentan-1-amine) (43). To a solution of compound 41 (74 mg, 0.2 mmol) in THF (2 mL) were added 4-cyanobutylzinc bromide (1.6 mL, 0.8 mmol, 0.5 M in THF) and Pd(PPh$_3$)$_4$ (23 mg, 0.02 mmol). The resulting reaction mixture was stirred at 65° C. under nitrogen atmosphere for 24 h. The reaction mixture was diluted with water and extracted with EtOAc (3×10 mL). The combined organic layer was dried over Na$_2$SO$_4$ and concentrated under reduced pressure. The crude material was purified by flash chromatography (20% MeOH/CH$_2$Cl$_2$) to obtain the compound 42 as a pale yellow solid (19 mg, 25%). MS (ESI-TOF) for $C_{24}H_{32}N_4$[M+H]$^+$ calculated 377.2700, found 377.2691. A solution of compound 42 (19 mg, 0.05 mmol) in THF (5 mL) was added slowly to a solution of LiAlH$_4$ (0.5 mL, 0.5 mmol, 1.0 M in THF) in THF (3 mL) at 0° C. under nitrogen atmosphere. The reaction mixture was stirred for 2 h at 25° C. and 2 h at 60° C. The reaction mixture was carefully quenched with ice-cold water (1 mL) at 0° C. and 10% NaOH (1 mL) was added. The resulting mixture was stirred for 10 min at room temperature, filtered through celite and washed with CH$_2$Cl$_2$ (25 mL). The resulting filtrate was dried over Na$_2$SO$_4$ and concentrated under reduced pressure and the crude material was purified by semi-preparative reverse phase HPLC to obtain the compound 43 as a white solid (5 mg, 26%). $^1$H NMR (400 MHz, MeOD) δ 8.33 (s, 1H), 7.39 (s, 1H), 7.28 (s, 1H), 3.07 (t, J=7.7 Hz, 2H), 2.94 (t, J=7.6 Hz, 4H), 2.86-2.73 (m, 4H), 1.82-1.66 (m, 10H), 1.58-1.40 (m, 8H), 0.95 (t, J=6.8 Hz, 3H). $^{13}$C NMR (126 MHz, MeOD) δ 154.80, 148.71, 141.75, 138.97, 136.98, 128.10, 125.79, 119.63, 115.24, 40.68, 40.68, 36.73, 32.74, 32.45, 32.12, 31.61, 30.84, 29.02, 28.52, 28.42, 27.37, 27.14, 23.63, 14.44. MS (ESI-TOF) for $C_{24}H_{40}N_4$[M+H]$^+$ calculated 385.3326, found 385.3330.

Protein expression, purification and crystallization. The extracellular domain of human TLR8 (hTLR8, residues 27-827) was prepared as described previously (Tanji, H. et al. *Science*. 2013, 339, 1426-1429), and was concentrated to 16 mg/mL in 10 mM MES (pH 5.5), 50 mM NaCl. The protein solutions for the crystallization of hTLR8/compound complexes contained hTLR8 (8.5 mg/mL) and compound (protein:compound molar ratio of 1:10) in a crystallization buffer containing 7 mM MES (pH 5.5), 35 mM NaCl. Crystallization experiments were performed with sitting-drop vapor-diffusion methods at 293 K. Crystals of hTLR8/compound were obtained with reservoir solutions containing 9-12% (w/v) PEG3350, 0.3 M potassium formate, and 0.1 M sodium citrate (pH 4.8-5.2).

Data collection and structure determination. Diffraction datasets were collected on beamlines PF-AR NE3A (Ibaraki, Japan) and SPring-8 BL41XU under cryogenic conditions at 100 K. Crystals of hTLR8/compound were soaked into a cryoprotectant solution containing 15% (w/v) PEG3350, 0.23 M potassium formate, 75 mM sodium citrate pH 4.8-5.2, 7.5 mM MES pH 5.5, 38 mM NaCl, and 25% glycerol. Datasets were processed using the HKL2000 package (Ostinowski, Z. M. et al. *Methods Enzymol*. 1997, 276, 307-32) or imosfim (Battye, T. G. et al. *Acta Crystallogr. D Biol. Crystallogr*. 2011, 67, 271-281). HTLR8/compound structures were determined by the molecular replacement method using the Molrep program (Vagin, A. et al. *Acta Crystallogr. D Biol. Crystallogr*. 2010, 66, 22-25) with the hTLR8/CL097 structure (PDB ID: 3W3J) as a search model. The model was further refined with stepwise cycles of manual model building using the COOT program (Emsley, P. et al. *Acta Crystallogr. D Biol. Crystallogr*. 2004, 60, 2126-2132) and restrained refinement using REFMAC (Murshudov, G. N. et al. *Acta Crystallogr. D Biol. Crystallogr*. 1997, 53, 240-255) until the R factor was converged. Compound molecule, N-glycans, and water molecules were modeled into the electron density maps at the latter cycles of the refinement. The quality of the final structure was evaluated with PROCHECK (Laskowski, R. A. M. et al. *J. Appl. Crystallogr*. 1993, 26, 283-291). The statistics of the data collection and refinement are also summarized in Table 2. The figures representing structures were prepared with PyMOL (Schrödinger, New York, NY). Coordinates have been deposited in the Protein Data Bank of the Research Collaboratory for Structural Bioinformatics; PDB codes for compounds 1 and 2 are, respectively, 5AWD and 5AWB.

Human TLR8-specific Reporter Gene assays (NF-κB induction), and TLR-2/-3/-4/-5/-7/-9- and NOD-1/NOD-2 Counter-screens: The induction of NF-κB was quantified using human TLR-2/3/-4/-5/-7/-8/-9 and NOD-1/NOD-2-specific, rapid-throughput, liquid handler-assisted reporter gene assays as previously described by us (Jenkins, M. K. et al. *Annu. Rev. Immunol*. 2001, 19, 23-45; Shukla, N. M. et al. *J. Med. Chem.* 2010, 53, 4450-4465; Agnihotri, G. et al. *J. Med. Chem.* 2011, 54, 1490-1510; Ukani, R. et al. *Bioorg. Med. Chem. Lett.* 2012, 22, 293-295). HEK293 cells stably co-transfected with the appropriate hTLR (or NOD) and secreted alkaline phosphatase (sAP) were maintained in HEK-BLUE™ Selection medium. Stable expression of secreted alkaline phosphatase (sAP) under control of NF-κB/AP-1 promoters is inducible by appropriate TLR/NOD agonists, and extracellular sAP in the supernatant is proportional to NF-κB induction. Reporter cells were incubated at a density of ~105 cells/ml in a volume of 80 μl/well, in 384-well, flat-bottomed cell culture-treated microtiter plates in the presence of graded concentrations of stimuli. sAP was assayed spectrophotometrically using an alkaline phosphatase-specific chromogen (present in HEK-detection medium as supplied by InvivoGen) at 620 nm.

Immunoassays for cytokines. Fresh human peripheral blood mononuclear cells (hPBMC) were isolated from human blood obtained by venipuncture with informed consent and as per institutional guidelines on Ficoll-Hypaque gradients. Aliquots of PBMCs (105 cells in 100 μL/well) were stimulated for 12 h with graded concentrations of test compounds. Supernatants were isolated by centrifugation, and were assayed in duplicates using analyte-specific multiplexed cytokine/chemokine bead array assays as reported by us previously (Beesu, M. et al. *J. Med. Chem.* 2014, 57, 7325-7341).

Rabbit Immunization and CRM197-specific Immunoassays: All experiments were performed at Harlan Laboratories (Indianapolis, IN) in accordance with institutional guidelines. All antigen/adjuvant preparations were entirely aqueous; no liposomal or emulsifying agents were used. Cohorts of adult female New Zealand White rabbits (n=4) were immunized intramuscularly in the flank region with (a) 10 μg of CRM197 (Malito, E. et al. *Proc. Natl. Acad. Sci. U.S.A.* 2012, 109, 5229-5234) in 0.2 mL saline (unadjuvanted control), or (b) 10 μg of CRM197 in 0.2 mL saline plus 100 μg of lead TLR8 agonists. Pre-immune test-bleeds were first obtained via venipuncture of the marginal vein of the ear. Animals were immunized on Days 1, 15 and 28. A final test-bleed was performed via the marginal vein of the ear on Day 38. Sera were stored at −80° C. until used. CRM197-specific ELISAs were performed in 384-well format using automated liquid handling methods as described by us elsewhere (Shukla, N. M. et al. *PLoS ONE*. 2012, 7, e43612). A precision 2000 liquid handler (Bio-Tek, Winooski, VT) was used for all serial dilution and reagent addition steps, and a Bio-Tek ELx405 384-well plate washer was employed for plate washes; 100 mM phosphate-buffered saline (PBS) pH 7.4, containing 0.1% Tween-20 was used as wash buffer. Nunc-Immuno MaxiSorp (384-well) plates were coated with 30 mL of CRM197 (10 μg/mL) in 100 mM carbonate buffer, pH 9.0 overnight at 4° C. After 3 washes, the plates were blocked with 3% bovine serum albumin (in PBS, pH 7.4) for 1 h at r. Serum samples (in quadruplicate) were serially diluted in a separate 384-well plate using the liquid handler, and 30 μL of the serum dilutions were transferred using the liquid handler, and the plate incubated at 37° C. for 2 h. The assay plate was washed three times, and 30 μl of 1:10,000 diluted appropriate anti-rabbit immunoglobulin (IgG, γ chain) conjugated with horseradish peroxidase was added to all wells. Following an incubation step at 37° C. for 1 h, and three washes, tetramethylbenzidine substrate was added at concentrations recommended by vendor (Sigma). The chromogenic reaction was terminated at 30 min by the addition of 2M $H_2SO_4$. Plates were then read at 450 nm using a SpectraMax M4 device (Molecular Devices, Sunnyvale, CA).

Eight-color Flow-cytometric immunostimulation experiments: Cell surface marker upregulation was determined by flow cytometry using protocols as described previously (Hood, J. D. et al. *Hum. Vaccin.* 2010, 6, 332-335), and modified for rapid-throughput. Briefly, heparin-anticoagulated whole blood samples were obtained by venipuncture from healthy human volunteers with informed consent and as per guidelines approved by the University of Kansas Human Subjects Experimentation Committee. Serial dilutions of selected compounds were performed using a Bio-Tek Precision 2000 XS liquid handler in sterile 96-well polypropylene plates, to which were added 100 mL aliquots of anticoagulated whole human blood. The plates were incubated at 37° C. for 16 h. Negative (endotoxin free water) controls were included in each experiment. The following fluorochrome-conjugated antibodies were used: CD3-PE, CD19-FITC, CD56-APC (eBioscience, San Diego, CA), CD14-V500, CD28 PE-Cy7, CD40 V450, CD80 APC-H7, CD86 PerCP-Cy5.5 (Becton-Dickinson Biosciences, San Jose, CA). Following incubation, 2.5 μg of each antibody was added to wells with a liquid handler, and incubated at 4° C. in the dark for 60 min. Following staining, erythrocytes were lysed and leukocytes fixed by mixing 200 mL of the samples in 800 mL pre-warmed Whole Blood Lyse/Fix Buffer (Becton-Dickinson Biosciences, San Jose, CA) in 96 deep-well plates. After washing the cells twice at 300 g for 10 minutes in RPMI, the cells were transferred to a 96-well plate. Flow cytometry was performed using a BD FACS-Verse instrument for acquisition on 100,000 gated events. Compensation for spillover was computed for each experiment on singly-stained Comp Beads (Becton-Dickinson Biosciences, San Jose, CA). CD28, CD40, CD80, and CD86 activation in the major leukocyte populations, viz., natural killer lymphocytes (NK cells: CD3-CD56+), cytokine-induced killer phenotype (CIK cells: CD3+CD56+), B lymphocytes (CD19+CD3-), T lymphocytes (CD3+CD56-), monocytes (CD14+), polymorphonuclear cells (CD14-) were quantified using FlowJo v 7.0 software (Treestar, Ashland, OR).

Results and Discussion

Figure 6A:
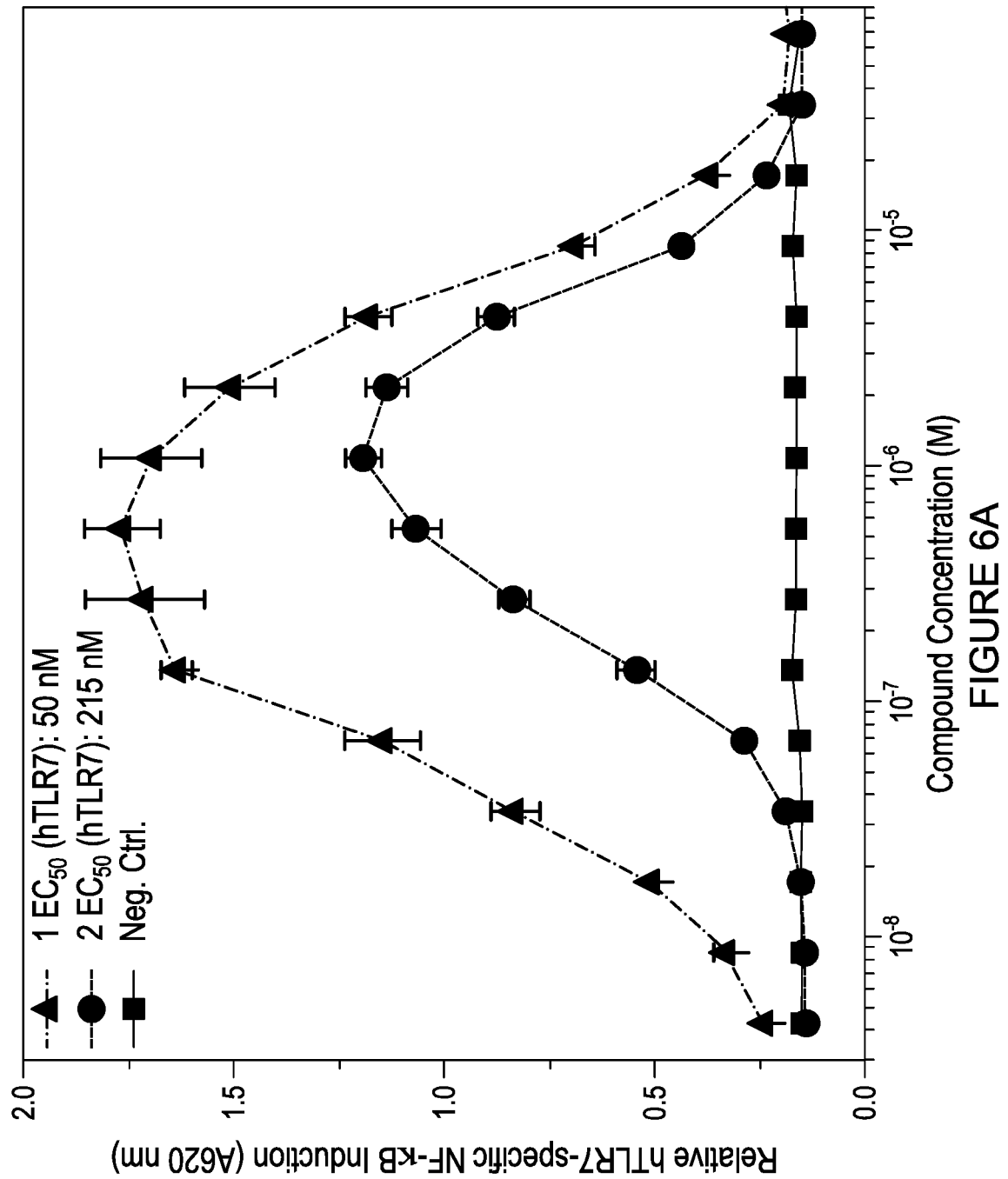
FIGS. 6A and 6B are graphs showing agonistic potencies of compounds 1 and 2 in human TLR7 (FIG. 6A) and TLR8 (FIG. 6B) primary screens.
Figure 6B:
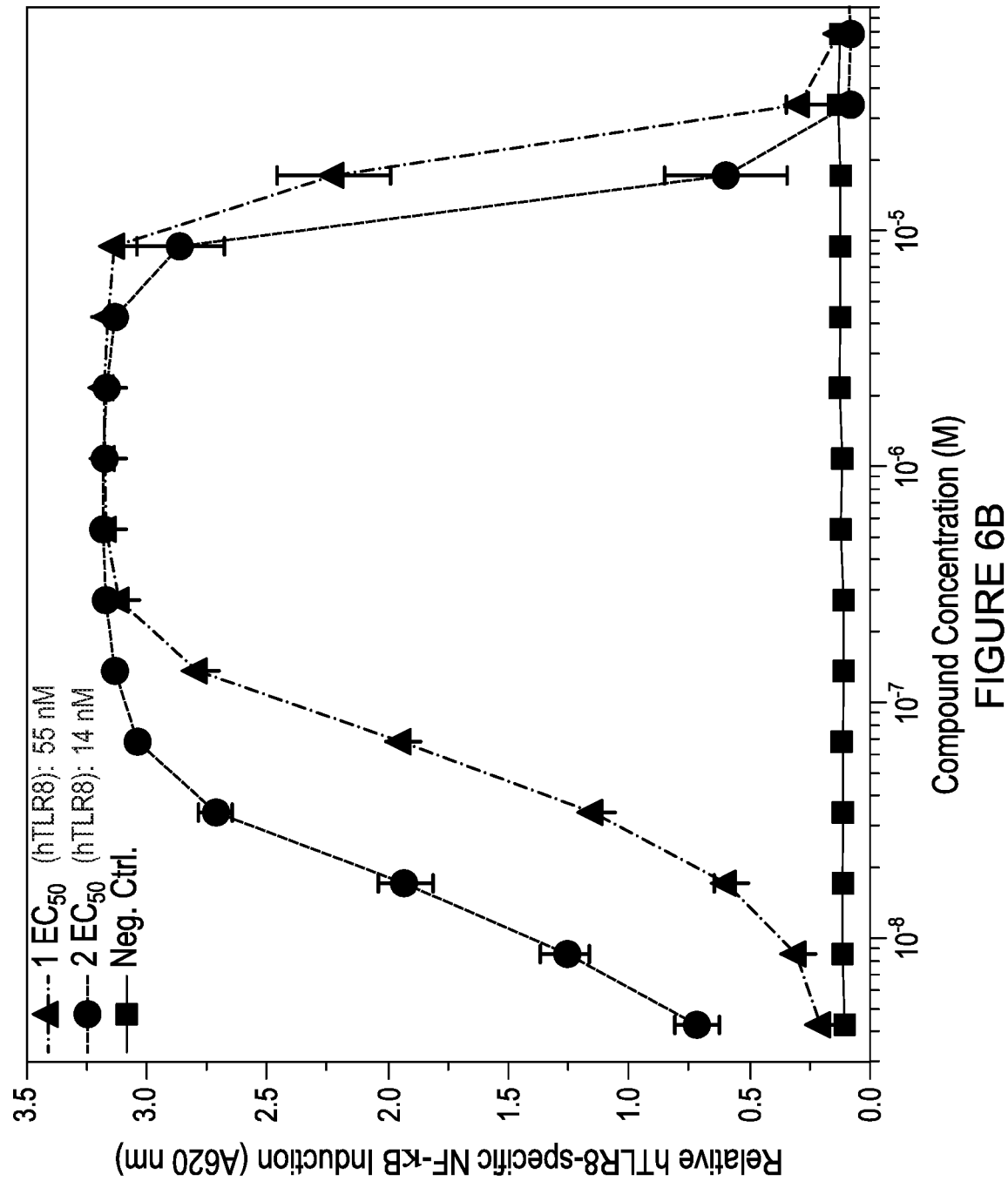

The dual TLR7/8-active regioisomeric imidazoquinolines 1 and 2 (FIG. 1), showed substantially different agonistic potencies in human TLR7 (1:50 nM; 2: 215 nM) and TLR8 (1: 55 nM; 2: 14 nM) primary screens (FIGS. 6A, 6B). The crystal structures of these two congeners bound to the ectodomain of human TLR8 revealed the structural basis of enhanced TLR8-agonistic potency of 2 relative to 1: the 3-aminomethylbenzyl substituent in 2 forms a strong ionic H-bond (salt bridge) with the side chain carboxylate of Asp545, while the 4-aminomethylbenzyl substituent in 1 was observed to engage the backbone carbonyl of Gly351 in a weaker H-bond (FIG. 1). The stronger interaction of 2 in its binding site not only resulted in enhancement of agonistic activity in primary screens (FIGS. 6A, 6B), but also in higher proinflammatory cytokine induction in whole human blood assays.

The question asked was whether grafting the aminomethylbenzyl group on the 3-pentyl-quinoline-2-amine structure which was previously reported to be a pure TLR8 agonist ($EC_{50}$ of 200 nM) (Kokatla, H. P. et al. *Chem. Med. Chem.* 2014, 9, 719-723) would result in augmented activity. Direct SNAr displacement of the 4-chloro-3-(pent-1-yn-1-yl)quinoline intermediate 4 (Kokatla, H. P. et al. 2014 supra) with 3- or 4-cyanobenzylzinc bromide as nucleophiles (Shiota, T. et al. *J. Org. Chem.* 1999, 64, 453-457) afforded the 4-substituted 3-pentynylquinolines 5a and 5b (Scheme 1); reduction of the nitriles with LiAlH$_4$ and subsequent Boc protection of the resultant amines yielded the intermediates 6a and 6b. Installation of the amine at C$_2$ was performed as reported earlier ((Kokatla, H. P. et al., 2014 supra). Hydrogenation of the alkynyl group and Boc-deprotection furnished the desired target compounds 9a and 9b (Scheme 1) which retained specificity for TLR8, but with marginal improvement in potency (150 nM and 120 nM, respectively; Table 1). In order to examine whether relieving possible steric bulk of the aminomethylbenzyl substituent at C4, the synthesis of the 4-aminobutyl (14a) and 5-aminopentyl (14b) analogues (Scheme 2) was undertaken, the lengths of which were found to be optimal in SAR studies on several TLR8-active chemotypes (Yoo, E. et al. *J. Med. Chem.* 2014, 57, 7955-7970; Salunke, D. B. et al. *J. Med. Chem.* 2012, 55, 8137-8151; Kokatla, H. P. et al. *J. Med. Chem.* 2013, 56, 6871-6885; Kokatla, H. P. et al. *Chem. Med. Chem.* 2014, 9, 719-723; Beesu, M. et al. *J. Med. Chem.* 2014, 57, 7325-7341). Installation of the 4-alkyl nitrile groups of 10a-b were carried out with cyanoalkylzinc bromides under Negishi conditions (Scheme 2), and the remainder of the sequence of reactions were similar to those described in Scheme 1. The potencies of 14a and 14b remained virtually unchanged (190 nM and 250 nM, respectively; Table 1).

The first attempts at attaching amine-bearing appendages on the quinoline core at C4 to allow for additional salt-bridge interactions with Asp545 appeared unfruitful, however, a systematic examination of substitutions at all other positions was carried out. The goal was to establish an efficient synthetic strategy to access 5-, 6-, 7- and 8-substituted 2-amino-3-pentylquinolines. A one-pot method for the syntheses of 2-aminoquinoline-3-carboxamides has been reported using 2-aminobenzaldehyde and active methylene group-bearing cyanoacetamides (Wang, K. et al. *ACS Comb. Sci.* 2012, 14, 316-322). ENREF_68 It was envisioned that a modified Friedlander synthesis of key bromo-substituted 2-amino-3-pentylquinolines could be directly obtained via condensation-cyclization reactions of 2-aminobromobenzaldehydes with heptanenitrile. The initial attempts at model reactions with alkane nitriles and the unsubstituted 2-aminobenzaldehyde proceeded very well in the presence of n-butyllithium. However, in order to preempt possible debromination, alternatives were sought and successfully utilized potassium tert-butoxide to generate the pivotal bromo-substituted 2-amino-3-pentylquinolines (Schemes 3-7).

Figure 2:
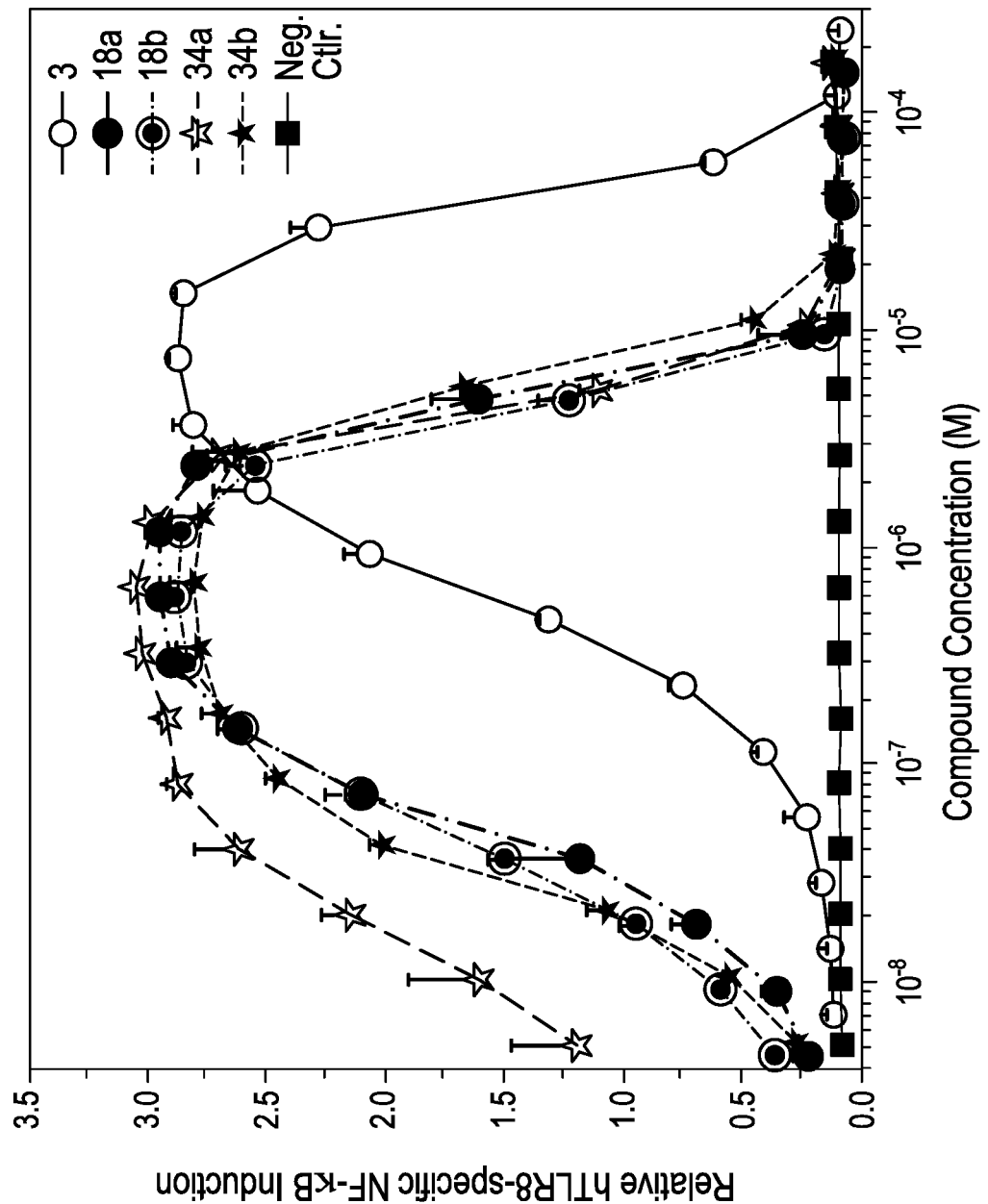
FIG. 2 is a graph showing the agonistic activities of analogues 18a, 18b, 34a, and 34b in human TLR8 reporter gene assays. Means±SD on quadruplicates are shown. Also included is 3, used as a reference/comparator compound.

2-amino-3-pentylquinolines substituted at C5 was targeted with 3-aminomethylbenzyl (18a), 4-aminomethylbenzyl (18b), and 2-aminomethylbenzyl (18c) substituents, which were obtained by Negishi coupling of corresponding cyanobenzylzinc bromides with 16 (Scheme 3). Substantially improved potencies were observed for both 18a and 18b (EC$_{50}$: 49 nM and 38 nM, respectively; FIG. 2, Table 1), whereas the 2-aminomethylbenzyl-substituted 18c was significantly weaker (EC$_{50}$: 1000 nM; Table 1) than the parent compound, 3, providing evidence that the placement of the amine on the benzyl substituent was an important determinant of activity. In order to formally test whether the amine was participating in the predicted salt bridge, the nitrile 17a was hydrolyzed to the carboxamide analogue 18d (Scheme 3). Compound 18d, as well as the 5-benzyl analogue 17d were found to be inactive (Table 1), lending support to our hypothesis.

The role of conformational flexibility of the aminomethylbenzyl substituent at C5 was explored, Accordingly, the aryl-aryl coupled 5-(aminomethyl)phenyl analogues 20a and 20b were synthesized via Suzuki reaction of cyanophenylboronic acids with 16 (Scheme 4). Compound 20a was entirely inactive and the activity of 20b was attenuated (699 nM), strongly pointing to the indispensability of conformational freedom. These findings prompted the synthesis of 5-aminoalkyl analogues (Schemes 5 and 6). The aminobutyl (34a), aminopentyl (34b), and aminohexyl (34c) derivatives could be accessed via Negishi couplings (Scheme 6); the reactivity of 2-cyanoethylzinc bromide with 16, however, was very poor even under microwave conditions, and the aminopropyl analogue 23 was accessed via Heck reaction of acrylonitrile with 16 (Scheme 5). A clear dependence on the length of the alkylamino substituent was observed in these homologues with progressive increases in potency from the aminopropyl (23: 91 nM), aminobutyl (34a: 27 nM; FIG. 2) and aminopentyl (34b: 9 nM; FIG. 2) analogues; a further in length (34c, aminohexyl) led to decreased activity (56 nM; Table 1). Conversion of the nitrile precursor 30a to the carboxamide derivative 34d (Scheme 6) resulted in a dramatic decrease in potency (2181 nM; Table 1), once again highlighting the importance of the presence of a free amino functional group.

The dramatic enhancement of potency in 34b seemed to unambiguously support the hypothesis of a salt-bridge between Asp545 and the 5-aminopentyl group of the lead compound. Given that guanidine-carboxylate interaction in proteins are consequential (Kumar, S. et al. *Chembiochem.* 2002, 3, 604-617; Singh, J. et al. *FEBS Lett.* 1987, 224, 161-171), and significant gains in interaction energies are observed in drugs such as zanamivir and peramivir whose crystal structures show strong salt-bridges between their guanidinium functional groups and the Asp/Glu residues that they interact with (Kerry, P. S. et al. *Sci. Rep.* 2013, 3, 2871), the guanidine derivative 34e was synthesized from 34a (Scheme 6), the length of the C5 substituent of which was calculated to be comparable to that of 34b. Surprisingly, a precipitous fall in activity (2862 nM; Table 1) was found, the reasons for which are yet to be understood.

Aminoalkyl substitutions at C6 (35a-35c), C7 (36a-36c), and C8 (37) (Scheme 6) were investigated. Compounds 35a-35c showed slight decreases in activity while analogues 36a-36c displayed modest gains in potency, with the most active compound being the 7-(5-aminopentyl)-3-pentylquinolin-2-amine, 36b (50 nM). The C8-substituted analogue 37 was entirely devoid of activity (Table 1). Noting that the most potent analogues possessed an aminopentyl substituent either at C5 (34b, 9 nM) or C7 (36b, 50 nM), a dually-substituted analogue was synthesized. The key precursor, 2-amino-4,6-dibromobenzaldehyde was synthesized from 2-amino-4,6-dibromobenzoic acid using conventional methods, and alkylamino substituents at C5 and C7 installed via Negishi reaction of 41 with 4-cyanobutylzinc bromide (Scheme 7). The disubstituted analogue 43, however, was found to be weaker (621 nM) than the parent compound.

Figures 3A, 3B:
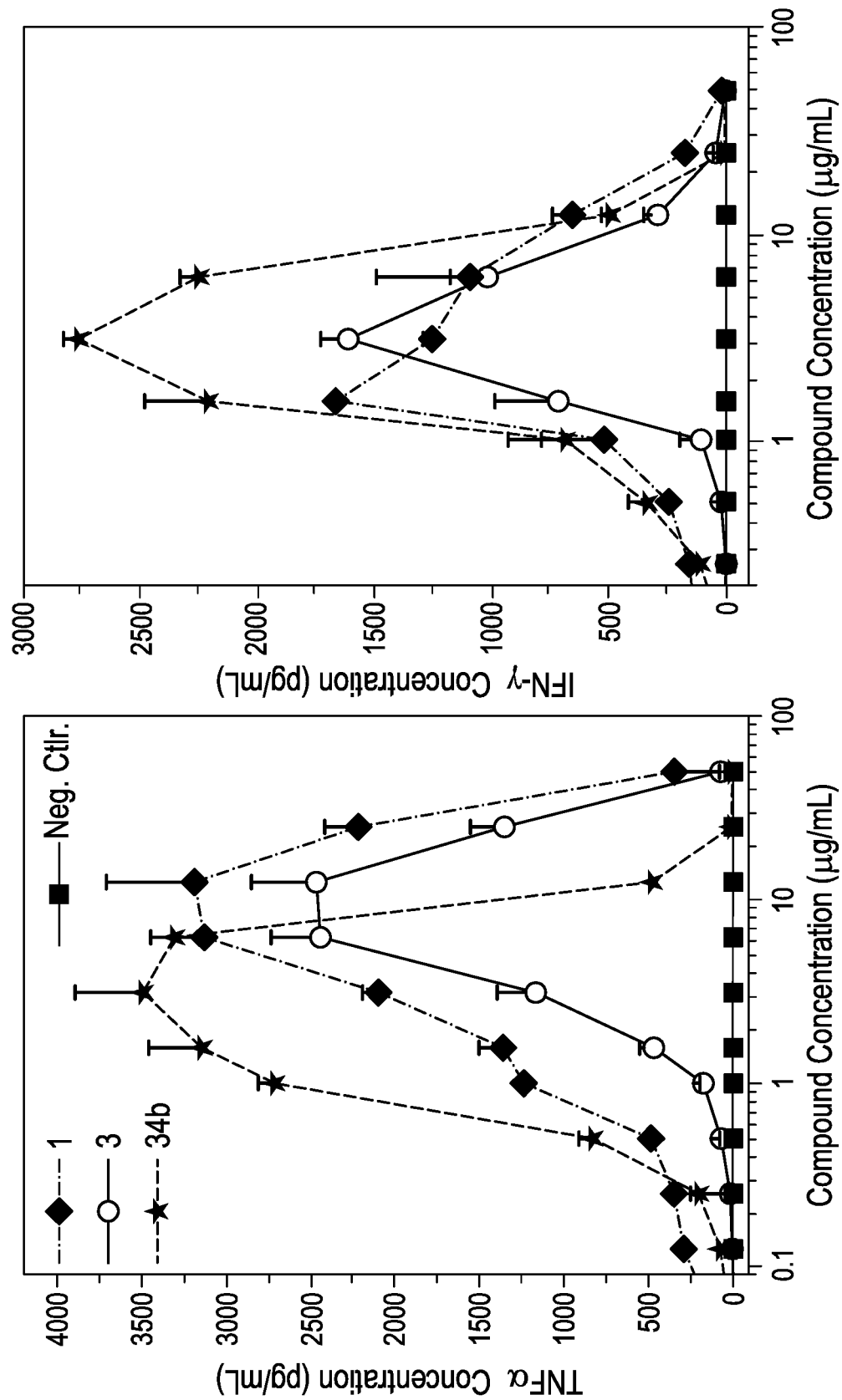

The most potent analogue 34b was characterized further in cytokine/chemokine induction profiles in a panel of secondary screens employing human peripheral blood mononuclear cells as well as whole human blood. Consistent with its specificity and potency for TLR8, not only was the induction of a specific set of proinflammatory cytokines was observed, including TNF-α, IL-12 and IFN-γ (FIG. 3), but also that the potency of 34b was significantly higher than that of both 3 (TLR8-specific) and 1 (dual TLR7/8-active).

Figure 4:
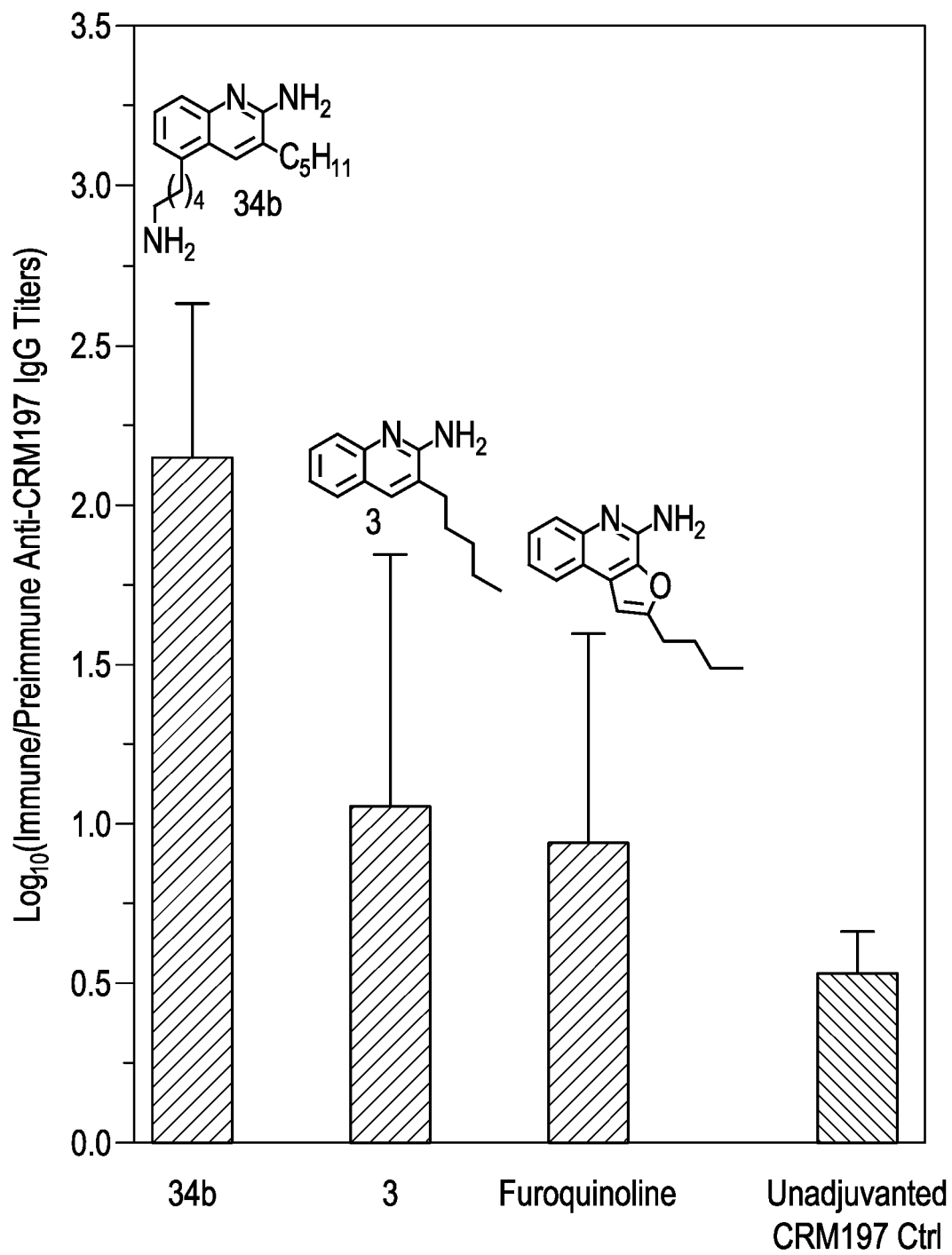
FIG. 4 is a graph showing the adjuvanticity of TLR8-active compounds. Cohorts of adult female New Zealand White rabbits (n=4) were immunized intramuscularly in the flank region with (a) 10 μg of CRM197 in 0.2 mL saline (unadjuvanted control), or (b) 10 μg of CRM197 in 0.2 mL saline plus 100 μg of lead TLR8 agonists (compounds 3, 34b, and a TLR8-specific furoquinoline agonist (Kokatla, H. P. et al. *J. Med. Chem.* 2013, 56, 6871-6885)). Pre-immune test-bleeds were obtained on Day 0, and animals were immunized on Days 1, 15 and 28. A final bleed was obtained on Day 38. CRM197-specific ELISAs were performed using automated liquid handling methods and are depicted as log 10 (immune/preimmune) titers.

The adjuvantic activity of 34b (TLR8 EC50: 9 nM) was compared with that of 3 (200 nM), as well as a first-generation C2-butyl furo[2,3-c]quinoline (1600 nM) (Kokatla, H. P. et al. *J. Med. Chem.* 2013, 56, 6871-6885) in a rabbit model of immunization, using the Diphtheria toxin mutein CRM197 as a model antigen (Malito, E. et al. *Proc. Natl. Acad. Sci. U.S.A.* 2012, 109, 5229-5234). A clear dependence between antigen-specific IgG titers and TLR8-agonistic potency was observed (FIG. 4).

One aspect of the inventors' work on vaccine adjuvant discovery, in addition to elucidating of structure-activity relationships in lead candidate vaccine adjuvants, is to delineate specific mechanisms by which these compounds elicit adjuvantic effects. As alluded to earlier, the understanding of how efferent signals arising from activation of the innate immune system engage particular pathways in downstream adaptive immune responses culminating, for instance, in the generation of antigen-specific humoral responses is nascent and fragmentary. One of the questions addressed is how various chemotypes acting on different innate immune receptors with divergent outcomes effect enhancement of immune responses. Pure TLR8 agonists, as discussed earlier, evoke the production of Th1-biased cytokines such as TNF-α, IL-1, IL-12, IL-18 and IFN-γ from cells of the monocytoid lineage; pure TLR7-active compounds induce the copious production of IFN-α from low-abundance plasmacytoid cells, activate natural killer (NK) (Hood, J. D. et al. *Hum. Vaccin.* 2010, 6, 332-335) and induce mitogenicity in B lymphocytes, and are much weaker in inducing TNF-α and IFN-γ; TLR2 agonists, in contrast, activate neutrophils as evidenced by rapid upregulation of CD11b and p38 MAP kinase activity (Salunke, D. B. et al. *J. Med. Chem.* 2012, 55, 3353-3363; Salunke, D. B. et al. *J. Med. Chem.* 2013, 56, 5885-5900). The observation that all these chemotypes display adjuvantic activities may signify that the disparate outcomes in different cell types may point to different mechanisms mediating adjuvantic activities such as, as discussed earlier, enhanced antigen uptake and presentation by APCs (Xu, W. et al. *Front. Immunol.* 2014, 4, 504; Platt, A. M. et al. *Adv. Immunol.* 2013, 120, 51-68; Teijeira, A. et al. *Front. Immunol.* 2013, 4, 433; Teijeira, A. et al. *Semin. Immunopathol.* 2014, 36, 261-274), enhanced CD4+ T cell help (Jenkins, M. K. et al. *Annu. Rev. Immunol.* 2001, 19, 23-45; Garside, P. et al. *Science* 1998, 281, 96-99; Miga, A. J. et al. *Eur. J. Immunol.* 2001, 31, 959-965), or affinity maturation of antibodies (McHeyzer-Williams, L. J. et al. *Curr. Opin. Immunol.* 2009, 21, 266-273; Nurieva, R. I. et al. *Cell. Molec. Immunol.* 2010, 7, 190-197).

Figure 5E:
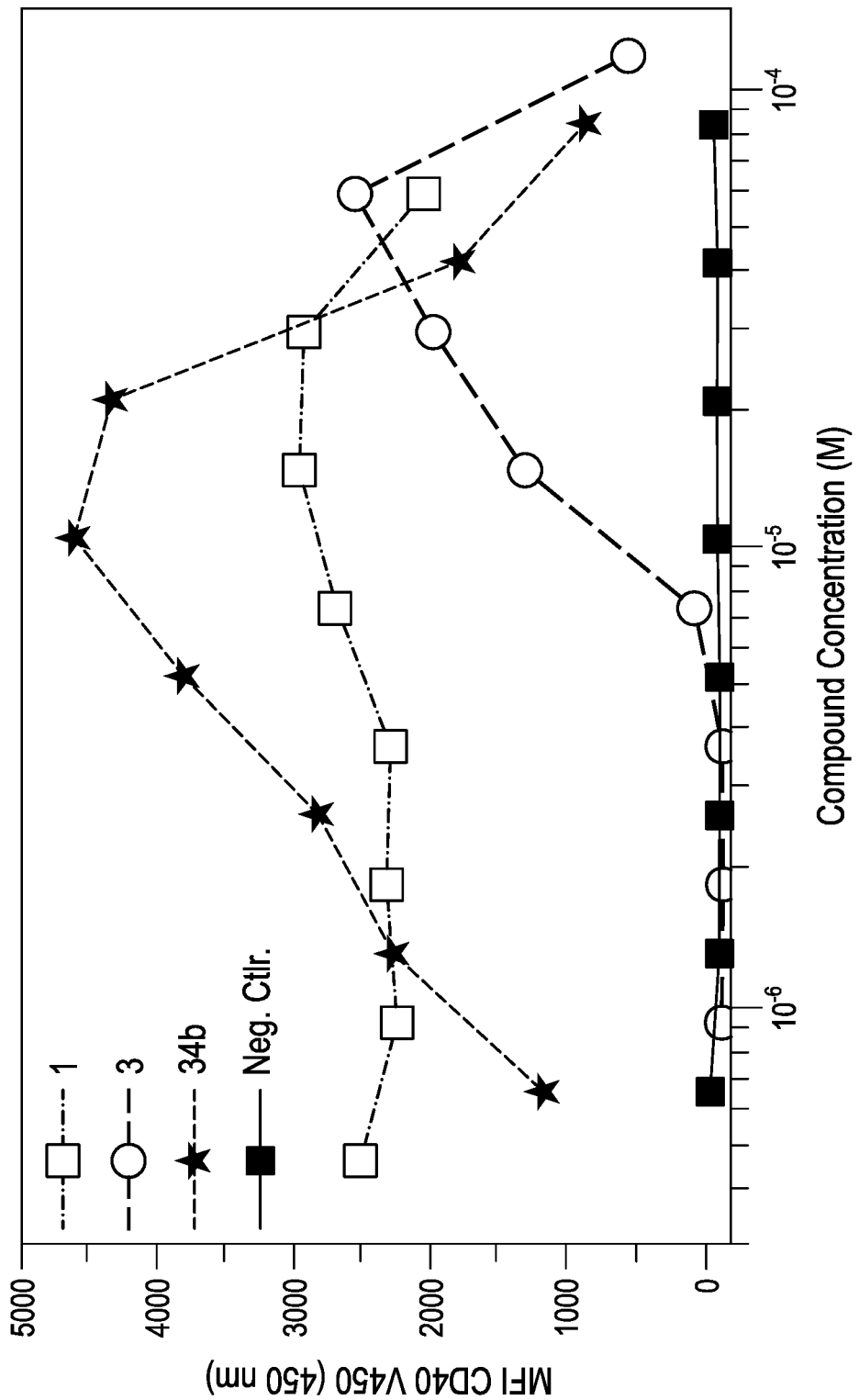
FIGS. 5E and 5F show upregulation of CD40 and CD80, respectively, in CD14+ monocytes by TLR8-active compounds.
Figure 5F:
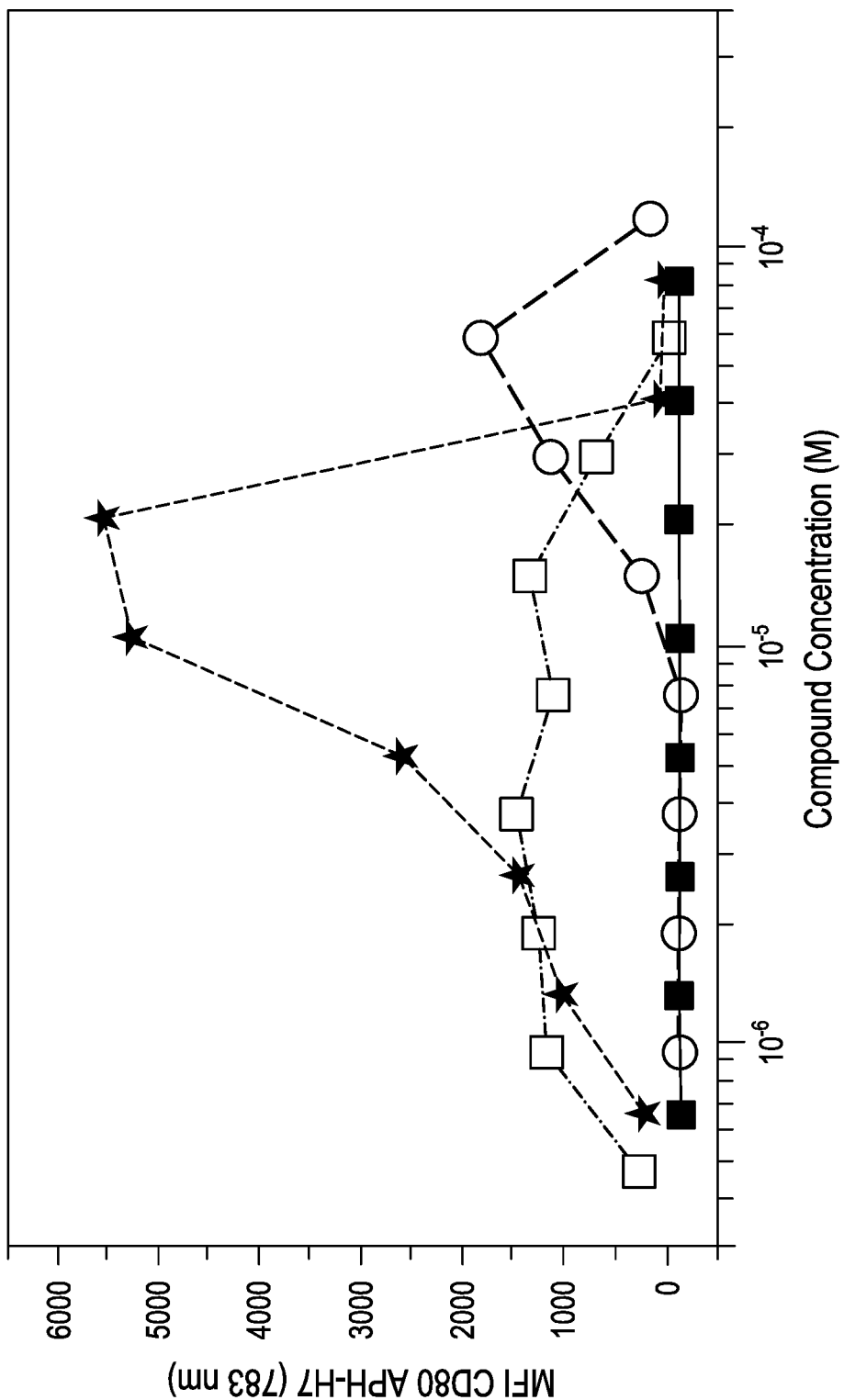

In an attempt to understand how TLR8 agonism may modulate adaptive immune functions, eight-color flow cytometry was used to interrogate activation markers (CD40, CD80) in major cellular subsets (granulocytes, monocytes (CD14+), T cells (CD3+), B cells (CD19+), NK cells (CD3−CD56+) and cytokine-induced killer cells (CD3+ CD56+) in human whole blood stimulated with 34b, the significantly weaker TLR8-specific 3, as well as the potent, dual TLR7/8-active 1; it was found that whereas both 34b and 1 upregulate CD40, specifically in CD14+ monocytes (and not in other subsets), the TLR8 stimulation with 34b strongly induces CD80 expression in the monocytes (FIG. 5) and, in these assays, differences in potency between 34b and 1 become readily evident (FIG. 5). These results hint at a possible specific role of TLR8 agonists at enhancing antigen presentation, and point a way forward to exploring this phenomenon in greater detail.

In conclusion, this approach of augmenting potency by exploiting key interactions identified in crystallographic studies of TLR8 has yielded novel analogues of extraordinary potency and specificity which are proving useful in understanding the immunological basis of adjuvanticity in this chemotype.

TABLE 1

$EC_{50}$ values of compounds in human TLR 8-specific reporter gene assays

| S. No. | Structure | TLR8 Agonistic Activity (nM) |
|---|---|---|
| 9a | 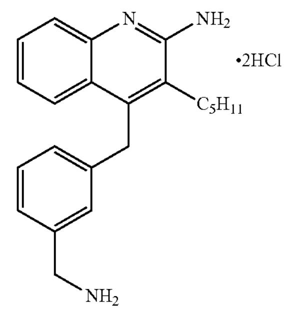 | 150 |
| 9b | 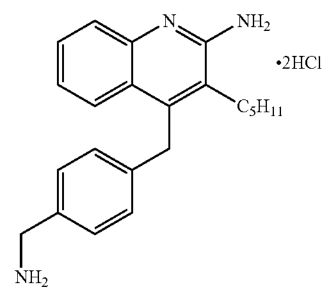 | 120 |
| 14a | 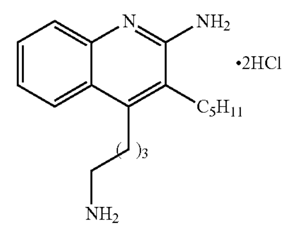 | 190 |
| 14b | 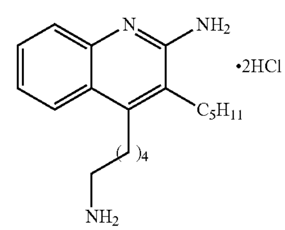 | 250 |
| 18a | 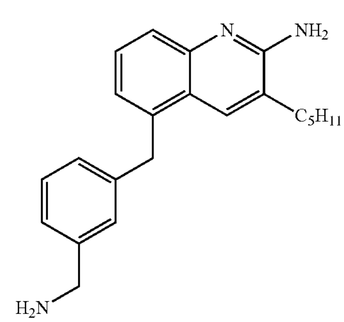 | 49 |

TABLE 1-continued

EC$_{50}$ values of compounds in human TLR 8-specific reporter gene assays

| S. No. | Structure | TLR8 Agonistic Activity (nM) |
|---|---|---|
| 18b | 5-(4-(aminomethyl)benzyl)-3-pentylquinolin-2-amine | 38 |
| 18c | 5-(2-(aminomethyl)benzyl)-3-pentylquinolin-2-amine | 1000 |
| 17d | 5-benzyl-3-pentylquinolin-2-amine | Inactive |
| 18d | 3-((2-amino-3-pentylquinolin-5-yl)methyl)benzamide | Inactive |
| 20a | 5-(3-(aminomethyl)phenyl)-3-pentylquinolin-2-amine | Inactive |
| 20b | 5-(4-(aminomethyl)phenyl)-3-pentylquinolin-2-amine | 699 |
| 23 | 5-(2-aminoethyl)-3-pentylquinolin-2-amine | 91 |
| 34a | 5-(3-aminopropyl)-3-pentylquinolin-2-amine | 27 |
| 34b | 5-(4-aminobutyl)-3-pentylquinolin-2-amine | 9 |
| 34c | 5-(5-aminopentyl)-3-pentylquinolin-2-amine | 56 |
| 34d | 3-(2-amino-3-pentylquinolin-5-yl)propanamide | 2181 |

TABLE 1-continued

EC$_{50}$ values of compounds in human TLR 8-specific reporter gene assays

| S. No. | Structure | TLR8 Agonistic Activity (nM) |
|---|---|---|
| 34e | 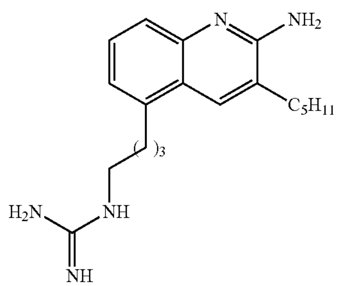 | 2862 |
| 35a | 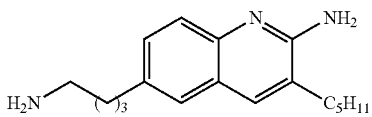 | 727 |
| 35b | 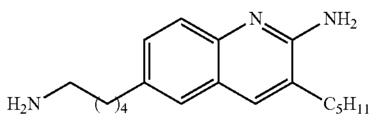 | 519 |
| 35c | 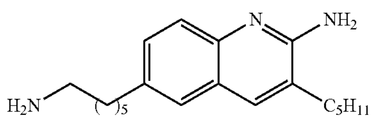 | 1016 |
| 36a | 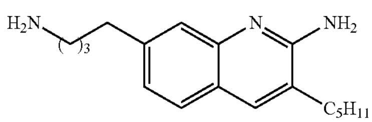 | 60 |
| 36b | 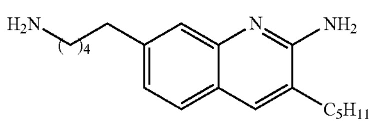 | 50 |
| 36c | 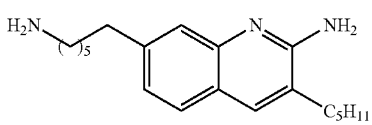 | 85 |
| 37 | 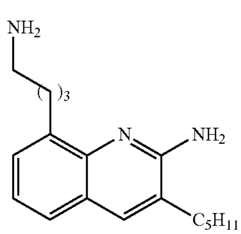 | Inactive |
| 43 | 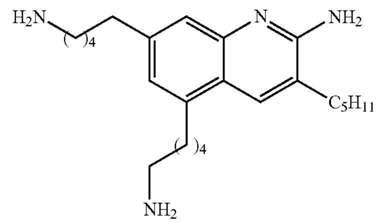 | 621 |

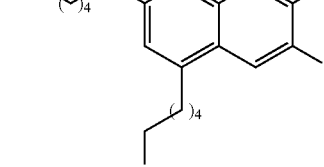

TABLE 2

Data collection and refinement statistics for TLR8/1, and TLR8/2

|  | TLR8/1 | TLR8/2 |
|---|---|---|
| Data Collection | | |
| X-ray source | PF-NE3A | PF-NE3A |
| Wavelength | 1.0000 | 1.0000 |
| Space group | C2 | C2 |
| Unit cell parameters | | |
| a (Å) | 135.7 | 134.9 |
| b (Å) | 106.7 | 107.1 |
| c (Å) | 72.2 | 72.1 |
| β (°) | 106.2 | 106.3 |
| Resolution (Å) | 2.05 | 2.10 |
| Completeness (%) | 99.8 (99.9) | 98.9 (99.6) |
| Redundancy | 3.5 (3.4) | 3.1 (2.8) |
| $R_{sym}$ (I)[b] | 0.077 (0.424) | 0.073 (0.759) |
| Average I/σ(I) | 9.6 (2.6) | 26.4 (2.0) |
| Refinement | | |
| Resolution range (Å) | 69.28-2.05 | 27.50-2.10 |
| No. of reflections used | 58,440 | 53,673 |
| Model | 1 × TLR8 | 1 × TLR8 |
| Average B-factor (Å$^2$) | 38.4 | 50.1 |
| R (%)[c] | 21.5 | 20.1 |
| $R_{free}$ (%)[d] | 26.9 | 25.9 |
| Rms deviations | | |
| Bond length (Å) | 0.011 | 0.016 |
| Bond angles (°) | 1.61 | 1.89 |

[a]Highest resolution shell is shown in parentheses.

[b]$R_{sym}$ (I) = Σ|I − <I>|/ΣI, where I is the diffraction intensity.

[c]$R = \Sigma|F_o - F_c|/\Sigma F_o$, where $F_o$ and $F_c$ are the observed and calculated structure amplitudes, respectively.

[d]$R_{free}$ is an R value for a 5% subset of all reflections, but was not used in the refinement.

EMBODIMENTS

The following are non-limiting embodiments of the present disclosure:

1. A compound represented by Formula (II):

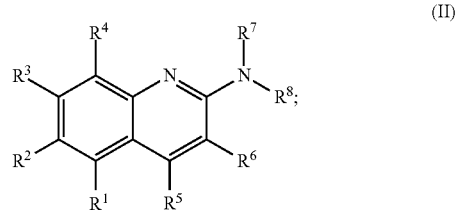

(II)

or a salt thereof, wherein:

$R^1$, $R^2$, $R^3$, $R^4$, and $R^5$ are independently selected from the group consisting of: H, halogen, —$OR^{10}$, —$N(R^{10})_2$, —$SR^{10}$, —CN, —$NO_2$, —$OC(O)R^{10}$, —$C(O)R^{10}$, —$C(O)OR^{10}$, —$C(O)N(R^{10})_2$, —$S(O)_2R'''$, —$S(O)_2OR^{10}$, optionally substituted $C_{1-20}$ alkyl, optionally substituted $C_{2-20}$ alkenyl, optionally substituted $C_{2-20}$ alkynyl, optionally substituted $C_{3-20}$ carbocycle, and optionally substituted 3- to 20-membered heterocycle, wherein at least one of $R^1$ and $R^3$ is selected from the group consisting of —$OR^{10}$, —$N(R^{10})_2$, —$SR^{10}$, —$OC(O)R^{10}$, —$C(O)R^{10}$, —$C(O)OR^{10}$, —$C(O)N(R^{10})_2$, —$S(O)_2R^{10}$, —$S(O)_2OR^{10}$, optionally substituted $C_{1-20}$ alkyl, optionally substituted $C_{2-20}$ alkenyl, optionally substituted $C_{2-20}$ alkynyl, optionally substituted $C_{3-20}$ carbocycle, and optionally substituted 3- to 20-membered heterocycle;

$R^6$ is selected from the group consisting of —$OR^{11}$, —$N(R^{11})_2$, —$SR^{11}$, optionally substituted $C_{1-20}$ alkyl, optionally substituted $C_{2-20}$ alkenyl, and optionally substituted $C_{2-20}$ alkynyl;

$R^7$ and $R^8$ are independently selected from H, optionally substituted $C_{1-10}$ alkyl, optionally substituted $C_{2-10}$ alkenyl, optionally substituted $C_{2-10}$ alkynyl, optionally substituted $C_{3-12}$ carbocycle and optionally substituted 3- to 12-membered heterocycle;

$R^{10}$ is independently selected at each occurrence from the group consisting of H, optionally substituted $C_{1-10}$ alkyl, optionally substituted $C_{2-10}$ alkenyl, optionally substituted $C_{2-10}$ alkynyl, optionally substituted $C_{3-12}$ carbocycle and optionally substituted 3- to 12-membered heterocycle; and $R^{11}$ is independently selected at each occurrence from the group consisting of optionally substituted $C_{1-10}$ alkyl, optionally substituted $C_{2-10}$ alkenyl, and optionally substituted $C_{2-10}$ alkynyl.

2. The compound or salt of embodiment 1, wherein at least one of $R^1$ and $R^3$ is selected from the group consisting of —$OR^{10}$, —$N(R^{10})_2$, —$OC(O)R'''$, —$C(O)R^{10}$, —$C(O)OR^{10}$, —$C(O)N(R^{10})_2$, —$S(O)_2R^{10}$, —$S(O)_2OR^{10}$, optionally substituted $C_{1-20}$ alkyl, optionally substituted $C_{2-20}$ alkenyl, and optionally substituted $C_{2-20}$ alkynyl.

3. The compound or salt of embodiment 2, wherein at least one of $R^1$ and $R^3$ is selected from the group consisting of optionally substituted $C_{1-20}$ alkyl, optionally substituted $C_{2-20}$ alkenyl, and optionally substituted $C_{2-20}$ alkynyl.

4. The compound or salt of embodiment 3, wherein $R^1$ is optionally substituted $C_{1-10}$ alkyl.

5. The compound or salt of embodiment 4, wherein $R^1$ is optionally substituted $C_{1-5}$ alkyl.

6. The compound of any one of embodiments 1 to 5, wherein $R^1$ is selected from the group consisting of:

optionally substituted $C_{1-20}$ alkyl, optionally substituted $C_{2-20}$ alkenyl, optionally substituted $C_{2-20}$ alkynyl, wherein the $C_{1-20}$ alkyl, $C_{2-20}$ alkenyl, and $C_{2-20}$ alkynyl optional substituents are one or more substituents independently selected from the group consisting of: halogen, —CN, —$NO_2$, —$OR^{50}$, —$SR^{50}$, —$N(R^{50})_2$, —$NR^{50}C(N(R^{50}))N(R^{50})_2$, —$OC(O)R^{50}$, —$C(O)R^{50}$, —$C(O)OR^{50}$, —$C(O)N(R^{50})_2$, —$S(O)_2R^{50}$, —$S(O)_2OR^{50}$, $C_{3-12}$ carbocycle, and 3- to 12-membered heterocycle, wherein the $C_{3-12}$ carbocycle and the 3- to 12-membered heterocycle are optionally substituted with one or more substituents selected from the group consisting of halogen, —CN, —$NO_2$, —$OR^{50}$, —$SR^{50}$, —$N(R^{50})_2$, $C_{1-10}$ alkyl, $C_{1-10}$ haloalkyl, —$C_{1-10}$ alkyl-$N(R^{50})_2$, —$C_{1-10}$ alkyl-$OR^{50}$, and —$C_{1-10}$ alkyl-$C(O)N(R^{50})_2$; and optionally substituted $C_{3-20}$ carbocycle and optionally substituted 3- to 20-membered heterocycle, wherein the $C_{3-20}$ carbocycle and 3- to 20-membered heterocycle optional substituents are one or more substituents independently selected from the group consisting of: halogen, —CN, —$NO_2$, —$OR^{50}$, —SR, —$N(R^{50})_2$, $C_{1-10}$ alkyl, $C_{1-10}$ haloalkyl, —$C_{1-10}$ alkyl-$N(R^{50})_2$, —$C_{1-10}$ alkyl-$OR^{50}$, and —$C_{1-10}$ alkyl-$C(O)N(R^{50})_2$; and wherein $R^{50}$ at each occurrence is independently selected from the group consisting of hydrogen, $C_{1-10}$ alkyl, and $C_{1-10}$ haloalkyl.

7. The compound or salt of embodiment 6, wherein $R^1$ is substituted with —$N(R^{50})_2$.

8. The compound or salt of embodiment 6, wherein $R^1$ is selected from:

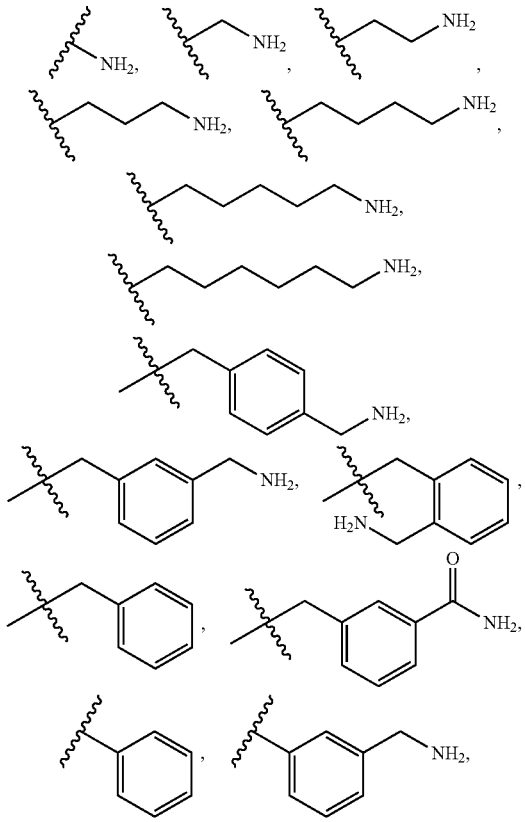

-continued

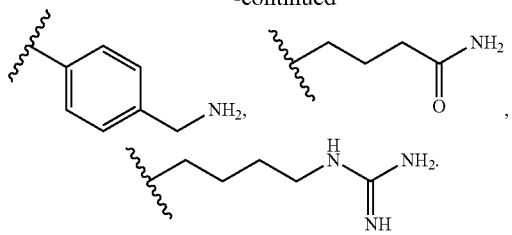

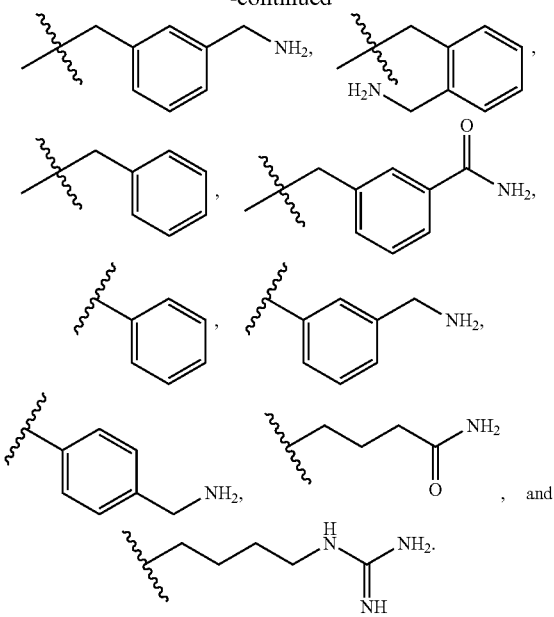

9. The compound or salt of embodiment 3, wherein $R^3$ is optionally substituted $C_{1-10}$ alkyl.

10. The compound or salt of embodiment 9, wherein $R^3$ is optionally substituted $C_{1-5}$ alkyl.

11. The compound of any one of embodiments 1 to 10, wherein $R^3$ is selected from the group consisting of:
optionally substituted $C_{1-20}$ alkyl, optionally substituted $C_{2-20}$ alkenyl, optionally substituted $C_{2-20}$ alkynyl, wherein the $C_{1-20}$ alkyl, $C_{2-20}$ alkenyl, and $C_{2-20}$ alkynyl optional substituents are one or more substituents independently selected from the group consisting of: halogen, —CN, —NO$_2$, —OR$^{50}$, —SR$^{50}$, —N(R$^{50}$)$_2$, —NR$^{50}$C(N(R$^{50}$))N(R$^{50}$)$_2$, —OC(O)R$^{50}$, —C(O)R$^{50}$, —C(O)OR$^{50}$, —C(O)N(R$^{50}$)$_2$, —S(O)$_2$R$^{50}$, —S(O)$_2$OR$^{50}$, $C_{3-12}$ carbocycle, and 3- to 12-membered heterocycle, wherein the $C_{3-12}$ carbocycle and 3- to 12-membered heterocycle are optionally substituted with one or more substituents selected from the group consisting of halogen, —CN, —NO$_2$, —OR$^{50}$, —SR$^{50}$, —N(R$^{50}$)$_2$, $C_{1-10}$ alkyl, $C_{1-10}$ haloalkyl, —C$_{1-10}$(alkyl-N(R$^{50}$)$_2$, —C$_{1-10}$ alkyl-OR$^{50}$, and —C$_{1-10}$ alkyl-C(O)N(R$^{50}$)$_2$; and
optionally substituted $C_{3-20}$ carbocycle and optionally substituted 3- to 20-membered heterocycle, wherein the $C_{3-20}$ carbocycle and 3- to 20-membered heterocycle optional substituents are one or more substituents independently selected from the group consisting of: halogen, —CN, —NO$_2$, —OR$^{50}$, —SR$^{50}$, —N(R$^{50}$)$_2$, $C_{1-10}$ alkyl, $C_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and
wherein R$^{50}$ at each occurrence is independently selected from the group consisting of hydrogen, $C_{1-10}$ alkyl, and $C_{1-10}$ haloalkyl.

12. The compound or salt of embodiment 11, wherein $R^3$ is substituted with —N(R$^{50}$)$_2$.

13. The compound or salt of embodiment 11, wherein $R^3$ is selected from:

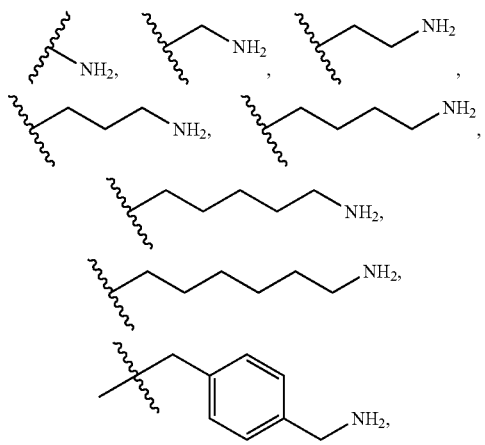

14. The compound or salt of embodiment 8, wherein R is selected from H, halogen, and —CN.

15. The compound or salt of embodiment 14, wherein $R^3$ is hydrogen.

16. The compound or salt of embodiment 13, wherein $R^1$ is selected from H, halogen, and —CN.

17. The compound or salt of embodiment 16, wherein $R^1$ is hydrogen.

18. The compound or salt of any one of embodiments 1 to 17, wherein $R^2$, $R^4$, and $R^5$ are independently selected from the group consisting of: H, halogen, —OR$^1$, —N(R$^{10}$)$_2$, —SR$^{10}$, —CN, —NO$_2$, —OC(O)R$^{10}$, —C(O)R$^{10}$, —C(O)OR$^{10}$, —C(O)N(R$^{10}$)$_2$, —S(O)$_2$R$^{10}$, —S(O)$_2$OR$^{10}$, and optionally substituted $C_{1-20}$ alkyl.

19. The compound or salt of embodiment 18, wherein $R^2$, $R^4$, and $R^5$ are independently selected from the group consisting of: H, halogen, —OR$^{10}$, —N(R$^{10}$)$_2$, —SR$^{10}$, —CN, —NO$_2$, and optionally substituted $C_{1-20}$ alkyl.

20. The compound or salt of any one of embodiments 1 to 19, wherein $R^2$, $R^4$, and $R^5$ are independently selected from the group consisting of:
optionally substituted $C_{1-20}$ alkyl, optionally substituted $C_{2-20}$ alkenyl, optionally substituted $C_{2-20}$ alkynyl, wherein the $C_{1-20}$ alkyl, $C_{2-20}$ alkenyl, and $C_{2-20}$ alkynyl optional substituents are one or more substituents independently selected from the group consisting of: halogen, —CN, —NO$_2$, —OR$^{50}$, —SR$^{50}$, —N(R$^{50}$)$_2$, —NR$^{50}$C(N(R$^{50}$))N(R$^{50}$)$_2$, —OC(O)R$^{50}$, —C(O)R$^{50}$, —C(O)OR$^{50}$, —C(O)N(R$^{50}$)$_2$, —S(O)$_2$R$^{50}$, —S(O)$_2$OR$^{50}$, $C_{3-12}$ carbocycle, and 3- to 12-membered heterocycle, wherein the $C_{3-12}$ carbocycle and 3- to 12-membered heterocycle are optionally substituted with one or more substituents selected from the group consisting of halogen, —CN, —NO$_2$, —OR$^{50}$, —SR$^{50}$, —N(R$^{50}$)$_2$, $C_{1-10}$ alkyl, $C_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and
optionally substituted $C_{3-20}$ carbocycle and optionally substituted 3- to 20-membered heterocycle, wherein the $C_{3-20}$ carbocycle and 3- to 20-membered heterocycle optional substituents are one or more substituents independently selected from the group consisting of: halogen, —CN, —NO$_2$, —OR$^{50}$, —SR$^{50}$, —N(R$^{50}$)$_2$, C$_{1-10}$ alkyl, C$_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and wherein R$^{50}$ at each occurrence is independently selected from the group consisting of hydrogen, C$_{1-10}$ alkyl, and C$_{1-10}$ haloalkyl.

21. The compound or salt of any one of embodiments 1 to 20, wherein R$^2$ is hydrogen.

22. The compound or salt of any one of embodiments 1 to 21, wherein R$^4$ is hydrogen.

23. The compound or salt of any one of embodiments 1 to 22, wherein R$^5$ is hydrogen.

24. The compound or salt of any one of embodiments 1 to 23, wherein R$^{10}$ is selected from the group consisting of:
optionally substituted C$_{1-20}$ alkyl, optionally substituted C$_{2-20}$ alkenyl, optionally substituted C$_{2-20}$ alkynyl, wherein the C$_{1-20}$ alkyl, C$_{2-20}$ alkenyl, and C$_{2-20}$ alkynyl optional substituents are one or more substituents independently selected from the group consisting of: halogen, —CN, —NO$_2$, —OR$^{50}$, —SR$^{50}$, —N(R$^{50}$)$_2$, —NR$^{50}$C(N(R$^{50}$))N(R$^{50}$)$_2$, —OC(O)R$^{50}$, —C(O)R$^{50}$, —C(O)OR$^{50}$, —C(O)N(R$^{50}$)$_2$, —S(O)$_2$R$^{50}$, —S(O)$_2$OR$^{50}$, C$_{3-12}$ carbocycle, and 3- to 12-membered heterocycle, wherein the C$_{3-12}$ carbocycle and 3- to 12-membered heterocycle are optionally substituted with one or more substituents selected from the group consisting of halogen, —CN, —NO$_2$, —OR$^{50}$, —SR$^{50}$, —N(R$^{50}$)$_2$, C$_{1-10}$ alkyl, C$_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and optionally substituted C$_{3-20}$ carbocycle and optionally substituted 3- to 20-membered heterocycle, wherein the C$_{3-20}$ carbocycle and 3- to 20-membered heterocycle optional substituents are one or more substituents independently selected from the group consisting of: halogen, —CN, —NO$_2$, —OR$^{50}$, —SR$^{50}$, —N(R$^{50}$)$_2$, C$_{1-10}$ alkyl, C$_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and wherein R$^{50}$ at each occurrence is independently selected from the group consisting of hydrogen, C$_{1-10}$ alkyl, and C$_{1-10}$ haloalkyl.

25. The compound or salt of any one of embodiments 1 to 24, wherein R$^6$ is selected from the group consisting of optionally substituted C$_{1-20}$ alkyl, optionally substituted C$_{2-20}$ alkenyl, and optionally substituted C$_{2-20}$ alkynyl.

26. The compound or salt of embodiment 25, wherein R$^6$ is selected from the group consisting of optionally substituted C$_{1-10}$ alkyl, optionally substituted C$_{2-10}$ alkenyl, and optionally substituted C$_{1-10}$ alkynyl.

27. The compound or salt of embodiment 26, wherein R$^6$ is selected from the group consisting of optionally substituted C$_{1-10}$ alkyl.

28. The compound or salt of any one of embodiments 1 to 27, wherein R$^6$ is selected from the group consisting of:
optionally substituted C$_{1-20}$ alkyl, optionally substituted C$_{2-20}$ alkenyl, optionally substituted C$_{2-20}$ alkynyl, wherein the C$_{1-20}$ alkyl, C$_{2-20}$ alkenyl, and C$_{2-20}$ alkynyl optional substituents are one or more substituents independently selected from the group consisting of: halogen, —CN, —NO$_2$, —OR$^{50}$, —SR$^{50}$, —N(R$^{50}$)$_2$, —NR$^{50}$C(N(R$^{50}$))N(R$^{50}$)$_2$, —OC(O)R$^{50}$, —C(O)R$^{50}$, —C(O)OR$^{50}$, —C(O)N(R$^{50}$)$_2$, —S(O)$_2$R$^{50}$, —S(O)$_2$OR$^{50}$, C$_{3-12}$ carbocycle, and 3- to 12-membered heterocycle, wherein the C$_{3-12}$ carbocycle and 3- to 12-membered heterocycle are optionally substituted with one or more substituents selected from the group consisting of halogen, —CN, —NO$_2$, —OR$^{50}$, —SR$^{50}$, —N(R$^{50}$)$_2$, C$_{1-10}$ alkyl, C$_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and optionally substituted C$_{3-20}$ carbocycle and optionally substituted 3- to 20-membered heterocycle, wherein the C$_{3-20}$ carbocycle and 3- to 20-membered heterocycle optional substituents are one or more substituents independently selected from the group consisting of: halogen, —CN, —NO$_2$, —OR$^{50}$, —SR$^{50}$, —N(R$^{50}$)$_2$, C$_{1-10}$ alkyl, C$_{1-10}$ haloalkyl, —C$_{1-10}$ alkyl-N(R$^{50}$))$_2$, —C$_{1-10}$ alkyl-OR$^{50}$, and —C$_{1-10}$ alkyl-C(O)N(R$^{50}$)$_2$; and wherein R$^{50}$ at each occurrence is independently selected from the group consisting of hydrogen, C$_{1-10}$ alkyl, and C$_{1-10}$ haloalkyl.

29. The compound or salt of embodiment 28, wherein R$^6$ is:

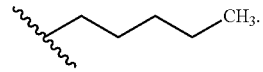 [SMILES: *CCCCC]

30. The compound or salt of any one of embodiments 1 to 29, wherein R$^7$ and R$^8$ are independently selected from H and optionally substituted C$_{1-10}$ alkyl.

31. The compound of any one of embodiments 1 to 30, wherein R$^7$ and R$^8$ are each H.

32. The compound or salt of any one of embodiments 1 to 31, wherein R$^7$ and R$^8$ are independently selected from the group consisting of:
optionally substituted C$_{1-20}$ alkyl, optionally substituted C$_{2-20}$ alkenyl, optionally substituted C$_{2-20}$ alkynyl, wherein the C$_{1-20}$ alkyl, C$_{2-20}$ alkenyl, and C$_{2-20}$ alkynyl optional substituents are one or more substituents independently selected from the group consisting of: halogen, —CN, —NO$_2$, —OR$^{50}$, —SR$^{50}$, —N(R$^{50}$)$_2$, —NR$^{50}$C(N(R$^{50}$))N(R$^{50}$)$_2$, —OC(O)R$^{50}$, —C(O)R$^{50}$, —C(O)OR$^{50}$, —C(O)N(R$^{50}$)$_2$, —S(O)$_2$R$^{50}$, —S(O)$_2$OR$^{50}$, C$_{3-12}$ carbocycle, and 3- to 12-membered heterocycle, wherein the C$_{3-12}$ carbocycle and 3- to 12-membered heterocycle are optionally substituted with one or more substituents selected from the group consisting of halogen, —CN, —NO$_2$, —OR$^{50}$, —SR$^{50}$, —N(R$^{50}$)$_2$, C$_{1-10}$ alkyl, C$_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and optionally substituted C$_{3-20}$ carbocycle and optionally substituted 3- to 20-membered heterocycle, wherein the C$_{3-20}$ carbocycle and 3- to 20-membered heterocycle optional substituents are one or more substituents independently selected from the group consisting of: halogen, —CN, —NO$_2$, —OR$^{50}$, —SR$^{50}$, —N(R$^{50}$)$_2$, C$_{1-10}$ alkyl, C$_{1-10}$ haloalkyl, —C$_{1-10}$ alkyl-N(R$^{50}$)$_2$, —C$_{1-10}$ alkyl-OR$^{50}$, and —C$_{1-10}$ alkyl-C(O)N(R$^{50}$)$_2$; and wherein R$^{50}$ at each occurrence is independently selected from the group consisting of hydrogen, C$_{1-10}$ alkyl, and C$_{1-10}$ haloalkyl.

33. The compound or salt of any one of embodiments 1 to 32, represented by the Formula:
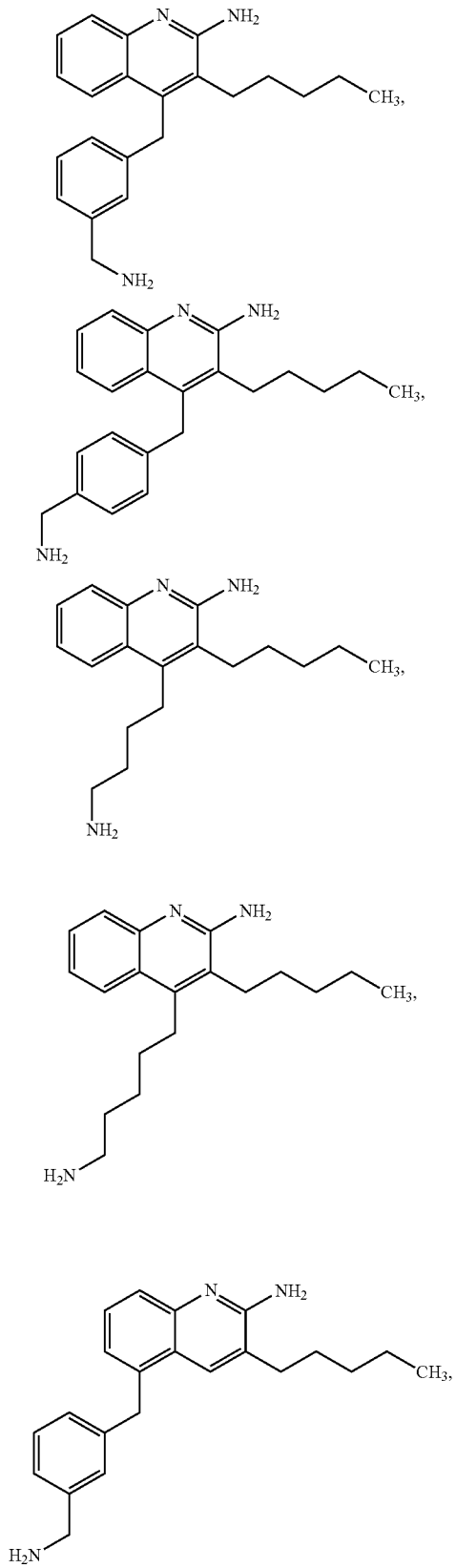
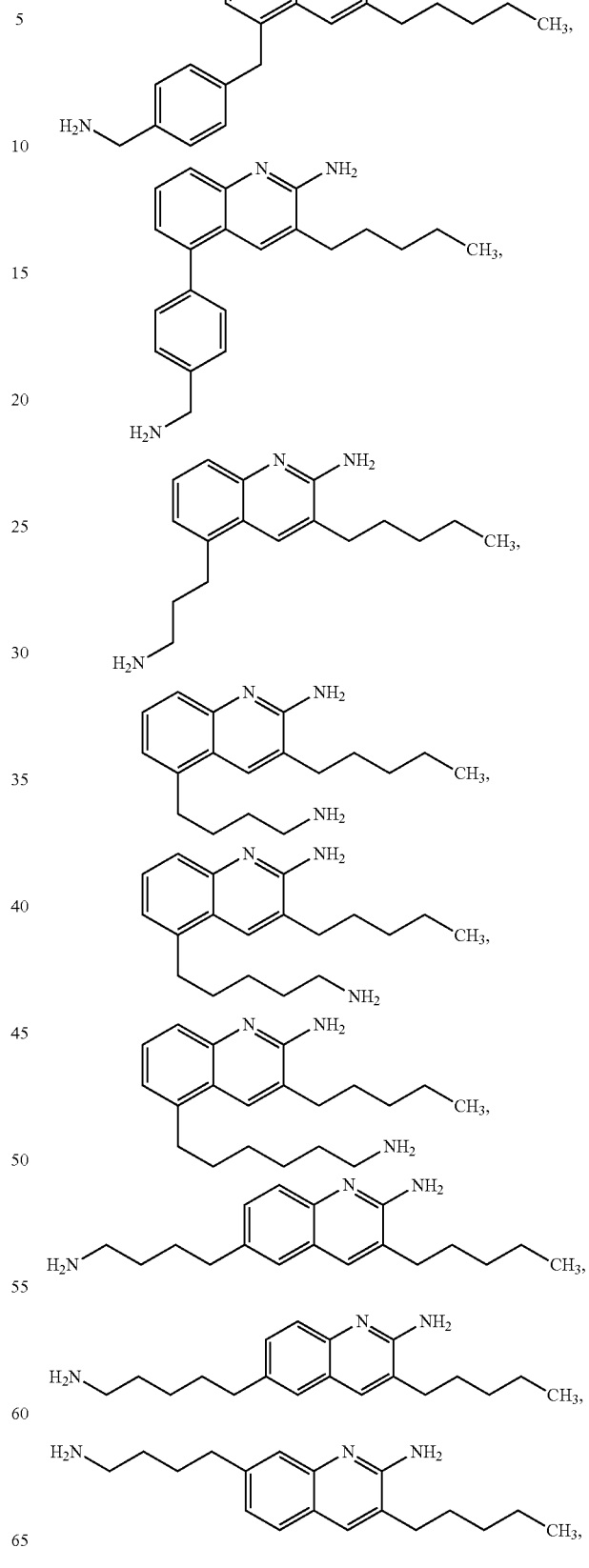

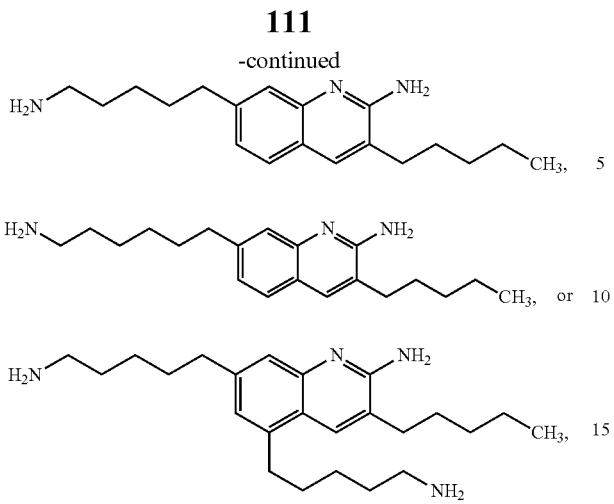

or a salt of any one thereof.

34. The compound or salt of any one of embodiments 1 to 32, represented by the Formula:

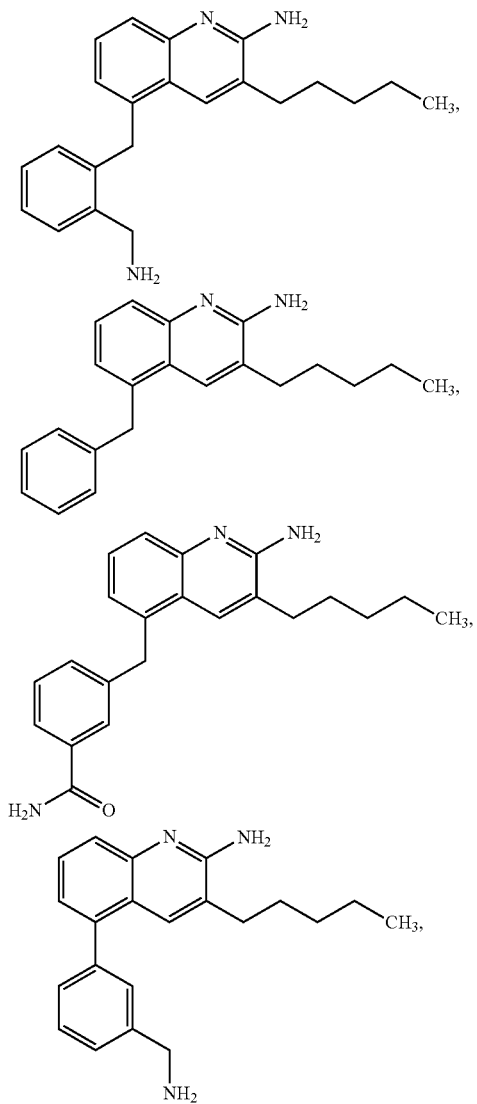

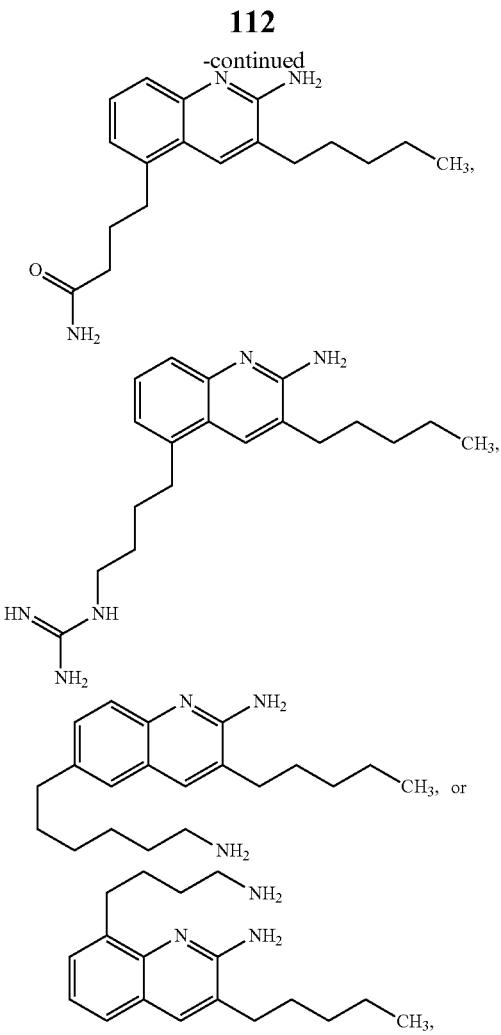

or a salt of any one thereof.

35. A pharmaceutical composition comprising a compound or salt of any one of embodiments 1 to 34, and pharmaceutically acceptable excipient.

36. The pharmaceutical composition of embodiment 35, wherein the composition further comprises a vaccine.

37. A method for modulating activity of a human toll-like receptor, comprising administering to a subject in need thereof, a compound of formula (III):

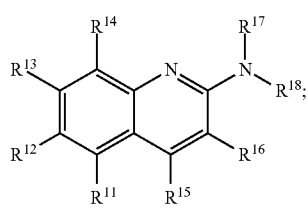

or a salt thereof, wherein:
$R^{11}$, $R^{12}$, $R^{13}$, $R^{14}$, and $R^{15}$ are independently selected from the group consisting of: H, halogen, —$OR^{20}$, —$N(R^{20})_2$, —$SR^{20}$, —CN, —$NO_2$, —OC(O)$R^{20}$, —C(O)$R^{20}$, —C(O)O$R^{20}$, —C(O)N$R^{20}$, —S(O)$_2$$R^{20}$, —S(O)$_2$O$R^{20}$, optionally substituted $C_{3-20}$ carbocycle, optionally substituted $C_{1-20}$ alkyl, optionally substituted $C_{2-20}$ alkenyl, optionally substituted $C_{2-20}$ alkynyl, and optionally substituted 3- to 20-membered heterocycle,
  wherein at least one of $R^{11}$, $R^{12}$, $R^{13}$, and $R^{14}$ is selected from the group consisting of —$OR^{20}$, —$NR^{20}{}_2$, —OC(O)$R^{20}$, —C(O)$R^{20}$, —C(O)O$R^{20}$, —C(O)N$R^{20}$, —S(O)$_2R^{20}$, —S(O)$_2OR^{20}$ optionally substituted $C_{3-20}$ carbocycle, optionally substituted $C_{1-20}$ alkyl, optionally substituted $C_{2-20}$ alkenyl, optionally substituted $C_{2-20}$ alkynyl, and optionally substituted 3- to 20-membered heterocycle;
  $R^{16}$ is optionally substituted $C_{1-20}$ alkyl, —$OR^{21}$, —$N(R^{21})_2$, —$SR^{21}$, optionally substituted $C_{2-20}$ alkenyl, and optionally substituted $C_{2-20}$ alkynyl;
  $R^{17}$ and $R^{18}$ are independently selected from H, optionally substituted $C_{1-10}$ alkyl, optionally substituted $C_{2-10}$ alkenyl, optionally substituted $C_{2-10}$ alkynyl, optionally substituted $C_{3-12}$ carbocycle and optionally substituted 3- to 12-membered heterocycle;
  $R^{20}$ is independently selected at each occurrence from the group consisting of H, optionally substituted $C_{1-10}$ alkyl, optionally substituted $C_{2-10}$ alkenyl, optionally substituted $C_{2-10}$ alkynyl, optionally substituted 3- to 12-membered heterocycle and optionally substituted $C_{3-2}$ carbocycle; and
  $R^{21}$ is independently selected at each occurrence from the group consisting of optionally substituted $C_{1-10}$ alkyl, optionally substituted $C_{2-10}$ alkenyl, and optionally substituted $C_{2-10}$ alkynyl.

38. The method of embodiment 37, wherein modulating the activity of the human toll-like receptor comprises agonizing the human toll-like receptor.

39. The method of embodiment 37 or 38, wherein the human toll-like receptor comprises hTLR8.

40. The method of any one of embodiments 37 to 39, wherein the method further comprises administering a vaccine to the subject before, in conjunction with, or after administration of the compound or salt.

41. A method of increasing an immune response to an antigen or vaccine, wherein the method comprises administering to a subject in need thereof a compound of Formula (III):

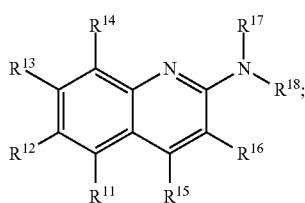

or a salt thereof, wherein:
  $R^{11}$, $R^2$, $R^{13}$, $R^{14}$, and $R^{15}$ are independently selected from the group consisting of: H, halogen, —$OR^{20}$, —$N(R^{20})_2$, —$SR^{20}$, —CN, —$NO_2$, —OC(O)$R^{20}$, —C(O)$R^{20}$, —C(O)O$R^{20}$, —C(O)N$R^{20}$, —S(O)$_2R^{20}$, —S(O)$_2OR^{20}$, optionally substituted $C_{3-20}$ carbocycle, optionally substituted $C_{1-20}$ alkyl, optionally substituted $C_{2-20}$ alkenyl, optionally substituted $C_{2-20}$ alkynyl, and optionally substituted 3- to 20-membered heterocycle,
  wherein at least one of $R^{11}$, $R^{12}$, $R^{13}$, and $R^{14}$ is selected from the group consisting of —$OR^{20}$, —$NR^{20}{}_2$, —OC(O)$R^{20}$, —C(O)$R^{20}$, —C(O)O$R^{20}$, —C(O)N$R^{20}$, —S(O)$_2R^{20}$, —S(O)$_2OR^{20}$, optionally substituted $C_{3-20}$ carbocycle, optionally substituted $C_{1-20}$ alkyl, optionally substituted $C_{2-20}$ alkenyl, optionally substituted $C_{2-20}$ alkynyl, and optionally substituted 3- to 20-membered heterocycle;
  $R^{16}$ is selected from the group consisting of optionally substituted $C_{1-20}$ alkyl, —OR, —$N(R^{21})_2$, —$SR^{21}$, optionally substituted $C_{2-20}$ alkenyl, and optionally substituted $C_{2-20}$ alkynyl;
  $R^{17}$ and $R^{18}$ are independently selected from the group consisting of H, optionally substituted $C_{1-10}$ alkyl, optionally substituted $C_{2-10}$ alkenyl, optionally substituted $C_{2-10}$ alkynyl, optionally substituted $C_{3-12}$ carbocycle and optionally substituted 3- to 12-membered heterocycle;
  $R^{20}$ is independently selected at each occurrence from the group consisting of H, optionally substituted $C_{1-10}$ alkyl, optionally substituted $C_{2-10}$ alkenyl, optionally substituted $C_{2-10}$ alkynyl, optionally substituted 3- to 12-membered heterocycle and optionally substituted $C_{3-12}$ carbocycle; and
  $R^{21}$ is independently selected at each occurrence from the group consisting of optionally substituted $C_{1-10}$ alkyl, optionally substituted $C_{2-10}$ alkenyl, and optionally substituted $C_{2-10}$ alkynyl.

42. The method of any one of embodiments 37 to 41, wherein at least one of $R^{11}$, $R^{12}$, $R^{13}$, and $R^{14}$ is selected from the group consisting of —$OR^{20}$, —$NR^{20}{}_2$, —OC(O)$R^{20}$, —C(O)$R^{20}$, —C(O)O$R^{20}$, —C(O)N($R^{20})_2$, —S(O)$_2R^{20}$, —S(O)$_2OR^{20}$ optionally substituted $C_1$–$2°$ alkyl, optionally substituted $C_{2-20}$ alkenyl, and optionally substituted $C_{2-20}$ alkynyl.

43. The method of embodiment 42, wherein at least one of $R^{11}$, $R^{12}$, $R^{13}$, and $R^{14}$ is selected from the group consisting of optionally substituted $C_{1-20}$ alkyl, optionally substituted $C_{2-20}$ alkenyl, and optionally substituted $C_{2-20}$ alkynyl.

44. The method of embodiment 43, wherein R" is optionally substituted $C_{1-10}$ alkyl.

45. The method of embodiment 44, wherein R" is optionally substituted $C_{1-5}$ alkyl.

46. The method of any one of embodiments 37 to 45, wherein $R^1$ is selected from the group consisting of:
  optionally substituted $C_{1-20}$ alkyl, optionally substituted $C_{2-20}$ alkenyl, optionally substituted $C_{2-20}$ alkynyl, wherein the $C_{1-20}$ alkyl, $C_{2-20}$ alkenyl, and $C_{2-20}$ alkynyl optional substituents are one or more substituents independently selected from the group consisting of: halogen, —CN, —$NO_2$, —$OR^{60}$, —$SR^{60}$, —$N(R^{60})_2$, —$NR^{60}C(N(R^{60}))N(R^{60})_2$, —OC(O)$R^{60}$, —C(O)$R^{60}$, —C(O)O$R^{60}$, —C(O)N($R^{60})_2$, —S(O)$_2R^{60}$, —S(O)$_2OR^{60}$, $C_{3-12}$ carbocycle, and 3- to 12-membered heterocycle, wherein the $C_{3-12}$ carbocycle, and 3- to 12-membered heterocycle are optionally substituted with one or more substituents selected from the group consisting of halogen, —CN, —$NO_2$, —$OR^{60}$, —$SR^{60}$, —$N(R^{60})_2$, $C_{1-10}$ alkyl, $C_{1-10}$ haloalkyl, —$C_{1-10}$ alkyl-$N(R^{60})_2$, —$C_{1-10}$ alkyl-$OR^{60}$, and —$C_{1-10}$ alkyl-C(O)$N(R^{60})_2$; and
  optionally substituted $C_{3-20}$ carbocycle and optionally substituted 3- to 20-membered heterocycle, wherein $C_{3-20}$ carbocycle and 3- to 20-membered heterocycle optional substituents are one or more substituents independently selected from the group consisting of: halogen, —CN, —$NO_2$, —$OR^{60}$, —$SR^6$, —$N(R^{60})_2$, $C_{1-10}$ alkyl, $C_{1-10}$ haloalkyl, —$C_{1-10}$ alkyl-$N(R^{60})_2$, —$C_{1-10}$ alkyl-$OR^{60}$, and —$C_{1-10}$ alkyl-C(O)$N(R^{60})_2$; and
  wherein $R^{60}$ at each occurrence is independently selected from the group consisting of hydrogen, $C_{1-10}$ alkyl, and $C_{1-10}$ haloalkyl.

47. The method of embodiment 46, wherein R" is substituted with —N(R$^{60}$)$_2$.

48. The method of embodiment 46, wherein R" is selected from:

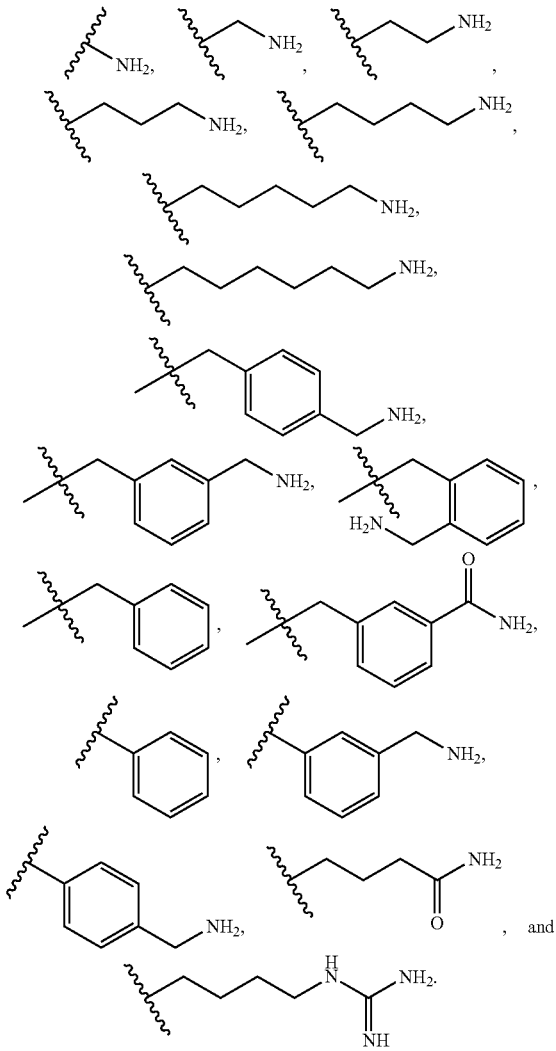

49. The method of any one of embodiments 44 to 48, wherein R$^{13}$ is optionally substituted C$_{1-10}$ alkyl.

50. The method of embodiment 49, wherein R$^{13}$ is optionally substituted C$_{1-5}$ alkyl.

51. The method of any one of embodiments 37 to 50, wherein R$^{13}$ is selected from the group consisting of:

optionally substituted C$_{1-20}$ alkyl, optionally substituted C$_{2-20}$ alkenyl, optionally substituted C$_{2-20}$ alkynyl, wherein the C$_{1-20}$ alkyl, C$_{2-20}$ alkenyl, and C$_{2-20}$ alkynyl optional substituents are one or more substituents independently selected from the group consisting of: halogen, —CN, —NO$_2$, —OR$^{60}$, —SR$^{60}$, —N(R$^{60}$)$_2$, —NR$^{60}$C(N(R$^{60}$))N(R$^{60}$)$_2$, —OC(O)R$^{60}$, —C(O)R$^{60}$, —C(O)OR$^{60}$, —C(O)N(R$^{60}$)$_2$, —S(O)$_2$R$^{60}$, —S(O)$_2$OR$^{60}$, C$_{3-12}$ carbocycle, and 3- to 12-membered heterocycle, wherein the C$_{3-12}$ carbocycle, and 3- to 12-membered heterocycle are optionally substituted with one or more substituents selected from the group consisting of halogen, —CN, —NO$_2$, —OR$^{60}$, —SR$^{60}$, —N(R$^{60}$)$_2$, C$_{1-10}$ alkyl, C$_{1-10}$ haloalkyl, —C$_{1-10}$ alkyl-N(R$^{60}$)$_2$, —C$_{1-10}$ alkyl-OR$^{60}$, and —C$_{1-10}$ alkyl-C(O)N(R$^{60}$)$_2$; and optionally substituted C$_{3-20}$ carbocycle and optionally substituted 3- to 20-membered heterocycle, wherein the C$_{3-20}$ carbocycle and 3- to 20-membered heterocycle optional substituents are one or more substituents independently selected from the group consisting of: halogen, —CN, —NO$_2$, —OR$^{60}$, —SR$^{60}$, —N(R$^{60}$)$_2$, C$_{1-10}$ alkyl, C$_{1-10}$ haloalkyl, —C$_{1-10}$ alkyl-N(R$^{60}$)$_2$, —C$_{1-10}$ alkyl-OR$^{60}$, and —C$_{1-10}$ alkyl-C(O)N(R$^{60}$)$_2$; and wherein R$^{60}$ at each occurrence is independently selected from the group consisting of hydrogen, C$_{1-10}$ alkyl, and C$_{1-10}$ haloalkyl.

52. The method of embodiment 51, wherein R$^{13}$ is substituted with —N(R$^{60}$)$_2$.

53. The method of embodiment 51, wherein R$^{13}$ is selected from:

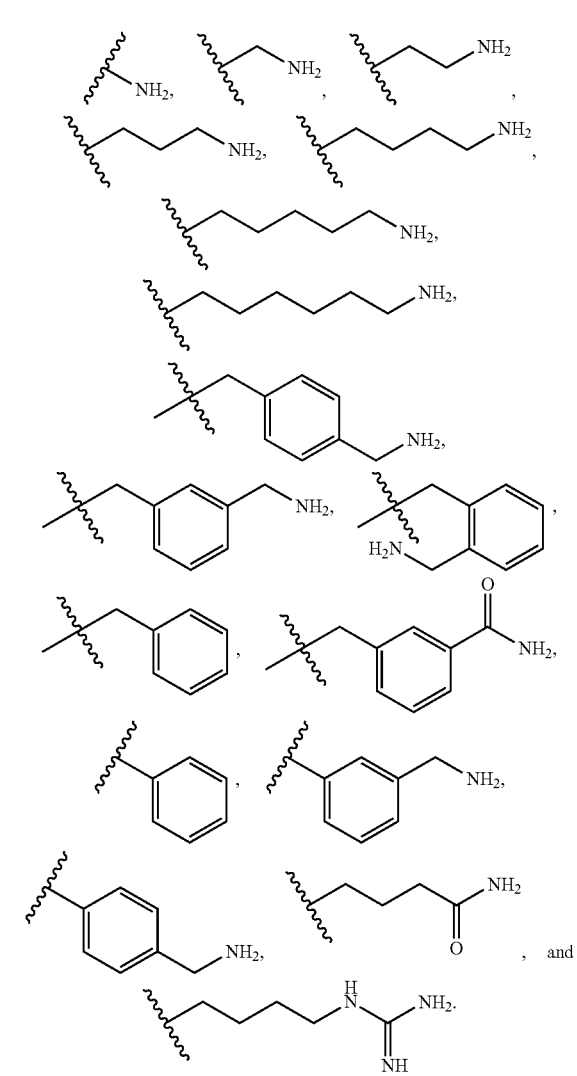

54. The method of any one of embodiments 37 to 48, wherein R$^{13}$ is selected from H, halogen, and —CN.

55. The method of embodiment 53, wherein R$^{13}$ is hydrogen.

56. The method of any one of embodiments 37 to 43 and 49 to 55, wherein R$^{11}$ is selected from H, halogen, and —CN.

57. The method of embodiment 56, wherein R$^{11}$ is hydrogen.

58. The method of any one of embodiments 37 to 57, wherein $R^{12}$, $R^{14}$, and $R^5$ are independently selected from the group consisting of: H, halogen, $-OR^{20}$, $-N(R^{20})_2$, $-SR^{20}$, $-CN$, $-NO_2$, $-OC(O)R^{20}$, $-C(O)R^{20}$, $-C(O)OR^{20}$, $-C(O)N(R^{20})_2$, $-S(O)_2R^{20}$, $-S(O)_2OR^{20}$, and optionally substituted $C_{1-20}$ alkyl.

59. The method of embodiment 58, wherein $R^{12}$, $R^{14}$, and $R^{15}$ are independently selected from the group consisting of: H, halogen, $-OR^{20}$, $-N(R^{20})_2$, $-SR^{20}$, $-CN$, $-NO_2$, and optionally substituted $C_{1-20}$ alkyl.

60. The method of any one of embodiments 37 to 58, wherein $R^{12}$, $R^{14}$, and $R^{15}$ are independently selected from the group consisting of:
  optionally substituted $C_{1-20}$ alkyl, optionally substituted $C_{2-20}$ alkenyl, optionally substituted $C_{2-20}$ alkynyl, wherein the $C_{1-20}$ alkyl, $C_{2-20}$ alkenyl, and $C_{2-20}$ alkynyl optional substituents are one or more substituents independently selected from the group consisting of: halogen, $-CN$, $-NO_2$, $-OR^{60}$, $-SR^{60}$, $-N(R^{60})_2$, $-NR^{60}C(N(R^{60}))N(R^{60})_2$, $-OC(O)R^{60}$, $-C(O)R^{60}$, $-C(O)OR^{60}$, $-C(O)N(R^{60})_2$, $-S(O)_2R^{60}$, $-S(O)_2OR^{60}$, $C_{3-12}$ carbocycle, and 3- to 12-membered heterocycle, wherein the $C_{3-12}$ carbocycle, and 3- to 12-membered heterocycle are optionally substituted with one or more substituents selected from the group consisting of halogen, $-CN$, $-NO_2$, $-OR^{60}$, $-SR^{60}$, $-N(R^{60})_2$, $C_{1-10}$ alkyl, $C_{1-10}$ haloalkyl, $-C_{1-10}$ alkyl-$N(R^{60})_2$, $-C_{1-10}$ alkyl-$OR^{60}$, and $-C_{1-10}$ alkyl-$C(O)N(R^{60})_2$; and
  optionally substituted $C_{3-20}$ carbocycle and optionally substituted 3- to 20-membered heterocycle, wherein the $C_{3-20}$ carbocycle and 3- to 20-membered heterocycle optional substituents are one or more substituents independently selected from the group consisting of: halogen, $-CN$, $-NO_2$, $-OR^{60}$, $-SR^{60}$, $-N(R^{60})_2$, $C_{1-10}$ alkyl, $C_{1-10}$ haloalkyl, $-C_{1-10}$ alkyl-$N(R^{60})_2$, $-C_{1-10}$ alkyl-$OR^{60}$, and $-C_{1-10}$ alkyl-$C(O)N(R^{60})_2$; and
  wherein $R^{60}$ at each occurrence is independently selected from the group consisting of hydrogen, $C_{1-10}$ alkyl, and $C_{1-10}$ haloalkyl.

61. The method of any one of embodiments 37 to 59, wherein $R^{12}$ is hydrogen.

62. The method of any one of embodiments 37 to 56, wherein $R^{14}$ is hydrogen.

63. The method of any one of embodiments 37 to 61, wherein $R^{15}$ is hydrogen.

64. The method of any one of embodiments 37 to 63, wherein $R^{20}$ is selected from the group consisting of:
  optionally substituted $C_{1-20}$ alkyl, optionally substituted $C_{2-20}$ alkenyl, optionally substituted $C_{2-20}$ alkynyl, wherein the $C_{1-20}$ alkyl, $C_{2-20}$ alkenyl, and $C_{2-20}$ alkynyl optional substituents are one or more substituents independently selected from the group consisting of: halogen, $-CN$, $-NO_2$, $-OR^{60}$, $-SR^{60}$, $-N(R^{60})_2$, $-NR^{60}C(N(R^{60}))N(R^{60})_2$, $-OC(O)R''^{\circ}$, $-C(O)R^{60}$, $-C(O)OR^{60}$, $-C(O)N(R^{60})_2$, $-S(O)_2R^{60}$, $-S(O)_2OR^{60}$, $C_{3-12}$ carbocycle, and 3- to 12-membered heterocycle, wherein the $C_{3-12}$ carbocycle, and 3- to 12-membered heterocycle are optionally substituted with one or more substituents selected from the group consisting of halogen, $-CN$, $-NO_2$, $-OR^{60}$, $-SR^{60}$, $-N(R^{60})_2$, $C_{1-10}$ alkyl, $C_{1-10}$ haloalkyl, $-C_{1-10}$ alkyl-$N(R^{60})_2$, $-C_{1-10}$ alkyl-$OR^{60}$, and $-C_{1-10}$ alkyl-$C(O)N(R^{60})_2$; and
  optionally substituted $C_{3-20}$ carbocycle and optionally substituted 3- to 20-membered heterocycle, wherein $C_{3-20}$ carbocycle and 3- to 20-membered heterocycle optional substituents are one or more substituents independently selected from the group consisting of: halogen, $-CN$, $-NO_2$, $-OR^{60}$, $-SR^{60}$, $-N(R^{60})_2$, $C_{1-10}$ alkyl, $C_{1-10}$ haloalkyl, $-C_{1-10}$ alkyl-$N(R^{60})_2$, $-C_{1-10}$ alkyl-$OR^{60}$, and $-C_{1-10}$ alkyl-$C(O)N(R^{60})_2$; and
  wherein $R^{60}$ at each occurrence is independently selected from the group consisting of hydrogen, $C_{1-10}$ alkyl, and $C_{1-10}$ haloalkyl.

65. The method of any one of embodiments 37 to 64, wherein $R^{16}$ is selected from the group consisting of optionally substituted $C_{1-20}$ alkyl, optionally substituted $C_{2-20}$ alkenyl, and optionally substituted $C_{2-20}$ alkynyl.

66. The method of embodiment 65, wherein $R^{16}$ is selected from the group consisting of optionally substituted $C_{1-10}$ alkyl, optionally substituted $C_{2-10}$ alkenyl, and optionally substituted $C_{1-20}$ alkynyl.

67. The method of embodiment 66, wherein $R^{16}$ is selected from the group consisting of optionally substituted $C_{1-10}$ alkyl.

68. The method of any one of embodiments embodiment 37 to 67, wherein $R^{16}$ is selected from the group consisting of:
  optionally substituted $C_{1-20}$ alkyl, optionally substituted $C_{2-20}$ alkenyl, optionally substituted $C_{2-20}$ alkynyl, wherein the $C_{1-20}$ alkyl, $C_{2-20}$ alkenyl, and $C_{2-20}$ alkynyl optional substituents are one or more substituents independently selected from the group consisting of: halogen, $-CN$, $-NO_2$, $-OR^{60}$, $-SR^{60}$, $-N(R^{60})_2$, $-NR^{60}C(N(R^{60}))N(R^{60})_2$, $-OC(O)R^{60}$, $-C(O)R^{60}$, $-C(O)OR^{60}$, $-C(O)N(R^{60})_2$, $-S(O)_2R^{60}$, $-S(O)_2OR^{60}$, $C_{3-12}$ carbocycle, and 3- to 12-membered heterocycle, wherein the $C_{3-12}$ carbocycle, and 3- to 12-membered heterocycle are optionally substituted with one or more substituents selected from the group consisting of halogen, $-CN$, $-NO_2$, $-OR^{60}$, $-SR^{60}$, $-N(R^{60})_2$, $C_{1-10}$ alkyl, $C_{1-10}$ haloalkyl, $-C_{1-10}$ alkyl-$N(R^{60})_2$, $-C_{1-10}$ alkyl-$OR^{60}$, and $-C_{1-10}$ alkyl-$C(O)N(R^{60})_2$; and
  optionally substituted $C_{3-20}$ carbocycle and optionally substituted 3- to 20-membered heterocycle, wherein $C_{3-20}$ carbocycle and 3- to 20-membered heterocycle optional substituents are one or more substituents independently selected from the group consisting of: halogen, $-CN$, $-NO_2$, $-OR^{60}$, $-SR^{60}$, $-N(R^{60})_2$, $C_{1-10}$ alkyl, $C_{1-10}$ haloalkyl, $-C_{1-10}$ alkyl-$N(R^{60})_2$, $-C_{1-10}$ alkyl-$OR^{60}$, and $-C_{1-10}$ alkyl-$C(O)N(R^{60})_2$; and
  wherein $R^{60}$ at each occurrence is independently selected from the group consisting of hydrogen, $C_{1-10}$ alkyl, and $C_{1-10}$ haloalkyl.

69. The method of embodiment 68, wherein $R^{16}$ is:

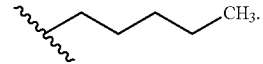 [SMILES: *CCCCC]

70. The method of any one of embodiments 37 to 69, wherein $R^{17}$ and $R^{18}$ are independently selected from H and optionally substituted $C_{1-10}$ alkyl.

71. The method of embodiment 70, wherein $R^{17}$ and $R^{18}$ are each H.

72. The method of any one of embodiments 37 to 71, wherein $R^{18}$ is selected from the group consisting of:
  optionally substituted $C_{1-20}$ alkyl, optionally substituted $C_{2-20}$ alkenyl, optionally substituted $C_{2-20}$ alkynyl, wherein the $C_{1-20}$ alkyl, $C_{2-20}$ alkenyl, and $C_{2-20}$ alkynyl optional substituents are one or more substituents independently selected from the group consisting of:

halogen, —CN, —NO$_2$, —OR$^{60}$, —SR$^{60}$, —N(R$^{60}$)$_2$, —NR$^{60}$C(N(R$^{60}$))N(R$^{60}$)$_2$, —OC(O)R$^{60}$, —C(O)R$^{60}$, —C(O)OR$^{60}$, —C(O)N(R$^{60}$)$_2$, —S(O)$_2$R$^{60}$, —S(O)$_2$OR$^{60}$, C$_{3-12}$ carbocycle, and 3- to 12-membered heterocycle, wherein the C$_{3-12}$ carbocycle, and 3- to 12-membered heterocycle are optionally substituted with one or more substituents selected from the group consisting of halogen, —CN, —NO$_2$, —OR$^{60}$, —SR$^{60}$, —N(R$^{60}$)$_2$, C$_{1-10}$ alkyl, C$_{1-10}$ haloalkyl, —C$_{1-10}$ alkyl-N(R$^{60}$)$_2$, —C$_{1-10}$ alkyl-OR$^{60}$, and —C$_{1-10}$ alkyl-C(O)N(R$^{60}$)$_2$; and optionally substituted C$_{3-20}$ carbocycle and optionally substituted 3- to 20-membered heterocycle, wherein the C$_{3-20}$ carbocycle and 3- to 20-membered heterocycle optional substituents are one or more substituents independently selected from the group consisting of: halogen, —CN, —NO$_2$, —OR$^{60}$, —SR$^{60}$, —N(R$^{60}$)$_2$, C$_{1-10}$ alkyl, C$_{1-10}$ haloalkyl, —C$_{1-10}$ alkyl-N(R$^{60}$)$_2$, —C$_{1-10}$ alkyl-OR$^{60}$, and —C$_{1-10}$ alkyl-C(O)N(R$^{60}$)$_2$; and wherein R$^{60}$ at each occurrence is independently selected from the group consisting of hydrogen, C$_{1-10}$ alkyl, and C$_{1-10}$ haloalkyl.

73. The method of any one of embodiments 37 to 72, wherein the compound is represented by the Formula:

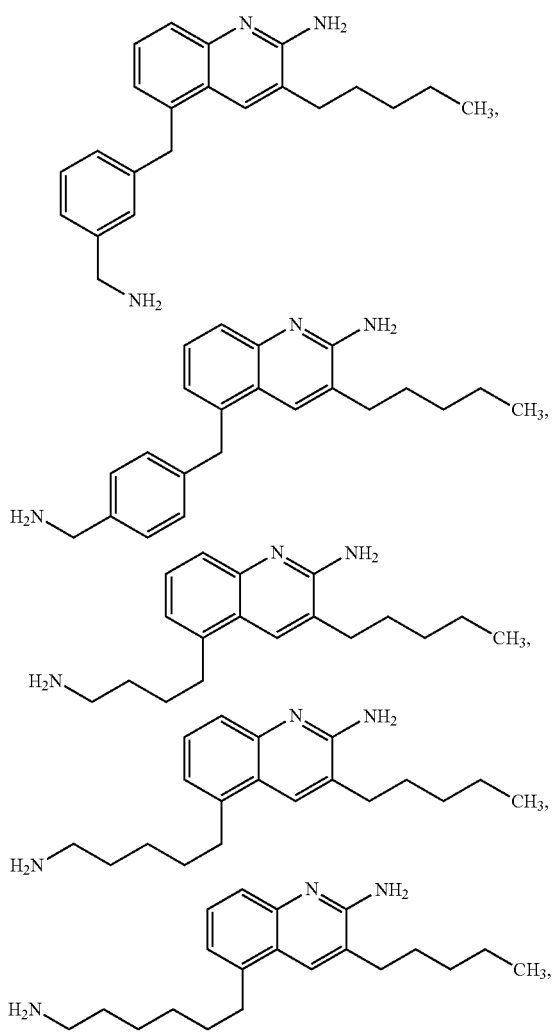

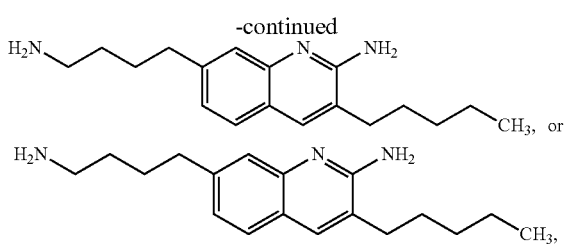

or a salt of any one thereof.

What is claimed is:

1. A compound represented by Formula (II):

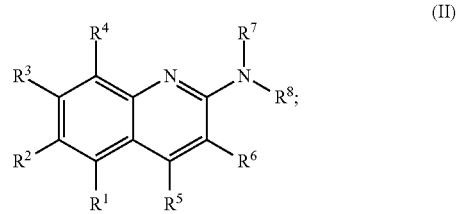

or a salt thereof, wherein:

R$^3$ is selected from the group consisting of

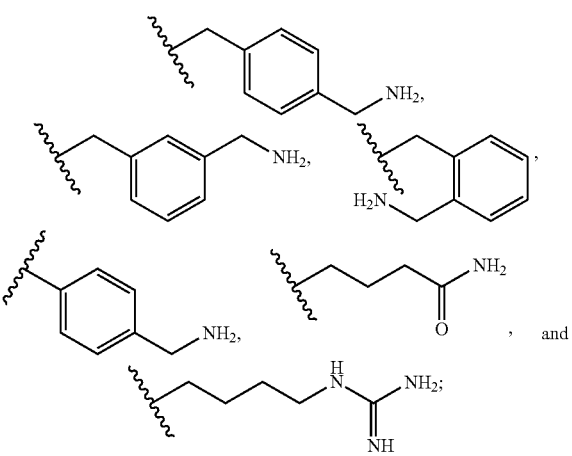

R$^1$ is selected from the group consisting of

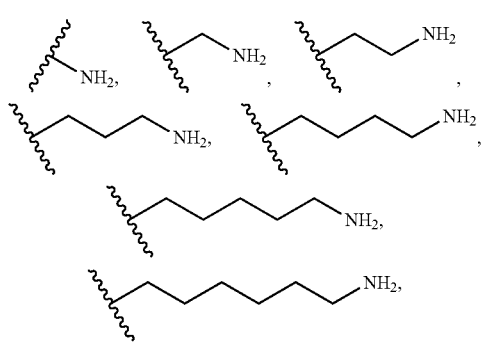

-continued

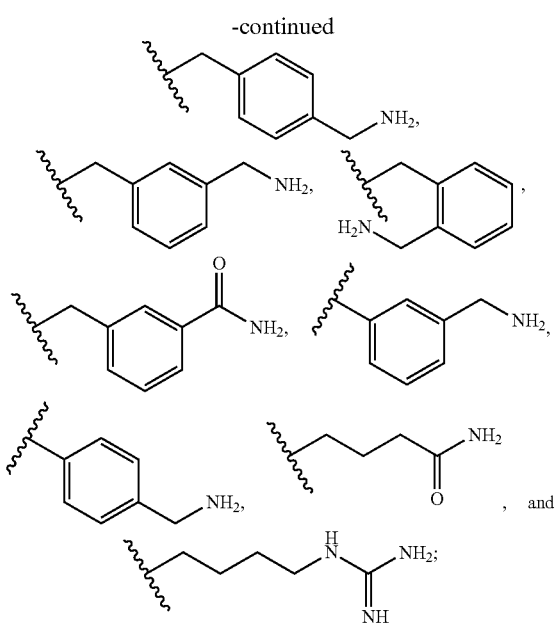

R², R⁴, and R⁵ are independently selected from the group consisting of H, halogen, $-OR^{10}$, $-N(R^{10})_2$, $-SR^{10}$, $-CN$, $-NO_2$, $-OC(O)R^{10}$, $-C(O)R^{10}$, $-C(O)OR^{10}$, $-C(O)N(R^{10})_2$, $-S(O)_2R^{10}$, $-S(O)_2OR^{10}$, optionally substituted $C_{1-20}$ alkyl, optionally substituted $C_{2-20}$ alkenyl, optionally substituted $C_{2-20}$ alkynyl, optionally substituted $C_{3-20}$ carbocycle, and optionally substituted 3-to 20-membered heterocycle;

R⁶ is selected from the group consisting of $-OR^{11}$, $-N(R^{11})_2$, $-SR^{11}$, optionally substituted $C_{1-20}$ alkyl, optionally substituted $C_{2-20}$ alkenyl, and optionally substituted $C_{2-20}$ alkynyl;

R⁷ and R⁸ are each independently H;

R¹⁰ is independently selected at each occurrence from the group consisting of H, optionally substituted $C_{1-10}$ alkyl, optionally substituted $C_{2-10}$ alkenyl, optionally substituted $C_{2-10}$ alkynyl, optionally substituted $C_{3-12}$ carbocycle and optionally substituted 3-to 12-membered heterocycle; and R¹¹ is independently selected at each occurrence from the group consisting of optionally substituted $C_{1-10}$ alkyl, optionally substituted $C_{2-10}$ alkenyl, and optionally substituted $C_{2-10}$ alkynyl.

2. The compound or salt of claim 1, wherein R², R⁴, and R⁵ are independently selected from the group consisting of H, halogen, $-OR^{10}$, $-N(R^{10})_2$, $-SR^{10}$, $-CN$, $-NO_2$, $-OC(O)R^{10}$, $-C(O)R^{10}$, $-C(O)OR^{10}$, $-C(O)N(R^{10})_2$, $-S(O)_2R^{10}$, $-S(O)_2OR^{10}$, and substituted $C_{1-20}$ alkyl.

3. The compound or salt of claim 1, wherein R¹⁰ is independently selected at each occurrence from the group consisting of:
optionally substituted $C_{1-10}$ alkyl, optionally substituted $C_{2-10}$ alkenyl, optionally substituted $C_{2-10}$ alkynyl, optionally substituted $C_{3-12}$ carbocycle and optionally substituted 3-to 12-membered heterocycle, wherein the $C_{1-10}$ alkyl, $C_{2-10}$ alkenyl, and $C_{2-10}$ alkynyl optional substituents are one or more substituents independently selected from the group consisting of: halogen, $-CN$, $-NO_2$, $-OR^{50}$, $-SR^{50}$, $-N(R^{50})_2$, $-NR^{50}C(N(R^{50}))N(R^{50})_2$, $-OC(O)R^{50}$, $-C(O)R^{50}$, $-C(O)OR^{50}$, $-C(O)N(R^{50})_2$, $-S(O)_2R^{50}$, and $-S(O)_2OR^{50}$, and wherein the $C_{3-12}$ carbocycle and 3-to 12-membered heterocycle optional substituents are one or more substituents selected from the group consisting of halogen, $-CN$, $-NO_2$, $-OR^{50}$, $-SR^{50}$, $-N(R^{50})_2$, $C_{1-10}$ alkyl, $C_{1-10}$ haloalkyl, $-C_{1-10}$ alkyl-$N(R^{50})_2$, $-C_{1-10}$ alkyl-$OR^{50}$, and $-C_{1-10}$ alkyl-$C(O)N(R^{50})_2$; and wherein R⁵⁰ at each occurrence is independently selected from the group consisting of hydrogen, $C_{1-10}$ alkyl, and $C_{1-10}$ haloalkyl.

4. The compound or salt of claim 1, wherein R⁶ is selected from the group consisting of optionally substituted $C_{1-20}$ alkyl, optionally substituted $C_{2-20}$ alkenyl, and optionally substituted $C_{2-20}$ alkynyl.

5. A compound that is represented by

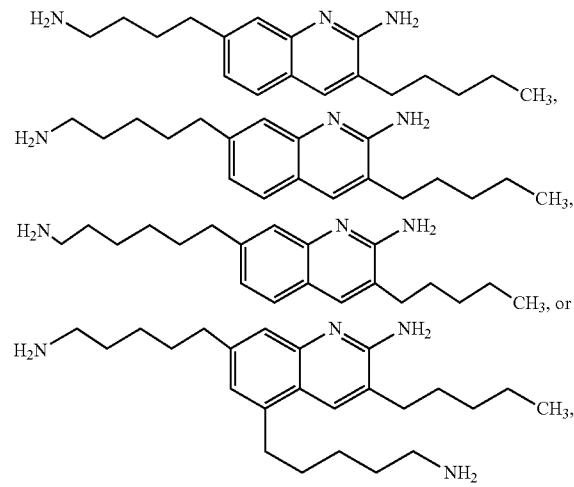

or a salt thereof.

6. A pharmaceutical composition comprising a compound or salt of claim 1, and a pharmaceutically acceptable excipient, optionally wherein the composition further comprises a vaccine.

7. A method for modulating activity of a human toll-like receptor, comprising administering to a subject in need thereof a compound of claim 1 or a salt thereof.

8. The method of claim 7, wherein modulating the activity of the human toll-like receptor comprises agonizing the human toll-like receptor.

9. The method of claim 7, wherein the human toll-like receptor comprises hTLR8.

10. The method of claim 7, wherein the method further comprises administering a vaccine to the subject before, in conjunction with, or after administration of the compound or salt thereof.

11. A method of increasing an immune response to an antigen or vaccine, wherein the method comprises administering to a subject in need thereof a compound of claim 1 or a salt thereof.

12. The method of claim 11, wherein the method further comprises administering a vaccine to the subject before, in conjunction with, or after administration of the compound or salt thereof.

* * * * *